US009850256B2

(12) United States Patent
Cren et al.

(10) Patent No.: US 9,850,256 B2
(45) Date of Patent: Dec. 26, 2017

(54) ANTIBACTERIAL BASIC BIAROMATIC DERIVATIVES WITH AMINOALKOXY SUBSTITUTION

(71) Applicant: Idorsia Pharmaceuticals Ltd, Allschwil (CH)

(72) Inventors: Sylvaine Cren, Allschwil (CH); Astrid Friedli, Allschwil (CH); Georg Rueedi, Allschwil (CH); Cornelia Zumbrunn, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 0 days.

(21) Appl. No.: 15/516,290

(22) PCT Filed: Oct. 14, 2015

(86) PCT No.: PCT/EP2015/073751
§ 371 (c)(1),
(2) Date: Mar. 31, 2017

(87) PCT Pub. No.: WO2016/059097
PCT Pub. Date: Apr. 21, 2016

(65) Prior Publication Data
US 2017/0305927 A1 Oct. 26, 2017

(30) Foreign Application Priority Data
Oct. 15, 2014 (EP) .................................. 14189026

(51) Int. Cl.
*C07D 498/04* (2006.01)
*C07D 417/14* (2006.01)
*C07D 498/00* (2006.01)
*A61K 31/5365* (2006.01)
*A61K 31/00* (2006.01)

(52) U.S. Cl.
CPC ........ *C07D 498/04* (2013.01); *A61K 31/5365* (2013.01); *C07D 417/14* (2013.01); *A61K 31/00* (2013.01); *C07D 498/00* (2013.01)

(58) Field of Classification Search
None
See application file for complete search history.

(56) References Cited

U.S. PATENT DOCUMENTS

| 8,114,867 | B2 | 2/2012 | Gude et al. |
| 8,217,029 | B2 | 7/2012 | Bur et al. |
| 8,349,826 | B2 | 1/2013 | Hubschwerlen et al. |
| 8,349,828 | B2 | 1/2013 | Hubschwerlen et al. |
| 8,507,478 | B2 | 8/2013 | Hubschwerlen et al. |
| 8,618,092 | B2 | 12/2013 | Hubschwerlen et al. |
| 9,079,922 | B2 | 7/2015 | Hubschwerlen et al. |
| 9,346,804 | B2 | 5/2016 | Hubschwerlen et al. |
| 9,505,750 | B2 | 11/2016 | Hubschwerlen et al. |
| 9,527,867 | B2 | 12/2016 | Cren et al. |

| 2010/0137290 | A1 | 6/2010 | Gude et al. |
| 2010/0331308 | A1 | 12/2010 | Hubschwerlen et al. |
| 2010/0331318 | A1 | 12/2010 | Hubschwerlen et al. |
| 2011/0003789 | A1 | 1/2011 | Hubschwerlen et al. |
| 2011/0039823 | A1 | 2/2011 | Bur et al. |

(Continued)

FOREIGN PATENT DOCUMENTS

WO  WO 99/37641 A1  7/1999
WO  WO 2004/002992 A1  1/2004

(Continued)

OTHER PUBLICATIONS

International Search Report and Written Opinion issued in PCT/EP2015/073751 dated Nov. 18, 2015.
"Remington, The Science and Practice of Pharmacy," 5 pages, 21st Edition (2005), Part 5, Pharmaceutical Manufacturing, published by Lippincott Williams & Wilkins.
Bellina et al., "Palladium Catalysts for the Suzuki Cross-Coupling Reaction: An Overview of Recent Advances," Synthesis, 2004, pp. 2419-2440, No. 15.
Cossio et al, "Mechanism and Stereoselectivity of the Aza-Wittig Reaction between Phosphazenes and Aldehydes," J. Org. Chem., 2006, pp. 2839-2847, vol. 71, No. 7, and references therin.
Fu, "The Development of Versatile Methods for Palladium-Catalyzed Coupling Reactions of Aryl Electrophiles through the Use of P(t-Bu)3 and PCy3 as Ligands," Accounts of chemical research, Nov. 2008, pp. 1555-1564, vol. 41, No. 11, and references therein.
Green et al, Protecting Groups in Organic Synthesis, 3rd edition, (1999), 52 pages.
Green et al, Protecting Groups in Organic Synthesis, 3rd edition, (1999), pp. 133-139 and 142-143 respectfully.
Green et al, Protecting Groups in Organic Synthesis, 3rd edition, (1999), pp. 23-147.
Green et al, Protecting Groups in Organic Synthesis, 3rd edition, (1999), pp. 293-329.

(Continued)

*Primary Examiner* — Kamal Saeed
(74) *Attorney, Agent, or Firm* — Arent Fox LLP

(57) ABSTRACT

The invention relates to antibacterial compounds of formula I wherein $R^{1a}$, $R^{2a}$, $R^{2b}$, $R^{3a}$, $R^{3b}$, $R^4$, $R^5$, $U^1$, $U^2$, $U^3$, $U^4$, $V^1$, $V^2$, $V^3$, $V^4$, X and Q and n are as defined in the specification. It further relates pharmaceutical compositions containing these compounds and the uses of these compounds in the manufacture of medicaments for the treatment of bacterial infections. These compounds are useful antimicrobial agents effective against a variety of human and veterinary pathogens including among others Gram-positive and Gram-negative aerobic and anaerobic bacteria.

15 Claims, No Drawings

(56) References Cited

U.S. PATENT DOCUMENTS

| | | |
|---|---|---|
| 2011/0195949 A1 | 8/2011 | Kaegi-Egger et al. |
| 2011/0195961 A1 | 8/2011 | Hubschwerlen et al. |
| 2011/0201595 A1 | 8/2011 | Hubschwerlen et al. |
| 2014/0142093 A1 | 5/2014 | Hubschwerlen et al. |
| 2015/0051188 A1 | 2/2015 | Hubschwerlen et al. |
| 2016/0075722 A1 | 3/2016 | Cren et al. |
| 2016/0237088 A1 | 8/2016 | Hubschwerlen et al. |

FOREIGN PATENT DOCUMENTS

| | | |
|---|---|---|
| WO | WO 2008/126024 A2 | 10/2008 |
| WO | WO 2008/126034 A2 | 10/2008 |
| WO | WO 2009/077989 A1 | 6/2009 |
| WO | WO 2009/104147 A2 | 8/2009 |
| WO | WO 2009/104159 A1 | 8/2009 |
| WO | WO 2009/005794 A2 | 10/2009 |
| WO | WO 2010/041194 A1 | 4/2010 |
| WO | WO 2010/041218 A2 | 4/2010 |
| WO | WO 2010/041219 A1 | 4/2010 |
| WO | WO 2010/059390 A1 | 5/2010 |
| WO | WO 2013/068948 A1 | 5/2013 |
| WO | WO 2014/170821 A1 | 10/2014 |

OTHER PUBLICATIONS

Green et al, Protecting Groups in Organic Synthesis, 3rd edition, (1999), pp. 494-653, John Wiley and Sons, Inc., New York, NY.

Kantchev et al., "Pd-N-Heterocyclic Carbene (NHC) Catalysts for Cross-Coupling Reactions," Aldrichimica ACTA, 2006, pp. 97-111, vol. 39, No. 4.

Mauger et al., "Synthetic Applications of Buchwald's Phosphines in Palladium-Catalyzed Aromatic-Bond-Forming Reactions," Aldrichimica ACTA, 2006, pp. 17-24, vol. 39, No. 1.

Methods for Dilution Antimicrobial Susceptibility Tests for Bacteria that Grow Aerobically, Approved standard, 7th ed., Clinical and Laboratory Standards Institute (CLSI) Document M7-A7, Wayne, PA, USA (2006).

Miyaura et al., "Palladium-Catalyzed Cross-Coupling Reactions of Organoboron Compounds," Chemical Reviews, 1995. pp. 2457-2483, vol. 95.

Sato et al, "One-pot reductive amination of aldehydes and ketones with α-picoline-borane in methanol, in water, and in neat conditions," Tetrahedron, 2004, pp. 7899-7906, vol. 60.

Solomon et al., "Antibiotic Resistance Threats in the United States: Stepping Back from the Brink," American Academy of Family Physicans, Jun. 15, 2014, pp. 938-941, vol. 89, No. 12.

Stahl et al, 'Handbook of Pharmaceutical Salts. Properties, Selection, and Use,' pp. 329-350, 2008, Wiley-VCH.

Wouters et al, "Pharmaceutical Salts and Co-crystals," vii-xiv, 2012, RSC Publishing.

ANTIBACTERIAL BASIC BIAROMATIC DERIVATIVES WITH AMINOALKOXY SUBSTITUTION

CROSS-REFERENCE TO RELATED APPLICATIONS

This application is a National Stage entry of International Application No.: PCT/EP2015/073751, filed Oct. 14, 2015, which claims priority to European Patent Application No. 14189026.9, filed Oct. 15, 2014. The disclosures of the priority applications are hereby incorporated in their entirety by reference.

The present invention concerns antibacterial basic biaromatic derivatives with aminoalkoxy substitution, pharmaceutical compositions containing them and uses of these compounds in the manufacture of medicaments for the treatment of bacterial infections. These compounds are useful antimicrobial agents effective against a variety of human and veterinary pathogens including among others Gram-positive and Gram-negative aerobic and anaerobic bacteria and especially against resistant strains of *Pseudomonas aeruginosa* and Enterobacteriaceae such as *Klebsiella pneumoniae*.

The intensive use of antibiotics has exerted a selective evolutionary pressure on microorganisms to produce genetically based resistance mechanisms. Modern medicine and socio-economic behaviour exacerbate the problem of resistance development by creating slow growth situations for pathogenic microbes, e.g. in artificial joints, and by supporting long-term host reservoirs, e.g. in immune-compromised patients.

In hospital settings, an increasing number of strains of *Staphylococcus aureus, Streptococcus pneumoniae, Enterococcus* spp., Enterobacteriacea and *Pseudomonas aeruginosa*, major sources of infections, are becoming multi-drug resistant and therefore difficult if not impossible to treat:

- *S. aureus* is resistant to β-lactams, quinolones and now even to vancomycin;
- *S. pneumoniae* is becoming resistant to penicillin or quinolone antibiotics and even to new macrolides;
- *Enteroccocci* are quinolone and vancomycin resistant and β-lactam antibiotics are inefficacious against these strains;
- Enterobacteriacea are cephalosporin and quinolone resistant and carbapenems are losing their efficacy (e.g. carbapenem-resistant *K. pneumoniae*);
- *P. aeruginosa* is β-lactam and quinolone resistant.

Furthermore, the incidence of multi-drug-resistant Gram-negative strains such as Enterobacteriacae and *Pseudomonas aeruginosa*, is steadily increasing and new emerging organisms like *Acinetobacter* spp. or *Clostridium difficile*, which have been selected during therapy with the currently used antibiotics, are becoming a real problem in hospital settings (S. L. Solomon et al., Antibiotic Resistance Threats In the United States: Stepping Back from the Brink, *Academy of Family Physician*, page 940 Volume 89, Number 12, Jun. 15, 2014). Therefore, there is a high medical need for new antibacterial agents which overcome these multidrug-resistant bacilli especially *Pseudomonas aeruginosa* and Enterobacteriacae such as *K. pneumoniae*.

WO 2008/126024 describes antibacterial compounds of formula (A1)

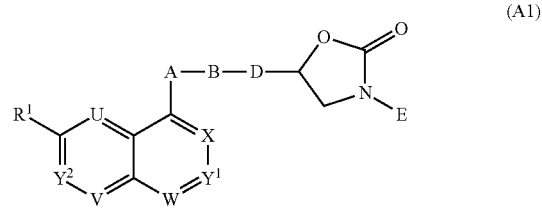

(A1)

wherein
$R^1$ is hydrogen, halogen, hydroxy, alkoxy or cyano;
$Y^1$ and $Y^2$ each represent CH and one or two of U, V, W and X represent(s) N and the remaining each represent CH or, in the case of X, may also represent $CR^a$, and, in the case of W, may also represent $CR^b$, or
each of U, V, W, X, $Y^1$ and $Y^2$ represents CH or each of U, V, W, X and $Y^1$ represents CH and $Y^2$ represents N, or also one or, provided $R^1$ is hydrogen, two of U, V, W, X, $Y^1$ and $Y^2$ represent(s) $CR^c$ and the remaining each represent CH;
$R^a$ represents halogen;
$R^b$ represents alkoxy, alkoxycarbonyl or alkoxyalkoxy;
$R^c$, each time it occurs, independently represents hydroxy or alkoxy;
A-B-D can (notably) be such that:
A is $CH_2N(R^7)$ and either B is $CH_2CH_2$, $COCH_2$ or $CH_2CH(OH)$ and D is $CH_2$ or B is $CH_2CH_2$ or $CH_2CH(OH)$ and D is $CH(OH)$ or $CH(NH_2)$, or
A is CONH or $CH_2O$, B is $CH_2CH_2$ and D is $CH_2$;
$R^7$ is hydrogen or $(CH_2)_r$—$COOR^{7'}$, or also $R^7$ is alkyl which may be substituted once or twice by groups independently selected from hydroxy, halogen, amino and dimethylamino, r being an integer from 1 to 4 and $R^{7'}$ being hydrogen or alkyl;
E can (notably) be one of the following groups:

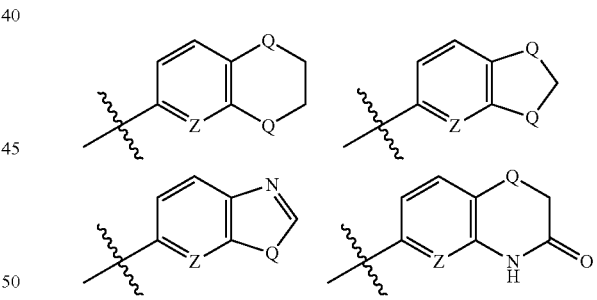

wherein Z is CH or N and Q is O or S.
WO 2010/041219 describes antibacterial compounds of formula (A2)

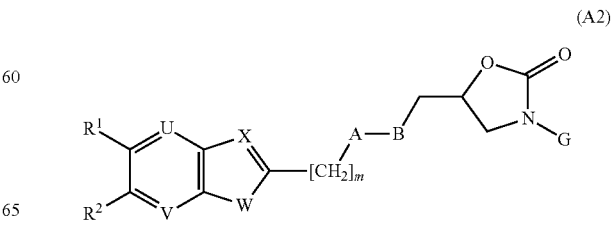

(A2)

wherein
R¹ represents hydrogen, $(C_1-C_4)$alkoxy or halogen;
R² represents hydrogen or $(C_1-C_4)$alkoxy;
U represents N or CH;
V represents N or $CR^b$, wherein $R^b$ is hydrogen or halogen;
W represents *—CH=$CR^a$—, *—N=CH— or S, wherein the asterisks indicate the bond which is linked to the carbon atom connecting V and W and wherein IV is hydrogen or halogen;
X represents N or $CR^c$, wherein $R^c$ is hydrogen, $(C_1-C_4)$ alkyl or halogen;
with the proviso that the group of formula (D)

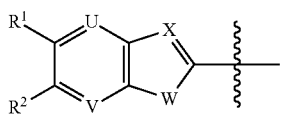

(D)

contains between none and three heteroatoms, wherein the heteroatoms are independently selected from nitrogen and, in case of W, sulfur;
m, A and B are (notably) such that m is 1, A is —NHCH₂—#, —CH₂NH—#, —NHCH₂CH₂—#, —CH₂NHCH₂—, —CH₂CH₂NH—#, —NHCH₂CH₂NH—, —CH₂NHCH₂CH₂—# or piperazin-1,4-diyl, wherein the hash indicates the bond which is linked to B, and B represents a bond; and
G represents (notably) a group of the formula (G1)

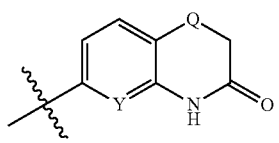

(G1)

wherein Y represents CH or N, and Q represents O or S.
Besides, WO 99/37641 describes antibacterial compounds of formula (A3)

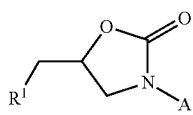

(A3)

wherein
A can notably represent a group of formula

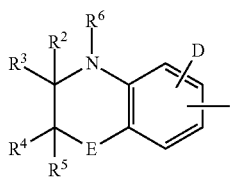

wherein
D, R⁴, R⁵ and R⁶ can each notably represent H;
E can notably represent O or S; and R² and R³ can notably represent together a group of formula =O; and
R¹ can notably represent a group of formula —NR¹⁸R¹⁹ wherein R¹⁸ and R¹⁹ can notably be such that R¹⁸ represents H and R¹⁹ represents a group —C(=O)—R²⁰ wherein R²⁰ can notably represent an aryl group with 6 to 10 carbon atoms or a heteroaromatic ring with up to 3 heteroatoms independently selected from S, N and O, which aryl or heteroaromatic ring may itself optionally be substituted with up to two identical or different substituents selected from halogen, cyano, nitro, hydroxy or phenyl.

In WO 2014/170821, the Applicants have described antibacterial compounds of formula (A4)

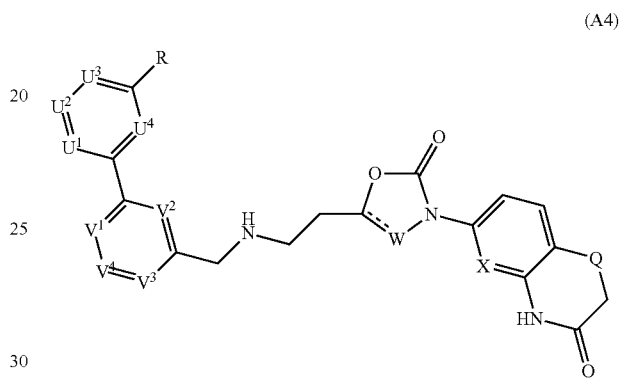

(A4)

wherein
R is H, cyano, $(C_1-C_3)$alkoxy, cyanomethoxy, $(C_3-C_6)$cycloalkylmethoxy, hydroxy$(C_2-C_4)$alkoxy, $(C_1-C_3)$alkoxy-$(C_2-C_3)$alkoxy, $(C_1-C_4)$alkoxycarbonyl, 2-ethoxy-2-oxoethoxy, 2-(methylamino)-2-oxoethoxy, (1-cyanocyclobutyl)methoxy, 3-hydroxy-pyrrolidin-1-yl or (3,4-dihydroxycyclopentyl)methoxy;
$U^1$ is N or $CR^1$, $U^2$ is N or $CR^2$, $U^3$ is N or $CR^3$ and $U^4$ is N or $CR^4$, it being understood that at most three of $U^1$, $U^2$, $U^3$ and $U^4$ can be N at the same time;
$V^1$ is N or $CR^5$, $V^2$ is N or $CR^6$, $V^3$ is N or $CR^7$ and $V^4$ is N or CH, it being understood that at most two of $V^1$, $V^2$, $V^3$ and $V^4$ can be N at the same time;
R¹ is H, cyano, hydroxy or $(C_1-C_3)$alkoxy;
R² is H, hydroxy or $(C_1-C_3)$alkoxy;
R³ is H, cyano, hydroxy, $(C_1-C_3)$alkoxy or carboxamido;
R⁴ is H, cyano, hydroxy or $(C_1-C_3)$alkoxy;
R⁵ is H, hydroxy or halogen;
R⁶ is H, hydroxy or halogen;
R⁷ is H;
the dotted line "-----" is a bond or is absent;
W is CH or N when the dotted line "-----" is a bond, or W represents CH₂ when the dotted line "-----" is absent;
X is CH or N; and
Q is O or S.

The instant invention provides new antibacterial biaromatic derivatives based on a biphenyl or heteroaromatic biphenyl-like motif, namely the compounds of formula I described herein.

Various embodiments of the invention are presented hereafter:

1) The invention relates to compounds of formula I

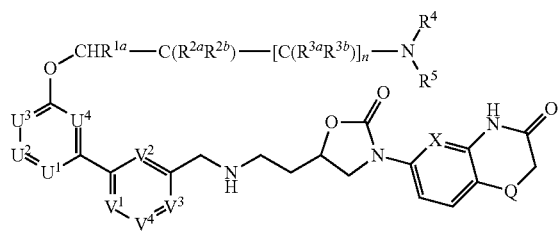

wherein n represents 0, 1, 2 or 3;

$R^{1a}$ represents H or $(C_1-C_3)$alkyl;

$R^{2a}$ and $R^{2b}$ independently from each other represent H or $(C_1-C_3)$alkyl;

$R^{3a}$ and $R^{3b}$ independently from each other represent H or $(C_1-C_3)$alkyl;

$R^4$ represents H, $(C_1-C_3)$alkyl, or $(C_2-C_3)$alkyl-$NR^{4a}R^{4b}$, wherein $R^{4a}$ and $R^{4b}$ are independently from each other H or $(C_1-C_3)$alkyl;

$R^5$ represents H, $(C_1-C_3)$alkyl, or $(C_2-C_3)$alkyl-$NR^{5a}R^{5b}$, wherein $R^{5a}$ and $R^{5b}$ are independently from each other H or $(C_1-C_3)$alkyl; or $R^{2a}$ and $R^{2b}$ together with the carbon atom which bears them form a 3 to 6-membered cycloalkyl ring; or $R^4$ and $R^5$ together with the nitrogen atom which bears them form a 4 to 6-membered heterocycloalkyl ring; or $R^4$ and $R^5$ together with the nitrogen atom which bears them form a 6 to 8-membered bicyclic heterocycloalkyl ring, which bicyclic heterocycloalkyl ring may optionally be substituted by a group $NR^6R^7$, wherein $R^6$ and $R^7$ are independently from each other H or $(C_1-C_3)$alkyl; or $R^4$ and $R^5$ together with the nitrogen atom which bears them and the adjacent $CR^{2a}R^{2b}$ or $CR^{3a}R^{3b}$ together form an amidine group; or $R^{1a}$ and $R^{3a}$, together with the carbon atoms which bear them and the carbon atom which connects these latter two atoms, form a 4 to 6-membered cycloalkyl ring, whereby $R^{2a}$, $R^{2b}$ and $R^{3b}$ each represent H, and n represents 1; or $R^{1a}$ and $R^4$, together with the carbon and nitrogen atoms which bear them and the carbon atom(s) which connect(s) the latter two atoms, form a 4 to 6-membered heterocycloalkyl ring, whereby $R^{2a}$, $R^{2b}$, optional $R^{3a}$ and optional $R^{3b}$ each represent H, n represents 0 or 1, and said 4 to 6-membered heterocycloalkyl ring optionally contains a substituent selected from $OCH_3$ and $CH_3$; or $R^{2a}$ and $R^4$ together with the carbon and nitrogen atoms which bear them and the optional carbon atom(s) which connect the latter two atoms, form a 4 to 6-membered heterocycloalkyl ring, whereby $R^{1a}$, optional $R^{3a}$ and optional $R^{3b}$ each represent H, $R^{2b}$ represents H, $NH_2$ or OH, and n represents 0, 1 or 2;

$U^1$ represents N or CH, $U^2$ represents N, CH, C—O$(C_1-C_3)$alkyl, or C—CN, $U^3$ represents N or CH and $U^4$ represents N or CH, it being understood that at most three of $U^1$, $U^2$, $U^3$ and $U^4$ can represent N at the same time;

$V^1$ represents N or CH, $V^2$ represents N or CH, $V^3$ represents N or CH and $V^4$ represents N or CH, it being understood that at most three of $V^1$, $V^2$, $V^3$ and $V^4$ can represent N at the same time;

X represents CH or N;

Q represents O or S;

and to salts (in particular pharmaceutically acceptable salts) of compounds of formula I.

It is to be understood that in embodiments where "$R^{1a}$ and $R^{3a}$, together with the carbon atoms which bear them and the carbon atom which connects these latter two atoms, form a 4 to 6-membered cycloalkyl ring", the way of counting within the ring occurs on the shortest or equally short way from $C^1$ to N. This way of counting leads to the smallest number for n as possible. For example:

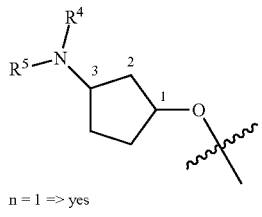

n = 1 => yes

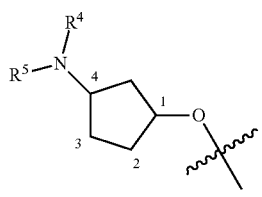

n = 2 => no

It is further to be understood that in embodiments where "$R^{1a}$ and $R^4$, together with the carbon and nitrogen atoms which bear them and the carbon atom(s) which connect(s) the latter two atoms, form a 4 to 6-membered heterocycloalkyl ring", the way of counting within the ring occurs on the shortest or equally short way from $C^1$ to N. This way of counting leads to the smallest number for n as possible. For example:

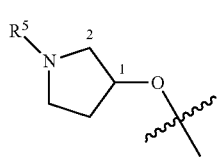

n = 0 => yes

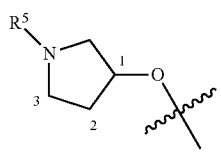

n = 1 => no

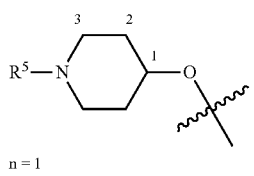

n = 1 equal to

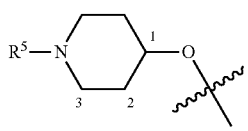

n = 1

It is further to be understood that in embodiments where "$R^{2a}$ and $R^4$ together with the carbon and nitrogen atoms which bear them and the optional carbon atom(s) which connect(s) the latter two atoms, form a 4 to 6-membered heterocycloalkyl ring", the way of counting within the ring occurs on the shortest or equally short way from $C^1$ to N. This way of counting leads to the smallest number for n as possible. For example:

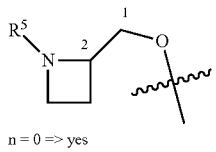

n = 0 => yes

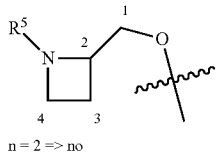

n = 2 => no

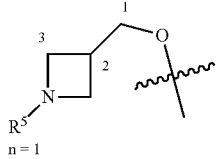

n = 1 equal to

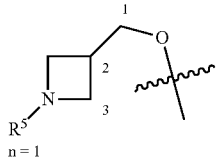

n = 1

It is to be understood that in case of n=1, 2 or 3, each of the $R^{3a}$ and $R^{3b}$ may independently from each other represent H or $(C_1$-$C_3)$alkyl, e.g. one of the $R^{3a}$ may be H whereas the other is $(C_1$-$C_3)$alkyl, for example:

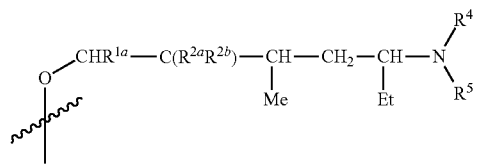

is included in the invention and definition of the embodiment relating to $R^{3a}$ and $R^{3b}$.

It is further to be understood that ring substituents being attached to the ring via a heteroatom such as O or N shall not be in ortho-position to the ring nitrogen atom, for example a $OCH_3$, $NH_2$ or a OH substituent shall not be at a position ortho to the ring nitrogen atom.

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a straight or branched chain alkyl group containing from one to three carbon atoms. The term "$(C_x$-$C_y)$alkyl" (x and y each being an integer) refers to a straight or branched chain alkyl group containing x to y carbon atoms. For example, a $(C_1$-$C_3)$alkyl group contains from one to three carbon atoms. Representative examples of alkyl groups include methyl, ethyl, propyl, and iso-propyl. Preferred are methyl and ethyl. Most preferred is methyl.

The term "amidine", used alone or in combination, refers to the group:

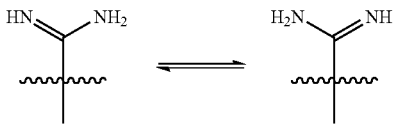

The term "3 to 6-membered cycloalkyl ring", used alone or in combination, refers to a saturated monocyclic hydrocarbon moiety containing 3 to 6 carbon atoms. The term "4 to 6-membered cycloalkyl ring", used alone or in combination, refers to a saturated monocyclic hydrocarbon moiety containing 4 to 6 carbon atoms. Representative examples of 3 to 6-membered cycloalkyl ring groups include cyclopropyl, cyclobutyl, cyclopentyl and cyclohexyl, preferred are cyclopropyl and cyclopentyl.

The term "4 to 6-membered heterocycloalkyl ring", used alone or in combination, refers to a 4-, 5-, or 6-membered saturated monocyclic hydrocarbon moiety containing 1 or 2 ring heteroatoms independently selected from nitrogen and oxygen. Representative examples of 4 to 6-membered heterocycloalkyl groups include, but are not limited to azetidinyl, pyrrolidinyl, piperidinyl, piperazinyl and morpholinyl. Preferred are azetidinyl, pyrrolidinyl, piperidinyl and morpholinyl. Optionally, the 4 to 6-membered heterocycloalkyl group may bear one or more substituents if explicitly mentioned.

The term "6 to 8-membered bicyclic heterocycloalkyl ring", used alone or in combination, refers to a 6-, 7-, or 8-membered saturated bicyclic hydrocarbon moiety containing one nitrogen atom. A preferred example is 3-azabicyclo[3.1.0]hexan-3-yl. Optionally, the 6 to 8-membered bicyclic heterocycloalkyl group may bear one or more substituents if explicitly mentioned (such 6 to 8-membered heterocycloalkyl group may for example then be 6-amino-3-azabicyclo[3.1.0]hexan-3-yl).

The term "quinolone-resistant", when used in this text, refers to a bacterial strain against which ciprofloxacin has a Minimal Inhibitory Concentration of at least 16 mg/l (said Minimal Inhibitory Concentration being measured with the standard method described in "Methods for Dilution Antimicrobial Susceptibility Tests for Bacteria that Grow Aerobically", Approved standard, 7th ed., Clinical and Laboratory Standards Institute (CLSI) Document M7-A7, Wayne, Pa., USA (2006)).

The term "methicillin-resistant", when used in this text, refers to a bacterial strain against which methicillin has a Minimal Inhibitory Concentration of at least 16 mg/l (said Minimal Inhibitory Concentration being measured with the standard method described in "Methods for Dilution Antimicrobial Susceptibility Tests for Bacteria that Grow Aerobically", Approved standard, 7th ed., Clinical and Laboratory Standards Institute (CLSI) Document M7-A7, Wayne, Pa., USA, 2006).

The term "cephalosporin-resistant", when used in this text, refers to a bacterial strain against which cephalosporins and in particular third generation cephalosporins have a Minimal Inhibitory Concentration of at least 16 mg/l (said Minimal Inhibitory Concentration being measured with the standard method described in "Methods for Dilution Antimicrobial Susceptibility Tests for Bacteria that Grow Aerobically", Approved standard, 7th ed., Clinical and Laboratory Standards Institute (CLSI) Document M7-A7, Wayne, Pa., USA, 2006).

The term "multiresistant" when used in this text, refers to a bacterial strain which is resistant against at least two classes of established classes of antibiotics e.g. quinolones and cephalosporins.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH (2008) and 'Pharmaceutical Salts and Co-crystals', Johan Wouters and Luc Quéré (Eds.), RSC Publishing (2012).

In this text, a bond interrupted by a wavy line shows a point of attachment of the radical drawn to the rest of the molecule. For example, the radical drawn below

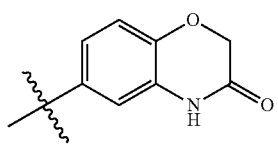 [SMILES: *c1ccc2c(c1)NC(=O)CO2]

is the 3-oxo-3,4-dihydro-2H-benzo[b][1,4]oxazin-6-yl group.

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

2) A second embodiment of the invention relates to the compounds of formula $I_A$

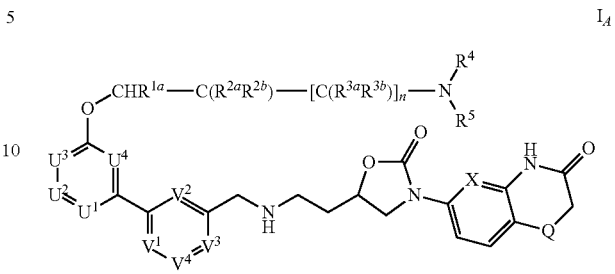

wherein n represents 0, 1, 2 or 3;

$R^{1a}$ represents H or $(C_1-C_3)$alkyl;

$R^{2a}$ and $R^{2b}$ independently from each other represent H or $(C_1-C_3)$alkyl;

$R^{3a}$ and $R^{3b}$ independently from each other represent H or $(C_1-C_3)$alkyl;

$R^4$ represents H, $(C_1-C_3)$alkyl, or $(C_2-C_3)$alkyl-$NR^{4a}R^{4b}$, wherein $R^{4a}$ and $R^{4b}$ are independently from each other H or $(C_1-C_3)$alkyl;

$R^5$ represents H, $(C_1-C_3)$alkyl, or $(C_2-C_3)$alkyl-$NR^{5a}R^{5b}$, wherein $R^{5a}$ and $R^{5b}$ are independently from each other H or $(C_1-C_3)$alkyl; or $R^{2a}$ and $R^{2b}$ together with the carbon atom which bears them form a 3 to 6-membered cycloalkyl ring; or $R^4$ and $R^5$ together with the nitrogen atom which bears them form a 4 to 6-membered heterocycloalkyl ring; or $R^4$ and $R^5$ together with the nitrogen atom which bears them form a 6 to 8-membered bicyclic heterocycloalkyl ring, which bicyclic heterocycloalkyl ring may optionally be substituted by a group $NR^6R^7$, wherein $R^6$ and $R^7$ are independently from each other H or $(C_1-C_3)$alkyl; or $R^4$ and $R^5$ together with the nitrogen atom which bears them and the adjacent $CR^{2a}R^{2b}$ or $CR^{3a}R^{3b}$ together form an amidine group; or $R^{1a}$ and $R^{3a}$, together with the carbon atoms which bear them and the carbon atom which connects these latter two atoms, form a 4 to 6-membered cycloalkyl ring, whereby $R^{2a}$, $R^{2b}$ and $R^{3b}$ each represent H, and n represents 1; $U^1$ represents N or CH, $U^2$ represents N, CH, C—O$(C_1-C_3)$ alkyl, or C—CN, $U^3$ represents N or CH and $U^4$ represents N or CH, it being understood that at most three of $U^1$, $U^2$, $U^3$ and $U^4$ can represent N at the same time;

$V^1$ represents N or CH, $V^2$ represents N or CH, $V^3$ represents N or CH and $V^4$ represents N or CH, it being understood that at most three of $V^1$, $V^2$, $V^3$ and $V^4$ can represent N at the same time;

X represents CH or N;

Q represents O or S;

and to salts (in particular pharmaceutically acceptable salts) of compounds of formula $I_A$.

3) A third embodiment of the invention relates to the compounds of formula $I_B$

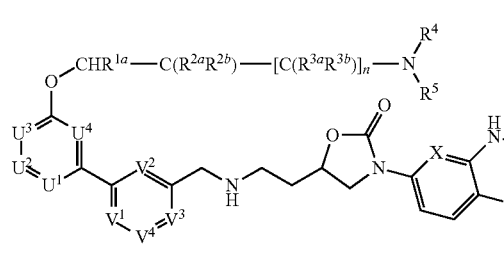

$I_B$ wherein
$R^{1a}$ and $R^4$, together with the carbon and nitrogen atoms which bear them and the carbon atom(s) which connect(s) the latter two atoms, form a 4 to 6-membered heterocycloalkyl ring, whereby $R^{2a}$, $R^{2b}$, optional $R^{3a}$, and optional $R^{3b}$ each represent H, n represents 0 or 1, and said 4 to 6-membered heterocycloalkyl ring optionally contains a substituent selected from $OCH_3$ and $CH_3$; or
$R^{2a}$ and $R^4$ together with the carbon and nitrogen atoms which bear them and the optional carbon atom(s) which connect(s) the latter two atoms, form a 4 to 6-membered heterocycloalkyl ring, whereby $R^{1a}$, optional $R^{3a}$ and optional $R^{3b}$ each represent H, $R^{2b}$ represents H, $NH_2$ or OH, and n represents 0, 1 or 2;
$R^5$ represents H, $(C_1-C_3)$alkyl, or $(C_2-C_3)$alkyl-$NR^{5a}R^{5b}$, wherein $R^{5a}$ and $R^{5b}$ are independently from each other H or $(C_1-C_3)$alkyl (preferably, $R^5$ represents H or $(C_1-C_3)$alkyl);
$U^1$ represents N or CH, $U^2$ represents N, CH, C—O($C_1$-$C_3$) alkyl, or C—CN, $U^3$ represents N or CH and $U^4$ represents N or CH, it being understood that at most three of $U^1$, $U^2$, $U^3$ and $U^4$ can represent N at the same time;
$V^1$ represents N or CH, $V^2$ represents N or CH, $V^3$ represents N or CH and $V^4$ represents N or CH, it being understood that at most three of $V^1$, $V^2$, $V^3$ and $V^4$ can represent N at the same time;
X represents CH or N;
Q represents O or S;
and to salts (in particular pharmaceutically acceptable salts) of compounds of formula $I_B$.

4) A fourth embodiment of the invention relates to the compounds of formulae I, $I_A$ or $I_B$, according to embodiments 1) to 3) which are also compounds of formula $I_{E1}$

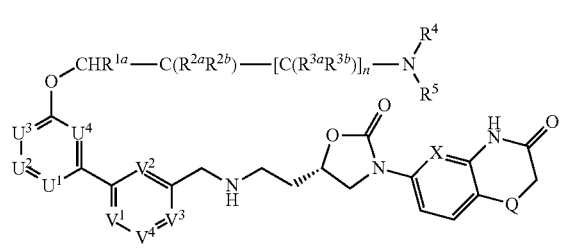

$I_{E1}$ wherein the absolute configuration of the asymmetric carbon of the oxazolidinone ring is as depicted in formula $I_{E1}$ [i.e. the absolute configuration of the asymmetric carbon of the oxazolidinone ring is (S)].

5) A fifth embodiment of the invention relates to the compounds of formulae I, $I_A$ or $I_B$, according to embodiments 1) to 3) which are also compounds of formula $I_{E2}$

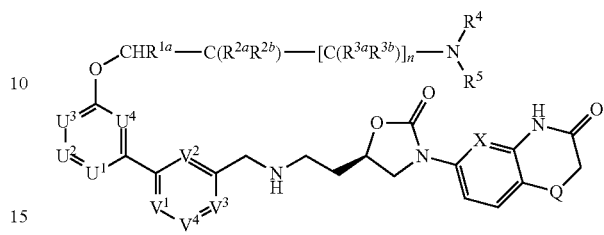

$I_{E2}$ wherein the absolute configuration of the asymmetric carbon of the oxazolidinone ring is as depicted in formula $I_{E2}$ [i.e. the absolute configuration of the asymmetric carbon of the oxazolidinone ring is (R)].

6) In particular, the invention relates to compounds of formulae I, $I_A$, $I_B$, $I_{E1}$ and $I_{E2}$ according to embodiments 1) to 5) that are also compounds of formula $I_S$

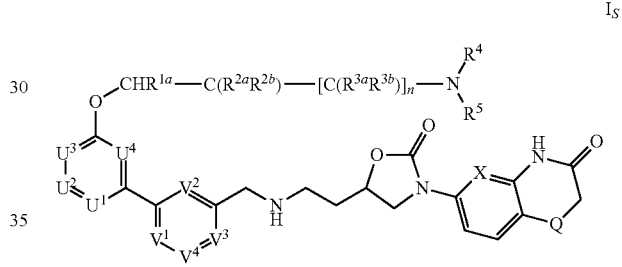

$I_S$ wherein
$R^{1a}$ represents H or $CH_3$;
$R^{2a}$ and $R^{2b}$ independently from each other represent H or $CH_3$;
$R^{3a}$ and $R^{3b}$ independently from each other represent H;
$R^4$ represents H, $CH_3$, or $CH_2CH_2NH_2$;
$R^5$ represents H, $CH_3$, or $CH_2CH_2NH_2$;
n represents 0, 1, 2 or 3; or
$R^{2a}$ and $R^{2b}$ together with the carbon atom which bears them form a cyclopropyl ring; or
$R^4$ and $R^5$ together with the nitrogen atom which bears them form a azetidinyl, pyrrolidinyl, piperidinyl or morpholinyl ring; or
$R^4$ and $R^5$ together with the nitrogen atom which bears them form a 6-amino-3-azabicyclo[3.1.0]hexan-3-yl group; or
$R^4$ and $R^5$ together with the nitrogen atom which bears them and the adjacent $CR^{2a}R^{2b}$ or $CR^{3a}R^{3b}$ together form an amidine group; or
$R^{1a}$ and $R^{3a}$, together with the carbon atom which bears them and the carbon atom which connects these latter two atoms, form a cyclopentyl ring; or
$R^{1a}$ and $R^4$, together with the carbon and nitrogen atoms which bear them and the carbon atom which connects the latter two atoms, form an azetidinyl, pyrrolidinyl or piperidinyl ring, whereby $R^{2a}$ and $R^{2b}$ each represent H, n represents 0, and said azetidinyl, pyrrolidinyl or piperidinyl ring optionally contains a $OCH_3$ substituent; or
$R^{2a}$ and $R^4$ together with the carbon and nitrogen atoms which bear them and the optional carbon atom which connects the latter two atoms, form an azetidinyl, pyrrolidinyl or morpholinyl ring, whereby $R^{1a}$, optional $R^{3a}$ and optional $R^{3b}$ each represent H, $R^{2b}$ represents H, $NH_2$ or OH, and n represents 0 or 1;

$U^1$ represents N or CH, $U^2$ represents N, CH, C—$OCH_3$, or C—CN, $U^3$ represents N or CH and $U^4$ represents N or CH, it being understood that at most three of $U^1$, $U^2$, $U^3$ and $U^4$ can represent N at the same time;

$V^1$ represents CH, $V^2$ represents CH, $V^3$ represents N or CH and $V^4$ represents CH;

X represents CH or N;

Q represents O or S;

and to salts (in particular pharmaceutically acceptable salts) of compounds of formula $I_S$.

7) Moreover, the invention relates to compounds of formulae I or $I_A$, $I_{E1}$ and $I_{E2}$ according to embodiments 1), 2), 4), 5) and compounds of formula $I_S$ according to embodiment 6) that are also compounds of formula $I_{SA}$ $$I_{SA}$$

wherein $R^{1a}$ represents H or $CH_3$;

$R^{2a}$ and $R^{2b}$ independently from each other represent H or $CH_3$;

$R^{3a}$ and $R^{3b}$ independently from each other represent H;

$R^4$ represents H, $CH_3$, or $CH_2CH_2NH_2$;

$R^5$ represents H, $CH_3$, or $CH_2CH_2NH_2$;

n represents 0, 1, 2 or 3; or $R^{2a}$ and $R^{2b}$ together with the carbon atom which bears them form a cyclopropyl ring; or $R^4$ and $R^5$ together with the nitrogen atom which bears them form a azetidinyl, pyrrolidinyl, piperidinyl or morpholinyl ring; or $R^4$ and $R^5$ together with the nitrogen atom which bears them form a 6-amino-3-azabicyclo[3.1.0]hexan-3-yl group; or $R^4$ and $R^5$ together with the nitrogen atom which bears them and the adjacent $CR^{2a}R^{2b}$ or $CR^{3a}R^{3b}$ together form an amidine group; or $R^{1a}$ and $R^{3a}$, together with the carbon atom which bears them and the carbon atom which connects these latter two atoms, form a cyclopentyl ring; or $U^1$ represents N or CH, $U^2$ represents N, CH, C—$OCH_3$, or C—CN, $U^3$ represents N or CH and $U^4$ represents N or CH, it being understood that at most three of $U^1$, $U^2$, $U^3$ and $U^4$ can represent N at the same time;

$V^1$ represents CH, $V^2$ represents CH, $V^3$ represents N or CH and $V^4$ represents CH;

X represents CH or N;

Q represents O or S;

and to salts (in particular pharmaceutically acceptable salts) of compounds of formula $I_{SA}$.

8) Moreover, the invention relates to compounds of formulae I or $I_B$, $I_{E1}$ and $IE_2$ according to embodiments 1), 3), 4), 5) and compounds of formula $I_S$ according to embodiment 6), that are also compounds of formula $I_{SB}$ $$I_{SB}$$

wherein $R^{1a}$ and $R^4$, together with the carbon and nitrogen atoms which bear them and the carbon atom which connects the latter two atoms, form an azetidinyl, pyrrolidinyl or piperidinyl ring, whereby $R^{2a}$ and $R^{2b}$ each represent H, n represents 0, and said azetidinyl, pyrrolidinyl or piperidinyl ring optionally contains a $OCH_3$ substituent; or $R^{2a}$ and $R^4$ together with the carbon and nitrogen atoms which bear them and the optional carbon atom which connects the latter two atoms, form an azetidinyl, pyrrolidinyl or morpholinyl ring, whereby $R^{1a}$, optional $R^{3a}$ and optional $R^{3b}$ each represent H, $R^{2b}$ represents H, $NH_2$ or OH, and n represents 0 or 1;

$R^5$ represents H or $CH_3$;

$U^1$ represents N or CH, $U^2$ represents N, CH, C—$OCH_3$, or C—CN, $U^3$ represents N or CH and $U^4$ represents N or CH, it being understood that at most three of $U^1$, $U^2$, $U^3$ and $U^4$ can represent N at the same time;

$V^1$ represents CH, $V^2$ represents CH, $V^3$ represents N or CH and $V^4$ represents CH;

X represents CH or N;

Q represents O or S;

and to salts (in particular pharmaceutically acceptable salts) of compounds of formula $I_{SB}$.

9) In particular, the invention relates to compounds of formulae I, $I_A$ and $I_B$, $I_{E1}$ and $IE_2$ according to embodiments 1) to 5), and compounds of formulae $I_S$, $I_{SA}$ and $I_{SB}$ according to embodiments 6) to 8), that are also compounds of formula $I_{PS}$ $$I_{PS}$$

wherein $R^{1a}$ represents H;

$R^{2a}$ and $R^{2b}$ independently from each other represent H or $CH_3$;

$R^4$ represents H;

$R^5$ represents H;

n represents 0; or $R^4$ and $R^5$ together with the nitrogen atom which bears them form a pyrrolidinyl ring; or $R^{1a}$ and $R^4$, together with the carbon and nitrogen atoms which bear them and the carbon atom which connects the latter two atoms, form an azetidinyl or pyrrolidinyl ring, whereby $R^{2a}$ and $R^{2b}$ each represent H, and n represents 0; or $R^{2a}$ and $R^4$, together with the carbon and nitrogen atoms which bear them and the optional carbon atom which connects the latter two atoms, form an azetidinyl or morpholinyl ring, whereby $R^{1a}$, $R^{2b}$, optional $R^{3a}$ and optional $R^{3b}$ each represent H, and n represents 0 or 1;

$U^1$ represents CH, $U^2$ represents N, CH, C—OCH$_3$, $U^3$ represents N or CH and $U^4$ represents N or CH;

$V^1$ represents CH, $V^2$ represents CH, $V^3$ represents N or CH and $V^4$ represents CH;

X represents CH or N;

Q represents O or S;

and to salts (in particular pharmaceutically acceptable salts) of compounds of formula $I_{PS}$.

10) Moreover, the invention relates to compounds of formulae I and $I_A$, $IE_1$ and $IE_2$ according to embodiments 1), 2), 4), 5), compounds of formulae $I_S$ and $I_{SA}$ according to embodiments 6) and 7), and compounds of formula $I_{PS}$ according to embodiment 9), that are also compounds of formula $I_{PSA}$ $$I_{PSA}$$

[Chemical structure diagram]

wherein $R^{1a}$ represents H;

$R^{2a}$ and $R^{2b}$ independently from each other represent H or CH$_3$;

$R^4$ represents H;

$R^5$ represents H;

n represents 0; or $R^4$ and $R^5$ together with the nitrogen atom which bears them form a pyrrolidinyl ring;

$U^1$ represents CH, $U^2$ represents N, CH, C—OCH$_3$, $U^3$ represents N or CH and $U^4$ represents N or CH;

$V^1$ represents CH, $V^2$ represents CH, $V^3$ represents N or CH and $V^4$ represents CH;

X represents CH or N;

Q represents O or S;

and to salts (in particular pharmaceutically acceptable salts) of compounds of formula $I_{PSA}$.

11) Moreover, the invention relates to compounds of formulae I and $I_B$, $IE_1$ and $IE_2$ according to embodiments 1), 3), 4), 5), compounds of formulae $I_S$ and $I_{SB}$ according to embodiments 6) and 8), and compounds of formula $I_{PS}$ according to embodiment 9), that are also compounds of formula $I_{PSB}$ $$I_{PSB}$$

[Chemical structure diagram]

wherein $R^{1a}$ and $R^4$, together with the carbon and nitrogen atoms which bear them and the carbon atom which connects the latter two atoms, form an azetidinyl or pyrrolidinyl ring, whereby $R^{2a}$ and $R^{2b}$ each represent H, and n represents 0; or $R^{2a}$ and $R^4$ together with the carbon and nitrogen atoms which bear them and the optional carbon atoms which connects the latter two atoms, form an azetidinyl or morpholinyl ring, whereby $R^{1a}$, $R^{2b}$, optional $R^{3a}$ and optional $R^{3b}$ each represent H, and n represents 0 or 1;

$R^5$ represents H;

$U^1$ represents CH, $U^2$ represents N, CH, C—OCH$_3$, $U^3$ represents N or CH and $U^4$ represents N or CH;

$V^1$ represents CH, $V^2$ represents CH, $V^3$ represents N or CH and $V^4$ represents CH;

X represents CH or N;

Q represents O or S;

and to salts (in particular pharmaceutically acceptable salts) of compounds of formula $I_{PSB}$.

12) According to one aspect of this invention, the compounds of formulae I, $I_A$, $I_{E1}$ and $I_{E2}$ as defined in one of embodiments 1), 2), 4) and 5) will be such that $R^{1a}$ represents H or (C$_1$-C$_3$)alkyl;

$R^{2a}$ and $R^{2b}$ independently from each other represent H or (C$_1$-C$_3$)alkyl;

$R^{3a}$ and $R^{3b}$ independently from each other represent H or (C$_1$-C$_3$)alkyl;

$R^4$ represents H, (C$_1$-C$_3$)alkyl, or (C$_2$-C$_3$)alkyl-NR$^{4a}$R$^{4b}$, wherein R$^{4a}$ and R$^{4b}$ are independently from each other H or (C$_1$-C$_3$)alkyl;

$R^5$ represents H, (C$_1$-C$_3$)alkyl, or (C$_2$-C$_3$)alkyl-NR$^{5a}$R$^{5b}$, wherein R$^{5a}$ and R$^{5b}$ are independently from each other H or (C$_1$-C$_3$)alkyl; and n represents 0, 1, 2 or 3.

13) According to one sub-embodiment of embodiment 12), the compounds of formula I, $I_A$, $IE_1$ and $IE_2$ as defined in embodiment 12) will be such that:

$R^{1a}$ represents H or CH$_3$;

$R^{2a}$ and $R^{2b}$ independently from each other represent H or CH$_3$;

$R^{3a}$ and $R^{3b}$ independently from each other represent H or CH$_3$;

$R^4$ represents H, CH$_3$, or CH$_2$CH$_2$NH$_2$;

$R^5$ represents H, CH$_3$, or CH$_2$CH$_2$NH$_2$; and n represents 0, 1, 2 or 3.

14) According to one sub-embodiment of embodiment 13), the compounds of formula I, $I_A$, $IE_1$ and $IE_2$ as defined in embodiment 13) will be such that:

$R^{1a}$ represents H or CH$_3$;

$R^{2a}$ and $R^{2b}$ independently from each other represent H or CH$_3$;

$R^{3a}$ and $R^{3b}$ independently from each other represent H;

$R^4$ represents H, CH$_3$ or CH$_2$CH$_2$NH$_2$;

$R^5$ represents H or $CH_3$; and n represents 0, 1, 2 or 3.

15) According to one sub-embodiment of embodiment 14), the compounds of formula I, $I_A$, $IE_1$ and $I_{E2}$ as defined in embodiment 14) will be such that:

$R^{2a}$ represents H;

$R^{2a}$ and $R^{2b}$, independently from each other represent H or $CH_3$;

$R^4$ represents H or $CH_3$, and preferably H;

$R^5$ represents H or $CH_3$, and preferably H; and n represents 0.

16) According to one aspect of this invention, the compounds of formulae I, $I_A$, $IE_1$ and $I_{E2}$ as defined in one of embodiments 1), 2), 4) and 5) will be such that $R^{1a}$ represents H or $(C_1-C_3)$alkyl;

$R^{2a}$ and $R^{2b}$ together with the carbon atom which bears them form a 3 to 6-membered cycloalkyl ring (preferably a cyclopropyl ring);

$R^{3a}$ and $R^{3b}$ independently from each other represent H or $(C_1-C_3)$alkyl;

$R^4$ represents H, $(C_1-C_3)$alkyl, or $(C_2-C_3)$alkyl-$NR^{4a}R^{4b}$, wherein $R^{4a}$ and $R^{4b}$ are independently from each other H or $(C_1-C_3)$alkyl;

$R^5$ represents H, $(C_1-C_3)$alkyl, or $(C_2-C_3)$alkyl-$NR^{5a}R^{5b}$, wherein $R^{5a}$ and $R^{5b}$ are independently from each other H or $(C_1-C_3)$alkyl; and n represents 0, 1, 2 or 3.

17) According to one sub-embodiment of embodiment 16), the compounds of formula I, $I_A$, $IE_1$ and $IE_2$ as defined in embodiment 16) will be such that $R^{1a}$ represents H;

$R^{2a}$ and $R^{2b}$ together with the carbon atom which bears them form a 3 to 6-membered cycloalkyl ring (preferably a cyclopropyl ring);

$R^{3a}$ and $R^{3b}$ independently from each other represent H;

$R^4$ represents H or $CH_3$;

$R^5$ represents H or $CH_3$; and n represents 0, 1, 2 or 3 (preferably n is 0).

18) According to one aspect of this invention, the compounds of formulae I, $I_A$, $IE_1$ and $I_{E2}$ as defined in one of embodiments 1), 2), 4) and 5) will be such that $R^{1a}$ represents H or $(C_1-C_3)$alkyl;

$R^{2a}$ and $R^{2b}$ independently from each other represent H or $(C_1-C_3)$alkyl;

$R^{3a}$ and $R^{3b}$ independently from each other represent H or $(C_1-C_3)$alkyl;

$R^4$ and $R^5$ together with the nitrogen atom which bears them form a 4 to 6-membered heterocycloalkyl ring; and n represents 0, 1, 2 or 3.

19) According to one sub-embodiment of embodiment 18), the compounds of formula I, $I_A$, $IE_1$ and $IE_2$ as defined in embodiment 18) will be such that $R^{1a}$ represents H or $CH_3$;

$R^{2a}$ and $R^{2b}$ independently from each other represent H or $CH_3$;

$R^{3a}$ and $R^{3b}$ independently from each other represent H or $CH_3$;

$R^4$ and $R^5$ together with the nitrogen atom which bears them form a 4 to 6-membered heterocycloalkyl ring; and n represents 0, 1, 2 or 3.

20) According to one sub-embodiment of embodiment 19), the compounds of formula I, $I_A$, $I_{E1}$ and $IE_2$ as defined in embodiment 19) will be such that $R^{1a}$, $R^{2a}$, $R^{2b}$, $R^{3a}$ and $R^{3b}$ each represent H;

$R^4$ and $R^5$ together with the nitrogen atom which bears them form an azetidinyl, pyrrolidinyl, piperidinyl or morpholinyl ring (preferably pyrrolidinyl); and n represents 0, 1, 2 or 3 (preferably n represents 0).

21) According to one aspect of this invention, the compounds of formulae I, $I_A$, $IE_1$ and $IE_2$ as defined in one of embodiments 1), 2), 4) and 5) will be such that $R^{1a}$ represents H or $(C_1-C_3)$alkyl;

$R^{2a}$ and $R^{2b}$, independently from each other represent H or $(C_1-C_3)$alkyl;

$R^{3a}$ and $R^{3b}$ independently from each other represent H or $(C_1-C_3)$alkyl;

$R^4$ and $R^5$ together with the nitrogen atom which bears them form a 6 to 8-membered bicyclic heterocycloalkyl ring, which bicyclic heterocycloalkyl ring may optionally be substituted by a group $NR^6R^7$, wherein $R^6$ and $R^7$ are independently from each other H or $(C_1-C_3)$alkyl; and n represents 0, 1, 2 or 3.

22) According to one sub-embodiment of embodiment 21), the compounds of formula I, $I_A$, $IE_1$ and $IE_2$ as defined in embodiment 21) will be such that $R^{1a}$ represents H or $CH_3$ (preferably H);

$R^{2a}$ and $R^{2b}$, independently from each other represent H or $CH_3$ (preferably H);

$R^{3a}$ and $R^{3b}$ independently from each other represent H or $CH_3$ (preferably H);

$R^4$ and $R^5$ together with the nitrogen atom which bears them form a 6-amino-3-azabicyclo[3.1.0]hexan-3-yl group; and n represents 0, 1, 2 or 3 (preferably n represents 0).

23) According to one aspect of this invention, the compounds of formulae I, $I_A$, $IE_1$ and $IE_2$ as defined in one of embodiments 1), 2), 4) and 5) will be such that $R^{1a}$ represents H or $(C_1-C_3)$alkyl;

$R^{2a}$ and $R^{2b}$ independently from each other represent H or $(C_1-C_3)$alkyl;

$R^{3a}$ and $R^{3b}$ independently from each other represent H or $(C_1-C_3)$alkyl;

$R^4$ and $R^5$ together with the nitrogen atom which bears them and the adjacent $CR^{2a}R^{2b}$ or $CR^{3a}R^{3b}$ together form an amidine group; and n represents 0, 1, 2 or 3.

24) According to one sub-embodiment of embodiment 23), the compounds of formula I, $I_A$, $IE_1$ and $IE_2$ as defined in embodiment 23) will be such that $R^{1a}$ represents H or $CH_3$ (preferably H);

$R^{2a}$ and $R^{2b}$ independently from each other represent H or $CH_3$ (preferably H);

$R^{3a}$ and $R^{3b}$ independently from each other represent H or $CH_3$ (preferably H);

$R^4$ and $R^5$ together with the nitrogen atom which bears them and the adjacent $CR^{2a}R^{2b}$ or $CR^{3a}R^{3b}$ together form an amidine group; and n represents 0, 1, 2 or 3 (preferably n represents 0).

25) According to one aspect of this invention, the compounds of formulae I, $I_A$, $I_{E1}$ and $IE_2$ as defined in one of embodiments 1), 2), 4) and 5) will be such that $R^{1a}$ and $R^{3a}$, together with the carbon atoms which bear them and the carbon atom which connects these latter two atoms, form a cyclobutyl, cyclopentyl or cyclohexyl ring (preferably a cyclopentyl ring);

$R^{2a}$, $R^{2b}$ and $R^{3b}$ each represent H;
$R^4$ represents H, $(C_1-C_3)$alkyl, or $(C_2-C_3)$alkyl-$NR^{4a}R^{4b}$, wherein $R^{4a}$ and $R^{4b}$ are independently from each other H or $(C_1-C_3)$alkyl;
$R^5$ represents H, $(C_1-C_3)$alkyl, or $(C_2-C_3)$alkyl-$NR^{5a}R^{5b}$, wherein $R^{5a}$ and $R^{5b}$ are independently from each other H or $(C_1-C_3)$alkyl; and
n represents 1.

26) According to one sub-embodiment of embodiment 25), the compounds of formula I, $I_A$, $IE_1$ and $IE_2$ as defined in embodiment 25) will be such that
$R^{1a}$ and $R^{3a}$, together with the carbon atoms which bear them and the carbon atom which connects these latter two atoms, form a cyclobutyl, cyclopentyl or cyclohexyl ring (preferably a cyclopentyl ring);
$R^{2a}$, $R^{2b}$ and $R^{3b}$ each represent H;
$R^4$ represents H or $CH_3$ (preferably H);
$R^5$ represents H or $CH_3$ (preferably H); and
n represents 1.

27) According to one aspect of this invention, the compounds of formulae I, $I_B$, $IE_1$ and $IE_2$ as defined in one of embodiments 1), 3), 4) and 5) will be such that
$R^{1a}$ and $R^4$, together with the carbon and nitrogen atoms which bear them and the carbon atom(s) which connect(s) the latter two atoms, form a 4 to 6-membered heterocycloalkyl ring containing one nitrogen atom, and the ring optionally contains a substituent selected from $OCH_3$ or $CH_3$;
$R^{2a}$ and $R^{2b}$ each represent H;
$R^{3a}$ and $R^{3b}$ each represent H;
$R^5$ represents H, $(C_1-C_3)$alkyl, or $(C_2-C_3)$alkyl-$NR^{5a}R^{5b}$, wherein $R^{5a}$ and $R^{5b}$ are independently from each other H or $(C_1-C_3)$alkyl; and
n represents 0 or 1.

28) According to one sub-embodiment of embodiment 27), the compounds of formula I, $I_B$, $I_{E1}$ and $IE_2$ as defined in embodiment 27) will be such that
$R^{1a}$ and $R^4$, together with the carbon and nitrogen atoms which bear them and the carbon atom(s) which connect(s) the latter two atoms, form a 4 to 6-membered heterocycloalkyl ring, and the ring optionally contains a substituent selected from $OCH_3$ or $CH_3$;
$R^{2a}$ and $R^{2b}$ each represent H;
$R^{3a}$ and $R^{3b}$ each represent H;
$R^5$ represents H or $CH_3$ (preferably H); and
n represents 0 or 1.

29) According to one sub-embodiment of embodiment 28), the compounds of formula I, $I_B$, $I_{E1}$ and $IE_2$ as defined in embodiment 28) will be such that
$R^{1a}$ and $R^4$, together with the carbon and nitrogen atoms which bear them and the carbon atom(s) which connect(s) the latter two atoms, form an azetinyl, pyrrolidinyl or piperidinyl ring, and said azetinyl, pyrrolidinyl or piperidinyl ring optionally contains a substituent selected from $OCH_3$ and $CH_3$ (preferably $OCH_3$);
$R^{2a}$ and $R^{2b}$ each represent H;
$R^{3a}$ and $R^{3b}$ each represent H;
$R^5$ represents H or $CH_3$ (preferably H); and
n represents 0 or 1.

30) According to one sub-embodiment of embodiment 29), the compounds of formula I, $I_B$, $I_{E1}$ and $IE_2$ as defined in embodiment 29) will be such that
$R^{1a}$ and $R^4$, together with the carbon and nitrogen atoms which bear them and the carbon atom(s) which connect(s) the latter two atoms, form an azetinyl or pyrrolidinyl ring;
$R^{2a}$ and $R^{2b}$ each represent H;
$R^{3a}$ and $R^{3b}$ each represent H;
$R^5$ represents H; and
n represents 0 or 1.

31) According to one aspect of this invention, the compounds of formulae I, $I_B$, $IE_1$ and $IE_2$ as defined in one of embodiments 1), 3), 4) and 5) will be such that
$R^{1a}$ represents H;
$R^{2a}$ and $R^4$ together with the carbon and nitrogen atoms which bear them and the optional carbon atom(s) which connect(s) the latter two atoms, form a 4 to 6-membered heterocycloalkyl ring;
$R^{2b}$ represents H, $NH_2$ or OH;
$R^{3a}$ and $R^{3b}$ each represent H;
$R^5$ represents H, $(C_1-C_3)$alkyl, or $(C_2-C_3)$alkyl-$NR^{5a}R^{5b}$, wherein $R^{5a}$ and $R^{5b}$ are independently from each other H or $(C_1-C_3)$alkyl; and
n represents 0, 1 or 2.

32) According to one sub-embodiment of embodiment 31), the compounds of formula I, $I_B$, $I_{E1}$ and $IE_2$ as defined in embodiment 31) will be such that
$R^{1a}$ represents H;
$R^{2a}$ and $R^4$ together with the carbon and nitrogen atoms which bear them and the optional carbon atom(s) which connect(s) the latter two atoms, form a 4 to 6-membered heterocycloalkyl ring;
$R^{2b}$ represents H, $NH_2$ or OH;
$R^{3a}$ and $R^{3b}$ represent H;
$R^5$ represents H or $CH_3$ (preferably H); and
n represents 0, 1 or 2 (preferably 0 or 1).

33) According to one sub-embodiment of embodiment 32), the compounds of formula I, $I_B$, $I_{E1}$ and $IE_2$ as defined in embodiment 32) will be such that
$R^{1a}$ represents H;
$R^{2a}$ and $R^4$ together with the carbon and nitrogen atoms which bear them and the optional carbon atom(s) which connect(s) the latter two atoms, form an azetidinyl, pyrrolidinyl or morpholinyl ring;
$R^{2b}$ represents H, $NH_2$ or OH;
$R^{3a}$ and $R^{3b}$ represent H;
$R^5$ represents H or $CH_3$ (preferably H); and
n represents 0, 1 or 2 (preferably 0 or 1).

34) According to one sub-embodiment of embodiment 33), the compounds of formula I, $I_B$, $I_{E1}$ and $IE_2$ as defined in embodiment 33) will be such that
$R^{1a}$ represents H;
$R^{2a}$ and $R^4$ together with the carbon and nitrogen atoms which bear them and the optional carbon atom(s) which connect(s) the latter two atoms, form an azetidinyl or morpholinyl ring;
$R^{2b}$ represents H;
$R^{3a}$ and $R^{3b}$ represent H;
$R^5$ represents H; and
n represents 0 or 1.

35) According to one aspect of this invention, the compounds of formulae I, $I_A$, $I_B$, $I_{E1}$, and $IE_2$ as defined in one of embodiments 1) to 5) as well as the compounds of anyone of the embodiments 13)-15), 17), 19)-22), 24), 26), 28)-30) and 32)-33) will be such that
$U^1$ represents N or CH;
$U^2$ represents N, CH, C—O$(C_1-C_3)$alkyl, or C—CN;
$U^3$ represents N or CH; and
$U^4$ represents N or CH;
it being understood that at most three of $U^1$, $U^2$, $U^3$ and $U^4$ can represent N at the same time.

36) According to one sub-embodiment of embodiment 35), the compounds of formulae I, $I_A$, $I_B$, $I_{E1}$, and $IE_2$ as defined in embodiment 35) will be such that $U^1$ represents N or CH;
$U^2$ represents N, CH, C—$OCH_3$ or C—CN;
$U^3$ represents N or CH; and
$U^4$ represents N or CH;

it being understood that at most three of $U^1$, $U^2$, $U^3$ and $U^4$ can represent N at the same time.

37) According to one aspect of this invention, the compounds of formulae I, $I_A$, $I_B$, $I_{E1}$, and $IE_2$ as defined in one of embodiments 1) to 5) as well as the compounds of anyone of the embodiments 13)-15), 17), 19)-22), 24), 26), 28)-30) and 32)-33) will be such that $V^1$ represents N or CH (preferably CH);
$V^2$ represents N or CH (preferably CH);
$V^3$ represents N or CH; and
$V^4$ represents N or CH (preferably CH);

it being understood that at most three of $V^1$, $V^2$, $V^3$ and $V^4$ can represent N at the same time.

38) Preferably the compounds of formulae I, $I_A$, $I_B$, $I_{E1}$, and $IE_2$ as defined in one of embodiments 1) to 5) as well as the compounds of anyone of the embodiments 13)-15), 17), 19)-22), 24), 26), 28)-30) and 32)-33) will be such that the meanings of $U^1$, $U^2$, $U^3$, $U^4$, $V^1$, $V^2$, $V^3$ and $V^4$ are as follows:

$U^1$, $U^2$, $U^3$, $U^4$, $V^1$, $V^2$, $V^3$ and $V^4$ each represent CH; or
$U^2$ represents N; $U^1$, $U^3$, $U^4$, $V^1$, $V^2$, $V^3$ and $V^4$ each represent CH; or
$U^2$ represents C—$OCH_3$; $U^1$, $U^3$, $U^4$, $V^1$, $V^2$, $V^3$ and $V^4$ each represent CH; or
$U^3$ represents N; $U^1$, $U^2$, $U^4$, $V^1$, $V^2$, $V^3$ and $V^4$ each represent CH; or
$U^4$ represents N; $U^1$, $U^2$, $U^3$, $V^1$, $V^2$, $V^3$ and $V^4$ each represent CH; or
$U^2$ and $U^4$ each represent N; $U^1$, $U^3$, $V^1$, $V^2$, $V^3$ and $V^4$ each represent CH; or
$U^4$ and $V^3$ each represent N; $U^1$, $U^2$, $U^3$, $V^1$, $V^2$ and $V^4$ each represent CH.

39) According to one sub-embodiment of embodiment 38), the compounds of formulae I, $I_A$, $I_B$, $I_{E1}$, and $IE_2$ as defined in embodiment 38) will be such that $U^1$, $U^2$, $U^3$, $U^4$, $V^1$, $V^2$, $V^3$ and $V^4$ each represent CH; or
$U^2$ represents C—$OCH_3$; $U^1$, $U^3$, $U^4$, $V^1$, $V^2$, $V^3$ and $V^4$ each represent CH; or
$U^4$ represents N; $U^1$, $U^2$, $U^3$, $V^1$, $V^2$, $V^3$ and $V^4$ each represent CH; or
$U^2$ and $U^4$ represent N; $U^1$, $U^3$, $V^1$, $V^2$, $V^3$ and $V^4$ each represent CH.

40) According to one sub-embodiment of embodiment 39), the compounds of formulae I, $I_A$, $I_B$, $I_{E1}$, and $IE_2$ as defined in embodiment 39) will be such that $U^1$, $U^2$, $U^3$, $U^4$, $V^1$, $V^2$, $V^3$ and $V^4$ each represent CH; or
$U^4$ represents N; $U^1$, $U^2$, $U^3$, $V^1$, $V^2$, $V^3$ and $V^4$ each represent CH.

41) According to one aspect of this invention, the compounds of formulae I, $I_A$, $I_B$, $I_{E1}$, and $IE_2$ as defined in one of embodiments 1) to 5) as well as the compounds of anyone of the embodiments 13)-15), 17), 19)-22), 24), 26), 28)-30) and 32)-33) will be such that the meanings of X and Q are as follows:

X represents N and Q represents O (preferred); or
X represents N and Q represents S (preferred); or
X represents CH and Q represents O; or
X represents CH and Q represents S.

42) Preferred are the following compounds of formula I:

6-[(S)-5-(2-{[3'-(2-amino-ethoxy)-biphenyl-3-ylmethyl]-amino}-ethyl)-2-oxo-oxazolidin-3-yl]-4H-pyrido[3,2-b][1,4]oxazin-3-one;
6-[(S)-5-(2-{[3'-(2-dimethylamino-ethoxy)-biphenyl-3-yl-methyl]-amino}-ethyl)-2-oxo-oxazolidin-3-yl]-4H-pyrido[3,2-b][1,4]oxazin-3-one;
6-[(S)-5-(2-{[3'-(3-amino-propoxy)-biphenyl-3-ylmethyl]-amino}-ethyl)-2-oxo-oxazolidin-3-yl]-4H-pyrido[3,2-b][1,4]oxazin-3-one;
6-[(S)-5-(2-{[3'-(2-methylamino-ethoxy)-biphenyl-3-ylm-ethyl]-amino}-ethyl)-2-oxo-oxazolidin-3-yl]-4H-pyrido[3,2-b][1,4]oxazin-3-one;
6-[(S)-5-(2-{[3'-(4-amino-butoxy)-biphenyl-3-ylmethyl]-amino}-ethyl)-2-oxo-oxazolidin-3-yl]-4H-pyrido[3,2-b][1,4]oxazin-3-one;
6-[(S)-5-(2-{[3'-(2-amino-1-methyl-ethoxy)-biphenyl-3-yl-methyl]-amino}-ethyl)-2-oxo-oxazolidin-3-yl]-4H-pyrido[3,2-b][1,4]oxazin-3-one;
6-[(S)-5-(2-{[3'-((1R,3R)-3-amino-cyclopentyloxy)-biphenyl-3-ylmethyl]-amino}-ethyl)-2-oxo-oxazolidin-3-yl]-4H-pyrido[3,2-b][1,4]oxazin-3-one;
6-[(S)-5-(2-{3-[6-(2-amino-ethoxy)-pyridin-2-yl]-benzy-lamino}-ethyl)-2-oxo-oxazolidin-3-yl]-4H-pyrido[3,2-b][1,4]oxazin-3-one;
6-[(S)-2-oxo-5-(2-{3-[6-(2-pyrrolidin-1-yl-ethoxy)-pyridin-2-yl]-benzylamino}-ethyl)-oxazolidin-3-yl]-4H-pyrido[3,2-b][1,4]oxazin-3-one;
6-[(S)-5-(2-{3-[5-(2-dimethylamino-ethoxy)-pyridazin-3-yl]-benzylamino}-ethyl)-2-oxo-oxazolidin-3-yl]-4H-pyrido[3,2-b][1,4]oxazin-3-one;
6-[(S)-5-(2-{3-[5-(2-amino-ethoxy)-pyridin-3-yl]-benzy-lamino}-ethyl)-2-oxo-oxazolidin-3-yl]-4H-pyrido[3,2-b][1,4]oxazin-3-one;
6-[(S)-2-oxo-5-(2-{3-[6-(2-piperidin-1-yl-ethoxy)-pyridin-2-yl]-benzylamino}-ethyl)-oxazolidin-3-yl]-4H-pyrido[3,2-b][1,4]oxazin-3-one;
6-[(S)-2-oxo-5-(2-{[3'-(2-piperidin-1-yl-ethoxy)-biphenyl-3-ylmethyl]-amino}-ethyl)-oxazolidin-3-yl]-4H-pyrido[3,2-b][1,4]oxazin-3-one;
6-[(S)-5-(2-{[3'-(1-amino-cyclopropylmethoxy)-biphenyl-3-ylmethyl]-amino}-ethyl)-2-oxo-oxazolidin-3-yl]-4H-pyrido[3,2-b][1,4]oxazin-3-one;
6-[(S)-5-(2-{3-[6-(2-amino-ethoxy)-pyrazin-2-yl]-benzy-lamino}-ethyl)-2-oxo-oxazolidin-3-yl]-4H-pyrido[3,2-b][1,4]oxazin-3-one;
6-[(S)-5-(2-{[6-(2-amino-ethoxy)-[2,4']bipyridinyl-2'-ylm-ethyl]-amino}-ethyl)-2-oxo-oxazolidin-3-yl]-4H-pyrido[3,2-b][1,4]oxazin-3-one;
6-[(5)-5-(2-{3-[6-((R)-2-amino-propoxy)-pyridin-2-yl]-benzylamino}-ethyl)-2-oxo-oxazolidin-3-yl]-4H-pyrido[3,2-b][1,4]oxazin-3-one;
6-[(5)-5-(2-{3-[6-((5)-2-amino-propoxy)-pyridin-2-yl]-ben-zylamino}-ethyl)-2-oxo-oxazolidin-3-yl]-4H-pyrido[3,2-b][1,4]oxazin-3-one;
6-[(5)-5-(2-{3-[2-(2-amino-ethoxy)-pyridin-4-yl]-benzy-lamino}-ethyl)-2-oxo-oxazolidin-3-yl]-4H-pyrido[3,2-b][1,4]oxazin-3-one;
6-[(5)-5-(2-{[3'-((S)-1-azetidin-2-ylmethoxy)-biphenyl-3-ylmethyl]-amino}-ethyl)-2-oxo-oxazolidin-3-yl]-4H-pyrido[3,2-b][1,4]oxazin-3-one;
6-[(5)-2-oxo-5-(2-{[3'-(S)-1-pyrrolidin-2-ylmethoxy)-bi-phenyl-3-ylmethyl]-amino}-ethyl)-oxazolidin-3-yl]-4H-pyrido[3,2-b][1,4]oxazin-3-one;
6-[(5)-2-oxo-5-(2-{[3'-(pyrrolidin-3-yloxy)-biphenyl-3-yl-methyl]-amino}-ethyl)-oxazolidin-3-yl]-4H-pyrido[3,2-b][1,4]oxazin-3-one;

6-[(5)-5-(2-{[3'-(S)-1-methyl-azetidin-2-ylmethoxy)-biphenyl-3-ylmethyl]-amino}-ethyl)-2-oxo-oxazolidin-3-yl]-4H-pyrido[3,2-b][1,4]oxazin-3-one;
6-[(5)-5-(2-{[3'-(azetidin-3-yloxy)-biphenyl-3-ylmethyl]-amino}-ethyl)-2-oxo-oxazolidin-3-yl]-4H-pyrido[3,2-b][1,4]oxazin-3-one;
6-[(5)-5-(2-{3-[6-(azetidin-3-ylmethoxy)-pyridin-2-yl]-benzylamino}-ethyl)-2-oxo-oxazolidin-3-yl]-4H-pyrido[3,2-b][1,4]oxazin-3-one;
6-[(5)-5-(2-{3-[6-(azetidin-3-yloxy)-pyridin-2-yl]-benzylamino}-ethyl)-2-oxo-oxazolidin-3-yl]-4H-pyrido[3,2-b][1,4]oxazin-3-one;
6-[(5)-5-(2-{3-[6-((S)-1-azetidin-2-ylmethoxy)-pyridin-2-yl]-benzylamino}-ethyl)-2-oxo-oxazolidin-3-yl]-4H-pyrido[3,2-b][1,4]oxazin-3-one;
6-[(5)-5-(2-{3-[6-(1-morpholin-2-ylmethoxy)-pyridin-2-yl]-benzylamino}-ethyl)-2-oxo-oxazolidin-3-yl]-4H-pyrido[3,2-b][1,4]oxazin-3-one;
6-[(5)-5-(2-{3-[6-(1-morpholin-3-ylmethoxy)-pyridin-2-yl]-benzylamino}-ethyl)-2-oxo-oxazolidin-3-yl]-4H-pyrido[3,2-b][1,4]oxazin-3-one;
6-[(5)-2-oxo-5-(2-{3 [6-(piperidin-3-yloxy)-pyridin-2-yl]-benzylamino}-ethyl)-oxazolidin-3-yl]-4H-pyrido[3,2-b][1,4]oxazin-3-one;
6-[(5)-5-(2-{[3'-(2-amino-ethoxy)-5'-methoxy-biphenyl-3-ylmethyl]-amino}-ethyl)-2-oxo-oxazolidin-3-yl]-4H-pyrido[3,2-b][1,4]oxazin-3-one;
6-[(R)-5-(2-{3-[6-(2-amino-ethoxy)-pyridin-2-yl]-benzylamino}-ethyl)-2-oxo-oxazolidin-3-yl]-4H-benzo[1,4]thiazin-3-one;
6-[(S)-5-(2-{3-[6-(5-amino-pentyloxy)-pyridin-2-yl]-benzylamino}-ethyl)-2-oxo-oxazolidin-3-yl]-4H-pyrido[3,2-b][1,4]oxazin-3-one;
6-[(S)-5-(2-{3-[6-(2-morpholin-4-yl-ethoxy)-pyridin-2-yl]-benzylamino}-ethyl)-2-oxo-oxazolidin-3-yl]-4H-pyrido[3,2-b][1,4]oxazin-3-one; or
(3S*,4S*)-6-[(S)-5-(2-{3-[6-(4-methoxy-pyrrolidin-3-yloxy)-pyridin-2-yl]-benzylamino}-ethyl)-2-oxo-oxazolidin-3-yl]-4H-pyrido[3,2-b][1,4]oxazin-3-one.

43) Particularly preferred are the following compounds of formula I:

6-[(S)-5-(2-{[3'-(2-amino-ethoxy)-biphenyl-3-ylmethyl]-amino}-ethyl)-2-oxo-oxazolidin-3-yl]-4H-pyrido[3,2-b][1,4]oxazin-3-one;
6-[(S)-5-(2-{3-[6-(2-amino-ethoxy)-pyridin-2-yl]-benzylamino}-ethyl)-2-oxo-oxazolidin-3-yl]-4H-pyrido[3,2-b][1,4]oxazin-3-one;
6-[(S)-2-oxo-5-(2-{3-[6-(2-pyrrolidin-1-yl-ethoxy)-pyridin-2-yl]-benzylamino}-ethyl)-oxazolidin-3-yl]-4H-pyrido[3,2-b][1,4]oxazin-3-one;
6-[(S)-5-(2-{3-[5-(2-amino-ethoxy)-pyridin-3-yl]-benzylamino}-ethyl)-2-oxo-oxazolidin-3-yl]-4H-pyrido[3,2-b][1,4]oxazin-3-one;
6-[(S)-5-(2-{3-[6-(2-amino-ethoxy)-pyrazin-2-yl]-benzylamino}-ethyl)-2-oxo-oxazolidin-3-yl]-4H-pyrido[3,2-b][1,4]oxazin-3-one;
6-[(S)-5-(2-{[6-(2-amino-ethoxy)-[2,4']bipyridinyl-2'-ylmethyl]-amino}-ethyl)-2-oxo-oxazolidin-3-yl]-4H-pyrido[3,2-b][1,4]oxazin-3-one;
6-[(S)-5-(2-{3-[6-((R)-2-amino-propoxy)-pyridin-2-yl]-benzylamino}-ethyl)-2-oxo-oxazolidin-3-yl]-4H-pyrido[3,2-b][1,4]oxazin-3-one;
6-[(S)-5-(2-{3-[6-((S)-2-amino-propoxy)-pyridin-2-yl]-benzylamino}-ethyl)-2-oxo-oxazolidin-3-yl]-4H-pyrido[3,2-b][1,4]oxazin-3-one;
6-[(S)-5-(2-{3-[2-(2-amino-ethoxy)-pyridin-4-yl]-benzylamino}-ethyl)-2-oxo-oxazolidin-3-yl]-4H-pyrido[3,2-b][1,4]oxazin-3-one;
6-[(S)-5-(2-{[3'-((S)-1-azetidin-2-ylmethoxy)-biphenyl-3-ylmethyl]-amino}-ethyl)-2-oxo-oxazolidin-3-yl]-4H-pyrido[3,2-b][1,4]oxazin-3-one;
6-[(S)-2-oxo-5-(2-{[3'-(pyrrolidin-3-yloxy)-biphenyl-3-ylmethyl]-amino}-ethyl)-oxazolidin-3-yl]-4H-pyrido[3,2-b][1,4]oxazin-3-one;
6-[(S)-5-(2-{[3'-(azetidin-3-yloxy)-biphenyl-3-ylmethyl]-amino}-ethyl)-2-oxo-oxazolidin-3-yl]-4H-pyrido[3,2-b][1,4]oxazin-3-one;
6-[(S)-5-(2-{3-[6-(azetidin-3-ylmethoxy)-pyridin-2-yl]-benzylamino}-ethyl)-2-oxo-oxazolidin-3-yl]-4H-pyrido[3,2-b][1,4]oxazin-3-one;
6-[(S)-5-(2-{3-[6-(azetidin-3-yloxy)-pyridin-2-yl]-benzylamino}-ethyl)-2-oxo-oxazolidin-3-yl]-4H-pyrido[3,2-b][1,4]oxazin-3-one;
6-[(S)-5-(2-{3-[6-((S)-1-azetidin-2-ylmethoxy)-pyridin-2-yl]-benzylamino}-ethyl)-2-oxo-oxazolidin-3-yl]-4H-pyrido[3,2-b][1,4]oxazin-3-one;
6-[(S)-5-(2-{3-[6-(1-morpholin-2-ylmethoxy)-pyridin-2-yl]-benzylamino}-ethyl)-2-oxo-oxazolidin-3-yl]-4H-pyrido[3,2-b][1,4]oxazin-3-one;
6-[(S)-5-(2-{[3'-(2-amino-ethoxy)-5'-methoxy-biphenyl-3-ylmethyl]-amino}-ethyl)-2-oxo-oxazolidin-3-yl]-4H-pyrido[3,2-b][1,4]oxazin-3-one; or
6-[(R)-5-(2-{3-[6-(2-amino-ethoxy)-pyridin-2-yl]-benzylamino}-ethyl)-2-oxo-oxazolidin-3-yl]-4H-benzo[1,4]thiazin-3-one.

44) More preferred are the following compounds of formula I:

6-[(S)-5-(2-{[3'-(2-amino-ethoxy)-biphenyl-3-ylmethyl]-amino}-ethyl)-2-oxo-oxazolidin-3-yl]-4H-pyrido[3,2-b][1,4]oxazin-3-one;
6-[(S)-5-(2-{3-[6-(2-amino-ethoxy)-pyridin-2-yl]-benzylamino}-ethyl)-2-oxo-oxazolidin-3-yl]-4H-pyrido[3,2-b][1,4]oxazin-3-one;
6-[(S)-5-(2-{3-[6-(2-amino-ethoxy)-pyrazin-2-yl]-benzylamino}-ethyl)-2-oxo-oxazolidin-3-yl]-4H-pyrido[3,2-b][1,4]oxazin-3-one;
6-[(S)-5-(2-{3-[6-((R)-2-amino-propoxy)-pyridin-2-yl]-benzylamino}-ethyl)-2-oxo-oxazolidin-3-yl]-4H-pyrido[3,2-b][1,4]oxazin-3-one;
6-[(S)-5-(2-{3-[6-((S)-2-amino-propoxy)-pyridin-2-yl]-benzylamino}-ethyl)-2-oxo-oxazolidin-3-yl]-4H-pyrido[3,2-b][1,4]oxazin-3-one;
6-[(S)-2-oxo-5-(2-{[3'-(pyrrolidin-3-yloxy)-biphenyl-3-ylmethyl]-amino}-ethyl)-oxazolidin-3-yl]-4H-pyrido[3,2-b][1,4]oxazin-3-one;
6-[(S)-5-(2-{3-[6-(azetidin-3-yloxy)-pyridin-2-yl]-benzylamino}-ethyl)-2-oxo-oxazolidin-3-yl]-4H-pyrido[3,2-b][1,4]oxazin-3-one;
6-[(S)-5-(2-{3-[6-((S)-1-azetidin-2-ylmethoxy)-pyridin-2-yl]-benzylamino}-ethyl)-2-oxo-oxazolidin-3-yl]-4H-pyrido[3,2-b][1,4]oxazin-3-one;
6-[(S)-5-(2-{3-[6-(1-morpholin-2-ylmethoxy)-pyridin-2-yl]-benzylamino}-ethyl)-2-oxo-oxazolidin-3-yl]-4H-pyrido[3,2-b][1,4]oxazin-3-one;
6-[(S)-5-(2-{[3'-(2-amino-ethoxy)-5'-methoxy-biphenyl-3-ylmethyl]-amino}-ethyl)-2-oxo-oxazolidin-3-yl]-4H-pyrido[3,2-b][1,4]oxazin-3-one; or
6-[(R)-5-(2-{3-[6-(2-amino-ethoxy)-pyridin-2-yl]-benzylamino}-ethyl)-2-oxo-oxazolidin-3-yl]-4H-benzo[1,4]thiazin-3-one.

45) Most preferred are the following compounds of formula I:

6-[(S)-5-(2-{[3'-(2-amino-ethoxy)-biphenyl-3-ylmethyl]-amino}-ethyl)-2-oxo-oxazolidin-3-yl]-4H-pyrido[3,2-b][1,4]oxazin-3-one;
6-[(S)-5-(2-{3-[6-(2-amino-ethoxy)-pyridin-2-yl]-benzylamino}-ethyl)-2-oxo-oxazolidin-3-yl]-4H-pyrido[3,2-b][1,4]oxazin-3-one;
6-[(S)-2-oxo-5-(2-{[3'-(pyrrolidin-3-yloxy)-biphenyl-3-ylmethyl]-amino}-ethyl)-oxazolidin-3-yl]-4H-pyrido[3,2-b][1,4]oxazin-3-one;
6-[(S)-5-(2-{3-[6-(azetidin-3-yloxy)-pyridin-2-yl]-benzylamino}-ethyl)-2-oxo-oxazolidin-3-yl]-4H-pyrido[3,2-b][1,4]oxazin-3-one;
6-[(S)-5-(2-{3-[6-((S)-1-azetidin-2-ylmethoxy)-pyridin-2-yl]-benzylamino}-ethyl)-2-oxo-oxazolidin-3-yl]-4H-pyrido[3,2-b][1,4]oxazin-3-one; and
6-[(R)-5-(2-{3-[6-(2-amino-ethoxy)-pyridin-2-yl]-benzylamino}-ethyl)-2-oxo-oxazolidin-3-yl]-4H-benzo[1,4]thiazin-3-one.

The compounds of formulae I, $I_A$, $I_B$, $IE_1$, $IE_2$, $I_S$, $I_{SA}$, $I_{SA}$, $I_{PS}$, $I_{PSA}$ and $I_{PSB}$ according to the invention, i.e. according to one of embodiments 1) to 45) above, are suitable for the use as chemotherapeutic active compounds in human and veterinary medicine and as substances for preserving inorganic and organic materials in particular all types of organic materials for example polymers, lubricants, paints, fibers, leather, paper and wood.

The compounds of formulae I, $I_A$, $I_B$, $I_{E1}$, $I_{E2}$, $I_S$, $I_{SA}$, $I_{SA}$, $I_{PS}$, $I_{PSA}$ and $I_{PSB}$ according to the invention are particularly active against bacteria and bacteria-like organisms. They may therefore be particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Moraxella catarrhalis, Staphylococcus aureus, Staphylococcus epidermidis, Staphylococcus haemolyticus*, or *Peptostreptococcus* spp.; pharyngitis, rheumatic fever, and glomerulonephritis related to infection by *Streptococcus pyogenes*, Groups C and G streptococci, *Corynebacterium diphtherias*, or *Actinobacillus haemolyticum*; respiratory tract infections related to infection by *Legionella pneumophila, S. pneumonia* or *Chlamydia pneumoniae*; blood and tissue infections, including endocarditis and osteomyelitis, caused by *S. aureus, S. haemolyticus*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *S. aureus*, coagulase-negative staphylococci (i.e., *S. epidermidis, S. haemolyticus*, etc.), *S. pyogenes, Streptococcus agalactiae*, Streptococcal groups C-F (minute colony streptococci), *viridans* streptococci, *Corynebacterium minutissimum, Clostridium* spp., or *Bartonella henselae*; uncomplicated acute urinary tract infections related to infection by *S. aureus* or coagulase-negative staphylococcal species; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and toxic shock syndrome), or Groups A, B and C streptococci; conjunctivitis, keratitis, and dacrocystitis related to infection by *C. trachomatis, N. gonorrhoeae, S. aureus, S. pneumoniae, S. pyogenes* or *Listeria* spp.

The preceding lists of infections and pathogens are to be interpreted merely as examples and in no way as limiting.

The compounds of formulae I, $I_A$, $I_B$, $I_{E1}$, $IE_2$, $I_S$, $I_{SA}$, $I_{SA}$, $I_{PS}$, $I_{PSA}$ and $I_{PSB}$ according to this invention, or the pharmaceutically acceptable salt thereof, may thus be used for the preparation of a medicament, and are suitable, for the prevention or treatment of a bacterial infection (notably for the prevention or treatment of a bacterial infection mediated by *Staphylococcus aureus* bacteria, especially for the prevention or treatment of a bacterial infection mediated by quinolone-resistant *Staphylococcus aureus*).

Accordingly, the compounds of formulae I, $I_A$, $I_B$, $I_{E1}$, $IE_2$, $I_S$, $I_{SA}$, $I_{SA}$, $I_{PS}$, $I_{PSA}$ and $I_{PSB}$ according to any one of embodiments 1) to 45), or the pharmaceutically acceptable salts thereof, may be used for the preparation of a medicament, and are suitable, for the prevention or treatment of a bacterial infection selected from the group consisting of respiratory tract infections, otitis media, meningitis, skin and soft tissue infections (whether complicated or uncomplicated), pneumonia (including hospital acquired pneumonia), bacteremia, endocarditis, intraabdominal infections, gastrointestinal infections, urinary tract infections, sexually transmitted infections, foreign body infections, osteomyelitis, Lyme disease, topical infections, or ophthalmological infections, and notably for the prevention or treatment of a bacterial infection selected from the group consisting of respiratory tract infections, otitis media, meningitis, skin and soft tissue infections (whether complicated or uncomplicated), pneumonia (including hospital acquired pneumonia) and bacteremia.

The compounds of formulae I, $I_A$, $I_B$, $I_{E1}$, $I_{E2}$, $I_S$, $I_{SA}$, $I_{SA}$, $I_{PS}$, $I_{PSA}$ and $I_{PSB}$ according to any one of embodiments 1) to 45), and the pharmaceutically acceptable salts thereof, may further be useful for the preparation of a medicament, and are suitable, for the treatment of infections that are mediated by Gram positive bacteria (such as *Staphylococcus aureus, Bacillus cereus, Bacillus anthracis, Corynebacterium* spp. and *Propionibacterium acnes*), notably by Gram positive bacteria selected from the group consisting of *Bacillus cereus, Bacillus anthracis* and *Propionibacterium acnes*. In particular, the compounds of formula I according to any one of embodiments 1) to 45), and the pharmaceutically acceptable salts thereof, can be used for the preparation of a medicament, and are suitable, for the treatment of a bacterial infection mediated by *Staphylococcus aureus* bacteria (especially quinolone-resistant *Staphylococcus aureus* bacteria).

The compounds of formulae I, $I_A$, $I_B$, $I_{E1}$, $I_{E2}$, $I_S$, $I_{SA}$, $I_{SA}$, $I_{PS}$, $I_{PSA}$ and $I_{PSB}$ according to any one of embodiments 1) to 45), and the pharmaceutically acceptable salts thereof, may further be useful for the preparation of a medicament, and are suitable, for the treatment of infections that are mediated by Gram negative bacteria (such as *E. coli, Klebsiella pneumoniae* and other Enterobacteriaceae, *Pseudomonas aeruginosa, Stenotrophomonas maltophilia, Neisseria meningitidis, Moraxella catarrhalis* and *Bacteroides* spp), notably by Gram negative bacteria selected from the group consisting of *Escherichia coli, Klebsiella pneumoniae, Pseudomonas aeruginosa, Stenotrophomonas maltophilia, Moraxella catarrhalis* and *Neisseria meningitidis*. In particular, the compounds of formula I according to any one of embodiments 1) to 45), and the pharmaceutically acceptable salts thereof, can be used for the preparation of a medicament, and are suitable, for the treatment of a bacterial infection mediated by *Klebsiella pneumoniae* bacteria (especially multiresistant or quinolone-resistant *Klebsiella pneumoniae* bacteria) and *Pseudomonas aeruginosa*.

One aspect of this invention therefore relates to the use of a compound of formulae I, $I_A$, $I_B$, $I_{E1}$, $I_{E2}$, $I_S$, $I_{SA}$, $I_{SA}$, $I_{PS}$, $I_{PSA}$ and $I_{PSB}$ according to one of embodiments 1) to 45), or of a pharmaceutically acceptable salt thereof, for the manufacture of a medicament for the prevention or treatment of a bacterial infection (in particular one of the previously mentioned infections mediated by Gram negative bacteria or one of the previously mentioned infections mediated by Gram positive bacteria). Another aspect of this invention relates to a compound of formulae I, $I_A$, $I_B$, $I_{E1}$, $IE_2$, $I_S$, $I_{SA}$, $I_{SA}$, $I_{PS}$, $I_{PSA}$ and $I_{PSB}$ according to one of embodiments 1) to 45), or a pharmaceutically acceptable salt thereof, for the prevention or treatment of a bacterial infection (in particular for the prevention or treatment of one of the previously mentioned infections mediated by Gram negative bacteria or of one of the previously mentioned infections mediated by Gram positive bacteria). Yet another aspect of this invention relates to a compound of formulae I, $I_A$, $I_B$, $I_{E1}$, $I_{E2}$, $I_S$, $I_{SA}$, $I_{SA}$, $I_{PS}$, $I_{PSA}$ and $I_{PSB}$ according to one of embodiments 1) to 45), or a pharmaceutically acceptable salt thereof, as a medicament. Yet a further aspect of this invention relates to a pharmaceutical composition containing, as active principle, a compound of formulae I, $I_A$, $I_B$, $I_{E1}$, $IE_2$, $I_S$, $I_{SA}$, $I_{SA}$, $I_{PS}$, $I_{PSA}$ and $I_{PSB}$ according to one of embodiments 1) to 45), or a pharmaceutically acceptable salt thereof, and at least one therapeutically inert excipient.

As well as in humans, bacterial infections can also be treated using compounds of formula I, $I_A$, $I_B$, $I_{E1}$, $IE_2$, $I_S$, $I_{SA}$, $I_{SA}$, $I_{PS}$, $I_{PSA}$ and $I_{PSB}$ (or pharmaceutically acceptable salts thereof) in other species like pigs, ruminants, horses, dogs, cats and poultry.

The present invention also relates to pharmacologically acceptable salts and to compositions and formulations of compounds of formulae I, $I_A$, $I_B$, $I_{E1}$, $IE_2$, $I_S$, $I_{SA}$, $I_{SA}$, $I_{PS}$, $I_{PSA}$ or $I_{PSB}$.

Any reference to a compound of formulae I, $I_A$, $I_B$, $I_{E1}$, $IE_2$, $I_S$, $I_{SA}$, $I_{SA}$, $I_{PS}$, $I_{PSA}$ or $I_{PSB}$ in this text is to be understood as referring also to the salts (and especially the pharmaceutically acceptable salts) of such compounds, as appropriate and expedient.

A pharmaceutical composition according to the present invention contains at least one compound of formulae I, $I_A$, $I_B$, $I_{E1}$, $IE_2$, $I_S$, $I_{SA}$, $I_{SA}$, $I_{PS}$, $I_{PSA}$ or $I_{PSB}$ (or a pharmaceutically acceptable salt thereof) as the active agent and optionally carriers and/or diluents and/or adjuvants, and may also contain additional known antibiotics.

The compounds of formulae I, $I_A$, $I_B$, $I_{E1}$, $IE_2$, $I_S$, $I_{SA}$, $I_{SA}$, $I_{PS}$, $I_{PSA}$ or $I_{PSB}$ and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a bacterial infection in a patient, comprising the administration to said patient of a pharmaceutically active amount of a compound of formula I according to one of embodiments 1) to 45) or a pharmaceutically acceptable salt thereof. Accordingly, the invention provides a method for the prevention or the treatment of a bacterial infection mediated by Gram negative bacteria (in particular a bacterial infection mediated by *Klebsiella pneumonia* bacteria, and especially by multiresistant or quinolone-resistant *Klebsiella pneumonia* bacteria and *Pseudomonas aeruginosa* bacteria) in a patient, comprising the administration to said patient of a pharmaceutically active amount of a compound of formula I according to one of embodiments 1) to 45) or a pharmaceutically acceptable salt thereof. The invention further provides a method for the prevention or the treatment of a bacterial infection mediated by Gram positive bacteria (in particular a bacterial infection mediated by *Staphylococcus aureus* bacteria, especially by quinolone-resistant *Staphylococcus aureus* bacteria) in a patient, comprising the administration to said patient of a pharmaceutically active amount of a compound of formula I according to one of embodiments 1) to 45) or a pharmaceutically acceptable salt thereof.

Moreover, the compounds of formulae I, $I_A$, $I_B$, $I_{E1}$, $IE_2$, $I_S$, $I_{SA}$, $I_{SA}$, $I_{PS}$, $I_{PSA}$ and $I_{PSB}$ according to this invention may also be used for cleaning purposes, e.g. to remove pathogenic microbes and bacteria from surgical instruments, catheters and artificial implants or to make a room or an area aseptic. For such purposes, the compounds of formula I could be contained in a solution or in a spray formulation.

This invention, thus, relates to the compounds of formulae I, $I_A$ and $I_B$ as defined in embodiments 1) to 3), or further limited under consideration of their respective dependencies by the characteristics of any one of embodiments 4) to 45), and to pharmaceutically acceptable salts thereof. It relates furthermore to the use of such compounds as medicaments, especially for the prevention or treatment of a bacterial infection, in particular for the prevention or treatment of a bacterial infection mediated by Gram positive bacteria (in particular a bacterial infection mediated by *Staphylococcus aureus* bacteria, especially by quinolone-resistant *Staphylococcus aureus* bacteria) or for the prevention or treatment of a bacterial infection mediated by Gram negative bacteria (in particular a bacterial infection mediated by *Klebsiella pneumonia* bacteria, and especially by multiresistant or quinolone-resistant *Klebsiella pneumonia* bacteria and *Pseudomonas aeruginosa* bacteria), and notably for the prevention or treatment of a bacterial infection mediated by quinolone-resistant *Staphylococcus aureus, Klebsiella pneumonia* or *Pseudomonas aeruginosa* bacteria. The following embodiments relating to the compounds of formulae I, $I_A$ and $I_B$ according to embodiments 1) to 3) are thus possible and intended and herewith specifically disclosed in individualised form:

1, 2+1, 3+1, 5+1, 5+2+1, 5+3+1, 6+1, 6+2+1, 6+3+1, 6+4, 6+5+1, 6+5+2+1, 6+5+3+1, 7+1, 7+2+1, 7+4, 7+5+1, 7+5+2+1, 7+5+3+1, 7+6+1, 7+6+2+1, 7+6+3+1, 7+6+4, 7+6+5+1, 7+6+5+2+1, 7+6+5+3+1, 8+1, 8+3+1, 8+4, 8+5+1, 8+5+2+1, 8+5+3+1, 8+6+1, 8+6+2+1, 8+6+3+1, 8+6+4, 8+6+5+1, 8+6+5+2+1, 8+6+5+3+1, 9+1, 9+2+1, 9+3+1, 9+4, 9+5+1, 9+5+2+1, 9+5+3+1, 9+6+1, 9+6+2+1, 9+6+3+1, 9+6+4, 9+6+5+1, 9+6+5+2+1, 9+6+5+3+1, 9+7+1, 9+7+2+1, 9+7+4, 9+7+5+1, 9+7+5+2+1, 9+7+5+3+1, 9+7+6+1, 9+7+6+2+1, 9+7+6+3+1, 9+7+6+4, 9+7+6+5+1, 9+7+6+5+2+1, 9+7+6+5+3+1, 9+8+1, 9+8+3+1, 9+8+4, 9+8+5+1, 9+8+5+2+1, 9+8+5+3+1, 9+8+6+1, 9+8+6+2+1, 9+8+6+3+1, 9+8+6+4, 9+8+6+5+1, 9+8+6+5+2+1, 9+8+6+5+3+1, 10+1, 10+2+1, 10+4, 10+5+1, 10+5+2+1, 10+5+3+1, 10+6+1, 10+6+2+1, 10+6+3+1, 10+6+4, 10+6+5+1, 10+6+5+2+1, 10+6+5+3+1, 10+7+1, 10+7+2+1, 10+7+4, 10+7+5+1, 10+7+5+2+1,

10+7+5+3+1, 10+7+6+1, 10+7+6+2+1, 10+7+6+3+1, 10+7+6+4, 10+7+6+5+1, 10+7+6+5+2+1, 10+7+6+5+3+1, 10+9+1, 10+9+2+1, 10+9+3+1, 10+9+4, 10+9+5+1, 10+9+5+2+1, 10+9+5+3+1, 10+9+6+1, 10+9+6+2+1, 10+9+6+3+1, 10+9+6+4, 10+9+6+5+1, 10+9+6+5+2+1, 10+9+6+5+3+1, 10+9+7+1, 10+9+7+2+1, 10+9+7+4, 10+9+7+5+1, 10+9+7+5+2+1, 10+9+7+5+3+1, 10+9+7+6+1, 10+9+7+6+2+1, 10+9+7+6+3+1, 10+9+7+6+4, 10+9+7+6+5+1, 10+9+7+6+5+2+1, 10+9+7+6+5+3+1, 10+9+8+1, 10+9+8+3+1, 10+9+8+4, 10+9+8+5+1, 10+9+8+5+2+1, 10+9+8+5+3+1, 10+9+8+6+1, 10+9+8+6+2+1, 10+9+8+6+3+1, 10+9+8+6+4, 10+9+8+6+5+1, 10+9+8+6+5+2+1, 10+9+8+6+5+3+1, 11+1, 11+3+1, 11+4, 11+5+1, 11+5+2+1, 11+5+3+1, 11+6+1, 11+6+2+1, 11+6+3+1, 11+6+4, 11+6+5+1, 11+6+5+2+1, 11+6+5+3+1, 11+8+1, 11+8+3+1, 11+8+4, 11+8+5+1, 11+8+5+2+1, 11+8+5+3+1, 11+8+6+1, 11+8+6+2+1, 11+8+6+3+1, 11+8+6+4, 11+8+6+5+1, 11+8+6+5+2+1, 11+8+6+5+3+1, 11+9+1, 11+9+2+1, 11+9+3+1, 11+9+4, 11+9+5+1, 11+9+5+2+1, 11+9+5+3+1, 11+9+6+1, 11+9+6+2+1, 11+9+6+3+1, 11+9+6+4, 11+9+6+5+1, 11+9+6+5+2+1, 11+9+6+5+3+1, 11+9+7+1, 11+9+7+2+1, 11+9+7+4, 11+9+7+5+1, 11+9+7+5+2+1, 11+9+7+5+3+1, 11+9+7+6+1, 11+9+7+6+2+1, 11+9+7+6+3+1, 11+9+7+6+4, 11+9+7+6+5+1, 11+9+7+6+5+2+1, 11+9+7+6+5+3+1, 11+9+8+1, 11+9+8+3+1, 11+9+8+4, 11+9+8+5+1, 11+9+8+5+2+1, 11+9+8+5+3+1, 11+9+8+6+1, 11+9+8+6+2+1, 11+9+8+6+3+1, 11+9+8+6+4, 11+9+8+6+5+1, 11+9+8+6+5+2+1, 11+9+8+6+5+3+1, 12+1, 12+2+1, 12+4, 12+5+1, 12+5+2+1, 12+5+3+1, 13+1, 13+2+1, 13+4, 13+5+1, 13+5+2+1, 13+5+3+1, 14+1, 14+2+1, 14+4, 14+5+1, 14+5+2+1, 14+5+3+1, 15+1, 15+2+1, 15+4, 15+5+1, 15+5+2+1, 15+5+3+1, 16+1, 16+2+1, 16+4, 16+5+1, 16+5+2+1, 16+5+3+1, 17+1, 17+2+1, 17+4, 17+5+1, 17+5+2+1, 17+5+3+1, 18+1, 18+2+1, 18+4, 18+5+1, 18+5+2+1, 18+5+3+1, 19+1, 19+2+1, 19+4, 19+5+1, 19+5+2+1, 19+5+3+1, 20+1, 20+2+1, 20+4, 20+5+1, 20+5+2+1, 20+5+3+1, 21+1, 21+2+1, 21+4, 21+5+1, 21+5+2+1, 21+5+3+1, 22+1, 22+2+1, 22+4, 22+5+1, 22+5+2+1, 22+5+3+1, 23+1, 23+2+1, 23+4, 23+5+1, 23+5+2+1, 23+5+3+1, 24+1, 24+2+1, 24+4, 24+5+1, 24+5+2+1, 24+5+3+1, 25+1, 25+2+1, 25+4, 25+5+1, 25+5+2+1, 25+5+3+1, 26+1, 26+2+1, 26+4, 26+5+1, 26+5+2+1, 26+5+3+1, 27+1, 27+3+1, 27+4, 27+5+1, 27+5+2+1, 27+5+3+1, 28+1, 28+3+1, 28+4, 28+5+1, 28+5+2+1, 28+5+3+1, 29+1, 29+3+1, 29+4, 29+5+1, 29+5+2+1, 29+5+3+1, 30+1, 30+3+1, 30+4, 30+5+1, 30+5+2+1, 30+5+3+1, 31+1, 31+3+1, 31+4, 31+5+1, 31+5+2+1, 31+5+3+1, 32+1, 32+3+1, 32+4, 32+5+1, 32+5+2+1, 32+5+3+1, 33+1, 33+3+1, 33+4, 33+5+1, 33+5+2+1, 33+5+3+1, 34+1, 34+3+1, 34+4, 34+5+1, 34+5+2+1, 34+5+3+1, 35+13+1, 35+13+2+1, 35+13+4, 35+13+5+1, 35+13+5+2+1, 35+13+5+3+1, 35+14+1, 35+14+2+1, 35+14+4, 35+14+5+1, 35+14+5+2+1, 35+14+5+3+1, 35+15+1, 35+15+2+1, 35+15+4, 35+15+5+1, 35+15+5+2+1, 35+15+5+3+1, 35+17+1, 35+17+2+1, 35+17+4, 35+17+5+1, 35+17+5+2+1, 35+17+5+3+1, 35+19+1, 35+19+2+1, 35+19+4, 35+19+5+1, 35+19+5+2+1, 35+19+5+3+1, 35+20+1, 35+20+2+1, 35+20+4, 35+20+5+1, 35+20+5+2+1, 35+20+5+3+1, 35+21+1, 35+21+2+1, 35+21+4, 35+21+5+1, 35+21+5+2+1, 35+21+5+3+1, 35+22+1, 35+22+2+1, 35+22+4, 35+22+5+1, 35+22+5+2+1, 35+22+5+3+1, 35+24+1, 35+24+2+1, 35+24+4, 35+24+5+1, 35+24+5+2+1, 35+24+5+3+1, 35+26+1, 35+26+2+1, 35+26+4, 35+26+5+1, 35+26+5+2+1, 35+26+5+3+1, 35+28+1, 35+28+3+1, 35+28+4, 35+28+5+1, 35+28+5+2+1, 35+28+5+3+1, 35+29+1, 35+29+3+1, 35+29+4, 35+29+5+1, 35+29+5+2+1, 35+29+5+3+1, 35+30+1, 35+30+3+1, 35+30+4, 35+30+5+1, 35+30+5+2+1, 35+30+5+3+1, 35+32+1, 35+32+3+1, 35+32+4, 35+32+5+1, 35+32+5+2+1, 35+32+5+3+1, 35+33+1, 35+33+3+1, 35+33+4, 35+33+5+1, 35+33+5+2+1, 35+33+5+3+1, 36+35+13+1, 36+35+13+2+1, 36+35+13+4, 36+35+13+5+1, 36+35+13+5+2+1, 36+35+13+5+3+1, 36+35+14+1, 36+35+14+2+1, 36+35+14+4, 36+35+14+5+1, 36+35+14+5+2+1, 36+35+14+5+3+1, 36+35+15+1, 36+35+15+2+1, 36+35+15+4, 36+35+15+5+1, 36+35+15+5+2+1, 36+35+15+5+3+1, 36+35+17+1, 36+35+17+2+1, 36+35+17+4, 36+35+17+5+1, 36+35+17+5+2+1, 36+35+17+5+3+1, 36+35+19+1, 36+35+19+2+1, 36+35+19+4, 36+35+19+5+1, 36+35+19+5+2+1, 36+35+19+5+3+1, 36+35+20+1, 36+35+20+2+1, 36+35+20+4, 36+35+20+5+1, 36+35+20+5+2+1, 36+35+20+5+3+1, 36+35+21+1, 36+35+21+2+1, 36+35+21+4, 36+35+21+5+1, 36+35+21+5+2+1, 36+35+21+5+3+1, 36+35+22+1, 36+35+22+2+1, 36+35+22+4, 36+35+22+5+1, 36+35+22+5+2+1, 36+35+22+5+3+1, 36+35+24+1, 36+35+24+2+1, 36+35+24+4, 36+35+24+5+1, 36+35+24+5+2+1, 36+35+24+5+3+1, 36+35+26+1, 36+35+26+2+1, 36+35+26+4, 36+35+26+5+1, 36+35+26+5+2+1, 36+35+26+5+3+1, 36+35+28+1, 36+35+28+3+1, 36+35+28+4, 36+35+28+5+1, 36+35+28+5+2+1, 36+35+28+5+3+1, 36+35+29+1, 36+35+29+3+1, 36+35+29+4, 36+35+29+5+1, 36+35+29+5+2+1, 36+35+29+5+3+1, 36+35+30+1, 36+35+30+3+1, 36+35+30+4, 36+35+30+5+1, 36+35+30+5+2+1, 36+35+30+5+3+1, 36+35+32+1, 36+35+32+3+1, 36+35+32+4, 36+35+32+5+1, 36+35+32+5+2+1, 36+35+32+5+3+1, 36+35+33+1, 36+35+33+3+1, 36+35+33+4, 36+35+33+5+1, 36+35+33+5+2+1, 36+35+33+5+3+1, 37+13+1, 37+13+2+1, 37+13+4, 37+13+5+1, 37+13+5+2+1, 37+13+5+3+1, 37+14+1, 37+14+2+1, 37+14+4, 37+14+5+1, 37+14+5+2+1, 37+14+5+3+1, 37+15+1, 37+15+2+1, 37+15+4, 37+15+5+1, 37+15+5+2+1, 37+15+5+3+1, 37+17+1, 37+17+2+1, 37+17+4, 37+17+5+1, 37+17+5+2+1, 37+17+5+3+1, 37+19+1, 37+19+2+1, 37+19+4, 37+19+5+1, 37+19+5+2+1, 37+19+5+3+1, 37+20+1, 37+20+2+1, 37+20+4, 37+20+5+1, 37+20+5+2+1, 37+20+5+3+1, 37+21+1, 37+21+2+1, 37+21+4, 37+21+5+1, 37+21+5+2+1, 37+21+5+3+1, 37+22+1, 37+22+2+1, 37+22+4, 37+22+5+1, 37+22+5+2+1, 37+22+5+3+1, 37+24+1, 37+24+2+1, 37+24+4, 37+24+5+1, 37+24+5+2+1, 37+24+5+3+1, 37+26+1, 37+26+2+1, 37+26+4, 37+26+5+1, 37+26+5+2+1, 37+26+5+3+1, 37+28+1, 37+28+3+1, 37+28+4, 37+28+5+1, 37+28+5+2+1, 37+28+5+3+1, 37+29+1, 37+29+3+1, 37+29+4, 37+29+5+1, 37+29+5+2+1, 37+29+5+3+1, 37+30+1, 37+30+3+1, 37+30+4, 37+30+5+1, 37+30+5+2+1, 37+30+5+3+1, 37+32+1, 37+32+3+1, 37+32+4, 37+32+5+1, 37+32+5+2+1, 37+32+5+3+1, 37+33+1, 37+33+3+1, 37+33+4, 37+33+5+1, 37+33+5+2+1, 37+33+5+3+1, 38+13+1, 38+13+2+1, 38+13+4, 38+13+5+1, 38+13+5+2+1, 38+13+5+3+1, 38+14+1, 38+14+2+1, 38+14+4, 38+14+5+1, 38+14+5+2+1, 38+14+5+3+1, 38+15+1, 38+15+2+1, 38+15+4, 38+15+5+1, 38+15+5+2+1, 38+15+5+3+1, 38+17+1, 38+17+2+1, 38+17+4, 38+17+5+1, 38+17+5+2+1, 38+17+5+3+1, 38+19+1, 38+19+2+1, 38+19+4, 38+19+5+1, 38+19+5+2+1, 38+19+5+3+1, 38+20+1, 38+20+2+1, 38+20+4, 38+20+5+1, 38+20+5+2+1, 38+20+5+3+1, 38+21+1, 38+21+2+1, 38+21+4, 38+21+5+1, 38+21+5+2+1, 38+21+5+3+1, 38+22+1, 38+22+2+1, 38+22+4, 38+22+5+1, 38+22+5+2+1, 38+22+5+3+1, 38+24+1, 38+24+2+1, 38+24+4, 38+24+5+1, 38+24+5+2+1, 38+24+5+3+1, 38+26+1, 38+26+2+1, 38+26+4, 38+26+5+1, 38+26+5+2+1, 38+26+5+3+1, 38+28+1, 38+28+3+1, 38+28+4, 38+28+5+1, 38+28+5+2+1, 38+28+5+3+1, 38+29+1, 38+29+3+1, 38+29+4, 38+29+5+1, 38+29+5+2+1, 38+29+5+3+1, 38+30+1, 38+30+3+1, 38+30+4, 38+30+5+1, 38+30+5+2+1, 38+30+5+3+1, 38+32+1, 38+32+3+1, 38+32+4, 38+32+5+1, 38+32+5+2+1, 38+32+5+3+1, 38+33+1, 38+33+3+1, 38+33+4, 38+33+5+1, 38+33+5+2+

1, 38+33+5+3+1, 39+38+13+1, 39+38+13+2+1, 39+38+13+ 4, 39+38+13+5+1, 39+38+13+5+2+1, 39+38+13+5+3+1, 39+38+14+1, 39+38+14+2+1, 39+38+14+4, 39+38+14+5+ 1, 39+38+14+5+2+1, 39+38+14+5+3+1, 39+38+15+1, 39+38+15+2+1, 39+38+15+4, 39+38+15+5+1, 39+38+15+ 5+2+1, 39+38+15+5+3+1, 39+38+17+1, 39+38+17+2+1, 39+38+17+4, 39+38+17+5+1, 39+38+17+5+2+1, 39+38+ 17+5+3+1, 39+38+19+1, 39+38+19+2+1, 39+38+19+4, 39+38+19+5+1, 39+38+19+5+2+1, 39+38+19+5+3+1, 39+38+20+1, 39+38+20+2+1, 39+38+20+4, 39+38+20+5+ 1, 39+38+20+5+2+1, 39+38+20+5+3+1, 39+38+21+1, 39+38+21+2+1, 39+38+21+4, 39+38+21+5+1, 39+38+21+ 5+2+1, 39+38+21+5+3+1, 39+38+22+1, 39+38+22+2+1, 39+38+22+4, 39+38+22+5+1, 39+38+22+5+2+1, 39+38+ 22+5+3+1, 39+38+24+1, 39+38+24+2+1, 39+38+24+4, 39+38+24+5+1, 39+38+24+5+2+1, 39+38+24+5+3+1, 39+38+26+1, 39+38+26+2+1, 39+38+26+4, 39+38+26+5+ 1, 39+38+26+5+2+1, 39+38+26+5+3+1, 39+38+28+1, 39+38+28+3+1, 39+38+28+4, 39+38+28+5+1, 39+38+28+ 5+2+1, 39+38+28+5+3+1, 39+38+29+1, 39+38+29+3+1, 39+38+29+4, 39+38+29+5+1, 39+38+29+5+2+1, 39+38+ 29+5+3+1, 39+38+30+1, 39+38+30+3+1, 39+38+30+4, 39+38+30+5+1, 39+38+30+5+2+1, 39+38+30+5+3+1, 39+38+32+1, 39+38+32+3+1, 39+38+32+4, 39+38+32+5+ 1, 39+38+32+5+2+1, 39+38+32+5+3+1, 39+38+33+1, 39+38+33+3+1, 39+38+33+4, 39+38+33+5+1, 39+38+33+ 5+2+1, 39+38+33+5+3+1, 40+39+38+13+1, 40+39+38+ 13+2+1, 40+39+38+13+4, 40+39+38+13+5+1, 40+39+38+ 13+5+2+1, 40+39+38+13+5+3+1, 40+39+38+14+1, 40+39+38+14+2+1, 40+39+38+14+4, 40+39+38+14+5+1, 40+39+38+14+5+2+1, 40+39+38+14+5+3+1, 40+39+38+ 15+1, 40+39+38+15+2+1, 40+39+38+15+4, 40+39+38+ 15+5+1, 40+39+38+15+5+2+1, 40+39+38+15+5+3+1, 40+39+38+17+1, 40+39+38+17+2+1, 40+39+38+17+4, 40+39+38+17+5+1, 40+39+38+17+5+2+1, 40+39+38+17+ 5+3+1, 40+39+38+19+1, 40+39+38+19+2+1, 40+39+38+ 19+4, 40+39+38+19+5+1, 40+39+38+19+5+2+1, 40+39+ 38+19+5+3+1, 40+39+38+20+1, 40+39+38+20+2+1, 40+39+38+20+4, 40+39+38+20+5+1, 40+39+38+20+5+2+ 1, 40+39+38+20+5+3+1, 40+39+38+21+1, 40+39+38+21+ 2+1, 40+39+38+21+4, 40+39+38+21+5+1, 40+39+38+21+ 5+2+1, 40+39+38+21+5+3+1, 40+39+38+22+1, 40+39+ 38+22+2+1, 40+39+38+22+4, 40+39+38+22+5+1, 40+39+ 38+22+5+2+1, 40+39+38+22+5+3+1, 40+39+38+24+1, 40+39+38+24+2+1, 40+39+38+24+4, 40+39+38+24+5+1, 40+39+38+24+5+2+1, 40+39+38+24+5+3+1, 40+39+38+ 26+1, 40+39+38+26+2+1, 40+39+38+26+4, 40+39+38+ 26+5+1, 40+39+38+26+5+2+1, 40+39+38+26+5+3+1, 40+39+38+28+1, 40+39+38+28+3+1, 40+39+38+28+4, 40+39+38+28+5+1, 40+39+38+28+5+2+1, 40+39+38+28+ 5+3+1, 40+39+38+29+1, 40+39+38+29+3+1, 40+39+38+ 29+4, 40+39+38+29+5+1, 40+39+38+29+5+2+1, 40+39+ 38+29+5+3+1, 40+39+38+30+1, 40+39+38+30+3+1, 40+39+38+30+4, 40+39+38+30+5+1, 40+39+38+30+5+2+ 1, 40+39+38+30+5+3+1, 40+39+38+32+1, 40+39+38+32+ 3+1, 40+39+38+32+4, 40+39+38+32+5+1, 40+39+38+32+ 5+2+1, 40+39+38+32+5+3+1, 40+39+38+33+1, 40+39+ 38+33+3+1, 40+39+38+33+4, 40+39+38+33+5+1, 40+39+ 38+33+5+2+1, 40+39+38+33+5+3+1, 41+13+1, 41+13+2+ 1, 41+13+4, 41+13+5+1, 41+13+5+2+1, 41+13+5+3+1, 41+14+1, 41+14+2+1, 41+14+4, 41+14+5+1, 41+14+5+2+ 1, 41+14+5+3+1, 41+15+1, 41+15+2+1, 41+15+4, 41+15+ 5+1, 41+15+5+2+1, 41+15+5+3+1, 41+17+1, 41+17+2+1, 41+17+4, 41+17+5+1, 41+17+5+2+1, 41+17+5+3+1, 41+19+1, 41+19+2+1, 41+19+4, 41+19+5+1, 41+19+5+2+ 1, 41+19+5+3+1, 41+20+1, 41+20+2+1, 41+20+4, 41+20+ 5+1, 41+20+5+2+1, 41+20+5+3+1, 41+21+1, 41+21+2+1, 41+21+4, 41+21+5+1, 41+21+5+2+1, 41+21+5+3+1, 41+22+1, 41+22+2+1, 41+22+4, 41+22+5+1, 41+22+5+2+ 1, 41+22+5+3+1, 41+24+1, 41+24+2+1, 41+24+4, 41+24+ 5+1, 41+24+5+2+1, 41+24+5+3+1, 41+26+1, 41+26+2+1, 41+26+4, 41+26+5+1, 41+26+5+2+1, 41+26+5+3+1, 41+28+1, 41+28+3+1, 41+28+4, 41+28+5+1, 41+28+5+2+ 1, 41+28+5+3+1, 41+29+1, 41+29+3+1, 41+29+4, 41+29+ 5+1, 41+29+5+2+1, 41+29+5+3+1, 41+30+1, 41+30+3+1, 41+30+4, 41+30+5+1, 41+30+5+2+1, 41+30+5+3+1, 41+32+1, 41+32+3+1, 41+32+4, 41+32+5+1, 41+32+5+2+ 1, 41+32+5+3+1, 41+33+1, 41+33+3+1, 41+33+4, 41+33+ 5+1, 41+33+5+2+1, 41+33+5+3+1, 42, 43, 44 and 45.

In the list above, the numbers refer to the embodiments according to their numbering provided hereinabove whereas "+" indicates the dependency from another embodiment. The different individualised embodiments are separated by commas. In other words, "8+5+1" for example refers to embodiment 8) depending on embodiment 5), depending on embodiment 1), i.e. embodiment "8+5+1" corresponds to embodiment 1) further limited by the features of embodiments 5) and 8). Likewise, "9+5+3+1" refers to embodiment 9) depending mutatis mutandis on embodiments 5) and 3), depending on embodiment 1), i.e. embodiment "9+5+3+1" corresponds to embodiment 1) further limited by the features of embodiment 3), further limited by the features of embodiments 5) and 9).

The compounds of formula I can be manufactured in accordance with the present invention using the procedures described hereafter.

Preparation of the Compounds of Formula I

Abbreviations

The following abbreviations are used throughout the specification and the examples:
Ac acetyl
AcOH acetic acid
Alloc allyloxycarbonyl
aq. aqueous
Boc tert-butoxycarbonyl
Bs 4-bromobenzenesulfonyl (brosylate)
BuLi n-butyllithium
Cbz benzyloxycarbonyl
CC column chromatography over silica gel
Cipro ciprofloxacin
Cy cyclohexyl
d day(s)
DAD diode array detection
dba dibenzylideneacetone
DCE 1,2-dichloroethane
DCM dichloromethane
DEAD diethyl azodicarboxylate
DIAD diisopropyl azodicarboxylate
DME 1,2-dimethoxyethane
DMF N,N-dimethylformamide
DMSO dimethylsulfoxide
DPPA diphenylphosphoryl azide
EA ethyl acetate
ELSD evaporative light scattering detector
ESI electron spray ionisation
eq. equivalent
Et ethyl
EtOH ethanol
Hept heptane
Hex hexane HPLC high pressure liquid chromatography
HV high vacuum conditions
LC liquid chromatography
min minutes
Me methyl
MeCN acetonitrile
MeOH methanol
MS mass spectroscopy
Ms methanesulfonyl (mesyl)
Nf nonafluorobutanesulfonyl
NMR Nuclear Magnetic Resonance
Ns 4-nitrobenzenesulfonyl (nosylate)
org. organic
PCy$_3$ tricyclohexylphosphine
Pd/C palladium on carbon
Pd(OH)$_2$/C palladium dihydroxide on carbon
Pd(PPh$_3$)$_4$ tetrakis(triphenylphosphine)palladium(0)
PEPPSI™-IPr [1,3 -bis(2,6-diisopropylphenyl)imidazol-2-ylidene](3 -chloropyridyl)palladium(II) dichloride
Ph phenyl
PPh$_3$ triphenylphosphine
PPh$_3$O triphenylphosphine oxide
prep-HPLC preparative high pressure liquid chromatography
PTSA para-toluenesulfonic acid
Pyr pyridine
Q-Phos pentaphenyl(di-tert-butylphosphino)ferrocene
quant. quantitative yield
tb 1,2,3,4,5-pentaphenyl-1'-(di-lerl-butylphosphino)ferrocene
rt room temperature
sat. saturated
SK-CC01-A 2'-(dimethylamino)-2-biphenylyl-palladium (II) chloride dinorbornylphosphine complex
S-Phos 2-dicyclohexylphosphino-2',6'-dimethoxybiphenyl
TBAF tetra-n-butylammonium fluoride
TBDMS tert-butyldimethylsilyl
TBDPS tert-butyldiphenylsilyl
tBu tert-butyl
TEA triethylamine
Tf trifluoromethanesulfonyl (triflyl)
TFA trifluoroacetic acid
THF tetrahydrofuran
TLC thin layer chromatography
t$_R$ retention time
Ts para-toluenesulfonyl General Reaction Techniques:

General Reaction Technique 1 (Reductive Amination):

The reaction between the amine and the aldehyde or ketone is performed in a solvent system allowing the removal of the formed water through physical or chemical means (e.g. distillation of the solvent-water azeotrope or presence of drying agents such as molecular sieves, MgSO$_4$ or Na$_2$SO$_4$). Such solvent is typically toluene, Hex, THF, DCM or DCE or a mixture of solvents such as DCE/MeOH. The reaction can be catalyzed by traces of acid (usually AcOH). The intermediate imine is reduced with a suitable reducing agent (e.g. NaBH$_4$, NaBH$_3$CN, or NaBH(OAc)$_3$ or through hydrogenation over a noble metal catalyst such as Pd/C. The reaction is carried out between −10° C. and 110° C., preferably between 0° C. and 60° C. The reaction can also be carried out in one pot. It can also be performed in protic solvents such as MeOH or water in presence of a picoline-borane complex (Sato et al., *Tetrahedron* (2004), 60, 7899-7906). Alternatively the imine intermediate can be obtained by aza-Wittig reaction between an iminophosphorane (generated in situ from an azide by reaction with PPh$_3$) and an aldehyde (*J. Org. Chem.* (2006), 71, 2839-2847 and references therein).

General Reaction Technique 2 (Removal of Amino Protecting Groups):

The Cbz protecting groups are removed by hydrogenolysis over a noble metal catalyst (e.g. Pd/C or Pd(OH)$_2$/C). The Boc group is removed under acidic conditions such as HCl in an org. solvent such as MeOH or dioxane, or TFA neat or diluted in a solvent such DCM. The Alloc group is removed in the presence of Pd(PPh$_3$)$_4$ in presence of an allyl cation scavenger such as morpholine, dimedone or tributyltin hydride between 0° C. and 50° C. in a solvent such as THF. The 4-methoxybenzyl group is removed using TFA neat or diluted in a solvent such as DCM. Further general methods to remove amine protecting groups have been described in T. W. Greene, P. G. M. Wuts, *Protecting Groups in Organic Synthesis*, 3$^{rd}$ Ed (1999), 494-653 (Publisher: John Wiley and Sons, Inc., New York, N.Y.).

General Reaction Technique 3 (Suzuki Coupling):

The aromatic halide (typically a bromide) is reacted with the required boronic acid derivative or its boronate ester equivalent (e.g. pinacol ester) in the presence of a palladium catalyst and a base such as K$_2$CO$_3$, Cs$_2$CO$_3$, K$_3$PO$_4$, tBuONa or tBuOK between 20 and 120° C. in a solvent such as toluene, EtOH, THF, dioxane, DME or DMF, usually in the presence of water (20 to 50%). Examples of typical palladium catalysts are triarylphosphine palladium complexes such as Pd(PPh$_3$)$_4$. These catalysts can also be prepared in situ from a common palladium source such as Pd(OAc)$_2$ or Pd$_2$(dba)$_3$ and a ligand such as trialkylphosphines (e.g. PCy$_3$ or P(tBu)$_3$), dialkylphosphinobiphenyls (e.g. S-Phos) or ferrocenylphosphines (e.g. Q-phos). Alternatively, one can use a commercially available precatalyst based on palladacycle (e.g. SK-CC01-A) or N-heterocyclic carbene complexes (e.g. PEPPSI™-IPr). The reaction can also be performed by using the corresponding aromatic triflate. Further variations of the reaction are described in Miyaura and Suzuki, *Chem. Rev.* (1995), 95, 2457-2483, Bellina et al., *Synthesis* (2004), 2419-2440, Mauger and Mignani, *Aldrichimica Acta* (2006), 39, 17-24, Kantchev et al., *Aldrichimica Acta* (2006), 39, 97-111, Fu, *Acc. Chem. Res.* (2008), 41, 1555-1564, and references cited therein.

General Reaction Technique 4 (Removal of Acetal Protecting Groups):

The acetal derivatives dissolved in a solvent such as THF or acetone were treated between 0° C. and +70° C. under acidic conditions such as aq. AcOH, aq. TFA, CBr$_4$ or HCl in MeOH, MeCN or THF. Further methods to remove acetal groups are given in T. W. Greene, P. G. M. Wuts, *Protecting Groups in Organic Synthesis*, 3$^{rd}$ Ed (1999), 293-329 (Publisher: John Wiley and Sons, Inc., New York, N.Y.)

General Reaction Technique 5 (Alcohol Activation):

The alcohol is reacted with MsCl, TfCl, BsCl, NfCl, NsCl or TsCl in the presence of a base such as TEA in a dry aprotic solvent such as Pyr, THF or DCM between −30° C. and +50° C. In the case of the triflate or mesylate, Tf$_2$O or Ms$_2$O can also be used.

General Reaction Technique 6 (Formation of Iodo, Chloro or Bromo Derivatives):

The sulfonates obtained using general reaction technique 5 can be reacted with a sodium halogenide such as NaI or NaBr in MeCN or DMF between 40° C. and 120° C., delivering the corresponding iodide derivatives. Alternatively the corresponding bromides or chlorides can also be obtained by reaction of the corresponding alcohol derivatives with PBr$_3$ or PCl$_3$ respectively.

General Reaction Technique 7 (Removal of Hydroxy Protecting Groups):

The silyl ether groups are removed either using fluoride anion sources such as TBAF in THF between 0° C. and +40° C. or HF in MeCN between 0° C. and +40° C. or using acidic conditions such as AcOH in THF/MeOH, aq. TFA or HCl in MeOH. Further methods to remove the TBDMS and TBDPS groups are given in T. W. Greene, P. G. M. Wuts, *Protecting Groups in Organic Synthesis*, 3$^{rd}$ Ed (1999), 133-139 and 142-143 respectively (Publisher: John Wiley and Sons, Inc., New York, N.Y.). Further general methods to remove alcohol protecting groups are described in T. W. Greene, P. G. M. Wuts, *Protecting Groups in Organic Synthesis*, 3$^{rd}$ Ed (1999), 23-147 (Publisher: John Wiley and Sons, Inc., New York, N.Y.).

General Preparation Methods:

Preparation of the Compounds of Formulae I, $I_A$ and $I_B$:

The compounds of formulae I, $I_A$ and $I_B$ can be manufactured by the methods given below, by the methods given in the examples or by analogous methods. Optimum reaction conditions may vary with the particular reactants or solvents used, but such conditions can be determined by a person skilled in the art by routine optimization procedures.

Sub-sections a) to c) hereafter describe general methods for preparing compounds of formulae I, $I_A$ or $I_B$. If not indicated otherwise, the generic groups $R^{1a}$, $R^{2a}$, $R^{2b}$, $R^{3a}$, $R^{3b}$, $R^4$, $R^5$, $U^1$, $U^2$, $U^3$, $U^4$, $V^1$, $V^2$, $V^3$, $V^4$, X and Q and n are as defined for formulae I, $I^A$ and $I_B$. General synthetic methods used repeatedly throughout the text below are referenced to and described in the above section entitled "General reaction techniques". In some instances certain generic groups might be incompatible with the assembly illustrated in the procedures and schemes below and so will require the use of protecting groups. The use of protecting groups is well known in the art (see for example "*Protective Groups in Organic Synthesis*", T. W. Greene, P. G. M. Wuts, Wiley-Interscience, 1999).

The compounds of formulae I, $I_A$ or $I_B$ can be obtained by:

a) reacting a compound of formula II

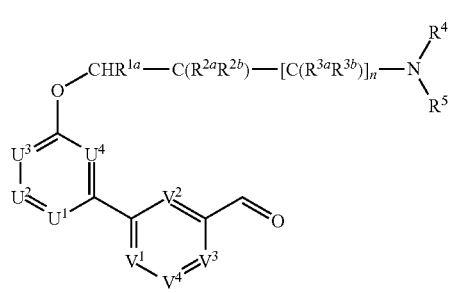

II wherein n, $R^{1a}$, $R^{2a}$, $R^{2b}$, $R^{3a}$, $R^{3b}$, $R^4$, $R^5$, $U^1$, $U^2$, $U^3$, $U^4$, $V^1$, $V^2$, $V^3$ and $V^4$ are as defined in formulae I, $I_A$ or $I_B$, with a compound of formula III

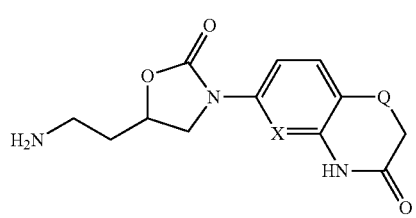

III wherein X and Q are as defined in formulae I, $I_A$ or $I_B$, using general reaction technique 1; or b) reacting a compound of formula IV

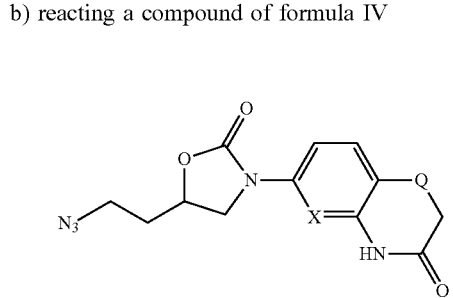

IV wherein X and Q are as defined in formulae I, $I_A$ or $I_B$, with PPh$_3$ in presence of water, followed by reaction with a compound of formula II as defined in section a), using general reaction technique 1; or c) Deprotecting a compound of formula V

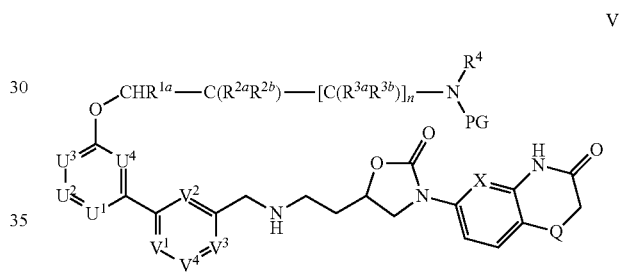

V wherein n, $R^{1a}$, $R^{2a}$, $R^{2b}$, $R^{3a}$, $R^{3b}$, $R^4$, $U^1$, $U^2$, $U^3$, $U^4$, $V^1$, $V^2$, $V^3$ and $V^4$ are as defined in formulae I, $I_A$ or $I_B$, and PG represents an amino protecting group such as Cbz or Boc following general reaction technique 2.

The compounds of formulae I, $I_A$ or $I_B$ thus obtained may, if desired, be converted into their salts, and notably into their pharmaceutically acceptable salts using standard methods. Besides, whenever the compounds of formulae I, $I_A$ or $I_B$ are obtained in the form of mixtures of enantiomers, the enantiomers can be separated using methods known to one skilled in the art, e.g. by formation and separation of diastereomeric salts or by HPLC over a chiral stationary phase such as a Regis Whelk-O1(R,R) (10 µm) column, a Daicel ChiralCel OD-H (5-10 µm) column, or a Daicel ChiralPak IA (10 µm) or AD-H (5 µm) column. Typical conditions of chiral HPLC are an isocratic mixture of eluent A (EtOH, in presence or absence of an amine such as TEA, diethylamine) and eluent B (Hex), at a flow rate of 0.8 to 150 ml/min.

Preparation of the Synthesis Intermediates of Formulae II, III, IV and V:

Compounds of Formulae II and II-PG:

The compounds of formulae II and II-PG can be prepared as summarized in Scheme 1 hereafter.

Scheme 1

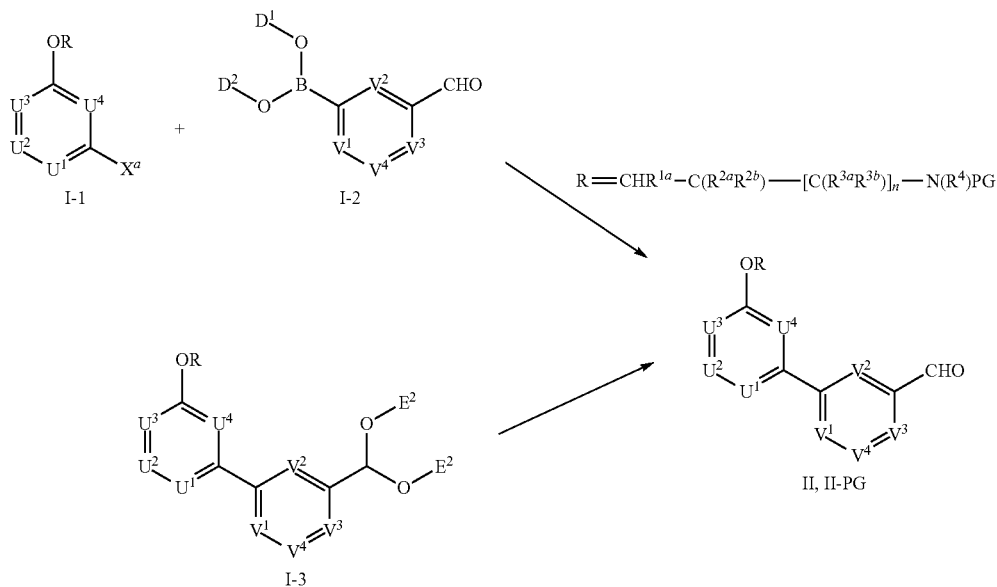

In Scheme 1, $U^1$, $U^2$, $U^3$, $U^4$, $V^1$, $V^2$, $V^3$ and $V^4$ are as defined in formulae I, $I_A$ or $I_B$, $X^a$ represents a halogen such as bromine or chlorine, $D^1$ and $D^2$ represent H, methyl or ethyl or $D^1$ and $D^2$ together represent $CH_2C(Me)_2CH_2$ or $C(Me)_2C(Me)_2$, $E^1$ and $E^2$ represent methyl or ethyl or $E^1$ and $E^2$ together represent $CH_2CH_2CH_2$ or $CH_2CH_2$ and R represents $CHR^{1a}$—$C(R^{2a}R^{2b})$—$[C(R^{3a}R^{3b})]_n$—$N(R^4)R^5)$ as defined in formulae I, $I_A$ or $I_B$ or $CHR^{1a}$—$C(R^{2a}R^{2b})$—$[C(R^{3a}R^{3b})]_n$—$N(R^4)$PG as defined in formula V.

The boronic esters or acids of formula I-2 can be reacted with the halogenides of formula I-1 using general reaction technique 3, affording the intermediates of formulae II and II-PG (R=$CHR^{1a}$—$C(R^{2a}R^{2b})$—$[C(R^{3a}R^{3b})]_n$—$N(R^4)$PG). Alternatively, the acetal of formula I-3 can be deprotected using general reaction technique 4, affording the compounds of formulae II and II-PG. Compounds of formula II can be also obtained from the compound of formula II-PG after removal of the protecting group PG using general reaction technique 2.

Compounds of Formulae III and IV:

The compounds of formulae III and IV can be prepared either as described in or in analogy to WO 2008/126024, WO 2009/104147 or WO 2010/041194, or as summarized in Scheme 2 hereafter.

Scheme 2

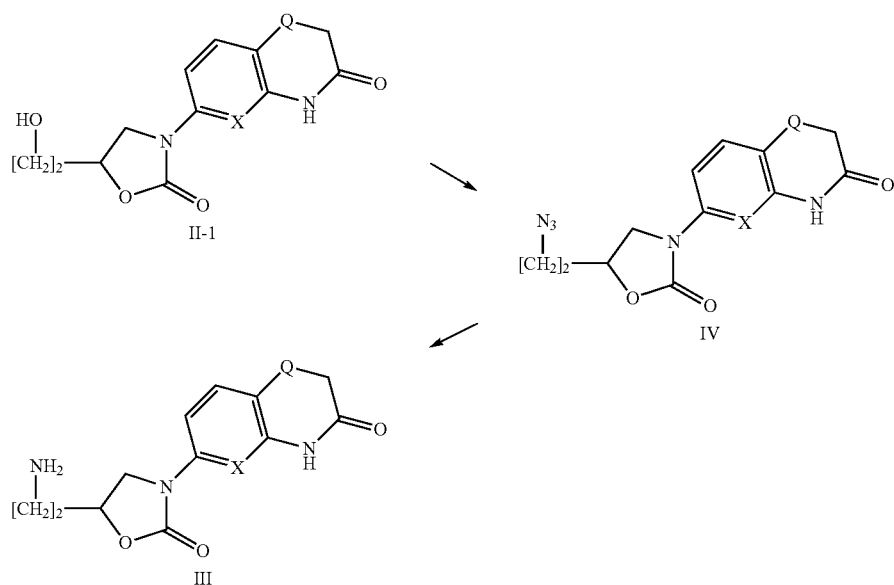

In Scheme 2, X and Q are as defined in formula I.

The alcohol derivatives of formula II-1 can be reacted with a compound of formula Cl—SO$_2$R$^A$ wherein R$^A$ represents methyl, trifluoromethyl or tolyl using general reaction technique 5. The resulting sulfonates can be optionally reacted with NaI using general reaction technique 6, and the resulting intermediates (sulfonates or iodides) can then be reacted with NaN$_3$. The compounds of formula IV thus obtained can be transformed into the derivatives of formula III by hydrogenation over a noble metal catalyst or by reaction with PPh$_3$ in the presence of water. The chiral compounds of formula III can be obtained starting from the chiral molecules of formula II-1 or through chiral separation at any stage of the synthesis.

Compounds of Formula V:

The compound of formula V are obtained by reacting a compound of formula II-PG

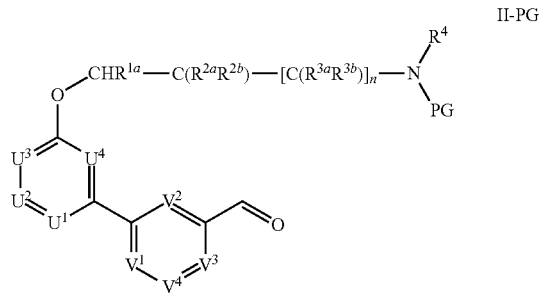

II-PG wherein n, R$^{1a}$, R$^{2a}$, R$^{2b}$, R$^{3a}$, R$^{3b}$, R$^4$, U$^1$, U$^2$, U$^3$, U$^4$, V$^1$, V$^2$, V$^3$ and V$^4$ are as defined in formulae I, I$_A$ or I$_B$, and PG represents an amine protecting group such as Cbz or Boc with a compound of formula III, using general reaction technique 1; or with a compound of formula IV as defined in section b), using general reaction technique 1.

Preparation of the Synthesis Intermediates of Formulae I-1, I-2, I-3 and II-1:

The compounds of formulae I-1 and I-2 are commercially available or can be prepared as described in the "EXAMPLES" section, in analogy thereto or by standard methods known to one skilled in the art.

The intermediates of formula I-3 can be prepared as described in Scheme 3 hereafter.

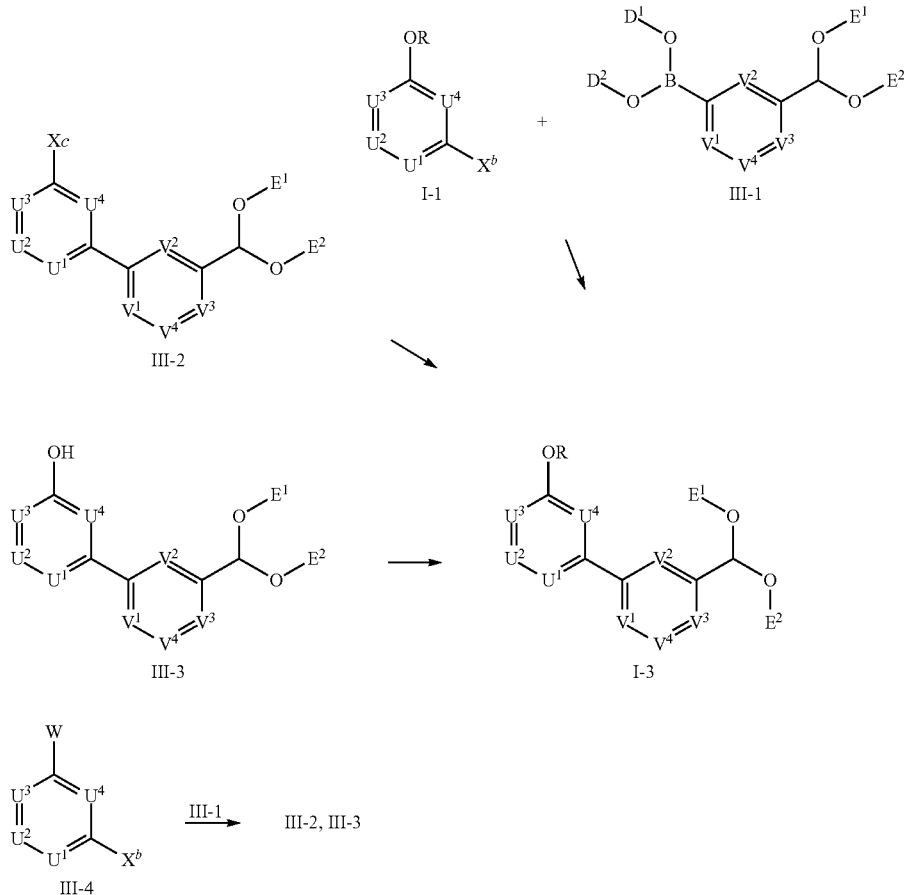

Scheme 3

In Scheme 3, $U^1$, $U^2$, $U^3$, $U^4$, $V^1$, $V^2$, $V^3$ and $V^4$ are as defined in formulae I, $I_A$ or $I_B$, $X^b$ and $X^c$ represent a halogen such as bromine or chlorine, $D^1$ and $D^2$ represent H, methyl or ethyl or $D^1$ and $D^2$ together represent $CH_2C(Me)_2CH_2$ or $C(Me)_2C(Me)_2$, $E^1$ and $E^2$ represent methyl or ethyl or $E^1$ and $E^2$ together represent $CH_2CH_2CH_2$ or $CH_2CH_2$, R represents $CHR^{1a}$—$C(R^{2a}R^{2b})$—$[C(R^{3a}R^{3b})]_n$—$N(R^4)R^5$ as defined in formulae I, $I_A$ or $I_B$ or $CHR^{1a}$—$C(R^{2a}R^{2b})$—$[C(R^{3a}R^{3b})]_n$—$N(R^4)PG$ as defined in formula V and W represents OH or $X^c$.

The compounds of formula I-3 are obtained by reacting the compounds of formulae I-1 and III-1 using general reaction technique 3. They can also be obtained by reacting a compound of formula III-2 with the compounds of formula ROH wherein R is defined as in Scheme 1, in presence of a base such as potassium tert-butoxide. The compounds of formula I-3 can also be obtained by reacting the compound of formula III-3 with the compounds of formula ROH wherein R is defined as in Scheme 1, in presence of $PPh_3$ and an alkyl azodicarboxylate such as DEAD or DIAD. Compounds III-2 and III-3 are prepared from compounds III-1 and III-4 wherein W represents $X^c$ or OH respectively using general reaction technique 3. The compounds of formulae III-1 and III-4 are commercially available or can be prepared as described in the "EXAMPLES" section, in analogy thereto or by standard methods known to one skilled in the art.

The intermediates of formula II-1 can be prepared either as described in or in analogy to WO 2009/104147 or WO 2009/104159, or, in the case wherein X is N and Q is O, as summarized in Scheme 4 hereafter.

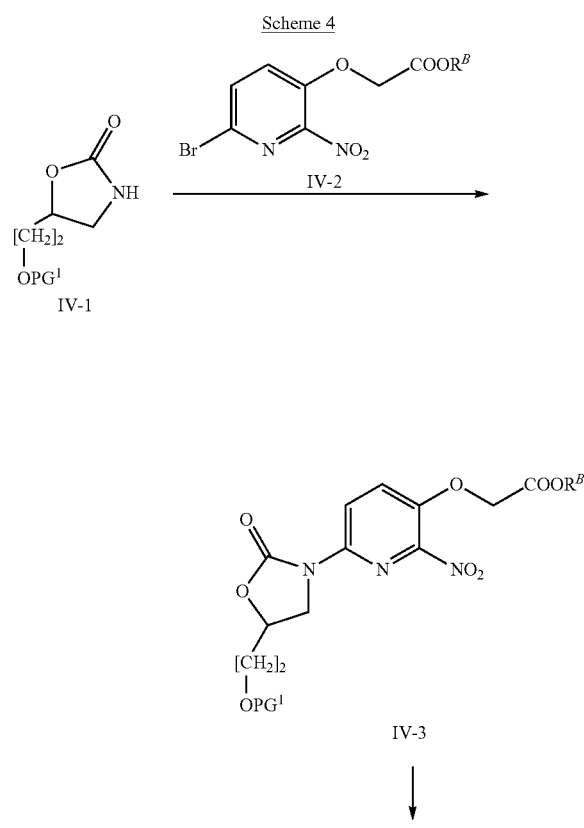

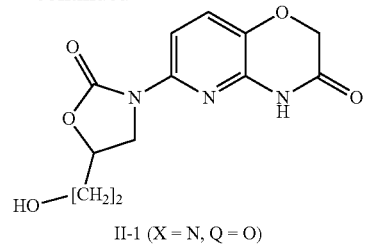

II-1 (X = N, Q = O)

In Scheme 4, $PG^1$ represents a hydroxy protecting group such as benzyl, TBDMS or TBDPS and $R^B$ represents $(C_1-C_4)$alkyl.

The compounds of formula IV-1 (either commercially available ($PG^1$=TBDPS) or prepared according to WO 2010/041194) can be reacted with the compounds of formula IV-2 (prepared according to WO 2004/002992) in the presence of CuI, an inorganic base such as $K_2CO_3$ and N,N-dimethyl-ethylenediamine, affording the compounds of formula IV-3. The latter can be heated between 50 and 70° C. in the presence of iron and ammonium chloride followed by reflux in AcOH, affording the compounds of formula II-1. If still present, the alcohol protecting group $PG^1$ can be removed using general reaction technique 7.

Particular embodiments of the invention are described in the following Examples, which serve to illustrate the invention in more detail without limiting its scope in any way.

EXAMPLES

All temperatures are stated in ° C. Unless otherwise indicated, the reactions take place at rt.

Analytical TLC characterizations were performed with 0.2 mm plates: Merck, Silica gel 60 $F_{254}$. Elution is performed with EA, Hept, DCM, MeOH or mixtures thereof. Detection was done with UV or with a solution of $KMnO_4$ (3 g), $K_2CO_3$ (20 g), 5% NaOH (3 mL) and $H_2O$ (300 mL) with subsequent heating.

CCs were performed using Brunschwig 60A silica gel (0.032-0.63 mm) or using an ISCO CombiFlash system and prepacked $SiO_2$ cartridges, elution being carried out with either Hept-EA or DCM-MeOH mixtures with an appropriate gradient.

The compounds were characterized by $^1$H-NMR (300 MHz, Varian Oxford; 400 MHz, Bruker Avance 400 or 500 MHz, Bruker Avance 500 Cryoprobe). Chemical shifts δ are given in ppm relative to the solvent used; multiplicities: s=singlet, d=doublet, t=triplet, q=quadruplet, p=pentuplet, hex=hexet, hep=heptet, m=multiplet, br.=broad; coupling constants J are given in Hz. Alternatively compounds were characterized by LC-MS (Sciex API 2000 with Agilent 1100 Binary Pump with DAD and ELSD or an Agilent quadrupole MS 6140 with Agilent 1200 Binary Pump, DAD and ELSD); by TLC (TLC plates from Merck, Silica gel 60 $F_{254}$); or by melting point.

The analytical LC-MS data have been obtained using the following respective conditions:

MS1 data:
Column: Zorbax SB-Aq, 3.5 μm, 4.6×50 mm;
Injection volume: 1 μL;
Column oven temperature: 40° C.;
Pump: Agilent G4220A;
Makeup pump: Dionex HPG-3200SD;
DAD: Agilent G4212A;
MS: Thermo MSQ Plus;

ELSD: Sedere Sedex 90;
Detection: UV 210 nm, ELSD and MS;
MS ionization mode: ESI+;
Eluents: A: H$_2$O+0.04% TFA; and B: MeCN;
Flow rate: 4.5 mL/min;
Gradient: 5% B (0.00 min-0.08 min), 5% B to 95% B (0.08 min-1.07 min), 95% B (1.07 min-1.57 min).
MS2 data:
Column: Waters X-Bridge C18, 2.5 µm, 4.6×30 mm;
Injection volume: 1 µL;
Column oven temperature: 40° C.;
Pump: Dionex HPG-320016;
Makeup pump: Dionex ISO-31005D;
DAD: Dionex DAD-3000016;
MS: Thermo MSQ Plus;
ELSD: Sedere Sedex 85;
Detection: UV 210 nm, ELSD and MS;
MS ionization mode: ESI+;
Eluents: A: H$_2$O+0.04% TFA; and B: MeCN;
Eluent flow rate: 4.5 mL/min;
Gradient: 5% B (0.00 min-0.01 min), 5% B to 95% B (0.01 min-1.0 min), 95% B (1.0 min-1.45 min).
MS3 data:
Column: Zorbax SB-Aq, 3.5 µm, 4.6×50 mm;
Otherwise same parameters as for obtaining MS2 data.
MS4 data:
Column: Phenomex Gemini, C18 110A, 3 µm, 2×50 mm;
Injection volume: 3 µL;
Eluents: A: H$_2$O (+0.1% HCOOH); and B: MeCN (+0.1% HCOOH);
Eluent flow rate: 0.3 mL/min;
Gradient: from 40% to 95% B in (0.00 min-9.00 min).
The number of decimals given for the corresponding [M+H] peak(s) of each tested compound depends upon the accuracy of the LC-MS device actually used.
The prep-HPLC purifications were performed on a Gilson HPLC system, equipped with a Gilson LH215 autosampler, Gilson 333/334 pumps, Thermo Finnigan MSQ Plus detector system, and a Dionex UVD340U (or Dionex DAD-3000) UV detector, using the following respective conditions:
Method 1:
Column: Waters Atlantis T3 OBD, 10 µm, 30×75 mm;
Flow rate: 75 mL/min;
Eluents: A: H$_2$O+0.5% HCOOH; B: MeCN;
Gradient: 90% A to 5% A (0.0 min-4.0 min), 5% A (4.0 min-6.0 min).
Method 2:
Column: Waters XBridge C18, 10 µm, 30×75 mm;
Flow rate: 75 mL/min;
Eluents: A: H$_2$O+0.5% NH$_4$OH; B: MeCN;
Gradient: 90% A to 5% A (0.0 min-4.0 min), 5% A (4.0 min-6.0 min).
Method 3:
Column: Waters XBridge C18, 10 µm, 30×75 mm;
Flow rate: 75 mL/min;
Eluents: A: H$_2$O+0.5% NH$_4$OH; B: MeCN;
Gradient: 95% A to 50% A (0.0-3.0 min), 50% A to 5% A (3.0-4.0 min), 5% A (4.0-6.0 min).
Method 4:
Column: Waters XBridge C18, 10 µm, 30×75 mm;
Flow rate: 75 mL/min;
Eluents: A: H$_2$O+0.5% HCOOH; B: MeCN;
Gradient: 90% A to 5% A (0.0 min-4.0 min), 5% A (4.0 min-6.0 min).

The following other purification methods were furthermore used:
Filtration over Si-carbonate: silica bound equivalent of tetramethyl ammonium carbonate, SiliaPrep SPE cartridges Carbonate, 200 mg, 3 mL (Silicycle SPE-R66030B-03G).
Filtration over Alumina cartridges: polar sorbent basic character, SiliaPrep SPE Cartridges Alumina Neutral, 1 g, 6 mL (Silicycle SPE-AUT-0054-065).

PREPARATIONS

General Building Blocks

Preparation BB1: 3'-(1,3-dioxolan-2-yl)-[1,1'-biphenyl]-3-ol 3-bromophenol (400 mg; commercial), 3-(1,3-dioxolan-2-yl)phenylboronic acid pinacol ester (638 mg; commercial), Pd(PPh$_3$)$_4$ (107 mg; commercial) and K$_2$CO$_3$ (959 mg) were suspended in water (5 mL) and dioxane (15 mL). Nitrogen was bubbled through the reaction mixture and it was further stirred at 100° C. for 2 h. The reaction mixture was cooled to rt and partitioned between water and EA. The aq. layer was extracted with EA and the combined org. layers were washed with brine and dried over MgSO$_4$, affording after CC purification (Combiflash; Hept/EA 1:0 to 0:1) 400 mg (71% yield) of a yellow oil.
MS3 (ESI, m/z): 243.04 [M−H$^+$]; $t_R$=0.77 min.

Preparation BB2: 6-(3-(1,3-dioxolan-2-yl)phenyl)pyridin-2-ol

Starting from 6-chloro-2-hydroxypyridine (383 mg; commercial), 3-(1,3-dioxolan-2-yl)phenylboronic acid pinacol ester (801 mg; commercial), Pd(PPh$_3$)$_4$ (134 mg; commercial) and K$_2$CO$_3$ (1.20 g) and proceeding in analogy to Preparation BB1, the title compound was obtained, after purification by CC (Combiflash; DCM to DCM/MeOH 4:1), as a brown oil (303 mg; 43% yield).
MS2 (ESI, m/z): 244.07 [M−H$^+$]; $t_R$=0.62 min.

Preparation BB3: 3-(3-(1,3-dioxolan-2-yl)phenyl)-5-chloropyridazine

A mixture of 3,5-dichloropyridazine (1.50 g; commercial), 3-(1,3-dioxolan-2-yl)phenylboronic acid pinacol ester (2.78 g; commercial), palladium acetate (113 mg; commercial), 1,1-bis(diphenylphosphino)ferrocene (288 mg; commercial) and Cs$_2$CO$_3$ (8.20 g) in dioxane (40 mL) and water (10 mL) was degased with nitrogen and stirred at 70° C. for 1 day. The mixture was allowed to reach rt, diluted with EA, filtered and partially concentrated under reduced pressure. The residue was diluted with water and the org. layer was separated, washed with brine, dried over MgSO$_4$, filtered, evaporated and purified CC (Combiflash; Hept to Hept/EA 1:1), affording an orange solid (2.05 g; 77.5% yield).
MS3 (ESI, m/z): 263.00 [M+H$^+$]; $t_R$=0.75 min.

Preparation BB4: 5-(3-(1,3-dioxolan-2-yl)phenyl)pyridin-3-ol

Starting from 5-bromo-5-hydroxypyridine (541 mg; commercial), 3-(1,3-dioxolan-2-yl)phenylboronic acid pinacol ester (859 mg; commercial), Pd(PPh$_3$)$_4$ (180 mg; commercial) and Na$_2$CO$_3$ (1M; 3.11 mL) and proceeding in analogy to Preparation BB1, but using EtOH and water as solvent, the title compound (540 mg; 71% yield) was obtained after purification by CC (Combiflash; Hept/EA 1:0 to 0:1) as a yellow oil.

MS3 (ESI, m/z): 244.07 [M+H$^+$]; $t_R$=0.52 min.

Preparation BB5:
6-(3-[1,3]dioxolan-2-yl-phenyl)-pyrazin-2-ol

Starting from 6-bromopyrazin-2-ol (450 mg) and 3-(1,3-dioxolan-2-yl)phenylboronic acid pinacol ester (710 mg) and proceeding in analogy to Preparation BB1, but using EtOH, toluene and water as solvent, the title compound was obtained as a yellow solid (466 mg; 74% yield).

MS3 (ESI, m/z): 245.04 [M+H$^+$]; $t_R$=0.59 min.

Preparation BB6: 2'-[1,3]dioxolan-2-yl-[2,4']bi-pyridinyl-6-ol

A mixture of 4-bromo-2-(1,3-dioxolan-2-yl)-pyridine (1500 mg), bis(pinacolato)diboron (1858 mg), potassium acetate (1600 mg) and dichloro[1,1'-bis(diphenylphosphino) ferrocene]palladium(II) dichloromethane adduct (626 mg) in dioxane (25 mL) was degassed for 5 min with N$_2$ and sealed in a Schlenk flask. The resulting dark brown suspension was stirred at 90° C. for 1.5 h. The mixture was cooled down to rt, diluted with EA, filtered through a glass fiber filter and concentrated under reduced pressure and used directly in the next step. The resulting crude 2-(1,3-dioxolan-2-yl)-4-(4,4,5,5-tetramethyl-1,3,2-dioxaborolan-2-yl) pyridine (1028 mg) was mixed with 6-chloro-2-hydroxypyridine (450 mg), palladium(II) acetate (38.2 mg), 1,1'-bis (diphenylphosphino)ferrocene (94.4 mg) and cesium carbonate (2773 mg) in dioxane (10 mL) and water (2.5 mL) and degassed for 5 min with N$_2$ and sealed in a Schlenk flask. The resulting dark brown suspension was stirred at 70° C. for 4 h. The mixture was cooled down to rt, diluted with EA, filtered through a glass fiber filter and concentrated under reduced pressure. The residue was purified by CC (Combiflash; Hept/EA 7:3 to EA/MeOH 9:1), affording a brown solid (431 mg; 52% yield).

MS3 (ESI, m/z): 245.06 [M+H$^+$]; $t_R$=0.49 min.

Preparation BB7:
4-(3-[1,3]dioxolan-2-yl-phenyl)-pyridin-2-ol

Starting from 4-bromo-2-hydroxypyridine (400 mg; commercial) and 3-(1,3-dioxolan-2-yl)phenylboronic acid pinacol ester (635 mg) and proceeding in analogy to Preparation BB1, the title compound was obtained as a brown oil (460 mg; 82% yield).

MS3 (ESI, m/z): 244.09 [M+H$^+$]; $t_R$=0.62 min.

Preparation BBB: 3'-[1,3]dioxolan-2-yl-5-methoxy-biphenyl-3-ol

Starting from 4-bromo-2-hydroxypyridine (467 mg; commercial), 3-(1,3-dioxolan-2-yl)phenylboronic acid pinacol ester (635 mg; commercial), Pd(PPh$_3$)$_4$ (106 mg; commercial) and K$_2$CO$_3$ (953 mg) and proceeding in analogy to Preparation BB1, the title compound was obtained, after purification by CC (Combiflash; DCM to DCM/MeOH 19:1), as a colourless oil (473 mg; 76% yield).

MS2 (ESI, m/z): 272.99 [M+H$^+$]; $t_R$=0.77 min.

Preparation BB9: 4-(4,4,5,5-tetramethyl-[1,3,2]di-oxaborolan-2-yl)-pyridine-2-carbaldehyde A mixture of 4-bromopyridine-2-carboxaldehyde (1.86 g; commercial), bis(pinacolato)-diboron (2.82 g), potassium acetate (2.48 g) and [1,1'-bis(diphenylphosphino)ferrocene]-dichloropalladium(II) dichloromethane complex (408 mg) in dioxane (20 mL) was degassed for 5 min with N$_2$ and stirred at 90° C. for 2 h. The mixture was cooled down to rt, diluted with EA, filtered through a pad of Celite, concentrated under reduced pressure and used directly in the next step.

$^1$H NMR (CDCl$_3$) δ: 10.13 (s, 1H); 8.82 (d, J=4.6 Hz, 1H); 8.34 (s, 1H); 7.87 (d, J=4.4 Hz, 1H); 1.33 (m, 12H).

Preparation BB10:
[2-(6-bromo-pyridin-2-yloxy)-ethyl]-carbamic acid tert-butyl ester DIAD (2.14 mL) was added dropwise to a 0° C. solution of 6-bromopyridin-2-ol (2.5 g; commercial), (Boc-amino) ethanolamine (2.32 mL; commercial) and P(Ph)$_3$ (3.94 g) in THF (45 mL). The mixture was stirred at rt for 3 h. The volatiles were removed under reduced pressure. The resulting residue was partitioned between EA and water, the aq. layer was extracted with EA and the combined org. layers were washed with brine and dried over MgSO$_4$. The title compound was obtained after purification by CC (Combiflash; Hept-EA, 1-0 to 0-1) as an off-white oil (3.6 g; 83% yield).

MS3 (ESI, m/z): 316.88 [M+H$^+$]; $t_R$=0.88 min.

Preparation BB11:
(3-(1,3-dioxolan-2-yl)phenyl)trihydroxyborate

BB11.i. 2-bromo-6-(1,3-dioxalan-2-yl)pyridine

A mixture of 2-bromo-6-formylpyridine (7.35 g), ethylene glycol (3.57 mL) and a catalytic amount of p-toluene sulfonic acid (0.49 g) in 175 mL benzene was heated at reflux using a Dean Stark trap for 1 day. Dilution with sat. aq. NaHCO$_3$ (40 mL) and extraction with DCM (2×100 mL), dried over Na$_2$SO$_4$ and concentrated under reduced pressure afforded the title compound, after purification by CC (DCM-DCM/EtOH 95:5), as a yellow oil (7.62 g; 84% yield).

$^1$H NMR (CDCl$_3$) δ: 7.74 (t, J=7.8 Hz, 1H); 7.57 (t, J=7.8 Hz, 2H); 5.72 (s, 1H); 4.13 (m, 2H); 4.04 (m, 2H).

BB11.ii. Lithium-(3-(1,3-dioxolan-2-yl)phenyl)tri-isopropoxyborate

An oven-dried round-bottomed flask was charged with toluene (83 mL) and THF (20 mL) and placed under argon atmosphere. The flask was charged with intermediate BB11.i (5.0 g) and cooled to −78° C. BuLi (14.25 mL) was added dropwise over 45 min, and the mixture was stirred for 45 min at −78° C. Triisopropylborate (4.27 g) was added dropwise via a syringe pump over 70 min, and the mixture was stirred for an additional 2 h at −78° C. The resulting solution was concentrated under reduced pressure. To the dark residue was added Et$_2$O (60 mL) and the mixture was left in an ultrasonic bath for 10 min. The brown precipitate was filtered, washed with Et$_2$O (3×15 mL) and dried under high vacuum for 3 h to yield the title compound as a brown solid (4.3 g; 61% yield).

$^1$H NMR (CDCl$_3$) δ: 7.64 (t, J=7.5 Hz, 1H); 7.52 (dd, J=1.2, 7.5 Hz, 1H); 7.28 (dd, J=1.2, 7.5 Hz, 1H); 5.77 (s, 1H); 4.13-4.02 (m, 4H).

BB11.iii. Lithium-(3-(1,3-dioxolan-2-yl)phenyl) trihydroxyborate

A mixture of intermediate BB11.ii (0.23 g), in 9 mL acetone and 1 mL water was stirred at rt for 24 h. The yellow precipitate was filtered, washed with 10 mL of mixture acetone/water (9:1) and dried at rt, to give the title compound as a yellow precipitate (0.11 g; 75% yield).

$^1$H NMR (CDCl$_3$) δ: 7.64 (t, J=7.5 Hz, 1H); 7.52 (dd, J=1.2, 7.5 Hz, 1H); 7.28 (dd, J=1.2, 7.5 Hz, 1H); 5.77 (s, 1H); 4.13-4.02 (m, 4H); 3.92 (m, 3H); 1.15 (m, 18H).

Specific Building Blocks

Preparation A1: [2-(3'-formyl-biphenyl-3-yloxy)-ethyl]-carbamic acid tert-butyl ester N-(2-(3-bromophenoxy)ethyl)carbamic acid tert-butyl ester (197 mg; prepared according to WO 2009/005794) and 3-formylphenylboronic acid (112 mg; commercial) were added to a mixture of aq. NaHCO$_3$ (10%; 1.3 mL) and DME (2.9 mL). N$_2$ was bubbled through the reaction mixture, Pd(PPh$_3$)$_4$ (29 mg) was added and the reaction mixture was further stirred at 80° C. overnight. The reaction mixture was cooled to rt and partitioned between water and EA. The aq. layer was extracted with EA and the combined org. layers were washed with brine and dried over MgSO$_4$, affording a brown oil (230 mg; 100% yield) which was further used without any purification.

MS1 (ESI, m/z): 342.16 [M+H$^+$]; $t_R$=0.94 min.

Preparation A2: 3'-(2-(dimethylamino)ethoxy)-[1,1'-biphenyl]-3-carbaldehyde

DIAD (82 mg) was added dropwise to a solution of the compound of Preparation BB1 (100 mg), dimethylethanolamine (0.04 mL) and PPh$_3$ (106 mg) in THF (1.2 mL) cooled to 0° C. The solution was allowed to reach rt and was further stirred overnight. The reaction mixture was evaporated under reduced pressure and the residue was partitioned between 1M HCl and EA. The aq. layer was washed with EA and neutralized with sat. NaHCO$_3$. The aq. layer was extracted with EA and dried over MgSO$_4$, affording a yellowish oil (44 mg; 44% yield) which was further used without any purification.

MS3 (ESI, m/z): 270.09 [M+H$^+$]; $t_R$=0.60 min.

Preparation A3: tert-butyl (2-((3'-formyl-[1,1'-biphenyl]-3-yl)oxy)ethyl)(methyl) carbamate A3.i. Tert-butyl (2-((3'-(1,3-dioxolan-2-yl)-[1,1'-biphenyl]-3-yl)oxy)ethyl)(methyl) carbamate A mixture of the compound of Preparation BB1 (100 mg), (2-hydroxyethyl)(methyl)carbamic acid tert-butyl ester (commercial; 80 mg) and PPh$_3$ (162 mg) in THF (4 mL) was treated dropwise with DEAD (40% in toluene; 0.18 mL) and the reaction mixture was further stirred at rt for 1 d. The solution was concentrated under reduced pressure and portioned between EA and water. The aq. layer was extracted with EA and the combined org. layers were washed with brine, dried over MgSO$_4$, filtered and concentrated under reduced pressure. The residue was purified by CC (Combiflash; Hept/EA 1:0 to 0:1), affording a colourless oil (31 mg; 19% yield).

MS2 (ESI, m/z): 300.00 [M+H$^+$]; $t_R$=0.96 min.

A3.ii. Tert-butyl (2-((3'-formyl-[1,1'-biphenyl]-3-yl)oxy)ethyl)(methyl)carbamate A solution of intermediate A3.i (25 mg) and PTSA (0.30 mg) in acetone (0.25 mL) was stirred at rt for 4 days. The solution was filtered and evaporated under reduced pressure, affording a brown oil (quant.) which was used without further purification.

MS2 (ESI, m/z): 355.91 [M+H$^+$]; $t_R$=0.95 min.

Preparation A4: tert-butyl (4-((3'-formyl-[1,1'-biphenyl]-3-yl)oxy)butyl)carbamate A4.i. Tert-butyl (4-((3'-(1,3-dioxolan-2-yl)-[1,1'-biphenyl]-3-yl)oxy)butyl)carbamate Starting from the compound of Preparation BB1 (300 mg) and 4-(Boc-amino)-1-butanol (commercial; 231 mg), and proceeding in analogy to Preparation A3, step A3.i, the title compound was obtained after purification by CC (Combiflash; Hept/EA 1:0 to 0:1) as an yellow oil (489 mg; contaminated by residual PPh$_3$O).

MS2 (ESI, m/z): 414.03 [M+H$^+$]; $t_R$=0.94 min.

A4.ii. Tert-butyl (4-((3'-formyl-[1,1'-biphenyl]-3-yl)oxy)butyl)carbamate

Starting from intermediate A4.i (470 mg) and proceeding in analogy to Preparation A3, step A3.ii, the title compound was obtained as a yellow oil (484 mg; 100% yield) and used directly in the subsequent step.

MS2 (ESI, m/z): 369.86 [M+H$^+$]; $t_R$=0.94 min.

Preparation A5: tert-butyl (RS)-(2-((3'-formyl-[1,1'-biphenyl]-3-yl)oxy)propyl) carbamate A5.i. Tert-butyl (RS)-(2-((3'-(1,3-dioxolan-2-yl)-[1,1'-biphenyl]-3-yl)oxy)propyl)carbamate Starting from the compound of Preparation BB1 (300 mg) and tert-butyl N-(2-hydroxypropyl)carbamate (commercial; 214 mg), and proceeding in analogy to Preparation A3, step A3.i, the title compound was obtained after purification by CC (Combiflash; Hept/EA 1:0 to 1:0) as a yellow oil (216 mg; 49% yield).

MS2 (ESI, m/z): 400.00 [M+H$^+$]; $t_R$=0.92 min.

A5.ii. Tert-butyl (RS)-(2-((3'-formyl-[1,1'-biphenyl]-3-yl)oxy)propyl) carbamate Starting from intermediate A5.i (200 mg) and proceeding in analogy to Preparation A3, step A3.ii, the title compound was obtained as a yellow oil (197 mg; 100% yield) and used directly in the subsequent step.

MS2 (ESI, m/z): 355.99 [M+H$^+$]; $t_R$=0.91 min.

Preparation A6: tert-butyl ((1R,3R)-3-((3'-formyl-[1,1'-biphenyl]-3-yl)oxy) cyclopentyl)carbamate A6.i. Tert-butyl ((1R,3R)-3-((3'-(1,3-dioxolan-2-yl)-[1,1'-biphenyl]-3-yl)oxy) cyclopentyl)carbamate The title compound can be prepared starting from the compound of Preparation BB1 and tert-butyl N-[(1R,3S)-3-hydroxycyclopentyl]carbamate (commercial), and proceeding in analogy to Preparation A3, step A3.i.

A6.ii. Tert-butyl ((1R,3R)-3-((3'-formyl-[1,1'-biphenyl]-3-yl)oxy) cyclopentyl)carbamate The title compound can be prepared starting from intermediate A6.i and proceeding in analogy to Preparation A3, step A3.ii.

Preparation A7: tert-butyl (2-((6-(3-formylphenyl)pyridin-2-yl)oxy)ethyl)carbamate

A7.i. Tert-butyl (2-((6-(3-(1,3-dioxolan-2-yl)phenyl)pyridin-2-yl)oxy)ethyl)carbamate Starting from the compound of Preparation BB2 (280 mg) and (Boc-amino)ethanolamine (commercial; 204 mg), and proceeding in analogy to Preparation A3, step A3.i, the title compound was obtained, after purification by CC (Combiflash; Hept/EA 0:1 to 1:0), as a colourless oil (340 mg; 76% yield).

MS3 (ESI, m/z): 386.98 [M−H$^+$]; $t_R$=0.92 min.

A7.ii. Tert-butyl (2-((6-(3-formylphenyl)pyridin-2-yl)oxy)ethyl)carbamate

A solution of intermediate A7.i (320 mg) in THF (4.6 mL) was heated at 50° C. for 5 min in presence of 1M HCl (1.55 mL). The reaction mixture was allowed to cool to rt, treated with excess sat. NaHCO$_3$ solution and extracted 5 times with DCM/MeOH. The combined org. layers were washed with brine, dried over MgSO$_4$, filtered and concentrated under reduced pressure, affording a yellow oil (300 mg; 100% yield) which was used directly in the subsequent step.

MS3 (ESI, m/z): 342.98 [M−H$^+$]; $t_R$=0.93 min.

Preparation A8: 3-(6-(2-(pyrrolidin-1-yl)ethoxy)pyridin-2-yl)benzaldehyde

A8.i. 2-(3-(1,3-dioxolan-2-yl)phenyl)-6-(2-(pyrrolidin-1-yl)ethoxy)pyridine Starting from 2-chloro-6-[2-(pyrrolidin-1-yl)ethoxy]pyridine (300 mg; commercial), 3-(1,3-dioxolan-2-yl)phenylboronic acid pinacol ester (365 mg; commercial), Pd(PPh$_3$)$_4$ (76 mg; commercial) and Na$_2$CO$_3$ (1M, 1.34 mL) and proceeding in analogy to Preparation BB1, but using EtOH and toluene as solvent, the title compound was obtained, after purification by CC (Combiflash; Hept/EA 1:0 to 0:1), as a brown oil (300 mg; 67% yield).

$^1$H NMR (CDCl$_3$) δ: 8.13 (m, 1H); 8.07 (m, 1H); 7.62-7.66 (m, 1H); 7.48-7.55 (m, 2H); 7.37-7.39 (m, 1H); 6.75 (dd, J=0.5, 8.2 Hz, 1H); 5.93 (s, 1H); 4.60-4.64 (m, 2H); 4.07-4.22 (m, 4H); 2.94-3.01 (m, 2H); 2.63-2.76 (m, 4H); 1.82-1.89 (m, 4H).

MS3 (ESI, m/z): 341.01 [M+H$^+$]; $t_R$=0.65 min.

A8.ii. 3-(6-(2-(pyrrolidin-1-yl)ethoxy)pyridin-2-yl)benzaldehyde

Starting from intermediate A8.i (280 mg) and proceeding in analogy to Preparation A7, step A7.ii, the title compound was obtained as a colourless oil (237 mg; 97% yield) and used directly in the subsequent step.

$^1$H NMR (CDCl$_3$) δ: 10.13 (s, 1H); 8.54 (t, J=1.7 Hz, 1H); 8.35 (ddd, J=1.4, 1.8, 7.8 Hz, 1H); 7.93 (m, 1H); 7.63-7.72 (m, 2H); 7.42-7.44 (m, 1H); 6.80-6.82 (m, 1H); 4.62-4.67 (m, 2H); 2.96-3.03 (m, 2H); 2.63-2.76 (m, 4H); 1.82-1.91 (m, 4H).

MS3 (ESI, m/z): 297.02 [M+H$^+$]; $t_R$=0.63 min.

Preparation A9: 3-(5-(2-(dimethylamino)ethoxy)pyridazin-3-yl)benzaldehyde

A9.i. 2-((6-(3-(1,3-dioxolan-2-yl)phenyl)pyridazin-4-yl)oxy)-N,N-dimethylethan-1-amine Potassium tert-butoxide (61 mg) was added to a solution of dimethylaminoethanol (33 mg) in THF (1.2 mL). The reaction mixture was stirred for 30 min at rt then treated with compound of Preparation BB3 (100 mg) and further stirred at rt for 30 min. The reaction mixture was diluted with EA, washed with water and brine, dried over MgSO$_4$, filtered, evaporated and purified by CC (Combiflash; DCM to DCM/MeOH 9:1), affording a yellow oil (101 mg; 88% yield).

MS3 (ESI, m/z): 316.01 [M+H$^+$]; $t_R$=0.47 min.

A9.ii. 3-(5-(2-(dimethylamino)ethoxy)pyridazin-3-yl)benzaldehyde

Starting from intermediate A9.i (70 mg) and proceeding in analogy to Preparation A7, step A7.ii, the title compound was obtained as an orange oil (44 mg; 63% yield). $^1$H NMR (CDCl$_3$) δ: 10.16 (s, 1H); 8.99 (d, J=2.8 Hz, 1H); 8.54 (t, J=1.6 Hz, 1H); 8.44 (ddd, J=1.3, 1.7, 7.8 Hz, 1H); 8.04 (dt, J=1.3, 7.6 Hz, 1H); 7.74 (t, J=7.7 Hz, 1H); 7.38 (d, J=2.8 Hz, 1H); 4.30 (t, J=5.5 Hz, 2H); 2.85 (t, J=5.5 Hz, 2H); 2.40 (s, 6H).

MS3 (ESI, m/z): 272.06 [M+H$^+$]; $t_R$=0.46 min.

Preparation A10: tert-butyl (2-((5-(3-formylphenyl)pyridin-3-yl)oxy)ethyl)carbamate

A10.i. Tert-butyl (2-((5-(3-(1,3-dioxolan-2-yl)phenyl)pyridin-3-yl)oxy)ethyl)carbamate Starting from the compound of Preparation BB4 (200 mg) and N-Boc-ethanolamine (0.14 mL) and proceeding in analogy to Preparation A2, the title compound was obtained, after purification by CC (Combiflash; Hept to Hept/EA 1:1), as a yellow oil (238 mg; 75% yield).

MS3 (ESI, m/z): 386.95 [M+H$^+$]; $t_R$=0.72 min.

A10.ii. Tert-butyl (2-((5-(3-formylphenyl)pyridin-3-yl)oxy)ethyl)carbamate

Starting from intermediate A10.i (235 mg) and proceeding in analogy to Preparation A7, step A7.ii, the title compound was obtained as a colourless solid (211 mg; 100% yield).

MS3 (ESI, m/z): 342.96 [M+H$^+$]; $t_R$=0.74 min.

Preparation A11: 3-(6-(2-(piperidin-1-yl)ethoxy)pyridin-2-yl)benzaldehyde

A11.i. 2-(3-(1,3-dioxolan-2-yl)phenyl)-6-(2-(piperidin-1-yl)ethoxy)pyridine Starting from the compound of Preparation BB2 (100 mg) and 1-(2-hydroxyethyl)piperidine (64 mg) and proceeding in analogy to Preparation A2, the title compound was obtained, after purification by CC (Combiflash; DCM to DCM/MeOH 19:1), as a yellow oil (99 mg; 68% yield).
MS1 (ESI, m/z): 355.13 [M+H$^+$]; $t_R$=0.67 min.

A11.ii. 3-(6-(2-(piperidin-1-yl)ethoxy)pyridin-2-yl) benzaldehyde

Starting from intermediate A11.i (72 mg) and proceeding in analogy to Preparation A7, step A7.ii, the title compound was obtained as a yellow oil (72 mg; 91% yield).
MS1 (ESI, m/z): 311.12 [M+H$^+$]; $t_R$=0.65 min.

Preparation A12: 3'-(2-(piperidin-1-yl)ethoxy)-[1,1'-biphenyl]-3-carbaldehyde

A12.i. 1-(2-((3'-(1,3-dioxolan-2-yl)-[1,1'-biphenyl]-3-yl)oxy)ethyl)piperidine

Starting from 1-[2-(3-bromophenoxy)ethyl]piperidine (150 mg; commercial) and 3-(1,3-dioxolan-2-yl)phenylboronic acid pinacol ester (146 mg; commercial), Pd(PPh$_3$)$_4$ (30 mg; commercial) and Na$_2$CO$_3$ (1M; 0.53 mL) and proceeding in analogy to Preparation BB1, but using EtOH, toluene and water as solvent, the title compound was obtained, after purification by CC (Combiflash; Hept/EA 2:1 to 0:1), as a yellow oil (145 mg; 78% yield).
MS3 (ESI, m/z): 353.90 [M+H$^+$]; $t_R$=0.64 min.

A12.ii. 3'-(2-(piperidin-1-yl)ethoxy)-[1,1'-biphenyl]-3-carbaldehyde

Starting from intermediate A12.i (135 mg) and proceeding in analogy to Preparation A7, step A7.ii, the title compound was obtained as a colourless solid (109 mg; 92% yield).
MS3 (ESI, m/z): 310.03 [M+H$^+$]; $t_R$=0.67 min.

Preparation A13: tert-butyl (1-(((3'-formyl-[1,1'-biphenyl]-3-yl)oxy)methyl) cyclopropyl)carbamate A13.i. Tert-butyl (1-(((3'-(1,3-dioxolan-2-yl)-[1,1'-biphenyl]-3-yl)oxy)methyl)cyclopropyl) carbamate Starting from the compound of Preparation BB1 (300 mg) and tert-butyl 1-(hydroxymethyl) cyclopropylcarbamate (commercial; 228 mg), and proceeding in analogy to preparation A3 step A3.i, the title compound was obtained after purification by CC (Combiflash; DCM to DCM/MeOH 4:1) as a yellow oil (131 mg; 29% yield).
MS2 (ESI, m/z): 412.00 [M+H$^+$]; $t_R$=0.92 min.

A13.ii. Tert-butyl (1-(((3'-formyl-[1,1'-biphenyl]-3-yl)oxy)methyl)cyclopropyl)carbamate Starting from intermediate A13.i (120 mg) and proceeding in analogy to Preparation A3, step A3.ii, the title compound was obtained as an yellow oil (123 mg; quant.) which was used directly in the subsequent step.
MS2 (ESI, m/z): 367.97 [M+H$^+$]; $t_R$=0.91 min.

Preparation A14: {2-[6-(3-formyl-phenyl)-pyrazin-2-yloxy]-ethyl}-carbamic acid tert-butyl ester A14.i. {2-[6-(3-[1,3]dioxolan-2-yl-phenyl)-pyrazin-2-yloxy]-ethyl}-carbamic acid tert-butyl ester Starting from intermediate BB5 (80 mg) and N-Boc-ethanolamine (0.0439 mL) and proceeding in analogy to preparation A3 step A3.i, the title compound was obtained after purification by CC (Combiflash; Hept to Hept/EA 1:1) as a yellow oil (85 mg; 79% yield).
MS3 (ESI, m/z): 387.97 [M+H$^+$]; $t_R$=0.89 min.

A14.ii. {2-[6-(3-formyl-phenyl)-pyrazin-2-yloxy]-ethyl}-carbamic acid tert-butyl ester Starting from intermediate A14.i (78 mg) and proceeding in analogy to Preparation A3, step A3.ii, the title compound was obtained as a colourless oil (66 mg; 95% yield) which was used directly in the subsequent step.
MS3 (ESI, m/z): 343.95 [M+H$^+$]; $t_R$=0.89 min.

Preparation A15: [2-(2'-formyl-[2,4']bipyridinyl-6-yloxy)-ethyl]-carbamic acid tert-butyl ester A15.i. [2-(2'-[1,3]dioxolan-2-yl-[2,4]bipyridinyl-6-yloxy)-ethyl]-carbamic acid tert-butyl ester Starting from intermediate BB6 (100 mg) and N-Boc-ethanolamine (0.0517 mL) and proceeding in analogy to Preparation A3, step A3.i, the title compound was obtained, after purification by CC (Combiflash; Hept to Hept/EA 1:2), as a colourless oil (136 mg; contaminated by residual PPh$_3$O).
MS3 (ESI, m/z): 387.98 [M+H$^+$]; $t_R$=0.75 min.

A15.ii. [2-(2'-formyl-[2,4']bipyridinyl-6-yloxy)-ethyl]-carbamic acid tert-butyl ester A solution of intermediate A15.i (105 mg) in MeCN/MeOH (1:1; 3 mL) was stirred at 80° C. overnight in presence of carbon tetrabromide (90 mg). The reaction mixture was concentrated under reduced pressure and purified by prep-HPLC (method 2), affording a yellow solid (8.5 mg; 18% yield).
MS3 (ESI, m/z): 343.96 [M+H$^+$]; $t_R$=0.88 min.

Preparation A16: {(R)-2-[6-(3-formyl-phenyl)-pyridin-2-yloxy]-1-methyl-ethyl}-carbamic acid tert-butyl ester A16.i. {(R)-2-[6-(3-[1,3]dioxolan-2-yl-phenyl)-pyridin-2-yloxy]-1-methyl-ethyl}-carbamic acid tert-butyl ester Starting from the compound of Preparation BB2 (280 mg) and Boc-(D)-alaninol (commercial; 223 mg), and proceeding in analogy to Preparation A3, step A3.i, the title compound was obtained, after purification by CC (Combiflash; Hept/EA 0:1 to 1:0), as a colourless oil (548 mg; contaminated by residual PPh$_3$O).
MS3 (ESI, m/z): 400.98 [M+H$^+$]; $t_R$=0.95 min.

A16.ii. {(R)-2-[6-(3-formyl-phenyl)-pyridin-2-yloxy]-1-methyl-ethyl}-carbamic acid tert-butyl ester Starting from intermediate A16.i (504 mg) and proceeding in analogy to Preparation A3, step A3.ii, the title compound was obtained as a off-white solid (463 mg; 100% yield) which was used directly in the subsequent step.
MS3 (ESI, m/z): 356.97 [M+H$^+$]; $t_R$=0.94 min.

Preparation A17: {(S)-2-[6-(3-formyl-phenyl)-pyridin-2-yloxy]-1-methyl-ethyl}-carbamic acid tert-butyl ester A17.i. {(S)-2-[6-(3-[1,3]dioxolan-2-yl-phenyl)-pyridin-2-yloxy]-1-methyl-ethyl}-carbamic acid tert-butyl ester Starting from the compound of Preparation BB2 (280 mg) and Boc-(L)-alaninol (commercial; 223 mg) and proceeding in analogy to Preparation A3, step A3.i, the title compound was obtained after purification by CC (Combiflash; Hept/EA 0:1 to 1:0) as a colourless oil (590 mg; contaminated by residual $PPh_3O$).
MS3 (ESI, m/z): 400.97 [M+H$^+$]; $t_R$=0.95 min.

A17.ii. {(S)-2-[6-(3-formyl-phenyl)-pyridin-2-yloxy]-1-methyl-ethyl}-carbamic acid tert-butyl ester Starting from intermediate A17.i (493 mg) and proceeding in analogy to Preparation A3, step A3.ii, the title compound was obtained as an off-white solid (462 mg; 100% yield) which was used directly in the subsequent step.
MS3 (ESI, m/z): 356.97 [M+H$^+$]; $t_R$=0.95 min.

Preparation A18: {2-[4-(3-formyl-phenyl)-pyridin-2-yloxy]-ethyl}-carbamic acid tert-butyl ester A18.i. {2-[4-(3-[1,3]dioxolan-2-yl-phenyl)-pyridin-2-yloxy]-ethyl}-carbamic acid tert-butyl ester Starting from the compound of Preparation BB7 (280 mg) and N-Boc-ethanolamine (commercial; 208 mg) and proceeding in analogy to Preparation A3, step A3.i, the title compound was obtained after purification by CC (Combiflash; Hept/EA 0:1 to 1:0) as a colourless solid (343 mg; 77% yield).
MS3 (ESI, m/z): 386.95 [M+H$^+$]; $t_R$=0.85 min.

A18.ii. {2-[4-(3-formyl-phenyl)-pyridin-2-yloxy]-ethyl}-carbamic acid tert-butyl ester Starting from intermediate A18.i (324 mg) and proceeding in analogy to Preparation A3, step A3.ii, the title compound was obtained as an off-white solid (338 mg) which was used directly in the subsequent step.
MS3 (ESI, m/z): 342.97 [M+H$^+$]; $t_R$=0.85 min.

Preparation A19: {5-[6-(3-formyl-phenyl)-pyridin-2-yloxy]-pentyl}-carbamic acid tert-butyl ester A19.i. {5-[6-(3-[1,3]dioxolan-2-yl-phenyl)-pyridin-2-yloxy]-pentyl}-carbamic acid tert-butyl ester Starting from compound of Preparation BB2 (280 mg) and 5-(Boc-amino)-1-pentanol (257 mg) and proceeding in analogy to Preparation A2, the title compound was obtained, after purification by CC (Combiflash; Hept/EA 1:0 to 0:1), as a colourless oil (338 mg; 69% yield).
MS3 (ESI, m/z): 429.06 [M+H$^+$]; $t_R$=0.99 min.

A19.ii. {5-[6-(3-formyl-phenyl)-pyridin-2-yloxy]-pentyl}-carbamic acid tert-butyl ester Starting from intermediate A19.i (303 mg) and proceeding in analogy to Preparation A7, step A7.ii the title compound was obtained as a yellow oil (300 mg; quant.).
MS3 (ESI, m/z): 384.94 [M+H$^+$]; $t_R$=1.00 min.

Preparation A20: [2-(3'-formyl-5-methoxy-biphenyl-3-yloxy)-ethyl]-carbamic acid tert-butyl ester A20.i. [2-(3'-[1,3]dioxolan-2-yl-5-methoxy-biphenyl-3-yloxy)-ethyl]-carbamic acid tert-butyl ester Starting from the compound of preparation BB8 (200 mg) and N-Boc-ethanolamine (133 mg) and proceeding in analogy to Preparation A2, the title compound was obtained after purification by CC (Combiflash; Hept/EA 1:0 to 0:1) as an off-white solid (238 mg; 78% yield).
MS3 (ESI, m/z): 416.01 [M+H$^+$]; $t_R$=0.94 min.

A20.ii. [2-(3'-formyl-5-methoxy-biphenyl-3-yloxy)-ethyl]-carbamic acid tert-butyl ester Starting from intermediate A20.i (219 mg) and proceeding in analogy to Preparation A7, step A7.ii the title compound was obtained as a yellow oil (213 mg; quant.).
MS3 (ESI, m/z): 371.92 [M+H$^+$]; $t_R$=0.94 min.

Preparation A21: 3-[6-(2-morpholin-4-yl-ethoxy)-pyridin-2-yl]-benzaldehyde

A21.i. 4-{2-[6-(3-[1,3]dioxolan-2-yl-phenyl)-pyridin-2-yloxy]-ethyl}-morpholine

Starting from the compound of Preparation BB2 (280 mg) and 4-(2-hydroxyethyl)morpholine (175 mg) and proceeding in analogy to Preparation A2, the title compound was obtained after purification by CC (Combiflash; Hept/EA 1:0 to 0:1) as a colourless oil (243 mg; 59% yield).
MS3 (ESI, m/z): 356.96 [M+H$^+$]; $t_R$=0.80 min.

A21.ii. 3-[6-(2-morpholin-4-yl-ethoxy)-pyridin-2-yl]-benzaldehyde

Starting from intermediate A21.i (235 mg) and proceeding in analogy to Preparation A7, step A7.ii the title compound was obtained as a yellow oil (180 mg; quant.).
MS3 (ESI, m/z): 313.01 [M+H$^+$]; $t_R$=0.595 min.

Preparation A22: tert-butyl ((1R,3S)-3-((3'-formyl-[1,1'-biphenyl]-3-yl)oxy) cyclopentyl)carbamate A22.i. Tert-butyl ((1R,3S)-3-((3'-(1,3-dioxolan-2-yl)-[1,1'-biphenyl]-3-yl)oxy) cyclopentyl)carbamate Starting from the compound of Preparation BB1 (300 mg) and tert-butyl N-[(1R,3S)-3-hydroxycyclopentyl]carbamate (commercial; 245 mg), and proceeding in analogy to Preparation A3, step A3.i, the title compound was obtained after purification by CC (Combiflash; DCM to DCM/MeOH 4:1) as a yellow oil (200 mg; 43% yield).
MS2 (ESI, m/z): 426.04 [M+H$^+$]; $t_R$=0.96 min.

A22.ii. Tert-butyl ((1R,3S)-3-((3'-formyl-[1,1'-biphenyl]-3-yl)oxy) cyclopentyl)carbamate Starting from intermediate A6.i (190 mg) and proceeding in analogy to Preparation A3, step A3.ii, the title compound was obtained as a yellow oil (185 mg; 100% yield) and used directly in the subsequent step.
MS2 (ESI, m/z): 381.99 [M+H$^+$]; $t_R$=0.94 min.

Preparation C1: (S)-2-(3'-formyl-biphenyl-3-yloxymethyl)-azetidine-1-carboxylic acid tert-butyl ester

C1.i. Tert-butyl (S)-2-(((3'-(1,3-dioxolan-2-yl)-[1,1'-biphenyl]-3-yl)oxy)methyl)azetidine-1-carboxylate A mixture of the compound of Preparation BB1 (100 mg), (S)-1-Boc-2-azetidinemethanol (commercial; 85 mg) and P(Ph)$_3$ (162 mg) in THF (4 mL) was treated dropwise with DEAD (40% in toluene; 0.18 mL) and the reaction mixture was further stirred at rt for 1 day. The solution was concentrated under reduced pressure and portioned between EA and water. The aq. layer was extracted with EA and the combined org. layers were washed with brine, dried over MgSO$_4$, filtered and concentrated under reduced pressure. The residue was purified by CC (Combiflash; Hept/EA 1:0 to 0:1) as a colourless oil (112 mg; 66% yield).

MS2 (ESI, m/z): 412.02 [M+H$^+$]; $t_R$=0.96 min.

C1.ii. (S)-2-(3'-formyl-biphenyl-3-yloxymethyl)-azetidine-1-carboxylic acid tert-butyl ester A solution of intermediate C1.i (100 mg) and PTSA (1.2 mg) in acetone (1 mL) was stirred at rt for 4 days. The solution was filtered and evaporated under reduced pressure, affording a brown oil (quant.) which was used without further purification.

MS2 (ESI, m/z): 367.99 [M+H$^+$]; $t_R$=0.94 min

Preparation C2: tert-butyl (S)-2-(((3'-formyl-[1,1'-biphenyl]-3-yl)oxy)methyl)pyrrolidine-1-carboxylate

C2.i. Tert-butyl (S)-2-(((3'-(1,3-dioxolan-2-yl)-[1,1'-biphenyl]-3-yl)oxy)methyl)pyrrolidine-1-carboxylate Starting from the compound of Preparation BB1 (300 mg) and N-Boc-(S)-prolinol (commercial; 250 mg), and proceeding in analogy to Preparation C1, step C1.i (using however DIAD instead of DEAD), the title compound was obtained after purification by CC (Combiflash; Hept-EA 1:0 to 1:0) as a colourless oil (376 mg; 80% yield).

MS2 (ESI, m/z): 426.06 [M+H$^+$]; $t_R$=1.02 min.

C2.ii. Tert-butyl (S)-2-(((3'-formyl-[1,1'-biphenyl]-3-yl)oxy)methyl)pyrrolidine-1-carboxylate Starting from intermediate C2.i (350 mg) and proceeding in analogy to Preparation C1, step C1.ii, the title compound was obtained as a brown oil and used directly in the subsequent step.

MS2 (ESI, m/z): 382.00 [M+H$^+$]; $t_R$=1.01 min.

Preparation C3: tert-butyl (RS)-3-((3'-formyl-[1,1'-biphenyl]-3-yl)oxy)pyrrolidine-1-carboxylate

C3.i. Tert-butyl (RS)-3-((3'-(1,3-dioxolan-2-yl)-[1,1'-biphenyl]-3-yl)oxy)pyrrolidine-1-carboxylate Starting from the compound of Preparation BB1 (300 mg) and N-Boc-3-hydroxypyrrolidine (commercial; 228 mg), and proceeding in analogy to Preparation C1, step C1.i, the title compound was obtained after purification by CC (Combiflash; Hept/EA 1:0 to 1:0) as a colourless oil (520 mg; contaminated by residual PPh$_3$O).

MS2 (ESI, m/z): 412.03 [M+H$^+$]; $t_R$=0.96 min.

C3.ii. Tert-butyl (RS)-3-((3'-formyl-[1,1'-biphenyl]-3-yl)oxy)pyrrolidine-1-carboxylate Starting from intermediate C3.i (500 mg) and proceeding in analogy to Preparation C1, step C1.ii, the title compound was obtained as an orange oil and used directly in the subsequent step.

MS2 (ESI, m/z): 368.00 [M+H$^+$]; $t_R$=0.95 min.

Preparation C4: (S)-3'-((1-methylazetidin-2-yl)methoxy)-[1,1'-biphenyl]-3-carbaldehyde

C4.i. (S)-2-(((3'-(1,3-dioxolan-2-yl)-[1,1'-biphenyl]-3-yl)oxy)methyl)-1-methylazetidine Starting from the compound of Preparation BB1 (300 mg) and (S)-1-methyl-2-azetidinemethanol (commercial; 125 mg) and proceeding in analogy to Preparation C1, step C1.i, the title compound was obtained after purification by CC (Combiflash; Hept/EA 0:1 to 1:0) as a brown oil (65 mg; 16% yield).

MS1 (ESI, m/z): 326.04 [M+H$^+$]; $t_R$=0.66 min.

C4.ii. (S)-3'-((1-methylazetidin-2-yl)methoxy)-[1,1'-biphenyl]-3-carbaldehyde Starting from intermediate C4.i (57 mg) and proceeding in analogy to Preparation C1, step C1.ii, the title compound was obtained as a colourless oil (42 mg; 85% yield) which was used directly in the subsequent step.

MS3 (ESI, m/z): 282.04 [M+H$^+$]; $t_R$=0.63 min.

Preparation C5: tert-butyl 3-((3'-formyl-[1,1'-biphenyl]-3-yl)oxy)azetidine-1-carboxylate

C5.i. Tert-butyl 3-((3'-(1,3-dioxolan-2-yl)-[1,1'-biphenyl]-3-yl)oxy)azetidine-1-carboxylate Starting from 3-(3-bromophenoxy)-1-azetidinecarboxylic acid tert-butyl ester (300 mg; prepared according to WO 2010/059390), 3-(1,3-dioxolan-2-yl)phenylboronic acid pinacol ester (252 mg; commercial), Pd(PPh$_3$)$_4$ (53 mg; commercial) and Na$_2$CO$_3$ (1M, 1.01 mL) and proceeding in analogy to Preparation BB1, but using EtOH and toluene as solvent, the title compound was obtained, after purification by CC (Combiflash; Hept/EA 1:0 to 0:1), as a yellow oil (114 mg; 31% yield).

MS3 (ESI, m/z): 397.98 [M+H$^+$]; $t_R$=0.98 min.

C5.ii. Tert-butyl 3-((3'-formyl-[1,1'-biphenyl]-3-yl)oxy)azetidine-1-carboxylate A solution of intermediate C5.i (110 mg) in THF (1.5 mL) was heated at 50° C. for 5 min in presence of 1M HCl (0.52 mL). The reaction mixture was allowed to cool to rt, treated with excess sat. NaHCO$_3$ solution and extracted 5 times with DCM/MeOH. The combined org. layers were washed with brine, dried over MgSO$_4$, filtered and concentrated under reduced pressure, affording an orange oil (85 mg; 87% yield).

MS3 (ESI, m/z): 297.96 [M+H$^+$]; $t_R$=0.97 min.

Preparation C6: tert-butyl 3-(((6-(3-formylphenyl)pyridin-2-yl)oxy)methyl)azetidine-1-carboxylate

C6.i. Tert-butyl 3-(((6-(3-(1,3-dioxolan-2-yl)phenyl)pyridin-2-yl)oxy)methyl)azetidine-1-carboxylate Starting from the compound of Preparation BB2 (108 mg) and tert-butyl 3-(hydroxymethyl)azetidine-1-carboxylate (100 mg; commercial) and proceeding in analogy to Preparation C1, step C1.i, the title compound (182 mg; 99% yield) was obtained, after purification by CC (Combiflash; Hept to Hept/EA 1:1), as a colourless oil.
MS1 (ESI, m/z): 413.17 [M+H$^+$]; $t_R$=0.97 min.

C6.ii. Tert-butyl 3-(((6-(3-formylphenyl)pyridin-2-yl)oxy)methyl)azetidine-1-carboxylate Starting from intermediate C6.i (170 mg) and proceeding in analogy to Preparation C5, step C5.ii. the title compound was obtained as a colourless solid (152 mg; 100% yield).
MS1 (ESI, m/z): 369.07 [M+H$^+$]; $t_R$=0.98 min.

Preparation C7: 3-[6-(3-formyl-phenyl)-pyridin-2-yloxy]-azetidine-1-carboxylic acid tert-butyl ester

C7.i. 3-[6-(3-[1,3]dioxolan-2-yl-phenyl)-pyridin-2-yloxy]-azetidine-1-carboxylic acid tert-butyl ester Starting from the compound of Preparation BB2 (150 mg) and 1-Boc-3-hydroxyazetidine (107 mg) and proceeding in analogy to Preparation C1, step C1.i, the title compound was obtained after purification by CC (Combiflash; Hept to Hept/EA 1:1) as a yellow oil (186 mg; 76% yield).
MS3 (ESI, m/z): 398.96 [M+H$^+$]; $t_R$=0.98 min.

C7.ii. 3-[6-(3-formyl-phenyl)-pyridin-2-yloxy]-azetidine-1-carboxylic acid tert-butyl ester Starting from intermediate C7.i (175 mg) and proceeding in analogy to Preparation C1, step C1.ii, the title compound was obtained as a colourless oil (151 mg; 100% yield) and used directly in the subsequent step.
MS3 (ESI, m/z): 354.94 [M+H$^+$]; $t_R$=0.89 min.

Preparation C8: (S)-2-[6-(3-formyl-phenyl)-pyridin-2-yloxymethyl]-azetidine-1-carboxylic acid tert-butyl ester

C8.i. (S)-2-[6-(3-[1,3]dioxolan-2-yl-phenyl)-pyridin-2-yloxymethyl]-azetidine-1-carboxylic acid tert-butyl ester Starting from the compound of Preparation BB2 (280 mg) and (S)-1-Boc-2-azetidinemethanol (237 mg; commercial) and proceeding in analogy to Preparation C1, step C1.i, the title compound was obtained, after purification by CC (Combiflash; Hept to Hept/EA 0:1), as a colourless oil (608 mg; contaminated by some PPh$_3$O).
MS3 (ESI, m/z): 413.01 [M+H$^+$]; $t_R$=0.97 min.

C8.ii. (S)-2-[6-(3-formyl-phenyl)-pyridin-2-yloxymethyl]-azetidine-1-carboxylic acid tert-butyl ester Starting from intermediate C8.i (591 mg) and proceeding in analogy to Preparation C1, step C1.ii, the title compound was obtained as an off-white solid (584 mg; 100% yield) and used directly in the subsequent step.
MS3 (ESI, m/z): 368.93 [M+H$^+$]; $t_R$=0.97 min.

Preparation C9: rac-2-[6-(3-formyl-phenyl)-pyridin-2-yloxymethyl]-morpholine-4-carboxylic acid tert-butyl ester

C9.i. Rac-2-[6-(3-[1,3]dioxolan-2-yl-phenyl)-pyridin-2-yloxymethyl]-morpholine-4-carboxylic acid tert-butyl ester Starting from the compound of Preparation BB2 (280 mg) and tert-butyl 2-(hydroxymethyl)morpholine-4-carboxylate (275 mg; commercial) and proceeding in analogy to Preparation C1, step C1.i, the title compound was obtained, after purification by CC (Combiflash; Hept to Hept/EA 0:1), as a colourless oil (670 mg; contaminated by some PPh$_3$O).
MS3 (ESI, m/z): 443.05 [M+H$^+$]; $t_R$=0.96 min.

C9.ii. Rac-2-[6-(3-formyl-phenyl)-pyridin-2-yloxymethyl]-morpholine-4-carboxylic acid tert-butyl ester Starting from intermediate C9.i (634 mg) and proceeding in analogy to Preparation C1, step C1.ii, the title compound was obtained as an off-white solid (616 mg; 100% yield) which was used directly in the subsequent step.
MS3 (ESI, m/z): 398.97 [M+H$^+$]; $t_R$=0.97 min.

Preparation C10: rac-3-[6-(3-formyl-phenyl)-pyridin-2-yloxymethyl]-morpholine-4-carboxylic acid tert-butyl ester

C10.i. Rac-3-[6-(3-[1,3]dioxolan-2-yl-phenyl)-pyridin-2-yloxymethyl]-morpholine-4-carboxylic acid tert-butyl ester Starting from the compound of Preparation BB2 (280 mg) and 4-Boc-(3-hydroxymethyl)morpholine (275 mg; commercial) and proceeding in analogy to Preparation C1, step C1.i, the title compound was obtained after purification by CC (Combiflash; Hept to Hept/EA 0:1) as a colourless oil (533 mg; contaminated by residual PPh$_3$O).
MS3 (ESI, m/z): 443.05 [M+H$^+$]; $t_R$=0.94 min.

C10.ii. Rac-3-[6-(3-formyl-phenyl)-pyridin-2-yloxymethyl]-morpholine-4-carboxylic acid tert-butyl ester Starting from intermediate C10.i (515 mg) and proceeding in analogy to Preparation C1, step C1.ii, the title compound was obtained as an off-white solid (494 mg; 100% yield) and used directly in the subsequent step.
MS3 (ESI, m/z): 398.99 [M+H$^+$]; $t_R$=0.95 min.

Preparation C11: rac-3-[6-(3-formyl-phenyl)-pyridin-2-yloxy]-piperidine-1-carboxylic acid tert-butyl ester

C11.i. Rac-3-[6-(3-[1,3]dioxolan-2-yl-phenyl)-pyridin-2-yloxy]-piperidine-1-carboxylic acid tert-butyl ester Starting from the compound of Preparation BB2 (280 mg) and 1-Boc-3-hydroxypiperidine (255 mg; commercial) and proceeding in analogy to Preparation C1, step C1.i, the title compound was obtained, after purification by CC (Combiflash; Hept to Hept/EA 0:1), as a colourless oil (412 mg; 84% yield).
MS3 (ESI, m/z): 427.05 [M+H$^+$]; $t_R$=0.99 min.

C11.ii. Rac-3-[6-(3-formyl-phenyl)-pyridin-2-yloxy]-piperidine-1-carboxylic acid tert-butyl ester Starting from intermediate C11.i (402 mg) and proceeding in analogy to Preparation C1, step C1.ii, the title compound was obtained as an off-white solid (382 mg; 100% yield) which was used directly in the subsequent step.
MS3 (ESI, m/z): 382.96 [M+H$^+$]; $t_R$=1.00 min.

Preparation C12: (3R*,4S*)-3-[6-(3-formyl-phenyl)-pyridin-2-yloxy]-4-methoxy-pyrrolidine-1-carboxylic acid tert-butyl ester C12.i. (3S*,4S*)-3-hydroxy-4-methoxy-pyrrolidine-1-carboxylic acid tert-butyl ester A solution of trans-4-methoxy-3-pyrrolidinol hydrochloride (256 mg) and TEA (0.58 mL) in water (1.2 mL) and dioxane (3 mL) was treated with di-tert-butyl dicarbonate (436 mg) and further stirred at rt for 2 h. The reaction mixture was diluted with EA and washed with water. The aq. layer was extracted with EA. The combined org. layers were dried over MgSO$_4$, filtered and concentrated under reduced pressure affording a light yellow oil (360 mg; 99% yield).
MS3 (ESI, m/z): 218.20 [M+H$^+$]; $t_R$=0.59 min.

C12.ii. (3R*,4S*)-3-(6-chloro-pyridin-2-yloxy)-4-methoxy-pyrrolidine-1-carboxylic acid tert-butyl ester Starting from 6-chloro-2-hydroxypyridine (150 mg) and intermediate C12.i (247 mg) and proceeding in analogy to Preparation C1, step C1.i, the title compound was obtained, after purification by CC (Combiflash; Hept to Hept/EA 0:1), as a colourless solid (240 mg; 64% yield).
MS3 (ESI, m/z): 328.92 [M+H$^+$]; $t_R$=0.90 min.

C12.iii. (3R*,4S*)-3-[6-(3-formyl-phenyl)-pyridin-2-yloxy]-4-methoxy-pyrrolidine-1-carboxylic acid tert-butyl ester Intermediate C12.ii (215 mg) and 3-formylphenylboronic acid (103 mg; commercial) were added to a mixture of aq. NaHCO$_3$ (2M; 0.33 mL), toluene (2 mL), EtOH (4 mL) and water (2 mL). N$_2$ was bubbled through the reaction mixture, Pd(PPh$_3$)$_4$ (38 mg) was added and the reaction mixture was further stirred at 90° C. for 90 min. The reaction mixture was cooled to rt and partitioned between water and EA. The aq. layer was extracted with EA and the combined org. layers were washed with brine and dried over MgSO$_4$, affording after purification by CC (Combiflash; Hept to Hept/EA 2:1) a light yellow oil (172 mg; 66% yield).
MS1 (ESI, m/z): 398.95 [M−H$^+$]; $t_R$=0.94 min.

Preparation C13: 3-[6-(1-methyl-azetidin-3-ylmethoxy)-pyridin-2-yl]-benzaldehyde C13.i. 3-(6-chloro-pyridin-2-yloxymethyl)-azetidine-1-carboxylic acid tert-butyl ester Starting from 6-chloro-2-hydroxypyridine (commercial; 300 mg) and tert-butyl 3-(hydroxymethyl)azetidine-1-carboxylate (commercial; 425 mg) and proceeding in analogy to Preparation C2, step C2.i, the title compound was obtained, after purification by CC (Combiflash; Hept/EA 1:0 to 4:1), as a colourless oil (610 mg; 89% yield).
MS3 (ESI, m/z): 298.96 [M−H$^+$]; $t_R$=0.92 min.

C13.ii. 2-(azetidin-3-ylmethoxy)-6-chloro-pyridine

A solution of intermediate C13.i (580 mg) in DCM (8 mL) was treated with TFA (3.31 mL) and further stirred at rt for 10 min. Sat. aq. NaHCO$_3$ was added and the mixture was extracted with DCM. The org. layer was dried over MgSO$_4$, filtered and concentrated under reduced pressure The residue was purified by prep-HPLC (method 2), affording a colourless foam (218 mg; 51% yield).
MS3 (ESI, m/z): 199.16 [M−H$^+$]; $t_R$=0.49 min.

C13.iii. 2-chloro-6-(1-methyl-azetidin-3-ylmethoxy)-pyridine

To a solution of intermediate C13.ii (100 mg) and TEA (0.558 mL) in DCM (3 mL) were added 37% aq. formaldehyde (0.511 mL) and NaBH(OAc)$_3$ (480 mg) and further stirred at rt for 2.5 h. The residue was partitioned between sat. aq. NaHCO$_3$ and DCM/MeOH 9:1. The org. layer was separated and dried over MgSO$_4$, filtered and concentrated under reduced pressure, affording a light yellow oil (51 mg; 48% yield).
MS3 (ESI, m/z): 213.15 [M+H$^+$]; $t_R$=0.50 min.

C13.iv. 3-[6-(1-methyl-azetidin-3-ylmethoxy)-pyridin-2-yl]-benzaldehyde

Starting from intermediate C13.iii (48 mg), 3-formylphenylboronic acid (35.5 mg; commercial), Pd(PPh$_3$)$_4$ (13 mg; commercial) and Na$_2$CO$_3$ (1M; 0.226 mL) and proceeding in analogy to Preparation BB1, but using EtOH and water as solvents, the title compound was obtained, after purification by CC (Combiflash; DCM to DCM/MeOH 9:1), as a yellow oil (37 mg; 58% yield).
MS3 (ESI, m/z): 283.02 [M+H$^+$]; $t_R$=0.62 min.

Preparation C14: 3-[6-(3-formyl-phenyl)-pyridazin-4-yloxy]-azetidine-1-carboxylic acid tert-butyl ester C14.i. 3-[6-(3-[1,3]dioxolan-2-yl-phenyl)-pyridazin-4-yloxy]-azetidine-1-carboxylic acid tert-butyl ester A suspension of NaH (301 mg) in dry THF (3 mL) was cooled to 0° C. A solution of 1-Boc-3-azetidinol (1.33 g; commercial) in dry THF (3 mL) was added and the mixture was stirred at 0° C. for 45 min. THF (3 mL) was added followed by a mixture of the compound of Preparation BB3 (263 mg) dissolved in THF (2 mL) at 0° C. and stirred at rt for 1 day. The mixture was concentrated under reduced pressure and the residue was portioned between EA and water. The layers were separated and the aq. phase was extracted twice with EA. The combined org. layers were dried over MgSO$_4$, filtered, evaporated and purified by CC (Combiflash; Hept/EA 1:0 to 1:4), affording a yellow sticky oil (144 mg; 36% yield).
MS1 (ESI, m/z): 400.14 [M+H$^+$]; $t_R$=0.83 min.

C14.ii. 3-[6-(3-formyl-phenyl)-pyridazin-4-yloxy]-azetidine-1-carboxylic acid tert-butyl ester A solution of intermediate C14.i (72 mg) in MeCN/MeOH (1:1; 2.6 mL) was stirred at 80° C. for 2 h in presence of CBr$_4$ (120 mg). The mixture was cooled to rt, basified with sat. aq. NaHCO$_3$ and extracted with EA. The org. layer was dried over MgSO$_4$, filtered and concentrated under reduced pressure, affording a yellow solid (144 mg; crude product) which was not further purified.
MS3 (ESI, m/z): 355.92 [M+H$^+$]; $t_R$=0.84 min.

Preparation C15: (R)-3-[2-(3-formyl-phenyl)-pyrimidin-4-yloxy]-pyrrolidine-1-carboxylic acid tert-butyl ester Starting from (R)-3-(2-chloro-pyrimidin-4-yloxy)-pyrrolidine-1-carboxylic acid tert-butyl ester (500 mg; commercial), 3-formylphenylboronic acid (250 mg; commercial), Pd(PPh$_3$)$_4$ (77 mg) and K$_2$CO$_3$ (692 mg) and proceeding in analogy to Preparation BB1, the title compound was obtained, after purification by CC (Combiflash; DCM to DCM/MeOH 4:1), as an orange oil (592 mg; 96% yield).
MS3 (ESI, m/z): 369.82 [M+H$^+$]; $t_R$=0.89 min.

Preparation C16: (R)-3-[6-(3-formyl-phenyl)-pyrimidin-4-yloxy]-pyrrolidine-1-carboxylic acid tert-butyl ester Starting from (R)-3-(6-chloro-pyrimidin-4-yloxy)-pyrrolidine-1-carboxylic acid tert-butyl ester (500 mg; commercial), 3-formylphenylboronic acid 250 mg; commercial), Pd(PPh$_3$)$_4$ (77 mg) and K$_2$CO$_3$ (692 mg) and proceeding in analogy to Preparation BB1, the title compound was obtained, after purification by CC (Combiflash; Hept/EA 1:0 to 0:1), as a colourless solid (328 mg; 53% yield).
MS3 (ESI, m/z): 369.87 [M+H$^+$]; $t_R$=0.91 min.

Preparation C17: {(1R*,5S*)-3-[2-(3'-formyl-biphenyl-3-yloxy)-ethyl]-3-aza-bicyclo[3.1.0]hex-6-yl}-carbamic acid tert-butyl ester C17.i. 3'-[1,3]dioxolan-2-yl-biphenyl-3-ol Starting from 3-hydroxyphenylboronic acid (5.00 g; commercial), 2-(3-bromophenyl)-1,3-dioxolane (8.30 g; commercial), Pd(PPh$_3$)$_4$ (1.68 g) and K$_2$CO$_3$ (15.0 g) and proceeding in analogy to Preparation BB1, the title compound was obtained, after purification by CC (Combiflash; Hept/EA 1:0 to 0:1), as a yellow oil (7.05 g; 80% yield).
MS3 (ESI, m/z): 243.07 [M+H$^+$]; $t_R$=0.78 min.
C17.ii. 2-[3'-(2-bromo-ethoxy)-biphenyl-3-yl]-[1,3]dioxolane
Starting from intermediate C17.i (279 mg) and 2-bromoethanol (0.189 mL; commercial) and proceeding in analogy to Preparation C2, step C2.i, the title compound was obtained, after purification by CC (Combiflash; Hept/EA 0:1 to 1:0), as a colourless oil (146 mg; 36% yield).
MS3 (ESI, m/z): 348.72 [M+H+]; $t_R$=0.94 min.

C17.iii. {(1R*,5S*)-3-[2-(3'-[1,3]dioxolan-2-yl-biphenyl-3-yloxy)-ethyl]-3-aza-bicyclo[3.1.0]hex-6-yl}-carbamic acid tert-butyl ester Intermediate C17.ii (130 mg) and K$_2$CO$_3$ (69 mg) were suspended with DMF. 6-(Boc-amino)-3-azabicyclo[3.1.0] hexane (81 mg; commercial) was added portionwise and the mixture was stirred at rt for 1 day. The mixture was concentrated under reduced pressure and the residue was portioned between EA and water. The aq. layer was extracted with EA and the combined org. layers were washed with water and brine, dried over MgSO$_4$ and concentrated under reduced pressure. The title compound was obtained, after purification by CC (Combiflash; Hept/EA 0:1 to 1:0), as a yellow oil (108 mg; 62% yield).
MS3 (ESI, m/z): 457.10 [M+H+]; $t_R$=0.73 min.

C17.iv. {(1R*,5S*)-3-[2-(3'-formyl-biphenyl-3-yloxy)-ethyl]-3-aza-bicyclo[3.1.0]hex-6-yl}-carbamic acid tert-butyl ester Starting from intermediate C17.iii (100 mg) and proceeding in analogy to Preparation A7, step A7.ii, the title compound was obtained as an off-white solid (70 mg; 77% yield).
MS3 (ESI, m/z): 423.06 [M+H+]; $t_R$=0.72 min.

Preparation C18: (R)-3-[6-(3-formyl-phenyl)-pyridin-2-yloxy]-pyrrolidine-1-carboxylic acid tert-butyl ester C18.i. (R)-3-[6-(3-[1,3]dioxolan-2-yl-phenyl)-pyridin-2-yloxy]-pyrrolidine-1-carboxylic acid tert-butyl ester Starting from the compound of Preparation BB2 (100 mg) and (S)—N-Boc-3-pyrrolidinol (85 mg; commercial) and proceeding in analogy to Preparation C2, step C2.i, the title compound was obtained as a yellow oil (421 mg; crude product) which was used in the next step without further purification.
MS3 (ESI, m/z): 413.04 [M+H$^+$]; $t_R$=0.98 min.

C18.ii. (R)-3-[6-(3-formyl-phenyl)-pyridin-2-yloxy]-pyrrolidine-1-carboxylic acid tert-butyl ester Starting from intermediate C18.i (420 mg) and proceeding in analogy to Preparation A7, step A7.ii, the title compound was obtained as a yellow oil (396 mg).
MS3 (ESI, m/z): 369.04 [M+H$^+$]; $t_R$=0.98 min.

Preparation C19: (S)-3-[6-(3-formyl-phenyl)-pyridin-2-yloxy]-pyrrolidine-1-carboxylic acid tert-butyl ester C19.i. (S)-3-[6-(3-[1,3]dioxolan-2-yl-phenyl)-pyridin-2-yloxy]-pyrrolidine-1-carboxylic acid tert-butyl ester Starting from the compound of Preparation BB2 (100 mg) and (R)—N-Boc-3-pyrrolidinol (85 mg; commercial) and proceeding in analogy to Preparation C2, step C2.i, the title compound was obtained as a yellow oil (402 mg; quant.).
MS3 (ESI, m/z): 413.06 [M+H$^+$]; $t_R$=0.98 min.

C19.ii. (S)-3-[6-(3-formyl-phenyl)-pyridin-2-yloxy]-pyrrolidine-1-carboxylic acid tert-butyl ester Starting from intermediate C19.i (420 mg) and proceeding in analogy to Preparation A7, step A7.ii, the title compound was obtained as a yellow oil (396 mg; quant.).
MS3 (ESI, m/z): 369.04 [M+H$^+$]; $t_R$=0.98 min.

Preparation C20: 3-[6-((R)-1-methyl-pyrrolidin-3-yloxy)-pyridin-2-yl]-benzaldehyde C20.i. 2-(3-[1,3]dioxolan-2-yl-phenyl)-6-((R)-1-methyl-pyrrolidin-3-yloxy)-pyridine Starting from the compound of Preparation BB2 (100 mg) and (S)-(+)-1-methyl-3-pyrrolidinol (0.050 mL; commercial) and proceeding in analogy to Preparation C2, step C2.i, the title compound was obtained as a yellow oil (396 mg; quant.).
MS3 (ESI, m/z): 327.04 [M+H$^+$]; $t_R$=0.63 min.

C20.ii. 3-[6-((R)-1-methyl-pyrrolidin-3-yloxy)-pyridin-2-yl]-benzaldehyde

Starting from intermediate C20.i (396 mg) and proceeding in analogy to Preparation A7, step A7.ii, the title compound was obtained as an orange oil (376 mg; quant.).
MS3 (ESI, m/z): 283.02 [M+H+]; $t_R$=0.61 min.

Preparation C21: 3-[6-((S)-1-methyl-pyrrolidin-3-yloxy)-pyridin-2-yl]-benzaldehyde C21.i. 2-(3-[1,3]dioxolan-2-yl-phenyl)-6-((S)-1-methyl-pyrrolidin-3-yloxy)-pyridine Starting from the compound of Preparation BB2 (100 mg) and (R)-(−)-1-methyl-3-pyrrolidinol (0.050 mL; commercial) and proceeding in analogy to Preparation C2, step C2.i, the title compound was obtained as a brown oil (419 mg; quant.).
MS3 (ESI, m/z): 327.04 [M+H$^+$]; $t_R$=0.63 min.

C21.ii. 3-[6-((S)-1-methyl-pyrrolidin-3-yloxy)-pyridin-2-yl]-benzaldehyde

Starting from intermediate C21.i (419 mg) and proceeding in analogy to Preparation A7, step A7.ii, the title compound was obtained as an orange oil (382 mg; quant.).
MS3 (ESI, m/z): 283.06 [M+H$^+$]; $t_R$=0.61 min.

Preparation C22: 3-[6-(1-methyl-azetidin-3-yloxy)-pyridin-2-yl]-benzaldehyde

C22.i. 2-(3-[1,3]dioxolan-2-yl-phenyl)-6-(1-methyl-azetidin-3-yloxy)-pyridine

Starting from the compound of Preparation BB2 (100 mg) and 1-methyl-azetidin-3-ol (39 mg; commercial) and proceeding in analogy to Preparation C2, step C2.i, the title compound was obtained, after purification by CC (Combiflash; DCM to DCM/MeOH 9:1), as a yellow oil (29 mg; 23% yield).
MS3 (ESI, m/z): 313.04 [M+H$^+$]; $t_R$=0.63 min.

C22.ii. 3-[6-(1-methyl-azetidin-3-yloxy)-pyridin-2-yl]-benzaldehyde

Starting from intermediate C22.i (25 mg) and proceeding in analogy to Preparation A7, step A7.ii, the title compound was obtained as a yellow oil (21 mg; 98% yield).
MS3 (ESI, m/z): 269.02 [M+H$^+$]; $t_R$=0.61 min.

Preparation C23: 3-[6-((S)-1-methyl-azetidin-2-ylmethoxy)-pyridin-2-yl]-benzaldehyde C23.i. 2-(3-[1,3]dioxolan-2-yl-phenyl)-6-((S)-1-methyl-azetidin-2-ylmethoxy)-pyridine Starting from the compound of Preparation BB2 (100 mg) and (S)-1-methyl-2-azetidinemethanol (45 mg; commercial) and proceeding in analogy to Preparation C2, step C2.i, the title compound was obtained, after purification by CC (Combiflash; DCM to DCM/MeOH 9:1), as a yellow oil (29 mg; 20% yield).
MS3 (ESI, m/z): 327.05 [M+H$^+$]; $t_R$=0.63 min.

C23.ii. 3-[6-((S)-1-methyl-azetidin-2-ylmethoxy)-pyridin-2-yl]-benzaldehyde

Starting from intermediate C23.i (25 mg) and proceeding in analogy to Preparation A7, step A7.ii, the title compound was obtained as a yellow oil (20 mg; quant.).
MS3 (ESI, m/z): 283.04 [M+H$^+$]; $t_R$=0.61 min.

Preparation C24: (R)-2-[6-(3-formyl-phenyl)-pyridin-2-yloxymethyl]-azetidine-1-carboxylic acid tert-butyl ester C24.i. (R)-2-[6-(3-[1,3]dioxolan-2-yl-phenyl)-pyridin-2-yloxymethyl]-azetidine-1-carboxylic acid tert-butyl ester Starting from the compound of Preparation BB2 (150 mg) and (R)-1-Boc-2-azetidinemethanol (138 mg; commercial) and proceeding in analogy to Preparation C2, step C2.i, the title compound was obtained, after purification by CC (Combiflash; Hept to Hept/EA 1:1), as a yellow oil (247 mg; 90% yield).
MS3 (ESI, m/z): 413.05 [M+H$^+$]; $t_R$=0.97 min.

C24.ii. (R)-2-[6-(3-formyl-phenyl)-pyridin-2-yloxymethyl]-azetidine-1-carboxylic acid tert-butyl ester Starting from intermediate C24.i (60 mg) and proceeding in analogy to Preparation A7, step A7.ii, the title compound was obtained as a colourless oil (56 mg; quant.).
MS3 (ESI, m/z): 369.00 [M+H$^+$]; $t_R$=0.97 min.

Preparation C25: 3-[6-((R)-1-methyl-azetidin-2-ylmethoxy)-pyridin-2-yl]-benzaldehyde C25.i. 3-[6-((R)-1-azetidin-2-ylmethoxy)-pyridin-2-yl]-benzaldehyde trifluoroacetate Starting from intermediate C24.i (170 mg) and proceeding in analogy to Preparation C13, step C13.ii, the title compound was obtained without further purification as a yellowish oil (171 mg; quant.).
MS3 (ESI, m/z): 269.06 [M+H$^+$]; $t_R$=0.61 min.

C25.ii. 2-((R)-1-azetidin-2-ylmethoxy)-6-(3-dimethoxymethyl-phenyl)-pyridine

A solution of intermediate C25.i (165 mg), trimethyl orthoformate (0.63 mL) and PTSA (2.46 mg) in MeOH (5.0 mL) was stirred at 50° C. for 1 day. Sat. aq. NaHCO$_3$ and EA were added, the layers were separated and the aq. layer was twice extracted with EA, dried over MgSO$_4$, filtered and concentrated under reduced pressure. The title compound was obtained as a yellow oil (119 mg; 88% yield; 25% pure).
MS3 (ESI, m/z): 315.03 [M+H$^+$]; $t_R$=0.65 min.

C25.iii. 2-(3-dimethoxymethyl-phenyl)-6-((R)-1-methyl-azetidin-2-ylmethoxy)-pyridine Starting from intermediate C25.ii (110 mg) and 37% aq. formaldehyde (0.089 mL) and proceeding in analogy to Preparation C13, step C13.iii, the title compound was obtained, after purification by prep-HPLC (method 2), as a colourless oil (15 mg; 52% yield).
MS3 (ESI, m/z): 239.04 [M+H+]; $t_R$=0.66 min.

C25.iv. 3-[6-((R)-1-methyl-azetidin-2-ylmethoxy)-pyridin-2-yl]-benzaldehyde

Starting from intermediate C25.iii (10 mg) and proceeding in analogy to Preparation A7, step A7.ii, the title compound was obtained as a yellowish oil (9 mg; quant.).
MS3 (ESI, m/z): 283.03 [M+H$^+$]; $t_R$=0.62 min.

Preparation C26: rac-3-[6-(1-ethyl-pyrrolidin-3-yloxy)-pyridin-2-yl]-benzaldehyde

C26.i. Rac-2-(3-[1,3]dioxolan-2-yl-phenyl)-6-(1-ethyl-pyrrolidin-3-yloxy)-pyridine Starting from the compound of Preparation BB2 (332 mg) and 1-ethyl-3-pyrrolidinol (0.188 mL; commercial) and proceeding in analogy to Preparation C2, step C2.i, the title compound was obtained, after purification by CC (Combiflash; Hept/EA 1:0 to 0:1), as a brown oil (180 mg; 39% yield).
MS3 (ESI, m/z): 341.05 [M+H$^+$]; $t_R$=0.66 min.

C26.ii. Rac-3-[6-(1-ethyl-pyrrolidin-3-yloxy)-pyridin-2-yl]-benzaldehyde

Starting from intermediate C26.i (156 mg) and proceeding in analogy to Preparation A7, step A7.ii, the title compound was obtained as a reddish solid (116 mg; 85% yield).
MS3 (ESI, m/z): 297.04 [M+H$^+$]; $t_R$=0.63 min.

Preparation C27: 3-[6-(1-methyl-piperidin-4-yloxy)-pyridin-2-yl]-benzaldehyde

C27.i. 2-(3-[1,3]dioxolan-2-yl-phenyl)-6-(1-methyl-piperidin-4-yloxy)-pyridine Starting from the compound of Preparation BB2 (200 mg) and 4-hydroxy-1-methylpiperidine (0.108 mL; commercial) and proceeding in analogy to Preparation C2, step C2.i, the title compound was obtained, after purification by CC (Combiflash; Hept/EA 1:0 to 0:1), as a yellow oil (106 mg; 38% yield).
MS3 (ESI, m/z): 341.05 [M+H$^+$]; $t_R$=0.65 min.

C27.ii. 3-[6-(1-methyl-piperidin-4-yloxy)-pyridin-2-yl]-benzaldehyde

Starting from intermediate C27.i (97 mg) and proceeding in analogy to Preparation A7, step A7.ii, the title compound was obtained as a reddish solid (80 mg; 95% yield).
MS3 (ESI, m/z): 297.06 [M+H$^+$]; $t_R$=0.64 min.

Preparation C28: 6-((S)-1-methyl-pyrrolidin-3-yloxy)-[2,4']bipyridinyl-2'-carbaldehyde

C28.i. 2-bromo-6-((S)-1-methyl-pyrrolidin-3-yloxy)-pyridine

Starting from 6-bromopyridin-2-ol (1.5 g; commercial) and (R)-(−)-1-methyl-3-pyrrolidinol (1.02 mL; commercial) and proceeding in analogy to Preparation C2, step C2.i, the title compound was obtained after purification by CC (Combiflash; DCM to DCM/MeOH 9:1) as a light yellow liquid (1.3 g; 60% yield).
MS3 (ESI, m/z): 258.94 [M+H$^+$]; $t_R$=0.51 min.

C28.ii. 2-((S)-1-methyl-pyrrolidin-3-yloxy)-6-(4,4,5,5-tetramethyl-[1,3,2]dioxaborolan-2-yl)-pyridine A mixture of intermediate C28.i (350 mg), bis(pinacolato)diboron (388 mg; commercial), potassium acetate (200 mg), Tris(dibenzylideneacetone)dipalladium(0) (37.4 mg) and tricyclohexylphosphine (45.8 mg) in dioxane (5 mL) was degassed for 5 min with N$_2$ and sealed in a Schlenk flask. The resulting dark brown suspension was stirred at 100° C. for 1.5 h. The mixture was cooled down to rt, diluted with EA, filtered through a glass fiber filter and concentrated under reduced pressure, the title compound was obtained as a yellow oil (895 mg; quant.) and used in the next step without further purification.
MS3 (ESI, m/z): 305.06 [M+H$^+$]; $t_R$=0.36 min.

C28.iii. 6-((S)-1-methyl-pyrrolidin-3-yloxy)-[2,4']bipyridinyl-2'-carbaldehyde A mixture of intermediate C28.ii (295 mg), 4-bromopyridine-2-carbaldehyde (73.6 mg; commercial), cesium carbonate (511 mg), copper(I) chloride (39.6 mg), palladium(II) acetate (4.44 mg) and 1,1'-bis(diphenylphosphino)ferrocene (22.2 mg) in dioxane (3 mL) was degassed for 10 min with N$_2$ and sealed in a glass vial. The resulting suspension was stirred at 100° C. for 1 h. The mixture was cooled down to rt suspended with EA and filtered through a pad of Celite. The filtrate was concentrated under reduced pressure. The title compound was obtained, after purification by CC (Combiflash; DCM; DCM/MeOH 9/1), as an orange oil (56 mg; 51% yield).
MS3 (ESI, m/z): 284.02 [M+H$^+$]; $t_R$=0.56 min.

Preparation C29: 6'-((S)-1-methyl-pyrrolidin-3-yloxy)-[2,2']bipyridinyl-6-carbaldehyde Starting from intermediate C28.ii (295 mg) and 6-bromo-2-pyridinecarboxaldehyde (74.4 mg; commercial) and proceeding in analogy to Preparation C28, step C28.iii, the title compound was obtained as a brown oil (61 mg; 56% yield).
MS3 (ESI, m/z): 284.04 [M+H$^+$]; $t_R$=0.59 min.

Preparation C30: 3-[6-((S)-1-methyl-pyrrolidin-2-ylmethoxy)-pyridin-2-yl]-benzaldehyde

C30.i. 2-(3-[1,3]dioxolan-2-yl-phenyl)-6-((S)-1-methyl-pyrrolidin-2-ylmethoxy)-pyridine Starting from the compound of Preparation BB2 (200 mg) and (S)-(−)-1-methyl-2-pyrrolidinemethanol (62.5 mg; commercial) and proceeding in analogy to Preparation C2, step C2.i, the title compound was obtained after purification by CC (Combiflash; Hept/EA 1:0 to 0:1) as a yellow oil (100 mg; 60% yield).
MS3 (ESI, m/z): 341.06 [M+H$^+$]; $t_R$=0.65 min.

C30.ii. 3-[6-((S)-1-methyl-pyrrolidin-2-ylmethoxy)-pyridin-2-yl]-benzaldehyde Starting from intermediate C30.i (96 mg) and proceeding in analogy to Preparation A7, step A7.ii, the title compound was obtained as a yellow solid (73 mg; 87% yield).
MS3 (ESI, m/z): 297.05 [M+H$^+$]; $t_R$=0.64 min.

Preparation C31: (2S,4S)-4-[6-(3-formyl-phenyl)-pyridin-2-yloxy]-2-methyl-pyrrolidine-1-carboxylic acid tert-butyl ester

C31.i. (2S,4S)-4-[6-(3-[1,3]dioxolan-2-yl-phenyl)-pyridin-2-yloxy]-2-methyl-pyrrolidine-1-carboxylic acid tert-butyl ester Starting from the compound of Preparation BB2 (120 mg) and (2S,4R)-4-hydroxy-2-methyl-pyrrolidine-1-carboxylic acid tert-butyl ester (109 mg; commercial) and proceeding in analogy to Preparation C2, step C2.i, the title compound was obtained, after purification by CC (Combiflash; Hept/EA 1:0 to 0:1), as a yellow oil (242 mg; quant.).
MS3 (ESI, m/z): 427.11 [M+H$^+$]; $t_R$=1.01 min.

C31.ii. (2S,4S)-4-[6-(3-formyl-phenyl)-pyridin-2-yloxy]-2-methyl-pyrrolidine-1-carboxylic acid tert-butyl ester Starting from intermediate C31.i (203 mg) and proceeding in analogy to Preparation A7, step A7.ii, the title compound was obtained as a yellow solid (217 mg; quant).
MS3 (ESI, m/z): 383.04 [M+H$^+$]; $t_R$=1.02 min.

Preparation C32: (R)-2-[6-(3-formyl-phenyl)-pyridin-2-yloxymethyl]-pyrrolidine-1-carboxylic acid tert-butyl ester

C32.i. (R)-2-[6-(3-[1,3]dioxolan-2-yl-phenyl)-pyridin-2-yloxymethyl]-pyrrolidine-1-carboxylic acid tert-butyl ester Starting from the compound of Preparation BB2 (120 mg) and N-Boc-D-prolinol (110 mg; commercial) and proceeding in analogy to Preparation C2, step C2.i, the title compound was obtained, after purification by CC (Combiflash; Hept/EA 1:0 to 0:1), as a yellow oil (200 mg; 95% yield).
MS3 (ESI, m/z): 427.10 [M+H$^+$]; $t_R$=1.00 min.

C32.ii. (R)-2-[6-(3-formyl-phenyl)-pyridin-2-yloxymethyl]-pyrrolidine-1-carboxylic acid tert-butyl ester Starting from intermediate C32.i (183 mg) and proceeding in analogy to Preparation A7, step A7.ii, the title compound was obtained as a colourless oil (179 mg; quant).
MS3 (ESI, m/z): 383.03 [M+H$^+$]; $t_R$=1.01 min.

Preparation C33: (S)-2-[6-(3-formyl-phenyl)-pyridin-2-yloxymethyl]-pyrrolidine-1-carboxylic acid tert-butyl ester

C33.i. (S)-2-[6-(3-[1,3]dioxolan-2-yl-phenyl)-pyridin-2-yloxymethyl]-pyrrolidine-1-carboxylic acid tert-butyl ester Starting from the compound of Preparation BB2 (120 mg) and N-Boc-L-prolinol (109 mg; commercial) and proceeding in analogy to Preparation C2, step C2.i, the title compound was obtained, after purification by CC (Combiflash; Hept/EA 1:0 to 0:1), as a yellow oil (238 mg; quant.).
MS3 (ESI, m/z): 427.10 [M+H$^+$]; $t_R$=1.00 min.

C33.ii. (S)-2-[6-(3-formyl-phenyl)-pyridin-2-yloxymethyl]-pyrrolidine-1-carboxylic acid tert-butyl ester Starting from intermediate C33.i (201 mg) and proceeding in analogy to Preparation A7, step A7.ii, the title compound was obtained as a colourless oil (213 mg; quant.).
MS3 (ESI, m/z): 383.01 [M+H$^+$]; $t_R$=1.01 min.

Preparation C34: rac-3-[6-(1-isopropyl-pyrrolidin-3-yloxy)-pyridin-2-yl]-benzaldehyde

C34.i. Rac-2-(3-[1,3]dioxolan-2-yl-phenyl)-6-(1-isopropyl-pyrrolidin-3-yloxy)-pyridine Starting from the compound of Preparation BB2 (120 mg) and 1-isopropyl-3-pyrrolidinol (73.8 mg; commercial) and proceeding in analogy to Preparation C2, step C2.i, the title compound was obtained, after purification by CC (Combiflash; Hept/EA 1:0 to 0:1), as a colourless oil (72 mg; 41% yield).
MS3 (ESI, m/z): 355.03 [M+H$^+$]; $t_R$=0.67 min.

C34.ii. Rac-3-[6-(1-isopropyl-pyrrolidin-3-yloxy)-pyridin-2-yl]-benzaldehyde Starting from intermediate C34.i (71 mg) and proceeding in analogy to Preparation A7, step A7.ii, the title compound was obtained as an off-white solid (54 mg; 87% yield).
MS3 (ESI, m/z): 311.05 [M+H$^+$]; $t_R$=0.77 min.

Preparation C35: (RS)-3-[6-(3-formyl-phenyl)-pyridin-2-yloxy]-(RS)-2-methyl-azetidine-1-carboxylic acid tert-butyl ester

C35.i. (RS)-3-[6-(3-[1,3]dioxolan-2-yl-phenyl)-pyridin-2-yloxy]-(RS)-2-methyl-azetidine-1-carboxylic acid tert-butyl ester Starting from the compound of Preparation BB2 (120 mg) and tert-butyl 3-hydroxy-2-methylazetidine-1-carboxylate (105 mg; commercial) and proceeding in analogy to Preparation C2, step C2.i, the title compound was obtained, after purification by CC (Combiflash; Hept/EA 1:0 to 0:1), as a colourless oil (56 mg; 28% yield).
MS3 (ESI, m/z): 413.08 [M+H$^+$]; $t_R$=1.00 min.

C35.ii. (RS)-3-[6-(3-formyl-phenyl)-pyridin-2-yloxy]-(RS)-2-methyl-azetidine-1-carboxylic acid tert-butyl ester Starting from intermediate C35.i (48 mg) and proceeding in analogy to Preparation A7, step A7.ii, the title compound was obtained as an off-white solid (47 mg; quant.).
MS3 (ESI, m/z): 369.00 [M+H$^+$]; $t_R$=0.67 min.

Preparation C36: 3-[4-methoxy-6-((S)-1-methyl-pyrrolidin-3-yloxy)-pyridin-2-yl]-benzaldehyde

C36.i. 6-bromo-4-methoxy-pyridin-2-ol

A dry tube was filled with (1,5-cyclooctadiene)(methoxy)iridium(I) dimer (18 mg) and 4,4'-di-tert-butyl-2,2'-dipyridyl (14.3 mg) and filled with N$_2$. 4,4,5,5-tetramethyl-1,3,2-dioxaborolane (0.232 mL) and 2-bromo-4-methoxypyridine (250 mg; commercial) in Hept (2.6 mL) were added and the brown solution was stirred at rt for 1 day.

(1,5-cyclooctadiene)(methoxy)iridium(I) dimer (18 mg) and 4,4'-di-tert-butyl-2,2'-dipyridyl (14.3 mg) were added again and the mixture was stirred at 50-80° C. for 3 days. The mixture was diluted with THF (10 mL) and oxone (monopersulfate compound in 10 mL H$_2$O; 899 mg) was added within 15 min under vigorous stirring. The reaction mixture was quenched with 40% aq. NaHSO$_3$ (10 mL), brine (10 mL) and the aq. mixture was extracted twice with EA. The combined org. layers were washed with water, dried over MgSO$_4$, filtered and concentrated under reduced pressure. The title compound was obtained, after purification by CC (Combiflash; Hept/EA 1:0 to 3:1), as a colourless solid (85 mg; 31% yield).

MS3 (ESI, m/z): 205.98 [M+H$^+$]; $t_R$=0.52 min.

C36.ii. 2-bromo-4-methoxy-6-((S)-1-methyl-pyrrolidin-3-yloxy)-pyridine

Starting from intermediate C36.i (60 mg) and (R)-(−)-1-methyl-3-pyrrolidinol (0.036 mL; commercial) and proceeding in analogy to Preparation C2, step C2.i, the title compound was obtained, after purification by CC (Combiflash; DCM to DCM/MeOH 4:1), as an orange oil (39 mg; 46% yield).

MS3 (ESI, m/z): 286.94 [M+H$^+$]; $t_R$=0.57 min.

C36.iii. 3-[4-methoxy-6-((S)-1-methyl-pyrrolidin-3-yloxy)-pyridin-2-yl]-benzaldehyde Starting from intermediate C36.ii (35 mg) and 3-formylphenylboronic acid (20 mg; commercial) and proceeding in analogy to Preparation BB1, but irradiate the reaction mixture in the microwave at 110° C. for 45 min, the title compound was obtained as an orange oil (35 mg; 92% yield).

MS3 (ESI, m/z): 313.05 [M+H$^+$]; $t_R$=0.65 min.

Preparation C37: 3-[4-((S)-1-methyl-pyrrolidin-3-yloxy)-pyrimidin-2-yl]-benzaldehyde

C37.i. 2-chloro-4-((S)-1-methyl-pyrrolidin-3-yloxy)-pyrimidine

Starting from 2-chloro-4-hydroxypyrimidine (70 mg; commercial) and (R)-(−)-1-methyl-3-pyrrolidinol (0.0628 mL; commercial) and proceeding in analogy to Preparation C2, step C2.i, the title compound was obtained, after purification by CC (Combiflash; DCM to DCM/MeOH 9:1), as a yellow solid (80 mg; 72% yield).

MS3 (ESI, m/z): 214.08 [M+H$^+$]; $t_R$=0.38 min.

C37.ii. 3-[4-((S)-1-methyl-pyrrolidin-3-yloxy)-pyrimidin-2-yl]-benzaldehyde Starting from intermediate C37.i (80 mg), 3-formylphenylboronic acid (30 mg; commercial), Pd(PPh$_3$)$_4$ (22 mg) and K$_2$CO$_3$ (78 mg) and proceeding in analogy to Preparation BB1, the title compound was obtained, after purification by CC (Combiflash; DCM to DCM/MeOH 9:1), as a yellow oil (11 mg; 10% yield).

MS3 (ESI, m/z): 284.02 [M+H$^+$]; $t_R$=0.56 min.

Preparation C38: 6-((S)-1-methyl-pyrrolidin-3-yloxy)-[2,3']bipyridinyl-5'-carbaldehyde Starting from intermediate C28.ii (250 mg) and 5-bromo-3-pyridinecarboxaldehyde (74.5 mg; commercial) and proceeding in analogy to Preparation C28, step C28.iii, the title compound was obtained as a yellow oil (62 mg; 59% yield).

MS3 (ESI, m/z): 284.02 [M+H$^+$]; $t_R$=0.54 min.

Preparation C39: 6'-((S)-1-methyl-pyrrolidin-3-yloxy)-[2,2']bipyridinyl-4-carbaldehyde Starting from intermediate C28.ii (250 mg) and 2-bromo-4-formylpyridine (74 mg; commercial) and proceeding in analogy to Preparation C28, step C28.iii, the title compound was obtained as a yellow oil (55 mg; 59% yield).

MS3 (ESI, m/z): 284.01 [M+H$^+$]; $t_R$=0.57 min.

Preparation C40: 3-[6-((R)-1-methyl-pyrrolidin-3-ylmethoxy)-pyridin-2-yl]-benzaldehyde

C40.i. 2-(3-[1,3]dioxolan-2-yl-phenyl)-6-((R)-1-methyl-pyrrolidin-3-ylmethoxy)-pyridine Starting from the compound of Preparation BB2 (200 mg) and (R)-(1-methyl-pyrrolidin-3-yl)-methanol (104 mg; commercial) and proceeding in analogy to Preparation C2, step C2.i, the title compound was obtained, after purification by CC (Combiflash; Hept/EA 1:0 to 0:1), as a colourless oil (120 mg; 43% yield).

MS3 (ESI, m/z): 341.04 [M+H$^+$]; $t_R$=0.63 min.

C40.ii. 3-[6-((R)-1-methyl-pyrrolidin-3-ylmethoxy)-pyridin-2-yl]-benzaldehyde Starting from intermediate C40.i (110 mg) and proceeding in analogy to Preparation A7, step A7.ii, the title compound was obtained as a colourless oil (82 mg; 85% yield).

MS3 (ESI, m/z): 297.02 [M+H$^+$]; $t_R$=0.62 min.

Preparation C41: 3-[6-((S)-1-methyl-pyrrolidin-3-ylmethoxy)-pyridin-2-yl]-benzaldehyde

C41.i. 2-(3-[1,3]dioxolan-2-yl-phenyl)-6-((S)-1-methyl-pyrrolidin-3-ylmethoxy)-pyridine Starting from the compound of Preparation BB2 (200 mg) and (S)-(1-methyl-pyrrolidin-3-yl)-methanol (109 mg; commercial) and proceeding in analogy to Preparation C2, step C2.i, the title compound was obtained, after purification by CC (Combiflash; Hept/EA 1:0 to 0:1), as a colourless oil (180 mg; 64% yield).

MS3 (ESI, m/z): 341.07 [M+H$^+$]; $t_R$=0.64 min.

C41.ii. 3-[6-((S)-1-methyl-pyrrolidin-3-ylmethoxy)-pyridin-2-yl]-benzaldehyde Starting from intermediate C41.i (177 mg) and proceeding in analogy to Preparation A7, step A7.ii, the title compound was obtained as a colourless oil (133 mg; 86% yield).

MS3 (ESI, m/z): 297.03 [M+H$^+$]; $t_R$=0.63 min.

Preparation C42: rac-3-[6-(1-methyl-piperidin-3-yloxy)-pyridin-2-yl]-benzaldehyde

C42.i. Rac-2-(3-[1,3]dioxolan-2-yl-phenyl)-6-(1-methyl-piperidin-3-yloxy)-pyridine Starting from the compound of Preparation BB2 (200 mg) and N-methyl-3-piperidinol (0.106 mL; 98% purity; commercial) and proceeding in analogy to Preparation C2, step C2.i, the title compound was obtained, after purification by CC (Combiflash; Hept/EA 1:0 to 0:1), as a yellow oil (51 mg; 18% yield).

MS3 (ESI, m/z): 341.06 [M+H$^+$]; $t_R$=0.64 min.

C42.ii. Rac-3-[6-(1-methyl-piperidin-3-yloxy)-pyridin-2-yl]-benzaldehyde

Starting from intermediate C42.i (45 mg) and proceeding in analogy to Preparation A7, step A7.ii, the title compound was obtained as a colourless oil (33 mg; 84% yield).

MS3 (ESI, m/z): 297.03 [M+H$^+$]; $t_R$=0.62 min.

Preparation C43: (R)-3-[6-(3-formyl-phenyl)-pyridin-2-yloxymethyl]-pyrrolidine-1-carboxylic acid tert-butyl ester

C43.i. (R)-3-[6-(3-[1,3]dioxolan-2-yl-phenyl)-pyridin-2-yloxymethyl]-pyrrolidine-1-carboxylic acid tert-butyl ester Starting from the compound of Preparation BB2 (200 mg) and (R)-3-hydroxymethyl-pyrrolidine-1-carboxylic acid tert-butyl ester (188 mg; commercial) and proceeding in analogy to Preparation C2, step C2.i, the title compound was obtained after purification by CC (Combiflash; Hept/EA 1:0 to 0:1) as a colourless oil (408 mg; quant.).

MS3 (ESI, m/z): 427.12 [M+H$^+$]; $t_R$=1.00 min.

C43.ii. (R)-3-[6-(3-formyl-phenyl)-pyridin-2-yloxymethyl]-pyrrolidine-1-carboxylic acid tert-butyl ester Starting from intermediate C43.i (384 mg) and proceeding in analogy to Preparation A7, step A7.ii, the title compound was obtained as a yellow oil (348 mg; quant.).

MS3 (ESI, m/z): 383.06 [M+H$^+$]; $t_R$=1.01 min.

Preparation C44: (S)-3-[6-(3-formyl-phenyl)-pyridin-2-yloxymethyl]-pyrrolidine-1-carboxylic acid tert-butyl ester

C44.i. (S)-3-[6-(3-[1,3]dioxolan-2-yl-phenyl)-pyridin-2-yloxymethyl]-pyrrolidine-1-carboxylic acid tert-butyl ester Starting from the compound of Preparation BB2 (200 mg) and (S)-3-hydroxymethyl-pyrrolidine-1-carboxylic acid tert-butyl ester (188 mg; commercial) and proceeding in analogy to Preparation C2, step C2.i, the title compound was obtained after purification by CC (Combiflash; Hept/EA 1:0 to 0:1) as a colourless oil (426 mg; quant.).

MS3 (ESI, m/z): 427.11 [M+H$^+$]; $t_R$=1.00 min.

C44.ii. (S)-3-[6-(3-formyl-phenyl)-pyridin-2-yloxymethyl]-pyrrolidine-1-carboxylic acid tert-butyl ester Starting from intermediate C44.i (423 mg) and proceeding in analogy to Preparation A7, step A7.ii, the title compound was obtained as a yellow oil (348 mg; quant.).

MS3 (ESI, m/z): 383.04 [M+H$^+$]; $t_R$=1.00 min.

Preparation C45: 6-[6-((S)-1-methyl-pyrrolidin-3-yloxy)-pyrazin-2-yl]-pyridine-2-carbaldehyde

C45.i. 2-bromo-6-((S)-1-methyl-pyrrolidin-3-yloxy)-pyrazine

Starting from 6-bromopyrazin-2-ol (1.5 g; commercial) and (R)-(−)-1-methyl-3-pyrrolidinol (1.02 mL; commercial) and proceeding in analogy to Preparation C2, step C2.i, the title compound was obtained, after purification by CC (Combiflash; DCM to DCM/MeOH 9:1), as a yellowish liquid (1.26 g; 57% yield).

MS3 (ESI, m/z): 259.95 [M+H$^+$]; $t_R$=0.44 min.

C45.ii. 2-((S)-1-methyl-pyrrolidin-3-yloxy)-6-(4,4,5,5-tetramethyl-[1,3,2]dioxaborolan-2-yl)-pyrazine Starting from intermediate C45.i (1.22 g) and proceeding in analogy to Preparation C28, step C28.ii, the title compound was obtained as an orange solid (3.08 g; quant.).

MS3 (ESI, m/z): 306.04 [M+H$^+$]; $t_R$=0.35 min.

C45.iii. 6-[6-((S)-1-methyl-pyrrolidin-3-yloxy)-pyrazin-2-yl]-pyridine-2-carbaldehyde Starting from intermediate C45.ii (250 mg) and 6-bromo-2-pyridinecarboxaldehyde (74.2 mg; commercial) and proceeding in analogy to Preparation C28, step C28.iii, the title compound was obtained as a light orange solid (49 mg; 47% yield).

MS3 (ESI, m/z): 285.01 [M+H$^+$]; $t_R$=0.53 min.

Preparation C46: 5-[6-((S)-1-methyl-pyrrolidin-3-yloxy)-pyrazin-2-yl]-pyridine-3-carbaldehyde Starting from intermediate C45.ii (250 mg) and 4-bromopyridine-2-carbaldehyde (73.5 mg; commercial) and proceeding in analogy to Preparation C28, step C28.iii, the title compound was obtained as an orange oil (54 mg; 52% yield).

MS3 (ESI, m/z): 285.00 [M+H$^+$]; $t_R$=0.50 min.

Preparation C47: 2-[6-((S)-1-methyl-pyrrolidin-3-yloxy)-pyrazin-2-yl]-pyridine-4-carbaldehyde Starting from intermediate C45.ii (250 mg) and 2-bromo-4-formylpyridine (73.5 mg; commercial) and proceeding in analogy to Preparation C28, step C28.iii, the title compound was obtained as a light orange solid (53 mg; 51% yield).

MS3 (ESI, m/z): 282.01 [M+H$^+$]; $t_R$=0.53 min.

Preparation C48: 4-[6-((S)-1-methyl-pyrrolidin-3-yloxy)-pyrazin-2-yl]-pyridine-2-carbaldehyde Starting from intermediate C45.ii (250 mg) and 4-bromopyridine-2-carbaldehyde (73.5 mg; commercial) and proceeding in analogy to Preparation C28, step C28.iii, the title compound was obtained, after purification by CC (Combiflash, DCM to DCM/MeOH 9:1), as an orange oil (54 mg; 52% yield).

MS3 (ESI, m/z): 285.00 [M+H$^+$]; $t_R$=0.50 min.

Preparation C49: 3-[5-((S)-1-methyl-pyrrolidin-3-yloxy)-pyridazin-3-yl]-benzaldehyde

C49.i. 3-(3-[1,3]dioxolan-2-yl-phenyl)-5-((S)-1-methyl-pyrrolidin-3-yloxy)-pyridazine Starting from the compound of Preparation BB3 (90 mg) and (S)-(+)-1-methyl-3-pyrrolidinol (329 mg; commercial) and proceeding in analogy to Preparation C14, step C14.i, the title compound was obtained as a light orange solid (142 mg; quant.).
MS3 (ESI, m/z): 328.05 [M+H$^+$]; $t_R$=0.49 min.

C49.ii. 3-[5-((S)-1-methyl-pyrrolidin-3-yloxy)-pyridazin-3-yl]-benzaldehyde Starting from intermediate C49.i (150 mg) and proceeding in analogy to Preparation A7, step A7.ii, the title compound was obtained as a brown sticky oil (98 mg; 84% yield).
MS3 (ESI, m/z): 284.19 [M+H$^+$]; $t_R$=0.47 min.

Preparation C50: {2-[2-(3-formyl-phenyl)-pyridin-4-yloxy]-ethyl}-carbamic acid tert-butyl ester

C50.i. [2-(2-chloro-pyridin-4-yloxy)-ethyl]-carbamic acid tert-butyl ester

Starting from 2-chloro-2-chloro-4-hydroxypyridine (250 mg; commercial) and N-(tert-butoxycarbonyl)ethanolamine (0.305 mL; commercial) and proceeding in analogy to Preparation C2, step C2.i, the title compound was obtained, after purification by CC (Combiflash; Hept to Hept/EA 1:2), as a colourless oil (560 mg; quant.).
MS3 (ESI, m/z): 272.98 [M+H$^+$]; $t_R$=0.78 min.

C50.ii. {2-[2-(3-formyl-phenyl)-pyridin-4-yloxy]-ethyl}-carbamic acid tert-butyl ester Starting from intermediate C50.i (535 mg), 3-formylphenylboronic acid (309 mg; commercial), Pd(PPh$_3$)$_4$ (113 mg) and 2M aq. Na$_2$CO$_3$ (0.98 mL) and proceeding in analogy to Preparation BB1, but using EtOH/water/toluene 2:1:1 as solvents, the title compound was obtained, after purification by CC (Combiflash; Hept to Hept/EA 1:1), as a yellow oil (408 mg; 61% yield).
MS3 (ESI, m/z): 342.90 [M+H$^+$]; $t_R$=0.63 min.

Preparation C51: (2-{(2-tert-butoxycarbonylamino-ethyl)-[2-(3'-formyl-biphenyl-3-yloxy)-ethyl]-amino}-ethyl)-carbamic acid tert-butyl ester

C51.i. (2-{(2-tert-butoxycarbonylamino-ethyl)-[2-(3'-[1,3]dioxolan-2-yl-biphenyl-3-yloxy)-ethyl]-amino}-ethyl)-carbamic acid tert-butyl ester Starting from intermediate C17.ii and di-tert-butyl (azanediylbis(ethane-2,1-diyl))dicarbamate (139 mg; commercial) and proceeding in analogy to Preparation C17, step C17.iii, the title compound was obtained, after purification by CC (Combiflash; Hept to Hept/EA 1:2), as a colourless oil (56 mg; 21% yield).
MS3 (ESI, m/z): 572.15 [M+H$^+$]; $t_R$=0.82 min.

C51.ii. (2-{(2-tert-butoxycarbonylamino-ethyl)-[2-(3'-formyl-biphenyl-3-yloxy)-ethyl]-amino}-ethyl)-carbamic acid tert-butyl ester Starting from intermediate C51.i (100 mg) and proceeding in analogy to Preparation A7, step A7.ii, the title compound was obtained as a colourless oil (21 mg; 46% yield).
MS3 (ESI, m/z): 528.14 [M+H$^+$]; $t_R$=0.81 min.

Preparation C52: (2-tert-butoxycarbonylamino-ethyl)-{2-[6-(3-formyl-phenyl)-pyridin-2-yloxy]-ethyl}-carbamic acid tert-butyl ester

C52.i. (2-tert-butoxycarbonylamino-ethyl)-(2-hydroxy-ethyl)-carbamic acid tert-butyl ester N-(2-Hydroxyethyl)ethylenediamine (2.06 g; commercial) and TEA (13.8 mL) were dissolved in EtOH (30 mL) and THF (30 mL), di-tert-butyl dicarbonate (10.8 g) was added and the mixture was stirred at rt for 1 day. TBME and 2M aq. HCl was added and the org. layer was washed with sat. aq. NaHCO$_3$ and brine, dried over MgSO$_4$ and concentrated under reduced pressure. The title compound was obtained as an off-white oil (6.98 g; quant.).
MS3 (ESI, m/z): 305.01 [M+H$^+$]; $t_R$=0.73 min.

C52.ii. (2-tert-butoxycarbonylamino-ethyl)-{2-[6-(3-[1,3]dioxolan-2-yl-phenyl)-pyridin-2-yloxy]-ethyl}-carbamic acid tert-butyl ester Starting from intermediate C52.i (332 mg) and the compound of Preparation BB2 (457 mg) and proceeding in analogy to Preparation C2, step C2.i, the title compound was obtained, after purification by CC (Combiflash; Hept/EA 1:0 to 0:1), as an off-white solid (1.1 g; quant.).
MS3 (ESI, m/z): 530.03 [M+H$^+$]; $t_R$=1.02 min.

C52.iii. (2-tert-butoxycarbonylamino-ethyl)-{2-[6-(3-formyl-phenyl)-pyridin-2-yloxy]-ethyl}-carbamic acid tert-butyl ester Starting from intermediate C52.ii (341 mg) and proceeding in analogy to Preparation A7, step A7.ii, the title compound was obtained as an off-white solid (295 mg; 95% yield).
MS3 (ESI, m/z): 486.12 [M+H$^+$]; $t_R$=1.02 min.

Preparation C53: [2-(2'-formyl-[2,4']bipyridinyl-4-yloxy)-ethyl]-carbamic acid tert-butyl ester

C53.i. [2-(2-chloro-pyridin-4-yloxy)-ethyl]-carbamic acid tert-butyl ester

Starting from 2-chloro-4-hydroxypyridine (200 mg; commercial) and (Boc-amino)ethanolamine (0.263 mL; commercial) and proceeding in analogy to Preparation C2, step C2.i, the title compound was obtained, after purification by CC (Combiflash; Hept to Hept/EA 1:1), as a colourless solid (471 mg; quant.).
MS3 (ESI, m/z): 273.01 [M+H$^+$]; $t_R$=0.79 min.

C53.ii. [2-(2'-formyl-[2,4']bipyridinyl-4-yloxy)-ethyl]-carbamic acid tert-butyl ester Starting from intermediate C53.i (200 mg) and the compound of Preparation BB9 (359 mg) and proceeding in analogy to Preparation BB3, the title compound was obtained as a yellow oil (26 mg; 10% yield).

MS3 (ESI, m/z): 343.99 [M+H+]; $t_R$=0.71 min.

Preparation C54: {2-[6-(2-formyl-pyridin-4-yl)-pyrazin-2-yloxy]-ethyl}-carbamic acid tert-butyl ester C54.i. [2-(6-bromo-pyrazin-2-yloxy)-ethyl]-carbamic acid tert-butyl ester Starting from 6-bromopyrazin-2-ol (250 mg, commercial) and (Boc-amino)ethanolamine (0.243 mL; commercial) and proceeding in analogy to Preparation C2, step C2.i, the title compound was obtained, after purification by CC (Combiflash; Hept to Hept/EA 1:1), as a colourless solid (348 mg; 77% yield).

MS3 (ESI, m/z): 319.92 [M+H$^+$]; $t_R$=0.84 min.

C54.ii. {2-[6-(2-formyl-pyridin-4-yl)-pyrazin-2-yloxy]-ethyl}-carbamic acid tert-butyl ester Starting from intermediate C54.i (120 mg) and the compound of Preparation BB9 (185 mg) and proceeding in analogy to Preparation BB1, the title compound was obtained, after purification by CC (Combiflash; Hept/EA 1:0 to 1:2), as a red foam (68 mg; 52% yield).

MS3 (ESI, m/z): 345.00 [M+H$^+$]; $t_R$=0.82 min.

Preparation C55: [2-(2'-formyl-[3,4']bipyridinyl-5-yloxy)-ethyl]-carbamic acid tert-butyl ester C55.i. [2-(5-bromo-pyridin-3-yloxy)-ethyl]-carbamic acid tert-butyl ester Starting from 3-bromo-5-hydroxypyridine (250 mg; commercial) and (Boc-amino)ethanolamine (0.245 mL; commercial) and proceeding in analogy to Preparation C2, step C2.i, the title compound was obtained after purification by CC (Combiflash; Hept to Hept/EA 1:1) as a colourless solid (512 mg; quant.).

MS3 (ESI, m/z): 316.92 [M+H$^+$]; $t_R$=0.82 min.

C55.ii. [2-(2'-formyl-[3,4']bipyridinyl-5-yloxy)-ethyl]-carbamic acid tert-butyl ester Starting from intermediate C55.i (200 mg) and the compound of Preparation BB9 (257 mg) and proceeding in analogy to Preparation BB1, the title compound was obtained, after purification by CC (Combiflash; DCM/MeOH 1:0 to 19:1), as a brown oil (97 mg; 45% yield).

MS3 (ESI, m/z): 344.02 [M+H$^+$]; $t_R$=0.74 min.

Preparation C56: {2-[4-(3-formyl-phenyl)-pyrimidin-2-yloxy]-ethyl}-carbamic acid tert-butyl ester C56.i. 2-chloro-4-(3-[1,3]dioxolan-2-yl-phenyl)-pyrimidine 3-(1,3-dioxolan-2-yl)phenylboronic acid pinacol ester (200 mg; commercial), 2,4-dichloropyrimidine (122 mg; commercial) and Na$_2$CO$_3$ (230 mg) were suspended with a mixture of dioxane/water 1:1 (3.6 mL). Pd(PPh$_3$)$_4$ (83.7 mg) was added and the mixture was degassed with N$_2$ and stirred in the microwave at 100° C. for 20 min. The mixture was partitioned between EA and water, the aq. layer was extracted with EA and the combined org. layers were washed with brine, dried over MgSO$_4$, filtered and concentrated under reduced pressure. The title compound was obtained, after purification by CC (Combiflash; Hept/EA 1:0 to 1:1), as a colourless oil (85 mg; 45% yield).

MS3 (ESI, m/z): 262.99 [M+H$^+$]; $t_R$=0.80 min.

C56.ii. 2-[4-(3-[1,3]dioxolan-2-yl-phenyl)-pyrimidin-2-yloxy]-ethylamine

To a solution of intermediate C56.i (70 mg) and (Boc-amino)ethanolamine (0.084 mL; commercial) in DMF (1.2 mL) at 0° C. was added NaH (32 mg) and the mixture was stirred at rt for 1 day. The title compound was obtained, after purification by prep-HPLC (method 2), as a light yellow oil (49 mg; 64% yield).

MS3 (ESI, m/z): 288.00 [M+H$^+$]; $t_R$=0.54 min.

C56.iii. {2-[4-(3-[1,3]dioxolan-2-yl-phenyl)-pyrimidin-2-yloxy]-ethyl}-carbamic acid tert-butyl ester Intermediate C56.ii (46 mg) and TEA (0.056 mL) were dissolved in water/dioxane 1:3.5 (0.9 mL). Di-tert-butyl dicarbonate (42 mg) was added and the mixture was stirred at rt for 1 day. EA was added and the mixture was washed with water. The aq. layer was extracted with EA. The combined org. layers were dried over MgSO$_4$, filtered and concentrated under reduced pressure. The title compound was obtained as a yellowish oil (62 mg; quant.).

MS3 (ESI, m/z): 388.04 [M+H$^+$]; $t_R$=0.85 min.

C56.iv. {2-[4-(3-formyl-phenyl)-pyrimidin-2-yloxy]-ethyl}-carbamic acid tert-butyl ester Starting from intermediate C56.iii (60 mg) and proceeding in analogy to Preparation A7, step A7.ii, the title compound was obtained as a light yellow oil (53 mg; quant.).

MS3 (ESI, m/z): 344.02 [M+H+]; $t_R$=0.84 min.

Preparation C57: {2-[2-(3-formyl-phenyl)-6-methoxy-pyridin-4-yloxy]-ethyl}-carbamic acid tert-butyl ester C57.i. 2-bromo-6-methoxy-pyridin-4-ol Starting from 2-bromo-6-methoxy-pyridine (0.163 mL; commercial) and proceeding in analogy to Preparation C36, step C36.i, the title compound was obtained, after purification by CC (Combiflash; Hept to Hept/EA 3:1), as a colourless solid (153 mg; 58% yield).

MS3 (ESI, m/z): 203.97 [M+H$^+$]; $t_R$=0.67 min.

C57.ii. [2-(2-bromo-6-methoxy-pyridin-4-yloxy)-ethyl]-carbamic acid tert-butyl ester Starting from intermediate C57.i (100 mg) and N-(Boc)-ethanolamine (0.077 mL; commercial) and proceeding in analogy to Preparation C2, step C2.i, the title compound was obtained, after purification by CC (Combiflash; DCM to DCM/MeOH 4:1), as a colourless oil (144 mg; 85% yield).

MS3 (ESI, m/z): 346.94 [M+H$^+$]; $t_R$=0.89 min.

C57.iii. {2-[2-(3-formyl-phenyl)-6-methoxy-pyridin-4-yloxy]-ethyl}-carbamic acid tert-butyl ester Starting from intermediate C57.ii (70 mg) and 3-formylphenylboronic acid (33 mg; commercial) and proceeding in analogy to Preparation BB1, irradiating however the reaction mixture in the microwave at 110° C. for 45 min, the title compound was obtained as a yellow foam (68 mg; 91% yield).

MS3 (ESI, m/z): 373.02 [M+H⁺]; $t_R$=0.93 min.

Preparation C58: [2-(2'-formyl-6-methoxy-[2,4']
bipyridinyl-4-yloxy)-ethyl]-carbamic acid tert-butyl
ester Starting from intermediate C57.ii (70 mg) and the compound of Preparation BB9 (99 mg; commercial) and proceeding in analogy to Preparation BB1, irradiating however the reaction mixture in the microwave at 110° C. for 45 min, the title compound was obtained as a yellowish solid (35 mg; 46% yield).

MS3 (ESI, m/z): 374.00 [M+H⁺]; $t_R$=0.91 min.

Preparation C59: {2-[6-(3-formyl-phenyl)-pyridin-2-yloxy]-ethyl}-methyl-carbamic acid tert-butyl ester C59.i. {2-[6-(3-[1,3]dioxolan-2-yl-phenyl)-pyridin-2-yloxy]-ethyl}-methyl-carbamic acid tert-butyl ester Starting from the compound of Preparation BB2 (100 mg) and N-Boc-N-methyl-aminoethanol (76 mg; commercial) and proceeding in analogy to Preparation C2, step C2.i, the title compound was obtained, after purification by CC (Combiflash; Hept to Hept/EA 0:1), as a colourless solid (227 mg; quant.).

MS3 (ESI, m/z): 400.99 [M+H⁺]; $t_R$=0.97 min.

C59.ii. {2-[6-(3-formyl-phenyl)-pyridin-2-yloxy]-ethyl}-methyl-carbamic acid tert-butyl ester Starting from intermediate C59.i (220 mg) and proceeding in analogy to Preparation A7, step A7.ii, the title compound was obtained as a light yellow oil (201 mg; quant.).

MS3 (ESI, m/z): 357.03 [M+H⁺]; $t_R$=0.97 min.

Preparation C60: {2-[6-(3-formyl-phenyl)-pyrazin-2-yloxy]-ethyl}-methyl-carbamic acid tert-butyl ester C60.i. {2-[6-(3-[1,3]dioxolan-2-yl-phenyl)-pyrazin-2-yloxy]-ethyl}-methyl-carbamic acid tert-butyl ester Starting from the compound of Preparation BB5 (100 mg) and N-Boc-N-methyl-aminoethanol (76 mg; commercial) and proceeding in analogy to Preparation C2, step C2.i, the title compound was obtained, after purification by CC (Combiflash; Hept to Hept/EA 0:1), as a colourless oil (123 mg; 75% yield).

MS3 (ESI, m/z): 401.88 [M+H⁺]; $t_R$=0.94 min.

C60.ii. {2-[6-(3-formyl-phenyl)-pyrazin-2-yloxy]-ethyl}-methyl-carbamic acid tert-butyl ester Starting from intermediate C60.i (110 mg) and proceeding in analogy to Preparation A7, step A7.ii, the title compound was obtained as a light yellow oil (101 mg; quant.).

MS3 (ESI, m/z): 358.02 [M+H⁺]; $t_R$=0.93 min.

Preparation C61: (2-{6-[2-(formyl)-pyrimidin-4-yl]-pyridin-2-yloxy}-ethyl)-carbamic acid tert-butyl ester C61.i. (E)-2-styrylpyrimidin-4-ol A solution of cinnamyl amidine hydrochloride (9.9 g; commercial) and sodium 3-ethoxy-3-oxoprop-1-en-1-olate (20.1 g, commercial) in water (300 mL) was stirred at rt for 2 days.

The mixture was concentrated under reduced pressure to ⅓ of the original volume and acidified to pH 3 with 1N aq. HCl. The formed yellow precipitate was collected by vacuum filtration, washed with water, ether and dried under vacuum (oil pump). The title compound (7.87 g; 73% yield) was obtained as a light yellow solid.

C61.ii. (E)-4-chloro-2-styrylpyrimidine

A solution of intermediate C61.i (7.860 g) in phosphorus oxychloride (110 mL) was stirred for 3 h at 100° C. The reaction mixture was then cooled and concentrated under reduced pressure. The yellow residue was cautiously poured into ice/water and stirred for 30 min. A yellow oily precipitate was extracted several times with EA, the org. layers were combined, washed with water and brine, dried over Na₂SO₄, filtered and concentrated under reduced pressure. The residue was washed with cold water, then Hex and dried on oil pump. The title compound was obtained as a light yellow solid (5.882 g; 68% yield).

C61.iii. (E)-4-chloro-2-styrylpyrimidine

To a solution of intermediate C61.ii (1.00 g) in dioxane (12.0 mL) under Ar was added Pd(PPh₃)₄ (0.096 g). After 5 min, bis(tri-butyltin) (2.700 g) was added portionwise: first 1.34 mL and then, after heating the mixture for 2 h at 100° C., another 1.0 mL dropwise. The reaction mixture was stirred under Ar at 100° C. for 36 h. The mixture was allowed to cool to rt, filtered over Celite and washed with EA. The solution was washed with brine, dried over Na₂SO₄ and evaporated. To the residue was added ether and the precipitate was filtered off. The ether filtrate was evaporated and the residue was purified by prep-HPLC to give the title compound (0.242 g; 11% yield).

C61.iv. (2-{6-[2-((E)-styryl)-pyrimidin-4-yl]-pyridin-2-yloxy}-ethyl)-carbamic acid tert-butyl ester A glass microwave reaction vessel was charged with intermediate C61.iii (64 mg) and the compound of Preparation BB10 (52 mg) in DMF (2 mL). Ar was bubbled through for 45 min. Tetrakis(triphenylphosphine)palladium (12 mg) and LiCl (anhydrous; 14 mg) were added and the reaction mixture was stirred at 115° C. for 1 day. The mixture was cooled to rt. DMF was evaporated, DCM was added and the mixture was filtered over Celite, washed with 10% MeOH in DCM, and the filtrate was concentrated under reduced pressure. The titled compound was obtained, after purification by CC (EA/Hex 1/7, then 1/4), as a colourless oil (34 mg; 61% yield).

¹H NMR (300 MHz, CDCl₃) δ: 8.82 (d, J=5.1 Hz, 1H); 8.25 (d, J=7.2 Hz, 1H); 8.11-8.06 (m, 2H); 7.79 (t, J=7.8 Hz,

1H); 7.67 (d, J=6.9 Hz, 2H); 7.44-7.30 (m, 4H); 6.89 (d, J=8.4 Hz, 1H); 4.53-4.05 (m, 2H); 3.63-3.58 (m, 2H); 1.45 (s, 9H).

MS4 (ESI, m/z): 419 [M+H$^+$]; $t_R$=7.55 min.

C61.v. (2-{6-[2-(formyl)-pyrimidin-4-yl]-pyridin-2-yloxy}-ethyl)-carbamic acid tert-butyl ester Intermediate C61.iv (35 mg) was dissolved in MeOH/DCM-1:1 (6 mL) and NaHCO$_3$ (32 mg) was added. The reaction mixture was cooled to −78° C. Ozone was passed through for 3 min until a blue solution was produced. Argon was then passed through at −78° C. for 10 min, then Me$_2$S (0.02 mL) was added at −78° C. The reaction mixture was warmed to rt, the solvent was evaporated, DCM was added, NaHCO$_3$ was filtered off and the solvent was evaporated. The product was used in the next step without further purification.

MS4 (ESI, m/z): 345 [M+H$^+$]; $t_R$=2.45 min.

Preparation C62: 3-[5-((R)-1-methyl-pyrrolidin-3-yloxy)-pyridazin-3-yl]-benzaldehyde C62.i. 3-(3-[1,3]dioxolan-2-yl-phenyl)-5-((R)-1-methyl-pyrrolidin-3-yloxy)-pyridazine Starting from the compound of Preparation BB3 (97 mg) and (R)-(−)-1-methyl-3-pyrrolidinol (322 mg; commercial) and proceeding in analogy to Preparation C14, step C14.i, the title compound was obtained as a red oil (199 mg; quant.).

MS1 (ESI, m/z): 328.10 [M+H$^+$]; $t_R$=0.49 min.

C62.ii. 3-[5-((R)-1-methyl-pyrrolidin-3-yloxy)-pyridazin-3-yl]-benzaldehyde

Starting from intermediate C62.i (150 mg) and proceeding in analogy to Preparation A7, step A7.ii, the title compound was obtained as a light brown sticky oil (107 mg; 92% yield).

MS1 (ESI, m/z): 284.19 [M+H$^+$]; $t_R$=0.48 min.

Preparation C63: 3-[6-methoxy-4-((S)-1-methyl-pyrrolidin-3-yloxy)-pyridin-2-yl]-benzaldehyde C63.i. 2-bromo-6-methoxy-4-((S)-1-methyl-pyrrolidin-3-yloxy)-pyridine Starting from intermediate C57.i (220 mg) and (R)-(−)-1-methyl-3-pyrrolidinol (0.13 mL; commercial) and proceeding in analogy to Preparation C2, step C2.i, the title compound was obtained, after purification by CC (Combiflash; DCM to DCM/MeOH 9:1), as a yellow oil (217 mg; 70% yield).

MS3 (ESI, m/z): 288.91 [M+H$^+$]; $t_R$=0.53 min.

C63.ii. 3-[6-methoxy-4-((S)-1-methyl-pyrrolidin-3-yloxy)-pyridin-2-yl]-benzaldehyde Starting from intermediate C63.i (40 mg) and 3-formylphenylboronic acid (22 mg; commercial) and proceeding in analogy to Preparation BB1, irradiating however the reaction mixture in the microwave at 110° C. for 45 min, the title compound was obtained as an orange oil (34 mg; 78% yield).

MS3 (ESI, m/z): 313.02 [M+H$^+$]; $t_R$=0.63 min.

Preparation C64: 3-[6-((R)-1-methyl-pyrrolidin-2-ylmethoxy)-pyridin-2-yl]-benzaldehyde C64.i. 2-(3-[1,3]dioxolan-2-yl-phenyl)-6-((R)-1-methyl-pyrrolidin-2-ylmethoxy)-pyridine Starting from the compound of Preparation BB2 (200 mg) and (R)-1-methyl-2-pyrrolidinemethanol (95 mg; commercial) and proceeding in analogy to Preparation C2, step C2.i, the title compound was obtained, after purification by CC (Combiflash; DCM to DCM/MeOH 19:1), as a light yellow oil (241 mg; 86% yield).

MS3 (ESI, m/z): 341.05 [M+H$^+$]; $t_R$=0.65 min.

C64.ii. 3-[6-((R)-1-methyl-pyrrolidin-2-ylmethoxy)-pyridin-2-yl]-benzaldehyde

Starting from intermediate C64.i (180 mg) and proceeding in analogy to Preparation A7, step A7.ii, the title compound was obtained as a light yellow oil (180 mg; 96% yield).

MS3 (ESI, m/z): 297.02 [M+H$^+$]; $t_R$=0.64 min.

Preparation C65: rac-(2S*,3S*)-3-[6-(3-formyl-phenyl)-pyridin-2-yloxy]-2-methyl-pyrrolidine-1-carboxylic acid tert-butyl ester C65.i. Rac-(2S*,3R*)-3-hydroxy-2-methyl-pyrrolidine-1-carboxylic acid tert-butyl ester Starting from trans-2-methylpyrrolidin-3-ol HCl (400 mg; commercial) and proceeding in analogy to Preparation C56, step C56.iii, the title compound was obtained as a light yellow oil (552 mg; 99% yield).

MS3 (ESI, m/z): 202.15 [M+H$^+$]; $t_R$=0.64 min.

C65.ii. Rac-(2S*,3S*)-3-[6-(3-[1,3]dioxolan-2-yl-phenyl)-pyridin-2-yloxy]-2-methyl-pyrrolidine-1-carboxylic acid tert-butyl ester Starting from the compound of Preparation BB2 (200 mg) and intermediate C65.i (182 mg) and proceeding in analogy to Preparation C2, step C2.i, the title compound was obtained, after purification by CC (Combiflash; Hept to Hept/EA 1:4), as a colourless oil (371 mg; quant.).

MS3 (ESI, m/z): 427.10 [M+H$^+$]; $t_R$=1.00 min.

C65.iii. Rac-(2S*,3S*)-3-[6-(3-formyl-phenyl)-pyridin-2-yloxy]-2-methyl-pyrrolidine-1-carboxylic acid tert-butyl ester Starting from intermediate C65.ii (350 mg) and proceeding in analogy to Preparation A7, step A7.ii, the title compound was obtained as a light yellow oil (247 mg; quant.).

MS3 (ESI, m/z): 383.04 [M+H$^+$]; $t_R$=1.01 min.

Preparation C66: rac-(3S*,4R*)-3-[6-(3-formyl-phenyl)-pyridin-2-yloxy]-4-methyl-pyrrolidine-1-carboxylic acid tert-butyl ester C66.i. Rac-(3R*,4R*)-3-hydroxy-4-methyl-pyrrolidine-1-carboxylic acid tert-butyl ester Starting from cis-4-methylpyrrolidin-3-ol hydrochloride (400 mg; commercial) and proceeding in analogy to Preparation C56, step C56.iii., the title compound was obtained as a light yellow oil (561 mg; quant.).

MS3 (ESI, m/z): 202.14 [M+H$^+$]; $t_R$=0.65 min.

C66.ii. Rac-(3S*,4R*)-3-[6-(3-[1,3]dioxolan-2-yl-phenyl)-pyridin-2-yloxy]-4-methyl-pyrrolidine-1-carboxylic acid tert-butyl ester Starting from the compound of Preparation BB2 (200 mg) and intermediate C66.i (200 mg) and proceeding in analogy to Preparation C2, step C2.i, the title compound was obtained, after purification by CC (Combiflash; Hept to Hept/EA 1:4), as a yellowish oil (327 mg; 93% yield).

MS3 (ESI, m/z): 427.11 [M+H$^+$]; $t_R$=1.01 min.

C66.iii. Rac-(3S*,4R*)-3-[6-(3-formyl-phenyl)-pyridin-2-yloxy]-4-methyl-pyrrolidine-1-carboxylic acid tert-butyl ester Starting from intermediate C66.ii (300 mg) and proceeding in analogy to Preparation A7, step A7.ii, the title compound was obtained as an orange oil (261 mg; quant.).

MS3 (ESI, m/z): 383.03 [M+H$^+$]; $t_R$=1.02 min.

Preparation C67: 3-[5-(1-methyl-azetidin-3-yloxy)-pyridazin-3-yl]-benzaldehyde

C67.i. 3-(3-[1,3]dioxolan-2-yl-phenyl)-5-(1-methyl-azetidin-3-yloxy)-pyridazine Starting from a compound of Preparation BB3. (108 mg) and 1-methyl-azetidin-3-ol (269 mg; commercial) and proceeding in analogy to Preparation C14, step C14.i, the title compound was obtained as an orange sticky oil (166 mg; quant.).

MS1 (ESI, m/z): 314.08 [M+H$^+$]; $t_R$=0.49 min.

C67.ii. 3-[5-(1-methyl-azetidin-3-yloxy)-pyridazin-3-yl]-benzaldehyde

Starting from intermediate C67.i (129 mg) and proceeding in analogy to Preparation A7, step A7.ii, the title compound was obtained as a light brown sticky oil (117 mg; quant.).

MS1 (ESI, m/z): 270.19 [M+H$^+$]; $t_R$=0.46 min.

Preparation C68: 3-[6-((3S,5S)-1,5-dimethyl-pyrrolidin-3-yloxy)-pyridin-2-yl]-benzaldehyde

C68.i. (2S,4S)-4-(6-bromo-pyridin-2-yloxy)-2-methyl-pyrrolidine-1-carboxylic acid tert-butyl ester Starting from 6-bromopyridin-2-ol (150 mg) and (2S,4R)-4-hydroxy-2-methyl-pyrrolidine-1-carboxylic acid tert-butyl ester (165 mg; commercial) and proceeding in analogy to Preparation C2, step C2.i, the title compound was obtained, after purification by CC (Combiflash; Hept to Hept/EA 1:4), as a yellowish oil (238 mg; 81% yield).

MS3 (ESI, m/z): 356.89 [M+H$^+$]; $t_R$=0.98 min.

C68.ii. 2-bromo-6-((3S,5S)-5-methyl-pyrrolidin-3-yloxy)-pyridine

Starting from intermediate C68.i (210 mg) and proceeding in analogy to Preparation C13, step C13.ii, the title compound was obtained without further purification as a yellow oil (146 mg; 97% yield).

MS3 (ESI, m/z): 259.90 [M+H$^+$]; $t_R$=0.55 min.

C68.iii. 2-bromo-6-((3S,5S)-1,5-dimethyl-pyrrolidin-3-yloxy)-pyridine

Starting from intermediate C68.ii (130 mg) and 37% aq. formaldehyde (0.513 mL) and proceeding in analogy to Preparation C13, step C13.iii, the title compound was obtained as a yellow oil (123 mg; 90% yield).

MS3 (ESI, m/z): 270.93 [M+H+]; $t_R$=0.55 min.

C68.iv. 3-[6-((3S,5S)-1,5-dimethyl-pyrrolidin-3-yloxy)-pyridin-2-yl]-benzaldehyde Starting from intermediate C68.iii (115 mg) and 3-formylphenylboronic acid (68 mg; commercial) and proceeding in analogy to Preparation BB1, irradiating however the reaction mixture in the microwave at 110° C. for 45 min, the title compound was obtained as a brown oil (121 mg; 96% yield).

MS3 (ESI, m/z): 297.05 [M+H$^+$]; $t_R$=0.65 min.

Preparation C69: rac-3-[6-((2S*,3S*)-1,2-dimethyl-pyrrolidin-3-yloxy)-pyridin-2-yl]-benzaldehyde

C69.i. Rac-(2S*,3S*)-3-(6-Bromo-pyridin-2-yloxy)-2-methyl-pyrrolidine-1-carboxylic acid tert-butyl ester Starting from 6-bromopyridin-2-ol (150 mg) and intermediate C65.i (165 mg; commercial) and proceeding in analogy to Preparation C2, step C2.i, the title compound was obtained, after purification by CC (Combiflash; DCM to DCM/MeOH 9:1), as a yellowish oil (165 mg; 56% yield).

MS3 (ESI, m/z): 356.89 [M+H$^+$]; $t_R$=0.97 min.

C69.ii. Rac-2-bromo-6-((2S*,3S*)-2-methyl-pyrrolidin-3-yloxy)-pyridine

Starting from intermediate C69.i (150 mg) and proceeding in analogy to Preparation C13, step C13.ii, the title compound was obtained without further purification as a yellow oil (101 mg; 94% yield).

MS3 (ESI, m/z): 258.90 [M+H$^+$]; $t_R$=0.56 min.

C69.iii. Rac-2-bromo-6-((2S*,3S*)-1,2-dimethyl-pyrrolidin-3-yloxy)-pyridine

Starting from intermediate C69.ii (90 mg) and 37% aq. formaldehyde (0.355 mL) and proceeding in analogy to Preparation C13, step C13.iii, the title compound was obtained as a yellow oil (70 mg; 74% yield).

MS3 (ESI, m/z): 270.93 [M+H+]; $t_R$=0.56 min.

C69.iv. Rac-3-[6-((2S*,3S*)-1,2-dimethyl-pyrrolidin-3-yloxy)-pyridin-2-yl]-benzaldehyde Starting from intermediate C69.iii (64 mg) and 3-formylphenylboronic acid (38 mg; commercial) and proceeding in analogy to Preparation BB1, irradiating however the reaction mixture in the microwave at 110° C. for 45 min, the title compound was obtained as a brown oil (69 mg; 99% yield).

MS3 (ESI, m/z): 297.03 [M+H$^+$]; $t_R$=0.65 min.

Preparation C70: rac-3-[6-((3S*,4R*)-1,4-dimethyl-pyrrolidin-3-yloxy)-pyridin-2-yl]-benzaldehyde

C70.i. Rac-(3S*,4R*)-3-(6-bromo-pyridin-2-yloxy)-4-methyl-pyrrolidine-1-carboxylic acid tert-butyl ester Starting from 6-bromopyridin-2-ol (150 mg) and intermediate C66.i (165 mg; commercial) and proceeding in analogy to Preparation C2, step C2.i, the title compound was obtained, after purification by CC (Combiflash; DCM to DCM/MeOH 9:1), as a yellowish oil (139 mg; 48% yield).
MS3 (ESI, m/z): 356.89 [M+H$^+$]; $t_R$=0.98 min.

C70.ii. Rac-2-bromo-6-((3S*,4R*)-4-methyl-pyrrolidin-3-yloxy)-pyridine

Starting from intermediate C70.i (120 mg) and proceeding in analogy to Preparation C13, step C13.ii, the title compound was obtained without further purification as a yellow oil (81 mg; 94% yield).
MS3 (ESI, m/z): 258.92 [M+H$^+$]; $t_R$=0.56 min.

C70.iii. Rac-2-bromo-6-((3S*,4R*)-1,4-dimethyl-pyrrolidin-3-yloxy)-pyridine Starting from intermediate C70.ii (70 mg) and 37% aq. formaldehyde (0.276 mL) and proceeding in analogy to Preparation C13, step C13.iii, the title compound was obtained as a yellow oil (71 mg; 96% yield).
MS3 (ESI, m/z): 270.93 [M+H+]; $t_R$=0.58 min.

C70.iv. Rac-3-[6-((3S*,4R*)-1,4-dimethyl-pyrrolidin-3-yloxy)-pyridin-2-yl]-benzaldehyde Starting from intermediate C70.iii (63 mg) and 3-formylphenylboronic acid (37 mg; commercial) and proceeding in analogy to Preparation BB1, irradiating however the reaction mixture in the microwave at 110° C. for 45 min, the title compound was obtained as a brown oil (54 mg; 78% yield).
MS3 (ESI, m/z): 297.05 [M+H$^+$]; $t_R$=0.66 min.

Preparation C71: (RS)-3-[6-((RS)-1,2-dimethyl-azetidin-3-yloxy)-pyridin-2-yl]-benzaldehyde

C71.i. (RS)-2-((RS)-1,2-dimethyl-azetidin-3-yloxy)-6-(3-[1,3]dioxolan-2-yl-phenyl)-pyridine To a suspension of LiAlH$_4$ (47.4 mg) in THF (0.5 mL) was added a solution of intermediate C35.i (100 mg) in THF (0.8 mL) and the resulting mixture was stirred at 65° C. for 1 h. After cooling to rt, water (0.25 mL), 2M aq. NaOH (0.250 mL), and water (0.750 mL) were added sequentially. The mixture was stirred at rt for 1 h and filtered through a pad of Celite. The filtrate was concentrated under reduced pressure to give the title compound as a light yellow oil (54 mg; 85% yield).
MS3 (ESI, m/z): 327.02 [M+H$^+$]; $t_R$=0.64 min.

C71.ii. (RS)-3-[6-((RS)-1,2-dimethyl-azetidin-3-yloxy)-pyridin-2-yl]-benzaldehyde Starting from intermediate C71.i (47 mg) and proceeding in analogy to Preparation A7, step A7.ii, the title compound was obtained as a light yellow oil (34 mg; 84% yield).
MS1 (ESI, m/z): 283.02 [M+H$^+$]; $t_R$=0.63 min.

Preparation C72: 6-[6-(1-methyl-azetidin-3-yloxy)-pyrazin-2-yl]-pyridine-2-carbaldehyde

C72.i. 2-chloro-6-(6-[1,3]dioxolan-2-yl-pyridin-2-yl)-pyrazine

To a mixture of 2-bromo-6-chloropyrazine (100 mg) and the compound of Preparation BB11 (113 mg) in dioxane (1.2 mL) was added a solution of K$_2$CO$_3$ (143 mg) in water (0.4 mL). The resulting suspension was degassed with N$_2$ for 10 min, tris(dibenzylideneacetone)-dipalladium(0) (23.7 mg) and PCy3 (17.4 mg) were added, the reaction flask was sealed and heated at 85° C. for 1 day. Water and EA were added, the layers were separated and the aq. layer was extracted twice with EA. The combined org. extracts were dried (MgSO$_4$), filtered and concentrated under reduced pressure. The title compound was obtained, after purification by CC (Combiflash; Hept to Hept/EA 1:1), as a yellowish oil (29 mg, 21% yield).
MS3 (ESI, m/z): 263.97 [M+H$^+$]; $t_R$=0.79 min.

C72.ii. 2-(6-[1,3]dioxolan-2-yl-pyridin-2-yl)-6-(1-methyl-azetidin-3-yloxy)-pyrazine Starting from intermediate C72.i (25 mg) and 1-methyl-azetidin-3-ol (65 mg; commercial) and proceeding in analogy to Preparation C14, step C14.i, the title compound was obtained as a yellow oil (28 mg; 94% yield).
MS1 (ESI, m/z): 315.01 [M−H$^+$]; $t_R$=0.51 min.

C72.iii. 6-[6-(1-methyl-azetidin-3-yloxy)-pyrazin-2-yl]-pyridine-2-carbaldehyde Starting from intermediate C72.ii (23 mg) and proceeding in analogy to Preparation A7, step A7.ii, the title compound was obtained as a light yellow solid (17 mg; 86% yield).
MS1 (ESI, m/z): 271.00 [M+H$^+$]; $t_R$=0.51 min.

Preparation C73: tert-butyl (R)-3-((6-(3-formylphenyl)pyridazin-4-yl)oxy)pyrrolidine-1-carboxylate

C73.i. (R)-3-[6-(3-[1,3]dioxolan-2-yl-phenyl)-pyridazin-4-yloxy]-pyrrolidine-1-carboxylic acid tert-butyl ester Starting from the compound of Preparation BB3 (108 mg) and (R)—N-Boc-3-pyrrolidinol (360 mg; commercial) and proceeding in analogy to Preparation C14, step C14.i, the title compound was obtained as a yellow sticky oil (463 mg; quant.).
MS1 (ESI, m/z): 414.19 [M+H$^+$]; $t_R$=0.84 min.

C73.ii. Tert-butyl (R)-3-((6-(3-formylphenyl)pyridazin-4-yl)oxy)pyrrolidine-1-carboxylate Starting from intermediate C73.i (170 mg) and proceeding in analogy to Preparation A7, step A7.ii, the title compound was obtained as a light yellow solid (386 mg; quant.).
MS1 (ESI, m/z): 370.04 [M+H$^+$]; $t_R$=0.86 min.

Preparation C74: (S)-3-[6-(3-formyl-phenyl)-pyridazin-4-yloxy]-pyrrolidine-1-carboxylic acid tert-butyl ester

C74.i. (S)-3-[6-(3-[1,3]dioxolan-2-yl-phenyl)-pyridazin-4-yloxy]-pyrrolidine-1-carboxylic acid tert-butyl ester Starting from compound of Preparation BB3 (108 mg) and (S)—N-Boc-3-pyrrolidinol (360 mg; commercial) and proceeding in analogy to Preparation C14, step C14.i, the title compound was obtained as an orange sticky oil (410 mg; quant.).
MS1 (ESI, m/z): 414.18 [M+H$^+$]; $t_R$=0.84 min.

C74.i. (S)-3-[6-(3-formyl-phenyl)-pyridazin-4-yloxy]-pyrrolidine-1-carboxylic acid tert-butyl ester Starting from intermediate C74.i (170 mg) and proceeding in analogy to Preparation A7, step A7.ii, the title compound was obtained as a light yellow sticky oil (363 mg; quant.).
MS1 (ESI, m/z): 370.03 [M+H$^+$]; $t_R$=0.86 min.

Preparation C75: tert-butyl (S)-2-(((6-(3-formylphenyl)pyridazin-4-yl)oxy)methyl)azetidine-1-carboxylate

C75.i. Tert-butyl (S)-2-(((6-(3-(1,3-dioxolan-2-yl)phenyl)pyridazin-4-yl)oxy)methyl)azetidine-1-carboxylate Starting from compound of Preparation BB3 (108 mg) and (S)-1-(tert-butoxycarbonyl)-2-azetidinemethanol (379 mg; commercial) and proceeding in analogy to Preparation C14, step C14.i, the title compound was obtained as an orange sticky oil (297 mg; quant.).
MS1 (ESI, m/z): 414.19 [M+H$^+$]; $t_R$=0.82 min.

C75.i. Tert-butyl (S)-2-(((6-(3-formylphenyl)pyridazin-4-yl)oxy)methyl)azetidine-1-carboxylate Starting from intermediate C75.i (170 mg) and proceeding in analogy to Preparation A7, step A7.ii, the title compound was obtained as a yellow sticky oil (258 mg; quant.).
MS1 (ESI, m/z): 370.06 [M+H$^+$]; $t_R$=0.84 min.

Preparation C76: 6'-(1-methyl-azetidin-3-yloxy)-[2,2']bipyridinyl-4-carbaldehyde C76.i. 6'-chloro-4-dimethoxymethyl-[2,2']bipyridinyl Starting from 2-bromo-6-chloropyridine (200 mg) and [4-(dimethoxymethyl)pyridin-2-yl]boronic acid (237 mg; commercial) and proceeding in analogy to Preparation BB1, irradiating however the reaction mixture in a microwave oven at 110° C. for 45 min, the title compound was obtained as a colourless oil (56 mg; 20% yield).
MS3 (ESI, m/z): 264.98 [M+H$^+$]; $t_R$=0.81 min.

C76.ii. 4-dimethoxymethyl-6'-(1-methyl-azetidin-3-yloxy)-[2,2']bipyridinyl

Starting from intermediate C76.i (25 mg) and 1-methyl-azetidin-3-ol (43 mg; commercial) and proceeding in analogy to Preparation C14, step C14.i, the title compound was obtained as a yellow oil (29 mg; 97% yield).
MS3 (ESI, m/z): 316.05 [M+H$^+$]; $t_R$=0.52 min.

C76.iii. 6'-(1-methyl-azetidin-3-yloxy)-[2,2']bipyridinyl-4-carbaldehyde

Starting from intermediate C76.ii (33 mg) and proceeding in analogy to Preparation A7, step A7.ii, the title compound was obtained as a yellowish oil (25 mg; quant.).
MS3 (ESI, m/z): 270.01 [M+H$^+$]; $t_R$=0.55 min.

Preparation C77: 6-(1-methyl-azetidin-3-yloxy)-[2,4']bipyridinyl-2'-carbaldehyde

C77.i. 6-chloro-[2,4']bipyridinyl-2'-carbaldehyde

Starting from 2-bromo-6-chloropyridine (150 mg) and the compound of Preparation BB9 (322 mg) and proceeding in analogy to Preparation BB1, irradiating however the reaction mixture in a microwave oven at 110° C. for 45 min, the title compound was obtained as an off-white solid (99 mg; 58% yield).
MS3 (ESI, m/z): 219.03 [M+H$^+$]; $t_R$=0.78 min.

C77.ii. 6-chloro-2'-[1,3]dioxolan-2-yl-[2,4']bipyridinyl

Starting from intermediate C77.i (85 mg) and ethylene glycol (0.044 mL; commercial) and proceeding in analogy to Preparation BB11, step BB11.i, the title compound was obtained as an orange oil (102 mg; quant.).
MS3 (ESI, m/z): 262.99 [M+H$^+$]; $t_R$=0.70 min.

C77.iii. 2'-[1,3]dioxolan-2-yl-6-(1-methyl-azetidin-3-yloxy)-[2,4']bipyridinyl Starting from 1-methyl-azetidin-3-ol (123 mg) and intermediate C77.ii (95 mg) and proceeding in analogy to Preparation C14, step C14.i, the title compound was obtained as a yellow oil (107 mg; quant.).
MS3 (ESI, m/z): 314.03 [M+H$^+$]; $t_R$=0.48 min.

C77.iv. 6-(1-methyl-azetidin-3-yloxy)-[2,4']bipyridinyl-2'-carbaldehyde

Starting from intermediate C77.iii (103 mg) and proceeding in analogy to Preparation A7, step A7.ii, the title compound was obtained as a yellow oil (66 mg; quant.).
MS3 (ESI, m/z): 270.01 [M+H$^+$]; $t_R$=0.53 min.

Preparation C78: 4-[6-(1-methyl-azetidin-3-yloxy)-pyrazin-2-yl]-pyridine-2-carbaldehyde

C78.i. 4-(6-chloro-pyrazin-2-yl)-pyridine-2-carbaldehyde

Starting from 2-bromo-6-chloropyrazine (100 mg) and the compound of Preparation BB9 (214 mg) and proceeding in analogy to Preparation BB1, irradiating however the reaction mixture in a microwave oven at 110° C. for 45 min, the title compound was obtained as a light yellow solid (51 mg; 45% yield).
MS3 (ESI, m/z): 220.01 [M+H$^+$]; $t_R$=0.72 min.

C78.ii. 2-chloro-6-(2-[1,3]dioxolan-2-yl-pyridin-4-yl)-pyrazine

Starting from intermediate C78.i (48 mg) and proceeding in analogy to Preparation BB11, step BB11.i, the title compound was obtained as an orange oil (49 mg; quant.).
MS3 (ESI, m/z): 264.98 [M+H$^+$]; $t_R$=0.68 min.

C78.iii. 2-(2-[1,3]dioxolan-2-yl-pyridin-4-yl)-6-(1-methyl-azetidin-3-yloxy)-pyrazine Starting from 1-methyl-azetidin-3-ol (47 mg) and intermediate C78.ii (45 mg) and proceeding in analogy to Preparation C14, step C14.i, the title compound was obtained as an orange oil (38 mg; quant.).
MS3 (ESI, m/z): 315.01 [M+H$^+$]; $t_R$=0.46 min.

C78.iv. 4-[6-(1-methyl-azetidin-3-yloxy)-pyrazin-2-yl]-pyridine-2-carbaldehyde Starting from intermediate C78.iii (35 mg) and proceeding in analogy to Preparation A7, step A7.ii, the title compound was obtained as a yellow oil (27 mg; quant.).
MS3 (ESI, m/z): 271.01 [M+H$^+$]; $t_R$=0.47 min.

Preparation C79: 6'-(1-methyl-azetidin-3-yloxy)-[2,2']bipyridinyl-6-carbaldehyde

C79.i. 6-chloro-6'-[1,3]dioxolan-2-yl-[2,2]bipyridinyl

Starting from 2-bromo-6-chloropyridine (200 mg) and the compound of Preparation BB11 (273 mg) and proceeding in analogy to Preparation C72, step C72.i, the titled compound was obtained as a light yellow solid (119 mg, 44% yield).
MS3 (ESI, m/z): 262.97 [M+H$^+$]; $t_R$=0.83 min.

C79.ii. 6'-[1,3]dioxolan-2-yl-6-(1-methyl-azetidin-3-yloxy)-[2,2']bipyridinyl Starting from intermediate C79.i (105 mg) and 1-methyl-azetidin-3-ol (181 mg; commercial) and proceeding in analogy to Preparation C14, step C14.i, the title compound was obtained as a light yellow oil (27 mg; 22% yield).
MS3 (ESI, m/z): 314.03 [M+H$^+$]; $t_R$=0.57 min.

C79.iii. 6'-(1-methyl-azetidin-3-yloxy)[2,2']bipyridinyl-6-carbaldehyde

Starting from intermediate C79.ii (24 mg) and proceeding in analogy to Preparation A7, step A7.ii, the title compound was obtained as a light yellow oil (19 mg; 92% yield).
MS3 (ESI, m/z): 270.00 [M+H$^+$]; $t_R$=0.58 min.

Preparation C80: 2-[6-(1-methyl-azetidin-3-yloxy)-pyrazin-2-yl]-pyridine-4-carbaldehyde

C80.i. 2-chloro-6-(4-dimethoxymethyl-pyridin-2-yl)-pyrazine

Starting from 2-bromo-6-chloropyrazine (200 mg; commercial) and [4-(dimethoxymethyl)pyridin-2-yl]boronic acid (229 mg; commercial) and proceeding in analogy to Preparation BB1, irradiating however the reaction mixture in a microwave oven at 110° C. for 45 min, the title compound was obtained as a yellow solid (25 mg; 9% yield).
MS3 (ESI, m/z): 265.96 [M+H$^+$]; $t_R$=0.82 min.

C80.ii. 2-(4-dimethoxymethyl-pyridin-2-yl)-6-(1-methyl-azetidin-3-yloxy)-pyrazine Starting from intermediate C80.i (23 mg) and 1-methyl-azetidin-3-ol (15 mg; commercial) and proceeding in analogy to Preparation C14, step C14.i, the title compound was obtained as a brown oil (19 mg; quant.).
MS3 (ESI, m/z): 317.07 [M+H$^+$]; $t_R$=0.53 min.

C80.iii. 2-[6-(1-methyl-azetidin-3-yloxy)-pyrazin-2-yl]-pyridine-4-carbaldehyde Starting from intermediate C80.ii (17 mg) and proceeding in analogy to Preparation A7, step A7.ii, the title compound was obtained as a brown oil (14 mg; quant.).
MS3 (ESI, m/z): 271.01 [M+H$^+$]; $t_R$=0.50 min.

Preparation C81: 5-[6-(1-methyl-azetidin-3-yloxy)-pyrazin-2-yl]-pyridine-3-carbaldehyde

C81.i. 2-chloro-6-(5-dimethoxymethyl-pyridin-3-yl)-pyrazine

Starting from 2-bromo-6-chloropyrazine (200 mg) and 5-(dimethoxymethyl)pyridine-3-boronic acid (208 mg; commercial) and proceeding in analogy to Preparation BB1, irradiating however the reaction mixture in a microwave oven at 110° C. for 45 min, the title compound was obtained as a yellow solid (220 mg; 83% yield).
MS3 (ESI, m/z): 265.96 [M+H$^+$]; $t_R$=0.71 min.

C81.ii. 2-(5-dimethoxymethyl-pyridin-3-yl)-6-(1-methyl-azetidin-3-yloxy)-pyrazine Starting from intermediate C81.i (195 mg) and 1-methyl-azetidin-3-ol (200 mg; commercial) and proceeding in analogy to Preparation C14, step C14.i, the title compound was obtained as an orange oil (238 mg; quant.).
MS3 (ESI, m/z): 317.04 [M+H$^+$]; $t_R$=0.48 min.

C81.iii. 5-[6-(1-methyl-azetidin-3-yloxy)-pyrazin-2-yl]-pyridine-3-carbaldehyde Starting from intermediate C81.ii (212 mg) and proceeding in analogy to Preparation A7, step A7.ii, the title compound was obtained as a yellow solid (157 mg; 87% yield).
MS3 (ESI, m/z): 271.02 [M+H$^+$]; $t_R$=0.47 min.

Preparation D1: 6-[(S)-5-(2-amino-ethyl)-2-oxo-oxazolidin-3-yl]-4H-pyrido[3,2-b][1,4]oxazin-3-one

D1.i. 3-[(S)-2-oxo-3-(3-oxo-3,4-dihydro-2H-pyrido[3,2-b][1,4]oxazin-6-yl)-oxazolidin-5-yl]-propionic acid A solution of 3-[(S)-2-oxo-3-(3-oxo-3,4-dihydro-2H-pyrido[3,2-b][1,4]oxazin-6-yl)-oxazolidin-5-yl]-propionaldehyde (8.0 g; prepared according to WO 2010/041194) in water (46 mL) and acetone (240 mL) was treated with KMnO$_4$ (9.8 g) and further stirred at rt for 2 h. The reaction mixture was treated with sodium bisulfite (9.0 g), further stirred for 15 min, filtered through a pad of Celite and the volatiles were removed under reduced pressure. The pH of the aq. layer was adjusted to 5 and the solid was collected by filtration. The crude product was dissolved with EA and extracted twice with 0.1M NaOH. The combined aq. layers were washed with EA, acidified (pH 3) with 1M HCl, the precipitate was filtered off, affording 4 g of title compound as a colourless solid. The aq. phase was extracted three times with DCM/MeOH. The combined org. layers were washed with brine, dried over $MgSO_4$ and concentrated under reduced pressure, affording another 670 mg of title compound as a colourless solid (total: 4.67 g; 62% yield).

MS4 (ESI, m/z): 507.9 [M–H$^+$]; $t_R$=0.58 min.

D1.ii. {2-[(S)-2-oxo-3-(3-oxo-3,4-dihydro-2H-pyrido[3,2-b][1,4]oxazin-6-yl)-oxazolidin-5-yl]-ethyl}-carbamic acid benzyl ester A solution of intermediate D1.i (1.60 g), benzyl alcohol (5.39 mL) and TEA (3.8 mL) in DMF (4.8 mL) was heated to 100° C. and treated dropwise with DPPA (1.26 mL) and further stirred at 100° C. for 4 h. The reaction mixture was diluted with EA, sequentially washed with sat. aq. $NH_4Cl$, sat. aq. $NaHCO_3$ and brine, dried over $MgSO_4$, filtered and concentrated to dryness. Water was added and the azeotrope was removed under reduced pressure. The crude product was purified by CC (EA/Hept 2:1), affording an off-white solid (0.8 g; 37% yield).

MS1 (ESI, m/z): 413.4 [M–H$^+$]; $t_R$=0.78 min.

D1.iii. 6-[(S)-5-(2-amino-ethyl)-2-oxo-oxazolidin-3-yl]-4H-pyrido[3,2-b][1,4]oxazin-3-one A solution of intermediate D1.ii (750 mg) in MeOH (30 mL) was hydrogenated over Pd(OH)$_2$/C (121 mg) for 1 h. The catalyst was filtered off and the filtrate was concentrated under reduced pressure, affording an off-white foam (530 mg; 100% yield).

MS1 (ESI, m/z): 279.32 [M–H$^+$]; $t_R$=0.45 min.

Examples of Compounds According to the Invention

Example 1: 6-[(S)-5-(2-{[3'-(2-amino-ethoxy)-biphenyl-3-ylmethyl]-amino}-ethyl)-2-oxo-oxazolidin-3-yl]-4H-pyrido[3,2-b][1,4]oxazin-3-one

1.i. {2-[3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-yloxy]-ethyl}-carbamic acid tert-butyl ester A solution of the compound of Preparation A1 (21.6 mg) and the compound of Preparation D1 (18.5 mg) in DMF/DCM (1:1; 7 mL) was treated with NaBH(OAc)$_3$ (40 mg) and further stirred at rt for 1 day. The residue was partioned between sat. aq. NaHCO$_3$ and EA. The org. layer was separated, washed with brine dried over MgSO$_4$, filtered and concentrated under reduced pressure. The residue was purified by prep-HPLC (method 1), affording a colourless lyophilisate (22 mg; 58% yield).

MS1 (ESI, m/z): 604.16 [M–H$^+$]; $t_R$=0.76 min.

1.ii. 6-[(S)-5-(2-{[3'-(2-amino-ethoxy)-biphenyl-3-ylmethyl]-amino}-ethyl)-2-oxo-oxazolidin-3-yl]-4H-pyrido[3,2-b][1,4]oxazin-3-one A solution of intermediate 1.i (10 mg) in DCM (0.05 mL) was treated with TFA (0.05 mL) and further stirred at rt for 1 h. The solution was concentrated to dryness and the residue was taken up in DCM and treated with NH$_4$OH. The aq. layer was extracted twice with DCM. The combined org. layers were washed with brine and dried over MgSO$_4$, filtered and concentrated under reduced pressure. The residue was purified by prep-HPLC (method 1), affording a colourless lyophilisate (5 mg; 66% yield).

MS1 (ESI, m/z): 504.06 [M–H$^+$]; $t_R$=0.54 min.

Example 2: 6-[(S)-5-(2-{[3'-(2-dimethylamino-ethoxy)-biphenyl-3-ylmethyl]-amino}-ethyl)-2-oxo-oxazolidin-3-yl]-4H-pyrido[3,2-b][1,4]oxazin-3-one Starting from the compound of Preparation A2 (40 mg) and the compound of Preparation D1 (44 mg) and proceeding in analogy to Example 1, step 1.i, the title compound was obtained as an off-white lyophilisate (9 mg; 12% yield).

MS3 (ESI, m/z): 532.12 [M+H$^+$]; $t_R$=0.54 min.

Example 3: 6-[(S)-5-(2-{[3'-(3-amino-propoxy)-biphenyl-3-ylmethyl]-amino}-ethyl)-2-oxo-oxazolidin-3-yl]-4H-pyrido[3,2-b][1,4]oxazin-3-one

3.i. [3-(3'-[1,3]dioxolan-2-yl-biphenyl-3-yloxy)-propyl]-carbamic acid tert-butyl ester A mixture of the compound of Preparation BB1 (100 mg), 3-(Boc-amino)-1-propanol (commercial; 0.082 mL) and PPh$_3$ (162 mg) in THF (4 mL) was treated dropwise with DEAD (40% in toluene; 0.18 mL) and the reaction mixture was further stirred at rt for 2 h. The solution was concentrated under reduced pressure and portioned between EA and water. The aq. layer was extracted with EA and the combined org. layers were washed with brine, dried over MgSO$_4$, filtered and concentrated under reduced pressure. The residue was purified by CC (Combiflash; Hept-EA 1:0 to 0:1), affording a colourless oil (131 mg; 79% yield).

MS2 (ESI, m/z): 400.04 [M+H$^+$]; $t_R$=0.92 min.

3.ii. [3-(3'-formyl-biphenyl-3-yloxy)-propyl]-carbamic acid tert-butyl ester A solution of intermediate 3.i (120 mg) and PTSA (1.5 mg) in acetone (1 mL) was stirred at rt for 1 day. The reaction mixture was filtered and evaporated under reduced pressure, affording a brown oil (115 mg; 100% yield).

MS2 (ESI, m/z): 355.93 [M+H$^+$]; $t_R$=0.91 min.

3.iii. 6-[(S)-5-(2-{[3'-(3-amino-propoxy)-biphenyl-3-ylmethyl]-amino}-ethyl)-2-oxo-oxazolidin-3-yl]-4H-pyrido[3,2-b][1,4]oxazin-3-one Intermediate 3.ii (80 mg) and the compound of Preparation D1 (58 mg) were reacted in analogy to Example 1, step 1.i. The resulting crude tert-butyl (S)-(3-((3'-(((2-(2-oxo-3-(3-oxo-3,4-dihydro-2H-pyrido[3,2-b][1,4]oxazin-6-yl)oxazolidin-5-yl)ethyl)amino)methyl)-[1,1'-biphenyl]-3-yl)oxy)propyl)carbamate intermediate (124 mg) was further reacted with TFA (0.6 mL) in analogy to Example 1, step 1.ii, affording after purification an off-white lyophilisate (11 mg; 10% yield).

MS2 (ESI, m/z): 518.08 [M+H$^+$]; $t_R$=0.46 min.

Example 4: 6-[(S)-5-(2-{[3'-(2-methylamino-ethoxy)-biphenyl-3-ylmethyl]-amino}-ethyl)-2-oxo-oxazolidin-3-yl]-4H-pyrido[3,2-b][1,4]oxazin-3-one The compound of Preparation A3 (30 mg) and the compound of Preparation D1 (22 mg) were reacted in analogy to Example 1, step 1.i. The resulting crude tert-butyl (S)-methyl-(2-((3'-(((2-(2-oxo-3-(3-oxo-3,4-dihydro-2H-pyrido[3,2-b][1,4]oxazin-6-yl)oxazolidin-5-yl)ethyl)amino)methyl)-[1,1'-biphenyl]-3-yl)oxy)ethyl)carbamate (46 mg) was further reacted with TFA (0.23 mL) in analogy to Example 1, step 1.ii, affording after purification an off-white solid (3 mg; 8% yield).
MS2 (ESI, m/z): 518.08 [M+H$^+$]; $t_R$=0.45 min.

Example 5: 6-[(S)-5-(2-{[3'-(4-amino-butoxy)-biphenyl-3-ylmethyl]-amino}-ethyl)-2-oxo-oxazolidin-3-yl]-4H-pyrido[3,2-b][1,4]oxazin-3-one 5.i. Tert-butyl (S)-(4-((3'-(((2-(2-oxo-3-(3-oxo-3,4-dihydro-2H-pyrido[3,2-b][1,4]oxazin-6-yl)oxazolidin-5-yl)ethyl)amino)methyl)-[1,1'-biphenyl]-3-yl)oxy)butyl)carbamate Starting from the compound of Preparation A4 (177 mg) and the compound of Preparation D1 (80 mg) and proceeding in analogy to Example 1, step 1.i, the title compound was obtained as a colourless solid (54 mg; 30% yield).
MS3 (ESI, m/z): 632.03 [M+H$^+$]; $t_R$=0.79 min.

5.ii. 6-[(S)-5-(2-{[3'-(4-Amino-butoxy)-biphenyl-3-ylmethyl]-amino}-ethyl)-2-oxo-oxazolidin-3-yl]-4H-pyrido[3,2-b][1,4]oxazin-3-one Starting from intermediate 5.i (45 mg) and proceeding in analogy to Example 1, step 1.ii, the title compound was obtained as a colourless solid (22 mg; 59% yield).
MS3 (ESI, m/z): 532.10 [M+H$^+$]; $t_R$=0.57 min.

Example 6: 6-((S)-5-(2-(((3'-(((RS)-1-aminopropan-2-yl)oxy)-[1,1'-biphenyl]-3-yl)methyl)amino)ethyl)-2-oxooxazolidin-3-yl)-2H-pyrido[3,2-b][1,4]oxazin-3(4H)-one 6.i. Tert-butyl ((RS)-2-(3'-(((2-((S)-2-oxo-3-(3-oxo-3,4-dihydro-2H-pyrido[3,2-b][1,4]oxazin-6-yl)oxazolidin-5-yl)ethyl)amino)methyl)-[1,1'-biphenyl]-3-yl)oxy)propyl)carbamate Starting from the compound of Preparation A5 (146 mg) and the compound of Preparation D1 (80 mg) and proceeding in analogy to Example 1, step 1.i, the title compound was obtained as an off-white oil (102 mg; 57% yield).
MS3 (ESI, m/z): 618.00 [M+H$^+$]; $t_R$=0.77 min.

6.ii. 6-((S)-5-(2-(((3'-(((RS)-1-aminopropan-2-yl)oxy)-[1,1'-biphenyl]-3-yl)methyl)amino)ethyl)-2-oxooxazolidin-3-yl)-2H-pyrido[3,2-b][1,4]oxazin-3(4H)-one Starting from intermediate 6.i (97 mg) and proceeding in analogy to Example 1, step 1.ii, the title compound was obtained as a colourless solid (51 mg; 63% yield).
MS3 (ESI, m/z): 518.09 [M+H$^+$]; $t_R$=0.56 min.

Example 7: 6-[(S)-5-(2-{[3'-((1R,3R)-3-amino-cyclopentyloxy)-biphenyl-3-ylmethyl]-amino}-ethyl)-2-oxo-oxazolidin-3-yl]-4H-pyrido[3,2-b][1,4]oxazin-3-one 7.i. Tert-butyl ((1R,3R)-3-((3'-(((2-((S)-2-oxo-3-(3-oxo-3,4-dihydro-2H-pyrido[3,2-b][1,4]oxazin-6-yl)oxazolidin-5-yl)ethyl)amino)methyl)-[1,1'-biphenyl]-3-yl)oxy)cyclopentyl)carbamate The title compound can be prepared starting from the compound of Preparation A6 and the compound of Preparation D1 and proceeding in analogy to Example 1, step 1.i.
MS3 (ESI, m/z): 644.01 [M+H$^+$]; $t_R$=0.79 min.

7.ii. 6-[(S)-5-(2-{[3'-((1R,3R)-3-amino-cyclopentyloxy)-biphenyl-3-ylmethyl]-amino}-ethyl)-2-oxo-oxazolidin-3-yl]-4H-pyrido[3,2-b][1,4]oxazin-3-one The title compound can be prepared starting from intermediate 7.i and proceeding in analogy to Example 1, step 1.ii.
MS3 (ESI, m/z): 544.09 [M+H$^+$]; $t_R$=0.57 min.

Example 8: 6-[(S)-5-(2-{3-[6-(2-amino-ethoxy)-pyridin-2-yl]-benzylamino}-ethyl)-2-oxo-oxazolidin-3-yl]-4H-pyrido[3,2-b][1,4]oxazin-3-one 8.i. Tert-butyl (S)-(2-((6-(3-(((2-(2-oxo-3-(3-oxo-3,4-dihydro-2H-pyrido[3,2-b][1,4]oxazin-6-yl)oxazolidin-5-yl)ethyl)amino)methyl)phenyl)pyridin-2-yl)oxy)ethyl)carbamate Starting from the compound of Preparation A7 (98 mg) and the compound of Preparation D1 (80 mg) and proceeding in analogy to Example 1, step 1.i, the title compound (39 mg; 22% yield) was obtained as a colourless solid.
MS3 (ESI, m/z): 604.97 [M+H$^+$]; $t_R$=0.74 min.

8.ii. 6-[(S)-5-(2-{3-[6-(2-amino-ethoxy)-pyridin-2-yl]-benzylamino}-ethyl)-2-oxo-oxazolidin-3-yl]-4H-pyrido[3,2-b][1,4]oxazin-3-one Starting from intermediate 8.i. (33 mg) and proceeding in analogy to Example 1, step 1.ii, the title compound was obtained as a colourless solid (10 mg; 37% yield).
MS3 (ESI, m/z): 505.02 [M+H$^+$]; $t_R$=0.52 min.

Example 9: 6-[(S)-2-oxo-5-(2-{3-[6-(2-pyrrolidin-1-yl-ethoxy)-pyridin-2-yl]-benzylamino}-ethyl)-oxazolidin-3-yl]-4H-pyrido[3,2-b][1,4]oxazin-3-one Starting from the compound of Preparation A8 (85 mg) and the compound of Preparation D1 (80 mg) and proceeding in analogy to Example 1, step 1.i, the title compound was obtained as a colourless solid (102 mg; 63% yield). $^1$H NMR (400 MHz, CDCl$_3$) δ: 8.49-8.59 (m, 1H); 8.25 (s, 1H); 7.86 (d, J=7.5 Hz, 1H); 7.62-7.68 (m, 2H); 7.37-7.46 (m, 3H); 7.26 (d, J=7.5 Hz, 1H); 6.69 (d, J=8.0 Hz, 1H); 4.84 (t, J=5.3 Hz, 2H); 4.68-4.75 (m, 1H); 4.58 (s, 2H); 4.20 (m, 1H); 4.12 (m, 2H); 3.84 (dd, J, =7.0 Hz, J$_2$=10.5 Hz, 1H); 3.45-3.50 (m, 2H); 3.23-3.30 (m, 4H); 3.00-3.12 (m, 2H); 2.18 (m, 2H); 2.04 (m, 4H).
MS3 (ESI, m/z): 559.09 [M+H$^+$]; $t_R$=0.54 min.

Example 10: 6-[(S)-5-(2-{3-[5-(2-dimethylamino-ethoxy)-pyridazin-3-yl]-benzylamino}-ethyl)-2-oxo-oxazolidin-3-yl]-4H-pyrido[3,2-b][1,4]oxazin-3-one Starting from the compound of Preparation A9 (35 mg) and the compound of Preparation D1 (38 mg) and proceeding in analogy to Example 1, step 1.i, the title compound (24 mg; 35% yield) was obtained as a yellowish foam.
$^1$H NMR (500 MHz, CDCl$_3$) δ: 9.13 (s, 1H); 8.28 (s, 1H); 7.79 (m, 2H); 7.47 (t, J=7.5 Hz, 1H); 7.41 (m, 1H); 7.34 (s, 1H); 7.27 (s, 1H); 4.78 (m, 1H); 4.64 (s, 2H); 4.39 (t, J=9.4 Hz, 1H); 4.30 (t, J=5.0 Hz, 2H); 3.94 (m, 3H); 2.95 (m, 1H); 2.84 (m, 3H); 2.39 (s, 6H); 2.15 (dd, J$_1$=6.3 Hz, J$_2$=13.6 Hz, 1H); 1.96 (m, 1H).
MS3 (ESI, m/z): 534.11 [M+H$^+$]; $t_R$=0.48 min.

Example 11: 6-[(S)-5-(2-{3-[5-(2-amino-ethoxy)-pyridin-3-yl]-benzylamino}-ethyl)-2-oxo-oxazolidin-3-yl]-4H-pyrido[3,2-b][1,4]oxazin-3-one

11.i. Tert-butyl (S)-(2-((5-(3-(((2-(2-oxo-3-(3-oxo-3,4-dihydro-2H-pyrido[3,2-b][1,4]oxazin-6-yl)oxazolidin-5-yl)ethyl)amino)methyl)phenyl)pyridin-3-yl)oxy)ethyl)carbamate Starting from the compound of Preparation A10 (90 mg) and the compound of Preparation D1 (38 mg) and proceeding in analogy to Example 1, step 1.i, the title compound was obtained as a yellowish foam (53 mg; 67% yield).

MS3 (ESI, m/z): 604.97 [M+H$^+$]; $t_R$=0.63 min.

11.ii. 6-[(S)-5-(2-{3-[5-(2-amino-ethoxy)-pyridin-3-yl]-benzylamino}-ethyl)-2-oxo-oxazolidin-3-yl]-4H-pyrido[3,2-b][1,4]oxazin-3-one Starting from intermediate 11.i. (45 mg) and proceeding in analogy to Example 1, step 1.ii, the title compound was obtained as a colourless solid (23 mg; 61% yield).

MS3 (ESI, m/z): 505.06 [M+H$^+$]; $t_R$=0.46 min.

Example 12: 6-[(S)-2-oxo-5-(2-{3-[6-(2-piperidin-1-yl-ethoxy)-pyridin-2-yl]-benzylamino}-ethyl)-oxazolidin-3-yl]-4H-pyrido[3,2-b][1,4]oxazin-3-one Starting from the compound of Preparation A11 (30 mg) and the compound of Preparation D1 (28 mg) and proceeding in analogy to Example 1, step 1.i, the title compound was obtained as a beige foam (19 mg; 34% yield).

MS3 (ESI, m/z): 573.05 [M+H$^+$]; $t_R$=0.56 min.

Example 13: 6-[(S)-2-oxo-5-(2-{[3'-(2-piperidin-1-yl-ethoxy)-biphenyl-3-ylmethyl]-amino}-ethyl)-oxazolidin-3-yl]-4H-pyrido[3,2-b][1,4]oxazin-3-one Starting from the compound of Preparation A12 (45 mg) and the compound of Preparation D1 (42 mg) and proceeding in analogy to Example 1, step 1.i, the title compound was obtained as an off-white foam (23 mg; 28% yield).

$^1$H NMR (500 MHz, CDCl$_3$) δ: 7.79 (d, J=8.7 Hz, 1H); 7.53 (s, 1H); 7.48 (m, 1H); 7.40 (t, J=7.6 Hz, 1H); 7.33 (t, J=7.9 Hz, 1H); 7.28 (m, 2H); 7.18 (d, J=7.7 Hz, 1H); 7.12 (s, 1H); 6.88 (dd, J$_1$=2.0 Hz, J$_2$=8.1 Hz, 1H); 4.77 (m, 1H); 4.60 (s, 2H); 4.20 (m, 3H); 3.88 (s, 2H); 3.77 (dd, J$_1$=7.4 Hz, J$_2$=10.2 Hz, 1H); 2.86 (m, 4H); 2.59 (s, 4H); 2.04 (m, 1H); 1.92 (m, 1H); 1.65 (m, 4H); 1.48 (d, J=4.3 Hz, 2H).

MS3 (ESI, m/z): 572.06 [M+H$^+$]; $t_R$=0.57 min.

Example 14: 6-[(S)-5-(2-{[3'-(1-amino-cyclopropylmethoxy)-biphenyl-3-ylmethyl]-amino}-ethyl)-2-oxo-oxazolidin-3-yl]-4H-pyrido[3,2-b][1,4]oxazin-3-one

14.i. {1-[3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-yloxymethyl]-cyclopropyl}-carbamic acid tert-butyl ester Starting from the compound of Preparation A13 (113 mg) and the compound of Preparation D1 (60 mg) and proceeding in analogy to Example 1, step 1.i, the title compound was obtained as an off-white oil (42 mg; 41% yield).

MS3 (ESI, m/z): 630.01 [M+H$^+$]; $t_R$=0.71 min.

14.ii. 6-[(S)-5-(2-{[3'-(1-amino-cyclopropylmethoxy)-biphenyl-3-ylmethyl]-amino}-ethyl)-2-oxo-oxazolidin-3-yl]-4H-pyrido[3,2-b][1,4]oxazin-3-one Starting from intermediate 14.i (39 mg) and proceeding in analogy to Example 1, step 1.ii, the title compound was obtained as a colourless solid (12 mg; 38% yield).

MS3 (ESI, m/z): 529.99 [M+H$^+$]; $t_R$=0.56 min.

Example 15: 6-[(S)-5-(2-{3-[6-(2-amino-ethoxy)-pyrazin-2-yl]-benzylamino}-ethyl)-2-oxo-oxazolidin-3-yl]-4H-pyrido[3,2-b][1,4]oxazin-3-one

15.i. (2-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyrazin-2-yloxy}-ethyl)-carbamic acid tert-butyl ester Starting from the compound of Preparation A14 (25 mg) and the compound of Preparation D1 (21 mg) and proceeding in analogy to Example 1, step 1.i, the title compound was obtained, after purification by CC (Combiflash; gradient DCM to DCM/MeOH 9:1), as a colourless foam (20 mg; 45% yield).

MS3 (ESI, m/z): 606.99 [M+H$^+$]; $t_R$=0.71 min.

15.ii. 6-[(S)-5-(2-{3-[6-(2-amino-ethoxy)-pyrazin-2-yl]-benzylamino}-ethyl)-2-oxo-oxazolidin-3-yl]-4H-pyrido[3,2-b][1,4]oxazin-3-one Starting from intermediate 15.i (15 mg) and proceeding in analogy to Example 1, step 1.ii, the title compound was obtained, after purification by prep-HPLC (method 1), as a beige solid (7 mg; 60% yield).

MS3 (ESI, m/z): 506.03 [M+H+]; $t_R$=0.50 min.

Example 16: 6-[(S)-5-(2-{[6-(2-amino-ethoxy)-[2,4']bipyridinyl-2'-ylmethyl]-amino}-ethyl)-2-oxo-oxazolidin-3-yl]-4H-pyrido[3,2-b][1,4]oxazin-3-one formate

16.i. 6-[(S)-5-(2-amino-ethyl)-2-oxo-oxazolidin-3-yl]-4H-pyrido[3,2-b][1,4]oxazin-3-one Starting from the compound of Preparation A15 (8 mg) and the compound of Preparation D1 (7 mg) and proceeding in analogy to Example 1, step 1.i, the title compound was obtained, after purification by prep-HPLC (method 2), as a colourless solid (9 mg; 66% yield).

MS3 (ESI, m/z): 617.97 [M+H$^+$]; $t_R$=0.78 min.

16.ii. 6-[(S)-5-(2-{[6-(2-amino-ethoxy)-[2,4']bipyridinyl-2'-ylmethyl]-amino}-ethyl)-2-oxo-oxazolidin-3-yl]-4H-pyrido[3,2-b][1,4]oxazin-3-one Starting from intermediate 16.i (9 mg) and proceeding in analogy to Example 1, step 1.ii, the title compound was obtained, after purification by prep-HPLC (method 1), as a light yellow foam (6 mg; 74% yield).

MS3 (ESI, m/z): 506.02 [M+H+]; $t_R$=0.50 min.

Example 17: 6-[(S)-5-(2-{3-[6-((R)-2-amino-propoxy)-pyridin-2-yl]-benzylamino}-ethyl)-2-oxo-oxazolidin-3-yl]-4H-pyrido[3,2-b][1,4]oxazin-3-one 17.i. ((R)-1-methyl-2-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxy}-ethyl)-carbamic acid tert-butyl ester Starting from the compound of Preparation A16 (103 mg) and the compound of Preparation D1 (80 mg) and proceeding in analogy to Example 1, step 1.i, the title compound was obtained, after purification by CC (Combiflash; DCM to DCM/MeOH 4:1). as a colourless solid (15 mg; 8% yield).
MS3 (ESI, m/z): 618.97 [M+H$^+$]; $t_R$=0.75 min.

17.ii. 6-[(S)-5-(2-{3-[6-((R)-2-amino-propoxy)-pyridin-2-yl]-benzylamino}-ethyl)-2-oxo-oxazolidin-3-yl]-4H-pyrido[3,2-b][1,4]oxazin-3-one Starting from intermediate 17.i (15 mg) and proceeding in analogy to Example 1, step 1.ii, the title compound was obtained, after purification by prep-HPLC (method 1), as a colourless solid (3 mg; 21% yield).
MS3 (ESI, m/z): 519.05 [M+H+]; $t_R$=0.53 min.

Example 18: 6-[(S)-5-(2-{3-[6-((S)-2-amino-propoxy)-pyridin-2-yl]-benzylamino}-ethyl)-2-oxo-oxazolidin-3-yl]-4H-pyrido[3,2-b][1,4]oxazin-3-one 18.i. ((S)-1-methyl-2-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxy}-ethyl)-carbamic acid tert-butyl ester Starting from the compound of Preparation A17 (103 mg) and the compound of Preparation D1 (80 mg) and proceeding in analogy to Example 1, step 1.i, the title compound was obtained, after purification by CC (Combiflash; DCM to DCM/MeOH 4:1), as a colourless solid (33 mg; 20% yield).
MS3 (ESI, m/z): 618.96 [M+H$^+$]; $t_R$=0.75 min.

18.ii. 6-[(S)-5-(2-{3-[6-((S)-2-amino-propoxy)-pyridin-2-yl]-benzylamino}-ethyl)-2-oxo-oxazolidin-3-yl]-4H-pyrido[3,2-b][1,4]oxazin-3-one Starting from intermediate 18.i (30 mg) and proceeding in analogy to Example 1, step 1.ii, the title compound was obtained, after purification by prep-HPLC (method 1), as a colourless solid (37 mg; quant.).
MS3 (ESI, m/z): 519.07 [M+H+]; $t_R$=0.53 min.

Example 19: 6-[(S)-5-(2-{3-[2-(2-amino-ethoxy)-pyridin-4-yl]-benzylamino}-ethyl)-2-oxo-oxazolidin-3-yl]-4H-pyrido[3,2-b][1,4]oxazin-3-one formate 19.i. (2-{4-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxy}-ethyl)-carbamic acid tert-butyl ester Starting from the compound of Preparation A18 (112 mg) and the compound of Preparation D1 (80 mg) and proceeding in analogy to Example 1, step 1.i, the title compound (57 mg; 33% yield) was obtained as a colourless solid after purification by CC (Combiflash; DCM to DCM/MeOH 4:1).
MS3 (ESI, m/z): 604.98 [M+H$^+$]; $t_R$=0.68 min.

19.ii. 6-[(S)-5-(2-{3-[2-(2-amino-ethoxy)-pyridin-4-yl]-benzylamino}-ethyl)-2-oxo-oxazolidin-3-yl]-4H-pyrido[3,2-b][1,4]oxazin-3-one formate Starting from intermediate 19.i (57 mg) and proceeding in analogy to Example 1, step 1.ii, the title compound was obtained, after purification by prep-HPLC (method 1), as a colourless solid (28 mg; 53% yield).
MS3 (ESI, m/z): 505.08 [M+H+]; $t_R$=0.51 min.

Example 20: 6-[(S)-5-(2-{3-[6-(5-amino-pentyloxy)-pyridin-2-yl]-benzylamino}-ethyl)-2-oxo-oxazolidin-3-yl]-4H-pyrido[3,2-b][1,4]oxazin-3-one 20.i. (5-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxy}-pentyl)-carbamic acid tert-butyl ester Starting from the compound of Preparation A19 (158 mg) and the compound of Preparation D1 (80 mg) and proceeding in analogy to Example 1, step 1.i, the title compound was obtained, after purification by CC (Combiflash; DCM to DCM/MeOH 4:1), as an off-white foam (70 mg; 38% yield).
MS3 (ESI, m/z): 646.96 [M+H$^+$]; $t_R$=0.79 min.

20.ii. 6-[(S)-5-(2-{3-[6-(5-amino-pentyloxy)-pyridin-2-yl]-benzylamino}-ethyl)-2-oxo-oxazolidin-3-yl]-4H-pyrido[3,2-b][1,4]oxazin-3-one Starting from intermediate 20.i (61 mg) and proceeding in analogy to Example 1, step 1.ii, the title compound was obtained, after purification by prep-HPLC (method 2), as an off-white solid (24 mg; 46% yield).
MS3 (ESI, m/z): 547.08 [M+H+]; $t_R$=0.57 min.

Example 21: 6-[(S)-5-(2-{[3'-(2-amino-ethoxy)-5'-methoxy-biphenyl-3-ylmethyl]-amino}-ethyl)-2-oxo-oxazolidin-3-yl]-4H-pyrido[3,2-b][1,4]oxazin-3-one 21.i. {2-[5-methoxy-3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-yloxy]-ethyl}-carbamic acid tert-butyl ester Starting from the compound of Preparation A20 (178 mg) and the compound of Preparation D1 (80 mg) and proceeding in analogy to Example 1, step 1.i, the title compound was obtained, after purification by CC (Combiflash; DCM to DCM/MeOH 4:1), as an off-white foam (17 mg; 10% yield).
MS3 (ESI, m/z): 633.95 [M+H$^+$]; $t_R$=0.76 min.

21.ii. 6-[(S)-5-(2-{[3'-(2-amino-ethoxy)-5'-methoxy-biphenyl-3-ylmethyl]-amino}-ethyl)-2-oxo-oxazolidin-3-yl]-4H-pyrido[3,2-b][1,4]oxazin-3-one Starting from intermediate 21.i (15 mg) and proceeding in analogy to Example 1, step 1.ii, the title compound was obtained, after purification by prep-HPLC (method 2), as an off-white solid (4 mg; 31% yield).
MS3 (ESI, m/z): 534.05 [M+H+]; $t_R$=0.55 min.

Example 22: 6-[(R)-5-(2-{3-[6-(2-amino-ethoxy)-pyridin-2-yl]-benzylamino}-ethyl)-2-oxo-oxazolidin-3-yl]-4H-benzo[1,4]thiazin-3-one

22.i. (2-{6-[3-({2-[(R)-2-oxo-3-(3-oxo-3,4-dihydro-2H-benzo[1,4]thiazin-6-yl)-oxazolidin-5-yl]-ethyl-amino}-methyl)-phenyl]-pyridin-2-yloxy}-ethyl)-carbamic acid tert-butyl ester Starting from the compound of Preparation A7 (116 mg) and 6-[(5R)-5-(2-aminoethyl)-2-oxo-3-oxazolidinyl]-2H-1,4-benzothiazin-3(4H)-one (84 mg; prepared according to WO 2010/041219) and proceeding in analogy to Example 1, step 1.i, the title compound was obtained, after purification by CC (Combiflash; DCM to DCM/MeOH 4:1), as a colourless oil (41 mg; 23% yield).

MS3 (ESI, m/z): 619.92 [M+H$^+$]; $t_R$=0.75 min.

22.ii. 6-[(R)-5-(2-{3-[6-(2-amino-ethoxy)-pyridin-2-yl]-benzylamino}-ethyl)-2-oxo-oxazolidin-3-yl]-4H-benzo[1,4]thiazin-3-one Starting from intermediate 22.i (35 mg) and proceeding in analogy to Example 1, step 1.ii, the title compound was obtained, after purification by prep-HPLC (method 2), as an off-white solid (14 mg; 47% yield).

MS3 (ESI, m/z): 520.02 [M+H+]; $t_R$=0.53 min.

Example 23: 6-[(S)-5-(2-{3-[6-(2-morpholin-4-yl-ethoxy)-pyridin-2-yl]-benzylamino}-ethyl)-2-oxo-oxazolidin-3-yl]-4H-pyrido[3,2-b][1,4]oxazin-3-one Starting from the compound of Preparation A21 (150 mg) and the compound of Preparation D1 (80 mg) and proceeding in analogy to Example 1, step 1.i, the title compound was obtained, after purification by CC (Combiflash; DCM to DCM/MeOH 4:1), as a colourless oil (138 mg; 84% yield).

MS3 (ESI, m/z): 575.02 [M+H$^+$]; $t_R$=0.52 min.

Example $101: 6-[(S)-5-(2-{[3'-((S)-1-azetidin-2-ylmethoxy)-biphenyl-3-ylmethyl]-amino}-ethyl)-2-oxo-oxazolidin-3-yl]-4H-pyrido[3,2-b][1,4]oxazin-3-one A solution of the compound of Preparation C1 (80 mg) and the compound of Preparation D1 (56 mg) in DMF/DCM (1:4; 2.5 mL) was treated with NaBH(OAc)$_3$ (125 mg) and further stirred at rt for 1 day. The residue was partioned between sat. aq. NaHCO$_3$ and EA. The org. layer was separated, washed with brine dried over MgSO$_4$, filtered and concentrated under reduced pressure. The residue was dissolved in DCM (0.5 mL) and treated with TFA (0.58 mL) and further stirred at rt for 1 h. The solution was concentrated to dryness and the residue was taken up in DCM and treated with NH$_4$OH. The aq. layer was extracted twice with DCM. The combined org. layers were washed with brine and dried over MgSO$_4$, filtered and concentrated under reduced pressure. The residue was purified by prep-HPLC (method 1), affording a colourless solid (3 mg; 8% yield).

MS2 (ESI, m/z): 529.95 [M+H$^+$]; $t_R$=0.45 min

Example $102: 6-((S)-2-oxo-5-(2-(((3'-(((S)-pyrrolidin-2-yl)methoxy)-[1,1'-biphenyl]-3-yl)methyl)amino)ethyl)oxazolidin-3-yl)-2H-pyrido[3,2-b][1,4]oxazin-3(4H)-one

$102.i. Tert-butyl 2-(((3'-(((2-((S)-2-oxo-3-(3-oxo-3,4-dihydro-2H-pyrido[3,2-b][1,4]oxazin-6-yl)oxazolidin-5-yl)ethyl)amino)methyl)-[1,1'-biphenyl]-3-yl)oxy)methyl)pyrrolidine-1-carboxylate A solution of the compound of Preparation C2 (229 mg) and the compound of Preparation D1 (100 mg) in DMF/DCM (1:4; 4.3 mL) was treated with NaBH(OAc)$_3$ (229 mg) and further stirred at rt for 1 day. The residue was diluted with DCM (5 mL), washed several times with water and brine, dried over MgSO$_4$, filtered, concentrated under reduced pressure and purified by CC (Combiflash; DCM to DCM/MeOH 4:1), affording a colourless solid (65 mg; 28% yield).

MS2 (ESI, m/z): 644.02 [M−H$^+$]; $t_R$=0.76 min.

$102.ii. 6-((S)-2-oxo-5-(2-(((3'-(((S)-pyrrolidin-2-yl)methoxy)-[1,1'-biphenyl]-3-yl)methyl)amino)ethyl)oxazolidin-3-yl)-2H-pyrido[3,2-b][1,4]oxazin-3(4H)-one A solution of intermediate $102.i (60 mg) in DCM (0.25 mL) was treated with TFA (0.29 mL) and further stirred at rt for 1 h. The reaction mixture was evaporated to dryness, diluted with DCM and washed with aq sat. NaHCO$_3$ solution, water and brine, dried over MgSO$_4$, filtered, concentrated under reduced pressure and purified by prep-HPLC (method 1), affording a colourless solid (24 mg; 47% yield).

MS2 (ESI, m/z): 544.09 [M−H$^+$]; $t_R$=0.46 min.

Example $103: 6-[(S)-2-oxo-5-(2-{[3'-((RS)-pyrrolidin-3-yloxy)-biphenyl-3-ylmethyl]-amino}-ethyl)-oxazolidin-3-yl]-4H-pyrido[3,2-b][1,4]oxazin-3-one

$103.i. Tert-butyl (RS)-3-((3'-(((2-((S)-2-oxo-3-(3-oxo-3,4-dihydro-2H-pyrido[3,2-b][1,4]oxazin-6-yl)oxazolidin-5-yl)ethyl)amino)methyl)-[1,1'-biphenyl]-3-yl)oxy)pyrrolidine-1-carboxylate Starting from the compound of Preparation C3 (176 mg) and the compound of Preparation D1 (80 mg) and proceeding in analogy to Example $102, step $102.i, the title compound was obtained as a colourless solid (39 mg; 22% yield).

MS2 (ESI, m/z): 630.01 [M−H$^+$]; $t_R$=0.73 min.

$103.ii. 6-[(S)-2-oxo-5-(2-{[3'-((RS)-pyrrolidin-3-yloxy)-biphenyl-3-ylmethyl]-amino}-ethyl)-oxazolidin-3-yl]-4H-pyrido[3,2-b][1,4]oxazin-3-one Starting from intermediate $103.i. (35 mg) and proceeding in analogy to Example $102, step $102.ii, the title compound was obtained as a colourless solid (13 mg; 45% yield).

MS2 (ESI, m/z): 529.95 [M+H$^+$]; $t_R$=0.47 min.

Example $104: 6-[(S)-5-(2-{[3'-((S)-1-methyl-azetidin-2-ylmethoxy)-biphenyl-3-ylmethyl]-amino}-ethyl)-2-oxo-oxazolidin-3-yl]-4H-pyrido[3,2-b][1,4]oxazin-3-one Starting from the compound of Preparation C4 (35 mg) and the compound of Preparation D1 (34 mg) and proceeding in analogy to Example S102, step S102.i, the title compound was obtained as an off-white foam (65 mg; 96% yield).

$^1$H NMR (CDCl$_3$) δ: 8.49-8.57 (m, 1H); 7.68-7.71 (m, 2H); 7.37-7.46 (m, 3H); 7.21-7.28 (m, 3H); 7.10-7.13 (m, 1H); 6.83-6.86 (m, 1H); 4.63 (m, 1H); 4.56 (m, 2H); 4.50 (m, 1H); 4.29 (m, 1H); 4.18 (m, 2H); 4.06 (m, 3H); 3.57 (m, 1H); 3.45-3.59 (m, 1H); 2.98-3.08 (m, 2H); 2.79-2.81 (m, 3H); 2.56-2.61 (m, 1H); 2.38-2.45 (m, 1H).

MS3 (ESI, m/z): 544.07 [M+H$^+$]; t$_R$=0.56 min.

Example S105: 6-[(S)-5-(2-{[3'-(azetidin-3-yloxy)-biphenyl-3-ylmethyl]-amino}-ethyl)-2-oxo-oxazolidin-3-yl]-4H-pyrido[3,2-b][1,4]oxazin-3-one

S105.i. Tert-butyl (S)-3-((3'-(((2-(2-oxo-3-(3-oxo-3,4-dihydro-2H-pyrido[3,2-b][1,4]oxazin-6-yl)oxazolidin-5-yl)ethyl)amino)methyl)-[1,1'-biphenyl]-3-yl)oxy)azetidine-1-carboxylate Starting from the compound of Preparation C5 (66 mg) and the compound of Preparation D1 (52 mg) and proceeding in analogy to Example S102, step S102.i, the title compound was obtained as a colourless oil (52 mg; 45% yield).

MS3 (ESI, m/z): 616.00 [M+H$^+$]; t$_R$=0.78 min.

S105.ii. 6-[(S)-5-(2-{[3'-(azetidin-3-yloxy)-biphenyl-3-ylmethyl]-amino}-ethyl)-2-oxo-oxazolidin-3-yl]-4H-pyrido[3,2-b][1,4]oxazin-3-one Starting from intermediate S105.i (48 mg) and proceeding in analogy to Example S102, step S102.ii, the title compound was obtained as a colourless solid (10 mg; 25% yield).

MS3 (ESI, m/z): 516.09 [M+H$^+$]; t$_R$=0.53 min.

Example S106: 6-[(S)-5-(2-{3-[6-(azetidin-3-ylmethoxy)-pyridin-2-yl]-benzylamino}-ethyl)-2-oxo-oxazolidin-3-yl]-4H-pyrido[3,2-b][1,4]oxazin-3-one

S106.i. Tert-butyl (S)-3-(((6-(3-(((2-(2-oxo-3-(3-oxo-3,4-dihydro-2H-pyrido[3,2-b][1,4]oxazin-6-yl)oxazolidin-5-yl)ethyl)amino)methyl)phenyl)pyridin-2-yl)oxy)methyl)azetidine-1-carboxylate Starting from the compound of Preparation C6 (40 mg) and the compound of Preparation D1 (32 mg) and proceeding in analogy to Example S102, step S102.i, the title compound was obtained as a light yellow oil (41 mg; 60% yield).

MS3 (ESI, m/z): 630.97 [M+H$^+$]; t$_R$=0.77 min.

S106.ii. 6-[(S)-5-(2-{3-[6-(azetidin-3-ylmethoxy)-pyridin-2-yl]-benzylamino}-ethyl)-2-oxo-oxazolidin-3-yl]-4H-pyrido[3,2-b][1,4]oxazin-3-one Starting from intermediate S106.i (35 mg) and proceeding in analogy to Example S102, step S102.ii, the title compound was obtained as a yellow foam (23 mg; 78% yield).

MS3 (ESI, m/z): 531.06 [M+H$^+$]; t$_R$=0.53 min.

Example S107: 6-[(S)-5-(2-{3-[6-(azetidin-3-yloxy)-pyridin-2-yl]-benzylamino}-ethyl)-2-oxo-oxazolidin-3-yl]-4H-pyrido[3,2-b][1,4]oxazin-3-one

S107.i. 3-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxy}-azetidine-1-carboxylic acid tert-butyl ester Starting from the compound of Preparation C7 (35 mg) and the compound of Preparation D1 (29 mg) and proceeding in analogy to Example S102, step S102.i, the title compound was obtained, after purification by CC (Combiflash; gradient DCM to DCM/MeOH 9:1), as a colourless foam (150 mg; 25% yield).

MS3 (ESI, m/z): 617.97 [M+H$^+$]; t$_R$=0.78 min.

S107.ii. 6-[(S)-5-(2-{3-[6-(azetidin-3-yloxy)-pyridin-2-yl]-benzylamino}-ethyl)-2-oxo-oxazolidin-3-yl]-4H-pyrido[3,2-b][1,4]oxazin-3-one Starting from intermediate S107.i (12 mg) and proceeding in analogy to Example S102, step S102.ii, the title compound was obtained, after purification by prep-HPLC (method 2), as an orange foam (4 mg; 41% yield).

MS3 (ESI, m/z): 517.06 [M+H+]; t$_R$=0.53 min.

Example S108: 6-[(S)-5-(2-{3-[6-((S)-1-azetidin-2-ylmethoxy)-pyridin-2-yl]-benzylamino}-ethyl)-2-oxo-oxazolidin-3-yl]-4H-pyrido[3,2-b][1,4]oxazin-3-one formate

S108.i. (S)-2-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxymethyl}-azetidine-1-carboxylic acid tert-butyl ester Starting from the compound of Preparation C8 (163 mg) and the compound of Preparation D1 (80 mg) and proceeding in analogy to Example S102, step S102.i, the title compound was obtained, after purification by CC (Combiflash; gradient DCM to DCM/MeOH 4:1), as a colourless foam (115 mg; 63% yield).

MS3 (ESI, m/z): 630.94 [M+H$^+$]; t$_R$=0.77 min.

S108.ii. 6-[(S)-5-(2-{3-[6-((S)-1-azetidin-2-ylmethoxy)-pyridin-2-yl]-benzylamino}-ethyl)-2-oxo-oxazolidin-3-yl]-4H-pyrido[3,2-b][1,4]oxazin-3-one formate Starting from intermediate S108.i (114 mg) and proceeding in analogy to Example S102, step S102.ii, the title compound was obtained, after purification by prep-HPLC (method 1), as a colourless solid (75 mg; 72% yield).

MS3 (ESI, m/z): 531.08 [M+H+]; t$_R$=0.53 min.

Example S109: 6-[(S)-5-(2-{3-[6-((RS)-1-morpholin-2-ylmethoxy)-pyridin-2-yl]-benzylamino}-ethyl)-2-oxo-oxazolidin-3-yl]-4H-pyrido[3,2-b][1,4]oxazin-3-one formate

S109.i. (RS)-2-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxymethyl}-morpholine-4-carboxylic acid tert-butyl ester Starting from the compound of Preparation C9 (153 mg) and the compound of Preparation D1 (80 mg) and proceeding in analogy to Example $102, step $102.i, the title compound was obtained, after purification by CC (Combiflash; gradient DCM to DCM/MeOH 4:1), as a colourless solid (75 mg; 39% yield).

MS3 (ESI, m/z): 660.92 [M+H$^+$]; $t_R$=0.76 min.

$109.ii. 6-[(S)-5-(2-{3-[6-((RS)-1-morpholin-2-ylmethoxy)-pyridin-2-yl]-benzylamino}-ethyl)-2-oxo-oxazolidin-3-yl]-4H-pyrido[3,2-b][1,4]oxazin-3-one formate Starting from intermediate $109.i (73 mg) and proceeding in analogy to Example $102, step $102.ii, the title compound was obtained, after purification by prep-HPLC (method 1), as a colourless solid (46 mg; 68% yield).

$^1$H NMR (500 MHz, CDCl$_3$) δ: 8.12 (s, 1H); 7.87 (d, J=7.8 Hz, 1H); 7.73 (d, J=8.7 Hz, 1H); 7.65-7.69 (m, 1H); 7.43-7.49 (m, 1H); 7.35-7.39 (m, 2H); 7.26-7.31 (m, 1H); 6.78 (d, J=8.2 Hz, 1H); 4.74-4.79 (m, 1H); 4.57-4.63 (m, 3H); 4.44 (m, 1H); 4.16-4.25 (m, 2H); 3.99-4.11 (m, 3H); 3.82-3.86 (m, 2H); 3.36-3.39 (m, 1H); 2.99-3.08 (m, 4H); 2.83-2.88 (m, 1H); 2.11-2.16 (m, 2H).

MS3 (ESI, m/z): 560.93 [M+H+]; $t_R$=0.53 min.

Example $110: 6-[(S)-5-(2-{3-[6-((RS)-1-morpholin-3-ylmethoxy)-pyridin-2-yl]-benzylamino}-ethyl)-2-oxo-oxazolidin-3-yl]-4H-pyrido[3,2-b][1,4]oxazin-3-one formate $110.i. (R)-3-{6-[3-({2-[(RS)-2-Oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxymethyl}-morpholine-4-carboxylic acid tert-butyl ester Starting from the compound of Preparation C10 (133 mg) and the compound of Preparation D1 (80 mg) and proceeding in analogy to Example $102, step $102.i, the title compound was obtained, after purification by CC (Combiflash; gradient DCM to DCM/MeOH 4:1), as a colourless solid (72 mg; 38% yield).

MS3 (ESI, m/z): 660.92 [M+H$^+$]; $t_R$=0.75 min.

$110.ii. 6-[(S)-5-(2-{3-[6-((RS)-1-Morpholin-3-ylmethoxy)-pyridin-2-yl]-benzylamino}-ethyl)-2-oxo-oxazolidin-3-yl]-4H-pyrido[3,2-b][1,4]oxazin-3-one formate Starting from intermediate $110.i (71 mg) and proceeding in analogy to Example $102, step $102.ii, the title compound was obtained, after purification by prep-HPLC (method 1), as a colourless solid (36 mg; 56% yield).

MS3 (ESI, m/z): 560.94 [M+H+]; $t_R$=0.53 min.

Example $111: 6-[(S)-2-oxo-5-(2-{3-[6-((RS)-piperidin-3-yloxy)-pyridin-2-yl]-benzylamino}-ethyl)-oxazolidin-3-yl]-4H-pyrido[3,2-b][1,4]oxazin-3-one formate $111.i. (RS)-3-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxy}-piperidine-1-carboxylic acid tert-butyl ester Starting from the compound of Preparation C11 (183 mg) and the compound of Preparation D1 (80 mg) and proceeding in analogy to Example $102, step $102.i, the title compound was obtained, after purification by CC (Combiflash; gradient DCM to DCM/MeOH 4:1), as a colourless solid (38 mg; 20% yield).

MS3 (ESI, m/z): 644.97 [M+H$^+$]; $t_R$=0.78 min.

$111.ii. 6-[(S)-2-oxo-5-(2-{3-[6-((RS)-piperidin-3-yloxy)-pyridin-2-yl]-benzylamino}-ethyl)-oxazolidin-3-yl]-4H-pyrido[3,2-b][1,4]oxazin-3-one formate Starting from intermediate $111.i (37 mg) and proceeding in analogy to Example $102, step $102.ii, the title compound was obtained, after purification by prep-HPLC (method 1), as a colourless solid (17 mg; 50% yield).

MS3 (ESI, m/z): 544.99 [M+H+]; $t_R$=0.54 min.

Example $112: (3S*,4S*)-6-[(S)-5-(2-{3-[6-(4-methoxy-pyrrolidin-3-yloxy)-pyridin-2-yl]-benzylamino}-ethyl)-2-oxo-oxazolidin-3-yl]-4H-pyrido[3,2-b][1,4]oxazin-3-one $112.i. (3S*,4S*)-3-methoxy-4-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxy}-pyrrolidine-1-carboxylic acid tert-butyl ester This compound can be prepared starting from cis-4-methoxy-3-pyrrolidinol hydrochloride and the compound of Preparation D1 and proceeding successively in analogy to Preparation C12 (all 3 steps) and Example $102, step $102.i.

$112.ii. (3S*,4S*)-6-[(S)-5-(2-{3-[6-(4-methoxy-pyrrolidin-3-yloxy)-pyridin-2-yl]-benzylamino}-ethyl)-2-oxo-oxazolidin-3-yl]-4H-pyrido[3,2-b][1,4]oxazin-3-one This compound can be prepared starting from intermediate $112.i and proceeding in analogy to Example $102, step $102.ii.

Example $113: 6-[(S)-5-(2-{3-[6-(1-methyl-azetidin-3-ylmethoxy)-pyridin-2-yl]-benzylamino}-ethyl)-2-oxo-oxazolidin-3-yl]-4H-pyrido[3,2-b][1,4]oxazin-3-one Starting from the compound of Preparation C13 (35 mg) and the compound of Preparation D1 (36 mg) and proceeding in analogy to Example $102, step $102.i, however using a 1/1 DCM/MeOH mixture as solvent, the title compound was obtained as an off-white foam (32 mg; 47% yield).

MS3 (ESI, m/z): 544.97 [M+H$^+$]; $t_R$=0.55 min.

Example $114: 6-[(S)-5-(2-{3-[5-(azetidin-3-yloxy)-pyridazin-3-yl]-benzylamino}-ethyl)-2-oxo-oxazolidin-3-yl]-4H-pyrido[3,2-b][1,4]oxazin-3-one $114.i. 3-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridazin-4-yloxy}-azetidine-1-carboxylic acid tert-butyl ester Starting from the compound of Preparation C14 (64 mg) and the compound of Preparation D1 (50 mg) and proceeding in analogy to Example 1, step 1.i, the title compound was obtained as a colourless solid (73 mg; 65% yield).

MS1 (ESI, m/z): 618.03 [M+H$^+$]; $t_R$=0.70 min.

$114.ii. 6-[(S)-5-(2-{3-[5-(azetidin-3-yloxy)-pyridazin-3-yl]-benzylamino}-ethyl)-2-oxo-oxazolidin-3-yl]-4H-pyrido[3,2-b][1,4]oxazin-3-one To a solution of intermediate $114.i (73 mg) in DCM (3.6 mL) was added 4.0M HCl in dioxane (0.29 mL) at 0° C. and further stirred at rt for 1.5 h. The reaction mixture was evaporated to dryness and purified by prep-HPLC (method 3), affording a colourless solid (40 mg; 66% yield).
MS1 (ESI, m/z): 517.96 [M+H$^+$]; $t_R$=0.48 min.

Example $115: 6-[(S)-2-oxo-5-(2-{3-[4-((R)-pyrrolidin-3-yloxy)-pyrimidin-2-yl]-benzylamino}-ethyl)-oxazolidin-3-yl]-4H-pyrido[3,2-b][1,4]oxazin-3-one $115.i. (R)-3-{2-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyrimidin-4-yloxy}-pyrrolidine-1-carboxylic acid tert-butyl ester Starting from the compound of Preparation C15 (142 mg) and the compound of Preparation D1 (80 mg) and proceeding in analogy to Example 1, step 1.i, however using a 3/1 DCM/MeOH mixture as solvent, the title compound was obtained as a colourless solid (98 mg; 54% yield).
MS3 (ESI, m/z): 631.94 [M+H$^+$]; $t_R$=0.71 min.

$115.ii. 6-[(S)-2-oxo-5-(2-{3-[4-((R)-pyrrolidin-3-yloxy)-pyrimidin-2-yl]-benzylamino}-ethyl)-oxazolidin-3-yl]-4H-pyrido[3,2-b][1,4]oxazin-3-one Starting from intermediate $115.i (90 mg) and proceeding in analogy to Example $102, step $102.ii, the title compound was obtained, after purification by prep-HPLC (method 2), as a colourless solid (30 mg; 40% yield).
$^1$H NMR (500 MHz, CDCl$_3$) δ: 8.54 (m, 1H); 8.06 (m, 1H); 7.94 (m, 1H); 7.75 (m, 1H); 7.47 (m, 2H); 7.39 (m, 1H); 7.28 (m, 1H); 5.62 (m, 1H); 4.78 (m, 1H); 4.61 (m, 2H); 4.24 (m, 1H); 3.90 (m, 2H); 3.79 (m, 1H); 3.24 (m, 3H); 3.01 (m, 1H); 2.86 (m, 2H); 2.20 (m, 3H); 1.99 (m, 2H).
MS3 (ESI, m/z): 532.06 [M+H$^+$]; $t_R$=0.49 min.

Example $116: 6-[(S)-2-oxo-5-(2-{3-[6-((R)-pyrrolidin-3-yloxy)-pyrimidin-4-yl]-benzylamino}-ethyl)-oxazolidin-3-yl]-4H-pyrido[3,2-b][1,4]oxazin-3-one $116.i. (R)-3-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyrimidin-4-yloxy}-pyrrolidine-1-carboxylic acid tert-butyl ester Starting from the compound of Preparation C16 (150 mg) and the compound of Preparation D1 (102 mg) and proceeding in analogy to Example 1, step 1.i, however using a 3/1 DCM/MeOH mixture as solvent, the title compound was obtained, after purification by CC (Combiflash; DCM to DCM/MeOH 4:1), as a colourless solid (198 mg; 86% yield).
MS3 (ESI, m/z): 631.95 [M+H$^+$]; $t_R$=0.72 min.

$116.ii. 6-[(S)-2-oxo-5-(2-{3-[6-((R)-pyrrolidin-3-yloxy)-pyrimidin-4-yl]-benzylamino}-ethyl)-oxazolidin-3-yl]-4H-pyrido[3,2-b][1,4]oxazin-3-one Starting from intermediate $116.i (190 mg) and proceeding in analogy to Example $102, step $102.ii, the title compound was obtained, after purification by prep-HPLC (method 2), as a colourless solid (77 mg; 48% yield).
MS3 (ESI, m/z): 532.02 [M+H$^+$]; $t_R$=0.49 min.

Example $117: 6-{(S)-5-[2-({3'-[2-((1R*,5S*,6RS)-6-amino-3-aza-bicyclo[3.1.0]hex-3-yl)-ethoxy]-biphenyl-3-ylmethyl}-amino)-ethyl]-2-oxo-oxazolidin-3-yl}-4H-pyrido[3,2-b][1,4]oxazin-3-one $117.i. ((1R*,5S*,6RS)-3-{2-[3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-yloxy]-ethyl}-3-aza-bicyclo[3.1.0]hex-6-yl)-carbamic acid tert-butyl ester Starting from the compound of Preparation C17 (60 mg) and the compound of Preparation D1 (40 mg) and proceeding in analogy to Example 1, step 1.i, however using a 2/1 DCM/MeOH mixture as solvent, the title compound was obtained, after purification by CC (Combiflash; DCM to DCM/MeOH 4:1), as a colourless oil (54 mg; 56% yield).
MS3 (ESI, m/z): 684.99 [M+H$^+$]; $t_R$=0.61 min.

$117.ii. 6-{(S)-5-[2-({3'-[2-((1R*,5S*,6RS)-6-amino-3-aza-bicyclo[3.1.0]hex-3-yl)-ethoxy]-biphenyl-3-ylmethyl}-amino)-ethyl]-2-oxo-oxazolidin-3-yl}-4H-pyrido[3,2-b][1,4]oxazin-3-one Starting from intermediate $117.i (49 mg) and proceeding in analogy to Example $102, step $102.ii, the title compound was obtained, after purification by prep-HPLC (method 2), as a colourless solid (14 mg; 33% yield).
MS3 (ESI, m/z): 585.05 [M+H$^+$]; $t_R$=0.48 min.

Example $118: 6-[(S)-2-oxo-5-(2-{3-[6-((R)-pyrrolidin-3-yloxy)-pyridin-2-yl]-benzylamino}-ethyl)-oxazolidin-3-yl]-4H-pyrido[3,2-b][1,4]oxazin-3-one $118.i. (R)-3-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxy}-pyrrolidine-1-carboxylic acid tert-butyl ester Starting from the compound of Preparation C18 (396 mg) and the compound of Preparation D1 (94 mg) and proceeding in analogy to Example $102, step $102.i, however using a 1/1 DCM/MeOH mixture as solvent, the title compound was obtained as a light yellow solid (133 mg; 65% yield).
MS3 (ESI, m/z): 631.15 [M+H$^+$]; $t_R$=0.76 min.

$118.ii. 6-[(S)-2-oxo-5-(2-{3-[6-((R)-pyrrolidin-3-yloxy)-pyridin-2-yl]-benzylamino}-ethyl)-oxazolidin-3-yl]-4H-pyrido[3,2-b][1,4]oxazin-3-one Starting from intermediate $118.i (115 mg) and proceeding in analogy to Example $102, step $102.ii, the title compound was obtained, after purification by prep-HPLC (method 2), as a colourless solid (42 mg; 43% yield).
MS3 (ESI, m/z): 531.13 [M+H$^+$]; $t_R$=0.55 min.

Example $119: 6-[(S)-2-oxo-5-(2-{3-[6-((S)-pyrrolidin-3-yloxy)-pyridin-2-yl]-benzylamino}-ethyl)-oxazolidin-3-yl]-4H-pyrido[3,2-b][1,4]oxazin-3-one $119.i. (S)-3-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxy}-pyrrolidine-1-carboxylic acid tert-butyl ester Starting from the compound of Preparation C19 (384 mg) and the compound of Preparation D1 (91 mg) and proceeding in analogy to Example $102, step $102.i, however using a 1/1 DCM/MeOH mixture as solvent, the title compound was obtained as a light yellow solid (132 mg; 67% yield).
MS3 (ESI, m/z): 631.13 [M+H$^+$]; $t_R$=0.76 min.

$119.ii. 6-[(S)-2-oxo-5-(2-{3-[6-((S)-pyrrolidin-3-yloxy)-pyridin-2-yl]-benzylamino}-ethyl)-oxazolidin-3-yl]-4H-pyrido[3,2-b][1,4]oxazin-3-one Starting from intermediate $119.i (115 mg) and proceeding in analogy to Example $102, step $102.ii, the title compound was obtained, after purification by prep-HPLC (method 2), as a colourless solid (69 mg; 71% yield).
MS3 (ESI, m/z): 531.15 [M+H$^+$]; $t_R$=0.54 min.

Example $120: 6-[(S)-5-(2-{3-[6-((R)-1-methyl-pyrrolidin-3-yloxy)-pyridin-2-yl]-benzylamino}-ethyl)-2-oxo-oxazolidin-3-yl]-4H-pyrido[3,2-b][1,4]oxazin-3-one Starting from the compound of Preparation C20 (376 mg) and the compound of Preparation D1 (97 mg) and proceeding in analogy to Example $102, step $102.i, however using a 1/1 DCM/MeOH mixture as solvent, the title compound was obtained, after purification by prep-HPLC (method 2), as a colourless solid (26 mg; 14% yield).
MS3 (ESI, m/z): 545.07 [M+H$^+$]; $t_R$=0.55 min.

Example $121: 6-[(S)-5-(2-{3-[6-((S)-1-methyl-pyrrolidin-3-yloxy)-pyridin-2-yl]-benzylamino}-ethyl)-2-oxo-oxazolidin-3-yl]-4H-pyrido[3,2-b][1,4]oxazin-3-one Starting from the compound of Preparation C21 (382 mg) and the compound of Preparation D1 (79 mg) and proceeding in analogy to Example $102, step $102.i, however using a 1/1 DCM/MeOH mixture as solvent, the title compound was obtained, after purification by prep-HPLC (method 2), as a colourless solid (16 mg; 11% yield).
MS3 (ESI, m/z): 545.06 [M+H$^+$]; $t_R$=0.55 min.

Example $122: 6-[(S)-5-(2-{3-[6-(1-methyl-azetidin-3-yloxy)-pyridin-2-yl]-benzylamino}-ethyl)-2-oxo-oxazolidin-3-yl]-4H-pyrido[3,2-b][1,4]oxazin-3-one Starting from the compound of Preparation C22 (19 mg) and the compound of Preparation D1 (21 mg) and proceeding in analogy to Example $102, step $102.i, however using a 1/1 DCM/MeOH mixture as solvent, the title compound was obtained, after purification by prep-HPLC (method 2), as a colourless solid (6 mg; 16% yield).
MS3 (ESI, m/z): 531.11 [M+H$^+$]; $t_R$=0.54 min.

Example $123: 6-[(S)-5-(2-{3-[6-((S)-1-methyl-azetidin-2-ylmethoxy)-pyridin-2-yl]-benzylamino}-ethyl)-2-oxo-oxazolidin-3-yl]-4H-pyrido[3,2-b][1,4]oxazin-3-one Starting from the compound of Preparation C23 (17 mg) and the compound of Preparation D1 (16 mg) and proceeding in analogy to Example $102, step $102.i, however using a 1/1 DCM/MeOH mixture as solvent, the title compound was obtained, after purification by prep-HPLC (method 2), as a colourless solid (14 mg; 47% yield).
MS3 (ESI, m/z): 545.07 [M+H$^+$]; $t_R$=0.55 min.

Example $124: 6-[(S)-5-(2-{3-[6-((R)-1-azetidin-2-ylmethoxy)-pyridin-2-yl]-benzylamino}-ethyl)-2-oxo-oxazolidin-3-yl]-4H-pyrido[3,2-b][1,4]oxazin-3-one $124.i. (R)-2-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxymethyl}-azetidine-1-carboxylic acid tert-butyl ester Starting from the compound of Preparation C24 (50 mg) and the compound of Preparation D1 (40 mg) and proceeding in analogy to Example $102, step $102.i, however using a 1/1 DCM/MeOH mixture as solvent, the title compound was obtained as a light off-white foam (43 mg; 50% yield).
MS3 (ESI, m/z): 631.12 [M+H$^+$]; $t_R$=0.77 min.

$124.ii. 6-[(S)-5-(2-{3-[6-((R)-1-azetidin-2-ylmethoxy)-pyridin-2-yl]-benzylamino}-ethyl)-2-oxo-oxazolidin-3-yl]-4H-pyrido[3,2-b][1,4]oxazin-3-one Starting from intermediate $124.i (40 mg) and proceeding in analogy to Example $102, step $102.ii, the title compound was obtained, after purification by prep-HPLC (method 2), as a colourless solid (21 mg; 62% yield).
MS3 (ESI, m/z): 531.10 [M+H$^+$]; $t_R$=0.54 min.

Example $125: 6-[(S)-5-(2-{3-[6-((R)-1-methyl-azetidin-2-ylmethoxy)-pyridin-2-yl]-benzylamino}-ethyl)-2-oxo-oxazolidin-3-yl]-4H-pyrido[3,2-b][1,4]oxazin-3-one Starting from the compound of Preparation C25 (8 mg) and the compound of Preparation D1 (8 mg) and proceeding in analogy to Example $102, step $102.i, however using a 1/1 DCM/MeOH mixture as solvent, the title compound was obtained, after purification by prep-HPLC (method 2), as a colourless solid (6 mg; 39% yield).
MS3 (ESI, m/z): 545.06 [M+H$^+$]; $t_R$=0.55 min.

Example $126: 6-[(S)-5-(2-{3-[6-((RS)-1-ethyl-pyrrolidin-3-yloxy)-pyridin-2-yl]-benzylamino}-ethyl)-2-oxo-oxazolidin-3-yl]-4H-pyrido[3,2-b][1,4]oxazin-3-one Starting from the compound of Preparation C26 (85 mg) and the compound of Preparation D1 (80 mg) and proceeding in analogy to Example $102, step $102.i, however using a 5/3 DCM/MeOH mixture as solvent, the title compound was obtained, after purification by CC (Combiflash; DCM to DCM/MeOH 4:1), as a colourless solid (39 mg; 24% yield).
MS3 (ESI, m/z): 599.13 [M+H$^+$]; $t_R$=0.55 min.

Example $127: 6-[(S)-5-(2-{3-[6-(1-methyl-piperidin-4-yloxy)-pyridin-2-yl]-benzylamino}-ethyl)-2-oxo-oxazolidin-3-yl]-4H-pyrido[3,2-b][1,4]oxazin-3-one Starting from the compound of Preparation C27 (69 mg) and the compound of Preparation D1 (65 mg) and proceeding in analogy to Example $102, step $102.i, however using a 5/3 DCM/MeOH mixture as solvent, the title compound was obtained, after purification by CC (Combiflash; DCM to DCM/MeOH 4:1), as a colourless solid (19 mg; 14% yield).
MS3 (ESI, m/z): 599.13 [M+H$^+$]; $t_R$=0.56 min.

Example $128: 6-[(S)-5-(2-{[6-((S)-1-methyl-pyrrolidin-3-yloxy)-[2,4']bipyridinyl-2'-ylmethyl]-amino}-ethyl)-2-oxo-oxazolidin-3-yl]-4H-pyrido[3,2-b][1,4]oxazin-3-one Starting from the compound of Preparation C28 (48 mg) and the compound of Preparation D1 (50 mg) and proceeding in analogy to Example $102, step $102.i, however using a 1/1 DCM/MeOH mixture as solvent, the title compound was obtained, after purification by prep-HPLC (method 2), as a colourless solid (34 mg; 37% yield).
MS3 (ESI, m/z): 546.13 [M+H$^+$]; t$_R$=0.52 min.

Example $129: 6-[(S)-5-(2-{[6'-((S)-1-methyl-pyrrolidin-3-yloxy)-[2,2']bipyridinyl-6-ylmethyl]-amino}-ethyl)-2-oxo-oxazolidin-3-yl]-4H-pyrido[3,2-b][1,4]oxazin-3-one Starting from the compound of Preparation C29 (52 mg) and the compound of Preparation D1 (54 mg) and proceeding in analogy to Example $102, step $102.i, however using a 1/1 DCM/MeOH mixture as solvent, the title compound was obtained, after purification by prep-HPLC (method 2), as a colourless solid (34 mg; 43% yield).
MS3 (ESI, m/z): 546.15 [M+H$^+$]; t$_R$=0.52 min.

Example $130: 6-[(S)-5-(2-{3-[6-((S)-1-methyl-pyrrolidin-2-ylmethoxy)-pyridin-2-yl]-benzylamino}-ethyl)-2-oxo-oxazolidin-3-yl]-4H-pyrido[3,2-b][1,4]oxazin-3-one Starting from the compound of Preparation C30 (69 mg) and the compound of Preparation D1 (65 mg) and proceeding in analogy to Example $102, step $102.i, however using a 5/3 DCM/MeOH mixture as solvent, the title compound was obtained, after purification by prep-HPLC (method 2), as a colourless solid (12 mg; 9% yield).
MS3 (ESI, m/z): 559.16 [M+H$^+$]; t$_R$=0.55 min.

Example $131: 6-[(S)-5-(2-{3-[6-((3S,5S)-5-methyl-pyrrolidin-3-yloxy)-pyridin-2-yl]-benzylamino}-ethyl)-2-oxo-oxazolidin-3-yl]-4H-pyrido[3,2-b][1,4]oxazin-3-one $131.i. (2S,4S)-2-methyl-4-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxy}-pyrrolidine-1-carboxylic acid tert-butyl ester Starting from the compound of Preparation C31 (183 mg) and the compound of Preparation D1 (80 mg) and proceeding in analogy to Example $102, step $102.i, however using a 5/3 DCM/MeOH mixture as solvent, the title compound was obtained as a colourless solid (110 mg; 59% yield).
MS3 (ESI, m/z): 645.15 [M+H$^+$]; t$_R$=0.80 min.

$131.ii. 6-[(S)-5-(2-{3-[6-((3S,5S)-5-methyl-pyrrolidin-3-yloxy)-pyridin-2-yl]-benzylamino}-ethyl)-2-oxo-oxazolidin-3-yl]-4H-pyrido[3,2-b][1,4]oxazin-3-one Starting from intermediate $131.i (106 mg) and proceeding in analogy to Example $102, step $102.ii, the title compound was obtained, after purification by prep-HPLC (method 2), as an off-white solid (23 mg; 26% yield).

$^1$H NMR (500 MHz, CDCl$_3$) δ: 7.99 (m, 1H); 7.88 (m, 1H); 7.75 (m, 1H); 7.61 (m, 1H); 7.41 (m, 1H); 7.33 (d, J=7.5 Hz, 2H); 7.27 (m, 1H); 6.63 (m, 1H); 5.64 (m, 1H); 4.75 (m, 1H); 4.60 (m, 2H); 4.21 (m, 1H); 3.87 (m, 2H); 3.77 (dd, J=7.3, 10.2 Hz, 1H); 3.62 (dd, J=5.7, 12.6 Hz, 1H); 3.54 (m, 1H); 3.12 (dd, J=3.0, 12.6 Hz, 1H); 2.85 (m, 2H); 2.24 (m, 1H); 2.01 (m, 3H); 1.88 (m, 1H); 1.70 (m, 1H); 1.26 (m, 3H).
MS3 (ESI, m/z): 545.05 [M+H$^+$]; t$_R$=0.54 min.

Example $132: 6-[(S)-2-oxo-5-(2-{3-[6-((R)-1-pyrrolidin-2-ylmethoxy)-pyridin-2-yl]-benzylamino}-ethyl)-oxazolidin-3-yl]-4H-pyrido[3,2-b][1,4]oxazin-3-one $132.i. (R)-2-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxymethyl}-pyrrolidine-1-carboxylic acid tert-butyl ester Starting from the compound of Preparation C32 (137 mg) and the compound of Preparation D1 (80 mg) and proceeding in analogy to Example $102, step $102.i, however using a 5/3 DCM/MeOH mixture as solvent, the title compound was obtained as a colourless solid (60 mg; 32% yield).
MS3 (ESI, m/z): 645.16 [M+H$^+$]; t$_R$=0.79 min.

$132.ii. 6-[(S)-2-oxo-5-(2-{3-[6-((R)-1-pyrrolidin-2-ylmethoxy)-pyridin-2-yl]-benzylamino}-ethyl)-oxazolidin-3-yl]-4H-pyrido[3,2-b][1,4]oxazin-3-one Starting from intermediate $132.i (53 mg) and proceeding in analogy to Example $102, step $102.ii, the title compound was obtained, after purification by prep-HPLC (method 2), as an off-white solid (25 mg; 56% yield).
MS3 (ESI, m/z): 545.06 [M+H$^+$]; t$_R$=0.54 min.

Example $133: 6-[(S)-2-oxo-5-(2-{3-[6-((S)-1-pyrrolidin-2-ylmethoxy)-pyridin-2-yl]-benzylamino}-ethyl)-oxazolidin-3-yl]-4H-pyrido[3,2-b][1,4]oxazin-3-one $133.i. (S)-2-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxymethyl}-pyrrolidine-1-carboxylic acid tert-butyl ester Starting from the compound of Preparation C33 (137 mg) and the compound of Preparation D1 (80 mg) and proceeding in analogy to Example $102, step $102.i, however using a 5/3 DCM/MeOH mixture as solvent, the title compound was obtained as a colourless foam (42 mg; 23% yield).
MS3 (ESI, m/z): 645.15 [M+H$^+$]; t$_R$=0.79 min.

$133.ii. 6-[(S)-2-oxo-5-(2-{3-[6-((S)-1-pyrrolidin-2-ylmethoxy)-pyridin-2-yl]-benzylamino}-ethyl)-oxazolidin-3-yl]-4H-pyrido[3,2-b][1,4]oxazin-3-one Starting from intermediate $133.i (38 mg) and proceeding in analogy to Example $102, step $102.ii, the title compound was obtained, after purification by prep-HPLC (method 2), as a colourless solid (22 mg; 68% yield).
MS3 (ESI, m/z): 545.05 [M+H$^+$]; t$_R$=0.54 min.

Example $134: 6-[(S)-5-(2-{3-[6-((RS)-1-isopropyl-
pyrrolidin-3-yloxy)-pyridin-2-yl]-benzylamino}-
ethyl)-2-oxo-oxazolidin-3-yl]-4H-pyrido[3,2-b][1,4]
oxazin-3-one Starting from the compound of Preparation C34 (48 mg) and the compound of Preparation D1 (43 mg) and proceeding in analogy to Example $102, step $102.i, however using a 5/3 DCM/MeOH mixture as solvent, the title compound was obtained, after purification by CC (Combiflash, gradient: DCM to DCM/MeOH 4:1), as a colourless solid (25 mg; 28% yield).
MS3 (ESI, m/z): 573.18 [M+H$^+$]; $t_R$=0.56 min.

Example $135: 6-[(S)-5-(2-{3-[6-((2RS,3RS)-2-
methyl-azetidin-3-yloxy)-pyridin-2-yl]-benzy-
lamino}-ethyl)-2-oxo-oxazolidin-3-yl]-4H-pyrido[3,
2-b][1,4]oxazin-3-one $135.i. (2RS,3RS)-2-methyl-3-{6-[3-({2-[(S)-2-oxo-
3-(3-oxo-3,4-dihydro-2H-pyrido[3,2-b][1,4]oxazin-
6-yl)-oxazolidin-5-yl]-ethylamino}-methyl)-phenyl]-
pyridin-2-yloxy}-azetidine-1-carboxylic acid tert-
butyl ester Starting from the compound of Preparation C35 (46 mg) and the compound of Preparation D1 (35 mg) and proceeding in analogy to Example $102, step $102.i, however using a 5/3 DCM/MeOH mixture as solvent, the title compound was obtained as a colourless oil (44 mg; 56% yield).
MS1 (ESI, m/z): 631.07 [M+H$^+$]; $t_R$=0.78 min.

$135.ii. 6-[(S)-5-(2-{3-[6-((2RS,3RS)-2-methyl-
azetidin-3-yloxy)-pyridin-2-yl]-benzylamino}-
ethyl)-2-oxo-oxazolidin-3-yl]-4H-pyrido[3,2-b][1,4]
oxazin-3-one Starting from intermediate $135.i (39 mg) and proceeding in analogy to Example $102, step $102.ii, the title compound was obtained, after purification by prep-HPLC (method 2), as a colourless solid (7 mg; 22% yield).
MS3 (ESI, m/z): 531.12 [M+H$^+$]; $t_R$=0.54 min.

Example $136: 6-[(S)-5-(2-{3-[4-methoxy-6-((S)-1-
methyl-pyrrolidin-3-yloxy)-pyridin-2-yl]-benzy-
lamino}-ethyl)-2-oxo-oxazolidin-3-yl]-4H-pyrido[3,
2-b][1,4]oxazin-3-one Starting from the compound of Preparation C36 (28 mg) and the compound of Preparation D1 (21 mg) and proceeding in analogy to Example $102, step $102.i, however using a 1/1 DCM/MeOH mixture as solvent, the title compound was obtained after purification by prep-HPLC (method 2 followed by method 1) as a colourless solid (5 mg; 11% yield).
MS3 (ESI, m/z): 575.16 [M+H$^+$]; $t_R$=0.56 min.

Example $137: 6-[(S)-5-(2-{3-[4-((S)-1-methyl-
pyrrolidin-3-yloxy)-pyrimidin-2-yl]-benzylamino}-
ethyl)-2-oxo-oxazolidin-3-yl]-4H-pyrido[3,2-b][1,4]
oxazin-3-one Starting from the compound of Preparation C37 (10 mg) and the compound of Preparation D1 (7 mg) and proceeding in analogy to Example $102, step $102.i, however using a 1/1 DCM/MeOH mixture as solvent, the title compound was obtained after purification by prep-HPLC (method 2 followed by method 1) as a beige lyophilisate (2 mg; 15% yield).
MS3 (ESI, m/z): 546.15 [M+H$^+$]; $t_R$=0.51 min.

Example $138: 6-[(S)-5-(2-{[6-((S)-1-methyl-pyrro-
lidin-3-yloxy)-[2,3']bipyridinyl-5'-ylmethyl]-
amino}-ethyl)-2-oxo-oxazolidin-3-yl]-4H-pyrido[3,
2-b][1,4]oxazin-3-one Starting from the compound of Preparation C38 (55 mg) and the compound of Preparation D1 (57 mg) and proceeding in analogy to Example $102, step $102.i, however using a 1/1 DCM/MeOH mixture as solvent, the title compound was obtained after purification by prep-HPLC (method 2) as an off-white solid (21 mg; 20% yield).
MS3 (ESI, m/z): 546.12 [M+H$^+$]; $t_R$=0.49 min.

Example $139: 6-[(S)-5-(2-{[6'-((S)-1-methyl-pyr-
rolidin-3-yloxy)-[2,2']bipyridinyl-4-ylmethyl]-
amino}-ethyl)-2-oxo-oxazolidin-3-yl]-4H-pyrido[3,
2-b][1,4]oxazin-3-one Starting from the compound of Preparation C39 (48 mg) and the compound of Preparation D1 (50 mg) and proceeding in analogy to Example $102, step $102.i, however using a 1/1 DCM/MeOH mixture as solvent, the title compound was obtained, after purification by prep-HPLC (method 2), as a colourless solid (34 mg; 37% yield).
$^1$H NMR (500 MHz, DMSO-d6) δ: 11.37-11.10 (m, 1H); 8.58 (d, J=4.9 Hz, 1H); 8.35 (s, 1H); 7.97 (d, J=7.3 Hz, 1H); 7.82 (m, 1H); 7.59 (d, J=8.7 Hz, 1H); 7.42 (d, J=8.7 Hz, 1H); 7.39 (dd, J=4.9, 1.1 Hz, 1H); 6.83 (d, J=8.1 Hz, 1H); 5.51-5.47 (m, 1H); 4.84 (m, 1H); 4.61 (s, 2H); 4.23 (m, 1H); 3.85 (s, 2H); 3.76 (dd, J=10.0, 7.3 Hz, 1H); 2.97-2.84 (m, 1H); 2.77-2.62 (m, 4H); 2.45-2.32 (m, 3H); 2.23 (s, 3H); 2.03-1.91 (m, 2H); 1.90-1.79 (m, 1H).
MS3 (ESI, m/z): 546.13 [M+H$^+$]; $t_R$=0.50 min.

Example $140: 6-[(S)-5-(2-{3-[6-((R)-1-methyl-
pyrrolidin-3-ylmethoxy)-pyridin-2-yl]-benzy-
lamino}-ethyl)-2-oxo-oxazolidin-3-yl]-4H-pyrido[3,
2-b][1,4]oxazin-3-one Starting from the compound of Preparation C40 (77 mg) and the compound of Preparation D1 (72 mg) and proceeding in analogy to Example $102, step $102.i, however using a 5/3 DCM/MeOH mixture as solvent, the title compound was obtained, after purification by CC (Combiflash; DCM to DCM/MeOH 4:1), as a colourless solid (16 mg; 11% yield).
MS3 (ESI, m/z): 300.56 [M+H$^+$]; $t_R$=0.55 min.

Example $141: 6-[(S)-5-(2-{3-[6-((S)-1-methyl-
pyrrolidin-3-ylmethoxy)-pyridin-2-yl]-benzy-
lamino}-ethyl)-2-oxo-oxazolidin-3-yl]-4H-pyrido[3,
2-b][1,4]oxazin-3-one Starting from the compound of Preparation C41 (77 mg) and the compound of Preparation D1 (72 mg) and proceeding in analogy to Example $102, step $102.i, however using a 5/3 DCM/MeOH mixture as solvent, the title compound was obtained, after purification by CC (Combiflash; DCM to DCM/MeOH 4:1), as a colourless solid (42 mg; 29% yield).
MS3 (ESI, m/z): 300.71 [M+H$^+$]; $t_R$=0.54 min.

Example $142: 6-[(RS)-5-(2-{3-[6-((S)-1-methyl-piperidin-3-yloxy)-pyridin-2-yl]-benzylamino}-ethyl)-2-oxo-oxazolidin-3-yl]-4H-pyrido[3,2-b][1,4]oxazin-3-one Starting from the compound of Preparation C42 (31 mg) and the compound of Preparation D1 (29 mg) and proceeding in analogy to Example $102, step $102.i, however using a 5/3 DCM/MeOH mixture as solvent, the title compound was obtained, after purification by CC (Combiflash; DCM to DCM/MeOH 4:1), as a colourless solid (16 mg; 28% yield).
MS3 (ESI, m/z): 300.70 [M+H$^+$]; $t_R$=0.54 min.

Example $143: 6-[(S)-2-oxo-5-(2-{3-[6-((R)-1-pyrrolidin-3-ylmethoxy)-pyridin-2-yl]-benzylamino}-ethyl)-oxazolidin-3-yl]-4H-pyrido[3,2-b][1,4]oxazin-3-one $143.i. (R)-3-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxymethyl}-pyrrolidine-1-carboxylic acid tert-butyl ester Starting from the compound of Preparation C43 (110 mg) and the compound of Preparation D1 (80 mg) and proceeding in analogy to Example $102, step $102.i, however using a 5/3 DCM/MeOH mixture as solvent, the title compound was obtained as a colourless solid (113 mg; 61% yield).
MS3 (ESI, m/z): 645.14 [M+H$^+$]; $t_R$=0.78 min.

$143.ii. 6-[(S)-2-oxo-5-(2-{3-[6-((R)-1-pyrrolidin-3-ylmethoxy)-pyridin-2-yl]-benzylamino}-ethyl)-oxazolidin-3-yl]-4H-pyrido[3,2-b][1,4]oxazin-3-one Starting from intermediate $143.i (100 mg) and proceeding in analogy to Example $102, step $102.ii, the title compound was obtained, after purification by prep-HPLC (method 2), as a colourless solid (36 mg; 43% yield).
MS3 (ESI, m/z): 545.04 [M+H$^+$]; $t_R$=0.54 min.

Example $144: 6-[(S)-2-oxo-5-(2-{3-[6-((S)-1-pyrrolidin-3-ylmethoxy)-pyridin-2-yl]-benzylamino}-ethyl)-oxazolidin-3-yl]-4H-pyrido[3,2-b][1,4]oxazin-3-one $144.i. (S)-3-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxymethyl}-pyrrolidine-1-carboxylic acid tert-butyl ester Starting from the compound of Preparation C44 (110 mg) and the compound of Preparation D1 (80 mg) and proceeding in analogy to Example $102, step $102.i, however using a 5/3 DCM/MeOH mixture as solvent, the title compound was obtained as a colourless oil (124 mg; 67% yield).
MS3 (ESI, m/z): 645.15 [M+H$^+$]; $t_R$=0.78 min.

$144.ii. 6-[(S)-2-oxo-5-(2-{3-[6-((S)-1-pyrrolidin-3-ylmethoxy)-pyridin-2-yl]-benzylamino}-ethyl)-oxazolidin-3-yl]-4H-pyrido[3,2-b][1,4]oxazin-3-one Starting from intermediate $144.i (100 mg) and proceeding in analogy to Example $102, step $102.ii, the title compound was obtained, after purification by prep-HPLC (method 2), as a colourless solid (51 mg; 61% yield).
MS3 (ESI, m/z): 545.03 [M+H$^+$]; $t_R$=0.54 min.

Example $145: 6-{(S)-5-[2-({6-[6-((S)-1-methyl-pyrrolidin-3-yloxy)-pyrazin-2-yl]-pyridin-2-ylmethyl}-amino)-ethyl]-2-oxo-oxazolidin-3-yl}-4H-pyrido[3,2-b][1,4]oxazin-3-one Starting from the compound of Preparation C45 (45 mg) and the compound of Preparation D1 (46 mg) and proceeding in analogy to Example $102, step $102.i, however using a 1/1 DCM/MeOH mixture as solvent, the title compound was obtained, after purification by prep-HPLC (method 2), as a colourless solid (46 mg; 53% yield).
MS3 (ESI, m/z): 547.09 [M+H$^+$]; $t_R$=0.50 min.

Example $146: 6-{(S)-5-[2-({5-[6-((S)-1-methyl-pyrrolidin-3-yloxy)-pyrazin-2-yl]-pyridin-3-ylmethyl}-amino)-ethyl]-2-oxo-oxazolidin-3-yl}-4H-pyrido[3,2-b][1,4]oxazin-3-one Starting from the compound of Preparation C46 (50 mg) and the compound of Preparation D1 (51 mg) and proceeding in analogy to Example $102, step $102.i, however using a 1/1 DCM/MeOH mixture as solvent, the title compound was obtained, after purification by prep-HPLC (method 2), as a light yellow solid (41 mg; 43% yield).
$^1$H NMR (500 MHz, DMSO-d6) δ: 11.19-11.24 (m, 1H); 9.18 (d, J=2.1 Hz, 1H); 8.89 (s, 1H); 8.64 (d, J=1.9 Hz, 1H); 8.43 (t, J=2.0 Hz, 1H); 8.29 (s, 1H); 7.58 (d, J=8.7 Hz, 1H); 7.42 (d, J=8.7 Hz, 1H); 5.51-5.49 (m, 1H); 4.83 (m, 1H); 4.61 (s, 2H); 4.22 (m, 1H); 3.94-3.81 (m, 2H); 3.77 (dd, J=10.1, 7.3 Hz, 1H); 2.84 (dd, J=10.7, 6.1 Hz, 1H); 2.70-2.64 (m, 4H); 2.42-2.32 (m, 3H); 2.26 (s, 3H); 2.03-1.83 (m, 3H).
MS3 (ESI, m/z): 547.11 [M+H$^+$]; $t_R$=0.48 min.

Example $147: 6-{(S)-5-[2-({2-[6-((S)-1-methyl-pyrrolidin-3-yloxy)-pyrazin-2-yl]-pyridin-4-ylmethyl}-amino)-ethyl]-2-oxo-oxazolidin-3-yl}-4H-pyrido[3,2-b][1,4]oxazin-3-one Starting from the compound of Preparation C47 (50 mg) and the compound of Preparation D1 (51 mg) and proceeding in analogy to Example $102, step $102.i, however using a 1/1 DCM/MeOH mixture as solvent, the title compound was obtained, after purification by prep-HPLC (method 2), as a light yellow solid (38 mg; 40% yield).
MS3 (ESI, m/z): 547.09 [M−H$^+$]; $t_R$=0.49 min.

Example $148: 6-{(S)-5-[2-({4-[6-((S)-1-methyl-pyrrolidin-3-yloxy)-pyrazin-2-yl]-pyridin-2-ylmethyl}-amino)-ethyl]-2-oxo-oxazolidin-3-yl}-4H-pyrido[3,2-b][1,4]oxazin-3-one Starting from the compound of Preparation C48 (48 mg) and the compound of Preparation D1 (49 mg) and proceeding in analogy to Example $102, step $102.i, however using a 1/1 DCM/MeOH mixture as solvent, the title compound was obtained, after purification by prep-HPLC (method 2), as a light yellow solid (28 mg; 30% yield).
MS3 (ESI, m/z): 547.10 [M−H$^+$]; $t_R$=0.49 min.

Example $149: 6-[(R)-5-(2-{3-[6-(1-methyl-azetidin-3-yloxy)-pyridin-2-yl]-benzylamino}-ethyl)-2-oxo-oxazolidin-3-yl]-4H-benzo[1,4]thiazin-3-one Starting from the compound of Preparation C22 (40 mg) and 6-[(5R)-5-(2-aminoethyl)-2-oxo-3-oxazolidinyl]-2H-1, 4-benzothiazin-3(4H)-one (44 mg; prepared according to WO 2010/041219) and proceeding in analogy to Example $102, step $102.i, however using a 1/1 DCM/MeOH mixture as solvent, the title compound was obtained, after purification by prep-HPLC (method 2), as a light yellow solid (19 mg; 23% yield).
MS3 (ESI, m/z): 546.10 [M−H$^+$]; $t_R$=0.56 min.

Example $150: 6-[(R)-5-(2-{3-[6-((S)-1-methyl-pyrrolidin-3-yloxy)-pyridin-2-yl]-benzylamino}-ethyl)-2-oxo-oxazolidin-3-yl]-4H-benzo[1,4]thiazin-3-one Starting from the compound of Preparation C21 (40 mg) and 6-[(5R)-5-(2-aminoethyl)-2-oxo-3-oxazolidinyl]-2H-1,4-benzothiazin-3(4H)-one (42 mg; prepared according to WO 2010/041219) and proceeding in analogy to Example $102, step $102.i, however using a 1/1 DCM/MeOH mixture as solvent, the title compound was obtained, after purification by prep-HPLC (method 2), as a light yellow solid (36 mg; 45% yield).
MS3 (ESI, m/z): 560.15 [M+H$^+$]; $t_R$=0.56 min.

Example $151: 6-[(R)-5-(2-{3-[6-((S)-1-azetidin-2-ylmethoxy)-pyridin-2-yl]-benzylamino}-ethyl)-2-oxo-oxazolidin-3-yl]-4H-pyrido[3,2-b][1,4]oxazin-3-one $151.i. (S)-2-{6-[3-({2-[(R)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxymethyl}-azetidine-1-carboxylic acid tert-butyl ester Starting from the compound of Preparation C8 (80 mg) and 6-[(R)-5-(2-amino-ethyl)-2-oxo-oxazolidin-3-yl]-4H-pyrido[3,2-b][1,4]oxazin-3-one (66 mg; prepared according to WO 2014/170821) and proceeding in analogy to Example $102, step $102.i, however using a 1/1 DCM/MeOH mixture as solvent, the title compound was obtained as a yellow oil (42 mg; 47% yield).
MS3 (ESI, m/z): 631.15 [M+H$^+$]; $t_R$=0.77 min.

$151.ii. 6-[(R)-5-(2-{3-[6-((S)-1-azetidin-2-ylmethoxy)-pyridin-2-yl]-benzylamino}-ethyl)-2-oxo-oxazolidin-3-yl]-4H-pyrido[3,2-b][1,4]oxazin-3-one Starting from intermediate $151.i (35 mg) and proceeding in analogy to Example $102, step $102.ii, the title compound was obtained, after purification by prep-HPLC (method 2), as a yellowish solid (15 mg; 64% yield).
MS3 (ESI, m/z): 531.16 [M+H$^+$]; $t_R$=0.54 min.

Example $152: 6-[(R)-5-(2-{3-[6-((S)-1-azetidin-2-ylmethoxy)-pyridin-2-yl]-benzylamino}-ethyl)-2-oxo-oxazolidin-3-yl]-4H-benzo[1,4]thiazin-3-one $152.i. (S)-2-{6-[3-({2-[(R)-2-oxo-3-(3-oxo-3,4-dihydro-2H-benzo[1,4]thiazin-6-yl)-oxazolidin-5-yl]-ethylamino}-methyl)-phenyl]-pyridin-2-yloxymethyl}-azetidine-1-carboxylic acid tert-butyl ester Starting from the compound of Preparation C8 (60 mg) and 6-[(5R)-5-(2-aminoethyl)-2-oxo-3-oxazolidinyl]-2H-1,4-benzothiazin-3(4H)-one (42 mg; prepared according to WO 2010/041219) and proceeding in analogy to Example $102, step $102.i, however using a 1/1 DCM/MeOH mixture as solvent, the title compound was obtained as a light yellowish oil (32 mg; 47% yield).
MS3 (ESI, m/z): 645.99 [M+H$^+$]; $t_R$=0.79 min.

$152.ii. 6-[(R)-5-(2-{3-[6-((S)-1-azetidin-2-ylmethoxy)-pyridin-2-yl]-benzylamino}-ethyl)-2-oxo-oxazolidin-3-yl]-4H-benzo[1,4]thiazin-3-one Starting from intermediate $152.i (27 mg) and proceeding in analogy to Example $102, step $102.ii, the title compound was obtained, after purification by prep-HPLC (method 2), as a colourless solid (17 mg; 75% yield).
MS3 (ESI, m/z): 546.13 [M+H$^+$]; $t_R$=0.56 min.

Example $153: 6-[(S)-5-(2-{3-[5-((S)-1-methyl-pyrrolidin-3-yloxy)-pyridazin-3-yl]-benzylamino}-ethyl)-2-oxo-oxazolidin-3-yl]-4H-pyrido[3,2-b][1,4]oxazin-3-one Starting from the compound of Preparation C49 (98 mg) and the compound of Preparation D1 (96 mg) and proceeding in analogy to Example $102, step $102.i, however using a 4/1 DCM/MeOH mixture as solvent and adding AcOH (0.020 mL), the title compound was obtained as a colourless oil (39 mg; 20% yield).
MS1 (ESI, m/z): 545.97 [M+H$^+$]; $t_R$=0.49 min.

Example $154: 6-[(S)-5-(2-{3-[4-(2-amino-ethoxy)-pyridin-2-yl]-benzylamino}-ethyl)-2-oxo-oxazolidin-3-yl]-4H-pyrido[3,2-b][1,4]oxazin-3-one $154.i. (2-{2-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-4-yloxy}-ethyl)-carbamic acid tert-butyl ester Starting from the compound of Preparation C50 (80 mg) and the compound of Preparation D1 (68 mg) and proceeding in analogy to Example $102, step $102.i, however using a 1/1 DCM/MeOH mixture as solvent, the title compound was obtained as a yellowish foam (53 mg; 38% yield).
MS3 (ESI, m/z): 605.98 [M+H$^+$]; $t_R$=0.58 min.

$154.ii. 6-[(S)-5-(2-{3-[4-(2-amino-ethoxy)-pyridin-2-yl]-benzylamino}-ethyl)-2-oxo-oxazolidin-3-yl]-4H-pyrido[3,2-b][1,4]oxazin-3-one Starting from intermediate $154.i (50 mg) and proceeding in analogy to Example $102, step $102.ii, the title compound was obtained, after purification by prep-HPLC (method 2), as a colourless solid (25 mg; 60% yield).
MS3 (ESI, m/z): 505.06 [M+H$^+$]; $t_R$=0.42 min.

Example $155: 6-((S)-5-{2-[(3'-{2-[bis-(2-amino-ethyl)-amino]-ethoxy}-biphenyl-3-ylmethyl)-amino]-ethyl}-2-oxo-oxazolidin-3-yl)-4H-pyrido[3,2-b][1,4]oxazin-3-one $155.i. [2-((2-tert-butoxycarbonylamino-ethyl)-{2-[3'-({2-[(S)-2-oxo-3-(3-oxo-3,4-dihydro-2H-pyrido[3,2-b][1,4]oxazin-6-yl)-oxazolidin-5-yl]-ethylamino}-methyl)-biphenyl-3-yloxy]-ethyl}-amino)-ethyl]-carbamic acid tert-butyl ester Starting from the compound of Preparation C51 (15 mg) and the compound of Preparation D1 (8 mg) and proceeding in analogy to Example $102, step $102.i, however using a 2/1 DCM/MeOH mixture as solvent, the title compound was obtained as an off-white solid (11 mg; 48% yield).
MS3 (ESI, m/z): 790.01 [M+H$^+$]; $t_R$=0.69 min.

$155.ii. 6-((S)-5-{2-[(3'-{2-[bis-(2-amino-ethyl)-amino]-ethoxy}-biphenyl-3-ylmethyl)-amino]-ethyl}-2-oxo-oxazolidin-3-yl)-4H-pyrido[3,2-b][1,4]oxazin-3-one Starting from intermediate $155.i (9 mg) and proceeding in analogy to Example $102, step $102.ii, the title compound was obtained, after purification by prep-HPLC (method 2), as a colourless solid (1 mg; 13% yield).
MS3 (ESI, m/z): 590.13 [M+H$^+$]; $t_R$=0.49 min.

Example $156: 6-{(S)-5-[2-(3-{6-[2-(2-amino-ethylamino)-ethoxy]-pyridin-2-yl}-benzylamino)-ethyl]-2-oxo-oxazolidin-3-yl}-4H-pyrido[3,2-b][1,4]oxazin-3-one $156.i. (2-tert-butoxycarbonylamino-ethyl)-(2-{6-[3-({2-[(S)-2-oxo-3-(3-oxo-3,4-dihydro-2H-pyrido[3,2-b][1,4]oxazin-6-yl)-oxazolidin-5-yl]-ethyl-amino}-methyl)-phenyl]-pyridin-2-yloxy}-ethyl)-carbamic acid tert-butyl ester Starting from the compound of Preparation C52 (138 mg) and the compound of Preparation D1 (79 mg) and proceeding in analogy to Example $102, step $102.i, however using a 2/1 DCM/MeOH mixture as solvent, the title compound was obtained as a colourless solid (58 mg; 28% yield).
MS3 (ESI, m/z): 749.07 [M+H$^+$]; $t_R$=0.80 min.

$156.ii. 6-{(S)-5-[2-(3-{6-[2-(2-amino-ethylamino)-ethoxy]-pyridin-2-yl}-benzylamino)-ethyl]-2-oxo-oxazolidin-3-yl}-4H-pyrido[3,2-b][1,4]oxazin-3-one Starting from intermediate $156.i (49 mg) and proceeding in analogy to Example $102, step $102.ii, the title compound was obtained, after purification by prep-HPLC (method 2), as a colourless solid (23 mg; 64% yield).
MS3 (ESI, m/z): 548.16 [M+H$^+$]; $t_R$=0.48 min.

Example $157: 6-[(S)-5-(2-{[4-(2-amino-ethoxy)-[2,4']bipyridinyl-2'-ylmethyl]-amino}-ethyl)-2-oxo-oxazolidin-3-yl]-4H-pyrido[3,2-b][1,4]oxazin-3-one $157.i. {2-[2'-({2-[(S)-2-oxo-3-(3-oxo-3,4-dihydro-2H-pyrido[3,2-b][1,4]oxazin-6-yl)-oxazolidin-5-yl]-ethylamino}-methyl)-[2,4']bipyridinyl-4-yloxy]-ethyl}-carbamic acid tert-butyl ester Starting from the compound of Preparation C53 (50 mg) and the compound of Preparation D1 (41 mg) and proceeding in analogy to Example $102, step $102.i, however using a 1/1 DCM/MeOH mixture as solvent, the title compound was obtained as a beige foam (38 mg; 43% yield).
MS3 (ESI, m/z): 606.15 [M+H$^+$]; $t_R$=0.61 min.

$157.ii. 6-[(S)-5-(2-{[4-(2-amino-ethoxy)-[2,4']bipyridinyl-2'-ylmethyl]-amino}-ethyl)-2-oxo-oxazolidin-3-yl]-4H-pyrido[3,2-b][1,4]oxazin-3-one Starting from intermediate $157.i (35 mg) and proceeding in analogy to Example $102, step $102.ii, the title compound was obtained, after purification by prep-HPLC (method 2), as a yellow solid (24 mg; 82% yield).
MS3 (ESI, m/z): 506.08 [M+H$^+$]; $t_R$=0.45 min.

Example $158: 6-{(S)-5-[2-({4-[6-(2-amino-ethoxy)-pyrazin-2-yl]-pyridin-2-ylmethyl}-amino)-ethyl]-2-oxo-oxazolidin-3-yl}-4H-pyrido[3,2-b][1,4]oxazin-3-one $158.i. (2-{6-[2-({2-[(S)-2-oxo-3-(3-oxo-3,4-dihydro-2H-pyrido[3,2-b][1,4]oxazin-6-yl)-oxazolidin-5-yl]-ethylamino}-methyl)-pyridin-4-yl]-pyrazin-2-yloxy}-ethyl)-carbamic acid tert-butyl ester Starting from the compound of Preparation C54 (60 mg) and the compound of Preparation D1 (49 mg) and proceeding in analogy to Example $102, step $102.i, however using a 1/1 DCM/MeOH mixture as solvent, the title compound was obtained as a beige foam (74 mg; 70% yield).
MS3 (ESI, m/z): 607.14 [M+H$^+$]; $t_R$=0.67 min.

$158.ii. 6-{(S)-5-[2-({4-[6-(2-amino-ethoxy)-pyrazin-2-yl]-pyridin-2-ylmethyl}-amino)-ethyl]-2-oxo-oxazolidin-3-yl}-4H-pyrido[3,2-b][1,4]oxazin-3-one Starting from intermediate $158.i (65 mg) and proceeding in analogy to Example $102, step $102.ii, the title compound was obtained, after purification by prep-HPLC (method 2), as a yellow solid (32 mg; 59% yield).
$^1$H NMR (500 MHz, DMSO-d6) δ: 8.93 (s, 1H); 8.66 (d, J=5.1 Hz, 1H); 8.37 (s, 1H); 8.13 (s, 1H); 7.95 (dd, J=1.3, 5.1 Hz, 1H); 7.58 (d, J=8.7 Hz, 1H); 7.42 (d, J=8.7 Hz, 1H); 4.84 (m, 1H); 4.60 (s, 2H); 4.39 (t, J=5.8 Hz, 2H); 4.23 (m, 1H); 3.91 (s, 2H); 3.77 (dd, J=7.4, 10.0 Hz, 1H); 2.95 (t, J=5.0 Hz, 2H); 2.69 (d, J=3.5 Hz, 2H); 2.02-1.85 (m, 2H).
MS3 (ESI, m/z): 507.09 [M+H$^+$]; $t_R$=0.47 min.

Example $159: 6-[(S)-5-(2-{[5-(2-amino-ethoxy)-[3,4']bipyridinyl-2'-ylmethyl]-amino}-ethyl)-2-oxo-oxazolidin-3-yl]-4H-pyrido[3,2-b][1,4]oxazin-3-one $159.i. {2-[2'-({2-[(S)-2-oxo-3-(3-oxo-3,4-dihydro-2H-pyrido[3,2-b][1,4]oxazin-6-yl)-oxazolidin-5-yl]-ethylamino}-methyl)-[3,4']bipyridinyl-5-yloxy]-ethyl}-carbamic acid tert-butyl ester Starting from the compound of Preparation C55 (80 mg) and the compound of Preparation D1 (65 mg) and proceeding in analogy to Example $102, step $102.i, however using a 1/1 DCM/MeOH mixture as solvent, the title compound was obtained, after purification by prep-HPLC (method 2), as an orange solid (58 mg; 41% yield).
MS3 (ESI, m/z): 605.15 [M+H$^+$]; $t_R$=0.64 min.

$159.ii. 6-[(S)-5-(2-{[5-(2-amino-ethoxy)-[3,4']bipyridinyl-2'-ylmethyl]-amino}-ethyl)-2-oxo-oxazolidin-3-yl]-4H-pyrido[3,2-b][1,4]oxazin-3-one Starting from intermediate $159.i (51 mg) and proceeding in analogy to Example $102, step $102.ii, the title compound was obtained after purification by prep-HPLC (method 2) as an off-white solid (23 mg; 54% yield).
MS3 (ESI, m/z): 506.09 [M+H$^+$]; $t_R$=0.46 min.

Example $160: 6-[(S)-5-(2-{3-[2-(2-amino-ethoxy)-pyrimidin-4-yl]-benzylamino}-ethyl)-2-oxo-oxazolidin-3-yl]-4H-pyrido[3,2-b][1,4]oxazin-3-one $160.i. (2-{4-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyrimidin-2-yloxy}-ethyl)-carbamic acid tert-butyl ester Starting from the compound of Preparation C56 (50 mg) and the compound of Preparation D1 (43 mg) and proceeding in analogy to Example $102, step $102.i, however using a 1/1 DCM/MeOH mixture as solvent, the title compound was obtained, after purification by prep-HPLC (method 2), as a light yellow solid (45 mg; 51% yield).
MS3 (ESI, m/z): 606.16 [M+H$^+$]; $t_R$=0.69 min.

$160.ii. 6-[(S)-5-(2-{3-[2-(2-amino-ethoxy)-pyrimidin-4-yl]-benzylamino}-ethyl)-2-oxo-oxazolidin-3-yl]-4H-pyrido[3,2-b][1,4]oxazin-3-one Starting from intermediate $160.i (31 mg) and proceeding in analogy to Example $102, step $102.ii, the title compound was obtained, after purification by prep-HPLC (method 2), as a yellowish solid (31 mg; 93% yield).
MS3 (ESI, m/z): 506.11 [M+H$^+$]; $t_R$=0.49 min.

Example $161: 6-[(S)-5-(2-{3-[4-(2-amino-ethoxy)-6-methoxy-pyridin-2-yl]-benzylamino}-ethyl)-2-oxo-oxazolidin-3-yl]-4H-pyrido[3,2-b][1,4]oxazin-3-one $161.i. (2-{2-methoxy-6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-4-yloxy}-ethyl)-carbamic acid tert-butyl ester Starting from the compound of Preparation C57 (55 mg) and the compound of Preparation D1 (35 mg) and proceeding in analogy to Example $102, step $102.i, however using a 1/1 DCM/MeOH mixture as solvent, the title compound was obtained, after purification by CC (Combiflash; DCM to DCM/MeOH 19:1), as a beige foam (29 mg; 39% yield).
MS3 (ESI, m/z): 635.16 [M+H$^+$]; $t_R$=0.74 min.

$161.ii. 6-[(S)-5-(2-{3-[4-(2-amino-ethoxy)-6-methoxy-pyridin-2-yl]-benzylamino}-ethyl)-2-oxo-oxazolidin-3-yl]-4H-pyrido[3,2-b][1,4]oxazin-3-one Starting from intermediate $161.i (25 mg) and proceeding in analogy to Example $102, step $102.ii, the title compound was obtained, after purification by prep-HPLC (method 2), as a colourless solid (20 mg; 95% yield).
MS3 (ESI, m/z): 535.12 [M+H$^+$]; $t_R$=0.53 min.

Example $162: 6-[(S)-5-(2-{[4-(2-amino-ethoxy)-6-methoxy-[2,4']bipyridinyl-2'-ylmethyl]-amino}-ethyl)-2-oxo-oxazolidin-3-yl]-4H-pyrido[3,2-b][1,4]oxazin-3-one $162.i. {2-[6-methoxy-2'-({2-[(S)-2-oxo-3-(3-oxo-3,4-dihydro-2H-pyrido[3,2-b][1,4]oxazin-6-yl)-oxazolidin-5-yl]-ethylamino}-methyl)-[2,4']bipyridinyl-4-yloxy]-ethyl}-carbamic acid tert-butyl ester Starting from the compound of Preparation C58 (25 mg) and the compound of Preparation D1 (20 mg) and proceeding in analogy to Example $102, step $102.i, however using a 1/1 DCM/MeOH mixture as solvent, the title compound was obtained, after purification by CC (Combiflash; DCM to DCM/MeOH 19:1), as an off-white foam (25 mg; 59% yield).
MS3 (ESI, m/z): 636.16 [M+H$^+$]; $t_R$=0.73 min.

$162.ii. 6-[(S)-5-(2-{[4-(2-amino-ethoxy)-6-methoxy-[2,4']bipyridinyl-2'-ylmethyl]-amino}-ethyl)-2-oxo-oxazolidin-3-yl]-4H-pyrido[3,2-b][1,4]oxazin-3-one Starting from intermediate $162.i (22 mg) and proceeding in analogy to Example $102, step $102.ii, the title compound was obtained, after purification by prep-HPLC (method 2), as a colourless solid (13 mg; 70% yield).
MS3 (ESI, m/z): 536.16 [M+H$^+$]; $t_R$=0.51 min.

Example $163: 6-[(S)-5-(2-{3-[6-(2-methylamino-ethoxy)-pyridin-2-yl]-benzylamino}-ethyl)-2-oxo-oxazolidin-3-yl]-4H-pyrido[3,2-b][1,4]oxazin-3-one $163.i. Methyl-(2-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxy}-ethyl)-carbamic acid tert-butyl ester Starting from the compound of Preparation C59 (70 mg) and the compound of Preparation D1 (57 mg) and proceeding in analogy to Example $102, step $102.i, however using a 1/1 DCM/MeOH mixture as solvent, the title compound was obtained, after purification by CC (Combiflash; DCM to DCM/MeOH 9:1), as an off-white foam (67 mg; 55% yield).
MS3 (ESI, m/z): 619.12 [M+H$^+$]; $t_R$=0.77 min.

$163.ii. 6-[(S)-5-(2-{3-[6-(2-methylamino-ethoxy)-pyridin-2-yl]-benzylamino}-ethyl)-2-oxo-oxazolidin-3-yl]-4H-pyrido[3,2-b][1,4]oxazin-3-one Starting from intermediate $163.i (60 mg) and proceeding in analogy to Example $102, step $102.ii, the title compound was obtained, after purification by prep-HPLC (method 2), as a colourless solid (41 mg; 82% yield).
MS3 (ESI, m/z): 520.11 [M+H$^+$]; $t_R$=0.50 min.

Example $164: 6-[(S)-5-(2-{3-[6-(2-methylamino-ethoxy)-pyrazin-2-yl]-benzylamino}-ethyl)-2-oxo-oxazolidin-3-yl]-4H-pyrido[3,2-b][1,4]oxazin-3-one $164.i. Methyl-(2-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyrazin-2-yloxy}-ethyl)-carbamic acid tert-butyl ester Starting from the compound of Preparation C60 (70 mg) and the compound of Preparation D1 (57 mg) and proceeding in analogy to Example $102, step $102.i, however using a 1/1 DCM/MeOH mixture as solvent, the title compound was obtained after purification by CC (Combiflash; DCM to DCM/MeOH 9:1) as a yellowish oil (69 mg; 57% yield).
MS3 (ESI, m/z): 620.11 [M+H$^+$]; $t_R$=0.74 min.

$164.ii. 6-[(S)-5-(2-{3-[6-(2-methylamino-ethoxy)-pyrazin-2-yl]-benzylamino}-ethyl)-2-oxo-oxazolidin-3-yl]-4H-pyrido[3,2-b][1,4]oxazin-3-one Starting from intermediate $164.i (60 mg) and proceeding in analogy to Example $102, step $102.ii, the title compound was obtained, after purification by prep-HPLC (method 2), as a colourless solid (31 mg; 62% yield).
MS3 (ESI, m/z): 519.10 [M+H$^+$]; $t_R$=0.53 min.

Example $165: 6-{(S)-5-[2-({4-[6-(2-amino-ethoxy)-pyridin-2-yl]-pyrimidin-2-ylmethyl}-amino)-ethyl]-2-oxo-oxazolidin-3-yl}-4H-pyrido[3,2-b][1,4]oxazin-3-one $165.i. Tert-butyl (S)-(2-((6-(2-(((2-(2-oxo-3-(3-oxo-3,4-dihydro-2H-pyrido[3,2-b][1,4]oxazin-6-yl)oxazolidin-5-yl)ethyl)amino)methyl)pyrimidin-4-yl)pyridin-2-yl)oxy)ethyl)carbamate The compound of Preparation C61 (20 mg) and the compound of Preparation D1 (16 mg) were dissolved in a 1/1 DMF/DCM mixture (2 mL). NaBH(OAc)$_3$ (44 mg) was added. The reaction mixture was stirred at rt for 1 h and the solvents were then evaporated. The residue was dissolved in EA and the mixture was washed with sat. aq. NaHCO$_3$. The org. layers was separated, dried over Na$_2$SO$_4$ and evaporated. The title compound was obtained, after purification by CC (EA, then EA/MeOH 9/1), as a colourless solid (12 mg; 34% yield).
$^1$H NMR (300 MHz, CDCl$_3$) δ: 1.44 (s, 9H); 1.98-1.86 (m, 2H); 2.18-2.01 (m, 1H); 2.97 (t, J=6.7 Hz, 2H); 3.59 (dd, J=11.1, 5.7 Hz, 2H); 3.81 (dd, J=10.2, 7.5 Hz, 1H); 4.14 (s, 2H); 4.26 (dd, J=10.5, 8.4 Hz, 1H); 4.51 (t, J=5.4 Hz, 1H); 4.63 (s, 2H); 4.88-4.79 (m, 1H); 5.06 (br. s, 1H); 6.87 (d, J=8.4 Hz, 1H); 7.30 (d, J=9.0 Hz, 1H); 7.75 (t, J=7.8 Hz, 1H); 7.82 (d, J=8.7 Hz, 1H); 8.15 (d, J=6.9 Hz, 1H); 8.80 (d, J=5.4 Hz, 1H).
MS3 (ESI, m/z): 607.10 [M+H$^+$]; $t_R$=0.70 min.

$165.ii. 6-{(S)-5-[2-({4-[6-(2-amino-ethoxy)-pyridin-2-yl]-pyrimidin-2-ylmethyl}-amino)-ethyl]-2-oxo-oxazolidin-3-yl}-4H-pyrido[3,2-b][1,4]oxazin-3-one Starting from intermediate $165.i (10 mg) and proceeding in analogy to Example $102, step $102.ii, the title compound was obtained, after purification by prep-HPLC (method 2), as a colourless solid (31 mg; 62% yield).
MS3 (ESI, m/z): 507.03 [M+H$^+$]; $t_R$=0.48 min.

Example $166: 6-[(S)-5-(2-{3-[5-((R)-1-methyl-pyrrolidin-3-yloxy)-pyridazin-3-yl]-benzylamino}-ethyl)-2-oxo-oxazolidin-3-yl]-4H-pyrido[3,2-b][1,4]oxazin-3-one Starting from the compound of Preparation C62 (107 mg) and the compound of Preparation D1 (105 mg) and proceeding in analogy to Example $102, step $102.i, however using a 4/1 DCM/MeOH mixture as solvent and performing the reaction in the presence of AcOH (0.022 mL), the title compound was obtained, after purification by CC (DCM to DCM/MeOH/NH$_4$OH 9:1:0.05), as a colourless solid (41 mg; 20% yield).
MS1 (ESI, m/z): 545.79 [M+H$^+$]; $t_R$=0.48 min.

Example $167: 6-[(S)-5-(2-{3-[6-((S)-1-methyl-pyrrolidin-3-yloxy)-pyridin-2-yl]-benzylamino}-ethyl)-2-oxo-oxazolidin-3-yl]-4H-benzo[1,4]thiazin-3-one Starting from the compound of Preparation C21 (60 mg) and 6-[(S)-5-(2-amino-ethyl)-2-oxo-oxazolidin-3-yl]-4H-benzo[1,4]thiazin-3-one (62 mg; prepared according to WO 2010/041194) and proceeding in analogy to Example $102, step $102.i, however using a 2/1 DCM/MeOH mixture as solvent, the title compound was obtained, after purification by prep-HPLC (method 2), as a colourless solid (3.6 mg; 3% yield).
MS3 (ESI, m/z): 560.10 [M+H$^+$]; $t_R$=0.56 min.

Example $168: 6-[(S)-5-(2-{3-[6-((R)-1-methyl-pyrrolidin-3-yloxy)-pyridin-2-yl]-benzylamino}-ethyl)-2-oxo-oxazolidin-3-yl]-4H-benzo[1,4]thiazin-3-one Starting from the compound of Preparation C20 (60 mg) and 6-[(S)-5-(2-amino-ethyl)-2-oxo-oxazolidin-3-yl]-4H-benzo[1,4]thiazin-3-one (62 mg; prepared according to WO 2010/041194) and proceeding in analogy to Example $102, step $102.i, however using a 2/1 DCM/MeOH mixture as solvent, the title compound was obtained, after purification by prep-HPLC (method 2), as a colourless solid (16 mg; 14% yield).
MS3 (ESI, m/z): 560.11 [M+H$^+$]; $t_R$=0.55 min.

Example $169: 6-[(R)-5-(2-{3-[6-((R)-1-methyl-pyrrolidin-3-yloxy)-pyridin-2-yl]-benzylamino}-ethyl)-2-oxo-oxazolidin-3-yl]-4H-benzo[1,4]thiazin-3-one Starting from the compound of Preparation C20 (60 mg) and 6-[(5R)-5-(2-aminoethyl)-2-oxo-3-oxazolidinyl]-2H-1,4-benzothiazin-3(4H)-one (42 mg; prepared according to WO 2010/041219) and proceeding in analogy to Example $102, step $102.i, however using a 2/1 DCM/MeOH mixture as solvent, the title compound was obtained, after purification by prep-HPLC (method 2), as a colourless solid (3.3 mg; 3% yield).
MS3 (ESI, m/z): 560.12 [M+H$^+$]; $t_R$=0.55 min.

Example $170: 6-[(S)-5-(2-{3-[6-methoxy-4-((S)-1-methyl-pyrrolidin-3-yloxy)-pyridin-2-yl]-benzylamino}-ethyl)-2-oxo-oxazolidin-3-yl]-4H-pyrido[3,2-b][1,4]oxazin-3-one Starting from the compound of Preparation C63 (30 mg) and the compound of Preparation D1 (28 mg) and proceeding in analogy to Example $102, step $102.i, however using a 1/1 DCM/MeOH mixture as solvent, the title compound was obtained after purification by prep-HPLC (method 2) as a colourless solid (19 mg; 34% yield). $^1$H NMR (500 MHz, DMSO-d6) δ: 8.02 (s, 1H); 7.94 (dt, J=6.9, 1.8 Hz, 1H); 7.59 (m, 1H); 7.43-7.37 (m, 3H); 7.08 (d, J=1.9 Hz, 1H); 6.23 (d, J=1.8 Hz, 1H); 5.04-5.01 (m, 1H); 4.81 (m, 1H); 4.61 (s, 2H); 4.22 (m, 1H); 3.93 (s, 3H); 3.78 (s, 2H); 3.76-3.74 (m, 1H); 2.77 (dd, J=10.6, 6.0 Hz, 1H); 2.70-2.62 (m, 4H); 2.36-2.31 (m, 2H); 2.26 (s, 3H); 1.92 (m, 2H); 1.81-1.76 (m, 1H).
MS3 (ESI, m/z): 575.14 [M+H$^+$]; $t_R$=0.55 min.

Example $171: 6-[(S)-5-(2-{3-[6-((R)-1-methyl-pyrrolidin-2-ylmethoxy)-pyridin-2-yl]-benzylamino}-ethyl)-2-oxo-oxazolidin-3-yl]-4H-pyrido[3,2-b][1,4]oxazin-3-one Starting from the compound of Preparation C64 (80 mg) and the compound of Preparation D1 (76 mg) and proceeding in analogy to Example $102, step $102.i, however using a 1/1 DCM/MeOH mixture as solvent, the title compound was obtained after purification by prep-HPLC (method 2) as a colourless solid (59 mg; 41% yield).
MS3 (ESI, m/z): 559.13 [M+H$^+$]; $t_R$=0.55 min.

Example $172: 6-[(S)-5-(2-{3-[6-((2S*,3S*)-2-methyl-pyrrolidin-3-yloxy)-pyridin-2-yl]-benzylamino}-ethyl)-2-oxo-oxazolidin-3-yl]-4H-pyrido[3,2-b][1,4]oxazin-3-one $172.i. Tert-butyl (2S*,3S*)-2-methyl-3-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxy}-pyrrolidine-1-carboxylate Starting from the compound of Preparation C65 (110 mg) and the compound of Preparation D1 (59 mg) and proceeding in analogy to Example $102, step $102.i, however using a 1/1 DCM/MeOH mixture as solvent, the title compound was obtained after purification by CC (Combiflash; DCM to DCM/MeOH 4:1) as a yellowish oil (88 mg; 68% yield).
MS3 (ESI, m/z): 645.13 [M+H$^+$]; $t_R$=0.79 min.

$172.ii. 6-[(S)-5-(2-{3-[6-((2S*,3S*)-2-methyl-pyrrolidin-3-yloxy)-pyridin-2-yl]-benzylamino}-ethyl)-2-oxo-oxazolidin-3-yl]-4H-pyrido[3,2-b][1,4]oxazin-3-one Starting from intermediate $172.i (82 mg) and proceeding in analogy to Example $102, step $102.ii, the title compound was obtained, after purification by prep-HPLC (method 2), as a colourless solid (21 mg; 40% yield).
MS3 (ESI, m/z): 545.03 [M+H$^+$]; $t_R$=0.55 min.

Example $173: 6-[(S)-5-(2-{3-[6-((3S*,4R*)-4-methyl-pyrrolidin-3-yloxy)-pyridin-2-yl]-benzylamino}-ethyl)-2-oxo-oxazolidin-3-yl]-4H-pyrido[3,2-b][1,4]oxazin-3-one $173.i. (3R*,4S*)-3-methyl-4-{6-[3-({2-[(S)-2-oxo-3-(3-oxo-3,4-dihydro-2H-pyrido[3,2-b][1,4]oxazin-6-yl)-oxazolidin-5-yl]-ethylamino}-methyl)-phenyl]-pyridin-2-yloxy}-pyrrolidine-1-carboxylic acid tert-butyl ester Starting from the compound of Preparation C66 (100 mg) and the compound of Preparation D1 (74 mg) and proceeding in analogy to Example $102, step $102.i, however using a 1/1 DCM/MeOH mixture as solvent, the title compound was obtained after purification by CC (Combiflash; DCM to DCM/MeOH 4:1) as a yellowish oil (72 mg; 44% yield).
MS3 (ESI, m/z): 645.13 [M+H$^+$]; $t_R$=0.80 min.

$173.ii. 6-[(S)-5-(2-{3-[6-((3S*,4R*)-4-methyl-pyrrolidin-3-yloxy)-pyridin-2-yl]-benzylamino}-ethyl)-2-oxo-oxazolidin-3-yl]-4H-pyrido[3,2-b][1,4]oxazin-3-one Starting from intermediate $173.i (65 mg) and proceeding in analogy to Example $102, step $102.ii, the title compound was obtained, after purification by prep-HPLC (method 2), as a colourless solid (35 mg; 64% yield).
MS3 (ESI, m/z): 545.05 [M+H$^+$]; $t_R$=0.56 min.

Example $174: 6-[(S)-5-(2-{3-[5-(1-methyl-azetidin-3-yloxy)-pyridazin-3-yl]-benzylamino}-ethyl)-2-oxo-oxazolidin-3-yl]-4H-pyrido[3,2-b][1,4]oxazin-3-one Starting from the compound of Preparation C67 (111 mg) and the compound of Preparation D1 (115 mg) and proceeding in analogy to Example $102, step $102.i, however using a 4/1 DCM/MeOH mixture as solvent and performing the reaction in the presence of AcOH (0.024 mL), the title compound was obtained, after purification by CC (DCM to DCM/MeOH/NH$_4$OH 9:1:0.05), as a colourless solid (41 mg; 19% yield).
MS1 (ESI, m/z): 532.07 [M+H$^+$]; $t_R$=0.47 min.

Example $175: 6-[(S)-5-(2-{3-[6-((3S,5S)-1,5-dimethyl-pyrrolidin-3-yloxy)-pyridin-2-yl]-benzylamino}-ethyl)-2-oxo-oxazolidin-3-yl]-4H-pyrido[3,2-b][1,4]oxazin-3-one Starting from the compound of Preparation C68 (60 mg) and the compound of Preparation D1 (59 mg) and proceeding in analogy to Example $102, step $102.i, however using a 1/1 DCM/MeOH mixture as solvent, the title compound was obtained, after purification by prep-HPLC (method 2), as a light yellow solid (59 mg; 52% yield).
MS3 (ESI, m/z): 559.13 [M+H$^+$]; $t_R$=0.56 min.

Example $176: 6-[(S)-5-(2-{3-[6-((2S*,3S*)-1,2-dimethyl-pyrrolidin-3-yloxy)-pyridin-2-yl]-benzylamino}-ethyl)-2-oxo-oxazolidin-3-yl]-4H-pyrido[3,2-b][1,4]oxazin-3-one Starting from the compound of Preparation C69 (60 mg) and the compound of Preparation D1 (59 mg) and proceeding in analogy to Example $102, step $102.i, however using a 1/1 DCM/MeOH mixture as solvent, the title compound was obtained after purification by prep-HPLC (method 2) as a light yellow solid (53 mg; 47% yield).
MS3 (ESI, m/z): 559.13 [M+H$^+$]; $t_R$=0.55 min.

Example $177: 6-[(S)-5-(2-{3-[6-((3S*,4R*)-1,4-dimethyl-pyrrolidin-3-yloxy)-pyridin-2-yl]-benzylamino}-ethyl)-2-oxo-oxazolidin-3-yl]-4H-pyrido[3,2-b][1,4]oxazin-3-one Starting from the compound of Preparation C70 (45 mg) and the compound of Preparation D1 (40 mg) and proceeding in analogy to Example $102, step $102.i, however using a 1/1 DCM/MeOH mixture as solvent, the title compound was obtained, after purification by prep-HPLC (method 2), as a light yellow solid (31 mg; 41% yield).
MS3 (ESI, m/z): 559.12 [M+H$^+$]; $t_R$=0.56 min.

Example $178: 6-[(S)-5-(2-{3-[6-((2RS,3RS)-1,2-dimethyl-azetidin-3-yloxy)-pyridin-2-yl]-benzylamino}-ethyl)-2-oxo-oxazolidin-3-yl]-4H-pyrido[3,2-b][1,4]oxazin-3-one Starting from the compound of Preparation C71 (28 mg) and the compound of Preparation D1 (29 mg) and proceeding in analogy to Example $102, step $102.i, however using a 1/1 DCM/MeOH mixture as solvent, the title compound was obtained, after purification by prep-HPLC (method 2), as a colourless solid (21 mg; 39% yield).
MS3 (ESI, m/z): 545.07 [M+H$^+$]; $t_R$=0.55 min.

Example $179: 6-{(S)-5-[2-({6-[6-(1-methyl-azetidin-3-yloxy)-pyrazin-2-yl]-pyridin-2-ylmethyl}-amino)-ethyl]-2-oxo-oxazolidin-3-yl}-4H-pyrido[3,2-b][1,4]oxazin-3-one Starting from the compound of Preparation C72 (13 mg) and the compound of Preparation D1 (14 mg) and proceeding in analogy to Example $102, step $102.i, however using a 1/1 DCM/MeOH mixture as solvent, the title compound was obtained, after purification by prep-HPLC (method 2), as a light yellow solid (9 mg; 35% yield).
MS3 (ESI, m/z): 533.13 [M+H$^+$]; $t_R$=0.48 min.

Example $180: 6-[(S)-2-oxo-5-(2-{3-[5-((R)-pyrrolidin-3-yloxy)-pyridazin-3-yl]-benzylamino}-ethyl)-oxazolidin-3-yl]-4H-pyrido[3,2-b][1,4]oxazin-3-one $180.i. Tert-butyl (R)-3-((6-(3-(((2-((S)-2-oxo-3-(3-oxo-3,4-dihydro-2H-pyrido[3,2-b][1,4]oxazin-6-yl) oxazolidin-5-yl)ethyl)amino)methyl)phenyl) pyridazin-4-yl)oxy)pyrrolidine-1-carboxylate Starting from the compound of Preparation C73 (152 mg) and the compound of Preparation D1 (115 mg) and proceeding in analogy to Example $102, step $102.i, however using a 4/1 DCM/MeOH mixture as solvent and performing the reaction in the presence of AcOH (0.024 mL), the title compound was obtained after purification by CC (DCM to DCM/MeOH/NH$_4$OH 9:1:0.1) as a yellow sticky oil (200 mg; 77% yield).
MS1 (ESI, m/z): 632.07 [M+H$^+$]; $t_R$=0.69 min.

$180.ii. 6-[(S)-2-oxo-5-(2-{3-[5-((R)-pyrrolidin-3-yloxy)-pyridazin-3-yl]-benzylamino}-ethyl)-oxazolidin-3-yl]-4H-pyrido[3,2-b][1,4]oxazin-3-one Starting from intermediate $180.i (200 mg) and proceeding in analogy to Example $102, step $102.ii, the title compound was obtained, after purification by prep-HPLC (method 4), as a colourless solid (35 mg; 64% yield).
MS1 (ESI, m/z): 532.08 [M+H$^+$]; $t_R$=0.48 min.

Example $181: 6-[(S)-2-oxo-5-(2-{3-[5-((S)-pyrrolidin-3-yloxy)-pyridazin-3-yl]-benzylamino}-ethyl)-oxazolidin-3-yl]-4H-pyrido[3,2-b][1,4]oxazin-3-one $181.i. Tert-butyl (S)-3-((6-(3-(((2-((S)-2-oxo-3-(3-oxo-3,4-dihydro-2H-pyrido[3,2-b][1,4]oxazin-6-yl) oxazolidin-5-yl)ethyl)amino)methyl)phenyl) pyridazin-4-yl)oxy)pyrrolidine-1-carboxylate Starting from the compound of Preparation C74 (152 mg) and the compound of Preparation D1 (115 mg) and proceeding in analogy to Example $102, step $102.i, however using a 4/1 DCM/MeOH mixture as solvent and performing the reaction in the presence of AcOH (0.024 mL), the title compound was obtained after purification by CC (DCM to DCM/MeOH/NH$_4$OH 9:1:0.05), as a brown sticky oil (138 mg; 53% yield).
MS1 (ESI, m/z): 632.11 [M+H$^+$]; $t_R$=0.70 min.

$181.ii. 6-[(S)-2-oxo-5-(2-{3-[5-((S)-pyrrolidin-3-yloxy)-pyridazin-3-yl]-benzylamino}-ethyl)-oxazolidin-3-yl]-4H-pyrido[3,2-b][1,4]oxazin-3-one Starting from intermediate $181.i (138 mg) and proceeding in analogy to Example $102, step $102.ii, the title compound was obtained, after purification by prep-HPLC (method 4), as a light brown solid (100 mg; 86% yield).
MS1 (ESI, m/z): 532.02 [M+H$^+$]; $t_R$=0.48 min.

Example $182: 6-[(S)-5-(2-{3-[5-((S)-1-azetidin-2-ylmethoxy)-pyridazin-3-yl]-benzylamino}-ethyl)-2-oxo-oxazolidin-3-yl]-4H-pyrido[3,2-b][1,4]oxazin-3-one $182.i. Tert-butyl (S)-2-(((6-(3-(((2-((S)-2-oxo-3-(3-oxo-3,4-dihydro-2H-pyrido[3,2-b][1,4]oxazin-6-yl) oxazolidin-5-yl)ethyl)amino)methyl)phenyl) pyridazin-4-yl)oxy)methyl)azetidine-1-carboxylate Starting from the compound of Preparation C75 (152 mg) and the compound of Preparation D1 (115 mg) and proceeding in analogy to Example $102, step $102.i, however using a 4/1 DCM/MeOH mixture as solvent and performing the reaction in the presence of AcOH (0.024 mL), the title compound was obtained after purification by CC (DCM to DCM/MeOH/NH$_4$OH 9:1:0.05) as a brown sticky oil (125 mg; 48% yield).
MS1 (ESI, m/z): 632.13 [M+H$^+$]; $t_R$=0.69 min.

$182.ii. 6-[(S)-5-(2-{3-[5-((S)-1-azetidin-2-ylmethoxy)-pyridazin-3-yl]-benzylamino}-ethyl)-2-oxo-oxazolidin-3-yl]-4H-pyrido[3,2-b][1,4]oxazin-3-one Starting from intermediate $182.i (125 mg) and proceeding in analogy to Example $102, step $102.ii, the title compound was obtained, after purification by prep-HPLC (method 4), as a light brown solid (18 mg; 17% yield).
MS1 (ESI, m/z): 531.99 [M+H$^+$]; $t_R$=0.49 min.

Example 183: 6-[(S)-5-(2-{[3'-((1S,3R)-3-aminocyclopentyloxy)-biphenyl-3-ylmethyl]-amino}-ethyl)-2-oxo-oxazolidin-3-yl]-4H-pyrido[3,2-b][1,4] oxazin-3-one $183.i. Tert-butyl ((1S,3R)-3-((3'-(((2-((S)-2-oxo-3-(3-oxo-3,4-dihydro-2H-pyrido[3,2-b][1,4]oxazin-6-yl)oxazolidin-5-yl)ethyl)amino)methyl)-[1,1'-biphenyl]-3-yl)oxy)cyclopentyl)carbamate Starting from the compound of Preparation A22 (169 mg) and the compound of Preparation D1 (80 mg) and proceeding in analogy to Example 1, step 1.i, the title compound was obtained as an off-white oil (107 mg; 58% yield).
MS3 (ESI, m/z): 644.01 [M+H$^+$]; $t_R$=0.79 min.

$183.ii. 6-[(S)-5-(2-{[3'-((1S,3R)-3-amino-cyclopentyloxy)-biphenyl-3-ylmethyl]-amino}-ethyl)-2-oxo-oxazolidin-3-yl]-4H-pyrido[3,2-b][1,4]oxazin-3-one Starting from intermediate $183.i (101 mg) and proceeding in analogy to Example 1, step 1.ii, the title compound was obtained as a colourless solid (50 mg; 59% yield).
MS3 (ESI, m/z): 544.09 [M+H$^+$]; $t_R$=0.57 min.

Example $184: (3R*,4S*)-6-[(S)-5-(2-{3-[6-(4-methoxy-pyrrolidin-3-yloxy)-pyridin-2-yl]-benzylamino}-ethyl)-2-oxo-oxazolidin-3-yl]-4H-pyrido[3,2-b][1,4]oxazin-3-one $184.i. (3R*,4S*)-3-methoxy-4-{6-[3-({2-[(S)-2-oxo-3-(3-oxo-3,4-dihydro-2H-pyrido[3,2-b][1,4] oxazin-6-yl)-oxazolidin-5-yl]-ethylamino}-methyl)-phenyl]-pyridin-2-yloxy}-pyrrolidine-1-carboxylic acid tert-butyl ester Starting from the compound of Preparation C12 (60 mg) and the compound of Preparation D1 (44 mg) and proceeding in analogy to Example $102, step $102.i, the title compound was obtained, after purification by CC (Combiflash; gradient DCM to DCM/MeOH 9:1), as a yellowish oil (65 mg; 65% yield).

MS3 (ESI, m/z): 661.99 [M+H$^+$]; $t_R$=0.75 min.

$184.ii. (3R*,4S*)-6-[(S)-5-(2-{3-[6-(4-methoxy-pyrrolidin-3-yloxy)-pyridin-2-yl]-benzylamino}-ethyl)-2-oxo-oxazolidin-3-yl]-4H-pyrido[3,2-b][1,4]oxazin-3-one Starting from intermediate $184.i (112 mg) and proceeding in analogy to Example $102, step $102.ii, the title compound was obtained, after purification by prep-HPLC (method 2), as a yellowish solid (31 mg; 61% yield).

MS3 (ESI, m/z): 561.04 [M+H+]; $t_R$=0.52 min.

Example $185: 6-[(S)-5-(2-{[6'-(1-methyl-azetidin-3-yloxy)-[2,2']bipyridinyl-4-ylmethyl]-amino}-ethyl)-2-oxo-oxazolidin-3-yl]-4H-pyrido[3,2-b][1,4]oxazin-3-one Starting from the compound of Preparation C76 (21 mg) and the compound of Preparation D1 (23 mg) and proceeding in analogy to Example $102, step $102.i, however using a 1/1 DCM/MeOH mixture as solvent, the title compound was obtained, after purification by prep-HPLC (method 2), as a yellowish solid (11 mg; 27% yield).

MS3 (ESI, m/z): 532.15 [M+H+]; $t_R$=0.51 min.

Example $186: 6-[(S)-5-(2-{[6-(1-methyl-azetidin-3-yloxy)-[2,4']bipyridinyl-2'-ylmethyl]-amino}-ethyl)-2-oxo-oxazolidin-3-yl]-4H-pyrido[3,2-b][1,4]oxazin-3-one Starting from the compound of Preparation C77 (60 mg) and the compound of Preparation D1 (65 mg) and proceeding in analogy to Example $102, step $102.i, however using a 1/1 DCM/MeOH mixture as solvent, the title compound was obtained, after purification by prep-HPLC (method 2), as a colourless solid (18 mg; 15% yield).

MS3 (ESI, m/z): 532.15 [M+H+]; $t_R$=0.52 min.

Example $187: 6-{(S)-5-[2-({4-[6-(1-methyl-azetidin-3-yloxy)-pyrazin-2-yl]-pyridin-2-ylmethyl}-amino)-ethyl]-2-oxo-oxazolidin-3-yl}-4H-pyrido[3,2-b][1,4]oxazin-3-one Starting from the compound of Preparation C78 (24 mg) and the compound of Preparation D1 (26 mg) and proceeding in analogy to Example $102, step $102.i, however using a 1/1 DCM/MeOH mixture as solvent, the title compound was obtained, after purification by prep-HPLC (method 2), as a colourless solid (14 mg; 30% yield).

MS3 (ESI, m/z): 533.15 [M+H+]; $t_R$=0.48 min.

Example $188: 6-[(S)-5-(2-{[6'-(1-methyl-azetidin-3-yloxy)-[2,2']bipyridinyl-6-ylmethyl]-amino}-ethyl)-2-oxo-oxazolidin-3-yl]-4H-pyrido[3,2-b][1,4]oxazin-3-one Starting from the compound of Preparation C79 (16 mg) and the compound of Preparation D1 (17 mg) and proceeding in analogy to Example $102, step $102.i, however using a 1/1 DCM/MeOH mixture as solvent, the title compound was obtained, after purification by prep-HPLC (method 2), as a colourless solid (9 mg; 29% yield).

MS3 (ESI, m/z): 532.13 [M+H+]; $t_R$=0.52 min.

Example $189: 6-{(S)-5-[2-({2-[6-(1-methyl-azetidin-3-yloxy)-pyrazin-2-yl]-pyridin-4-ylmethyl}-amino)-ethyl]-2-oxo-oxazolidin-3-yl}-4H-pyrido[3,2-b][1,4]oxazin-3-one Starting from the compound of Preparation C80 (11 mg) and the compound of Preparation D1 (12 mg) and proceeding in analogy to Example $102, step $102.i, however using a 1/1 DCM/MeOH mixture as solvent, the title compound was obtained, after purification by prep-HPLC (method 2), as a colourless solid (3 mg; 14% yield).

MS3 (ESI, m/z): 533.14 [M+H+]; $t_R$=0.48 min.

Example $190: 6-{(S)-5-[2-({5-[6-(1-methyl-azetidin-3-yloxy)-pyrazin-2-yl]-pyridin-3-ylmethyl}-amino)-ethyl]-2-oxo-oxazolidin-3-yl}-4H-pyrido[3,2-b][1,4]oxazin-3-one Starting from the compound of Preparation C81 (80 mg) and the compound of Preparation D1 (87 mg) and proceeding in analogy to Example $102, step $102.i, however using a 1/1 DCM/MeOH mixture as solvent, the title compound was obtained, after purification by prep-HPLC (method 2), as a light yellow solid (41 mg; 26% yield).

MS3 (ESI, m/z): 533.14 [M+H+]; $t_R$=0.47 min.

Pharmacological Properties of the Invention Compounds
In Vitro Assays
Bacterial Growth Minimal Inhibitory Concentrations:
Experimental Methods:

Minimal Inhibitory Concentrations (MICs; mg/L) were determined in cation-adjusted Mueller-Hinton Broth by a microdilution method following the description given in "Methods for Dilution Antimicrobial Susceptibility Tests for Bacteria that Grow Aerobically", Approved standard, 7$^{th}$ ed., Clinical and Laboratory Standards Institute (CLSI) Document M7-A7, Wayne, Pa., USA (2006).

Results:

All Example compounds were tested against several Gram positive and Gram negative bacteria. Typical antibacterial test results are given in Table 1 hereafter (MICs in mg/L). *Staphylococcus aureus* A798 is a multiply-resistant strain (methicillin- and quinolone-resistant), *Klebsiella pneumoniae* T6474 is a multiply-resistant strain (penicillin-, cephalosporin- and in particular quinolone-resistant), while *E. coli* ATCC25922 and *Pseudomonas aeruginosa* ATCC 27853 are quinolone-sensitive strains.

TABLE 1

| Example No. | MIC for S. aureus A798 | MIC for E. coli ATCC25922 | MIC for K. pneumoniae T6474 | MIC for P. aeruginosa ATCC 27853 |
|---|---|---|---|---|
| 1 | 2 | 1 | 1 | 2 |
| 2 | 0.5 | 2 | 2 | 4 |
| 3 | 2 | 1 | 2 | 2 |
| 4 | 2 | 1 | 2 | 2 |
| 5 | 2 | 4 | 4 | 4 |
| 6 | 4 | 4 | 4 | 4 |
| 8 | 0.25 | 0.5 | 1 | 0.25 |
| 9 | 0.125 | 2 | 1 | 2 |
| 10 | 8 | 2 | 4 | 4 |
| 11 | 2 | 2 | 4 | 1 |
| 12 | 0.063 | 1 | 2 | 2 |
| 13 | 0.5 | 2 | 2 | 8 |
| 14 | 1 | 2 | 2 | 8 |
| 15 | 0.5 | 1 | 2 | 1 |
| 16 | 0.5 | 2 | 4 | 0.5 |

TABLE 1-continued

| Example No. | MIC for S. aureus A798 | MIC for E. coli ATCC25922 | MIC for K. pneumoniae T6474 | MIC for P. aeruginosa ATCC 27853 |
|---|---|---|---|---|
| 17 | 0.5 | 1 | 2 | 1 |
| 18 | 0.5 | 1 | 2 | 1 |
| 19 | 8 | 1 | 4 | 1 |
| 20 | 0.5 | 2 | 8 | 2 |
| 21 | 0.5 | 1 | 2 | 1 |
| 22 | 0.5 | 0.5 | 2 | 0.5 |
| 23 | 0.125 | 4 | 8 | 8 |
| \$101 | 2 | 1 | 2 | 1 |
| \$102 | 2 | 1 | 2 | 2 |
| \$103 | 2 | 1 | 1 | 1 |
| \$104 | 1 | 2 | 4 | 4 |
| \$105 | 2 | 2 | 2 | 2 |
| \$106 | 2 | 2 | 4 | 1 |
| \$107 | 1 | 0.5 | 2 | 0.5 |
| \$108 | 2 | 1 | 2 | 0.5 |
| \$109 | 0.5 | 1 | 2 | 1 |
| \$110 | 0.25 | 1 | 2 | 2 |
| \$111 | 1 | 2 | 2 | 2 |
| \$113 | 0.5 | 2 | 2 | 2 |
| \$114 | 16 | 4 | 8 | 1 |
| \$115 | 4 | 4 | 16 | 2 |
| \$116 | 4 | 2 | 8 | 2 |
| \$117 | 1 | 1 | 1 | 4 |
| \$118 | 2 | 1 | 2 | 1 |
| \$119 | 0.5 | 1 | 1 | 0.5 |
| \$120 | 0.5 | 1 | 2 | 2 |
| \$121 | 0.25 | 0.5 | 0.5 | 1 |
| \$122 | 0.25 | 0.25 | 0.5 | 0.5 |
| \$123 | 0.25 | 1 | 1 | 1 |
| \$124 | 1 | 1 | 2 | 0.5 |
| \$125 | 0.5 | 1 | 2 | 4 |
| \$126 | 0.5 | 1 | 2 | 2 |
| \$127 | 1 | 2 | 8 | 4 |
| \$128 | 0.25 | 0.5 | 1 | 1 |
| \$129 | 2 | 4 | 4 | 8 |
| \$130 | 0.25 | 1 | 2 | 4 |
| \$131 | 0.25 | 0.5 | 1 | 0.5 |
| \$132 | 0.25 | 0.5 | 1 | 0.5 |
| \$133 | 1 | 1 | 2 | 0.5 |
| \$134 | 0.5 | 2 | 4 | 4 |
| \$135 | 0.5 | 0.5 | 1 | 0.5 |
| \$136 | 0.25 | 1 | 2 | 2 |
| \$137 | 0.5 | 1 | 1 | 1 |
| \$138 | 2 | 1 | 2 | 2 |
| \$139 | 0.25 | 1 | 1 | 2 |
| \$140 | 0.5 | 2 | 2 | 2 |
| \$141 | 0.5 | 2 | 2 | 2 |
| \$142 | 0.5 | 2 | 2 | 2 |
| \$143 | 2 | 2 | 4 | 1 |
| \$144 | 2 | 4 | 4 | 1 |
| \$145 | 2 | 4 | 2 | 8 |
| \$146 | 4 | 2 | 4 | 4 |
| \$147 | 1 | 1 | 1 | 4 |
| \$148 | 1 | 1 | 1 | 1 |
| \$149 | 0.5 | 0.5 | 1 | 1 |
| \$150 | 2 | 2 | 2 | 2 |
| \$151 | 4 | 2 | 2 | 1 |
| \$152 | 4 | 2 | 4 | 1 |
| \$153 | 4 | 2 | 4 | 4 |
| \$154 | 4 | 1 | 4 | 0.5 |
| \$155 | 1 | 2 | 16 | 2 |
| \$156 | 1 | 1 | 2 | 0.5 |
| \$157 | 8 | 4 | 16 | 1 |
| \$158 | 4 | 8 | 16 | 2 |
| \$159 | 8 | 16 | 8 | 4 |
| \$160 | 4 | 2 | 8 | 1 |
| \$161 | 0.5 | 0.5 | 1 | 1 |
| \$162 | 1 | 1 | 1 | 1 |
| \$163 | 0.5 | 0.5 | 2 | 0.5 |
| \$164 | 0.5 | 1 | 1 | 0.5 |
| \$165 | 8 | 4 | 4 | 2 |
| \$166 | 4 | 2 | 4 | 4 |
| \$167 | 0.25 | 1 | 1 | 1 |
| \$168 | 1 | 2 | 2 | 2 |
| \$169 | 0.25 | 1 | 2 | 2 |
| \$170 | 0.25 | 2 | 4 | 2 |
| \$171 | 0.25 | 1 | 1 | 1 |
| \$172 | 0.5 | 1 | 2 | 0.5 |
| \$173 | 0.5 | 1 | 2 | 1 |
| \$174 | 2 | 1 | 2 | 2 |
| \$175 | 0.25 | 2 | 4 | 4 |
| \$176 | 0.25 | 2 | 2 | 2 |
| \$177 | 0.5 | 2 | 4 | 4 |
| \$178 | 0.125 | 0.5 | 1 | 1 |
| \$179 | 0.5 | 1 | 1 | 2 |
| \$180 | >16 | 16 | >16 | 4 |
| \$181 | 16 | 16 | >16 | 4 |
| \$182 | 8 | 16 | 16 | 16 |
| \$183 | 2 | 4 | 4 | 4 |
| \$184 | 8 | 4 | 8 | 2 |
| \$185 | 0.125 | 0.5 | 0.5 | 1 |
| \$186 | 0.25 | 0.5 | 1 | 0.5 |
| \$187 | 0.5 | 0.5 | 1 | 0.5 |
| \$188 | 1 | 1 | 2 | 4 |
| \$189 | 0.25 | 1 | 1 | 2 |
| \$190 | 4 | 2 | 4 | 4 |
| Cipro | >8 | ≤0.016 | >8 | 0.25 |

The invention claimed is:

1. A compound of formula I

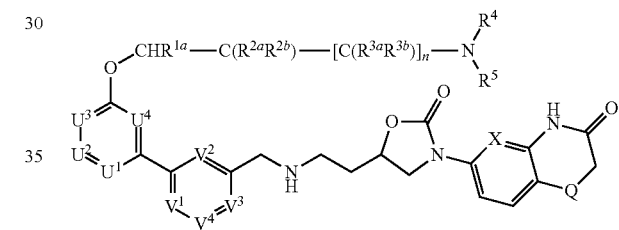

wherein n represents 0, 1, 2 or 3;

$R^{1a}$ represents H or $(C_1-C_3)$alkyl;

$R^{2a}$ and $R^{2b}$ each independently represents H or $(C_1-C_3)$alkyl;

$R^{3a}$ and $R^{3b}$ each independently represents H or $(C_1-C_3)$alkyl;

$R^4$ represents H, $(C_1-C_3)$alkyl, or $(C_2-C_3)$alkyl-$NR^{4a}R^{4b}$, wherein $R^{4a}$ and $R^{4b}$ are independently from each other H or $(C_1-C_3)$alkyl;

$R^5$ represents H, $(C_1-C_3)$alkyl, or $(C_2-C_3)$alkyl-$NR^{5a}R^{5b}$, wherein $R^{5a}$ and $R^{5b}$ are independently from each other H or $(C_1-C_3)$alkyl; or $R^{2a}$ and $R^{2b}$ together with the carbon atom which bears them, form a 3 to 6-membered cycloalkyl ring; or $R^4$ and $R^5$ together with the nitrogen atom which bears them, form a 4 to 6-membered heterocycloalkyl ring; or $R^4$ and $R^5$ together with the nitrogen atom which bears them, form a 6 to 8-membered bicyclic heterocycloalkyl ring, which bicyclic heterocycloalkyl ring may optionally be substituted by a group $NR^6R^7$, wherein $R^6$ and $R^7$ are independently from each other H or $(C_1-C_3)$alkyl; or $R^4$ and $R^5$ together with the nitrogen atom which bears them and the adjacent $CR^{2a}R^{2b}$ or $CR^{3a}R^{3b}$ together form an amidine group; or $R^{1a}$ and $R^{3a}$, together with the carbon atoms which bear them and the carbon atom which connects these latter two atoms, form a 4 to 6-membered cycloalkyl ring, whereby $R^{2a}$, $R^{2b}$ and $R^{3b}$ each represent H, and n represents 1; or $R^{1a}$ and $R^4$, together with the carbon and nitrogen atoms which bear them and the carbon atom(s) which connect(s) the latter two atoms, form a 4 to 6-membered heterocycloalkyl ring, whereby $R^{2a}$, $R^{2b}$, optional $R^{3a}$ and optional $R^{3b}$ each represent H, n represents 0 or 1, and said 4 to 6-membered heterocycloalkyl ring optionally comprises a substituent selected from $OCH_3$ or $CH_3$; or $R^{2a}$ and $R^4$ together with the carbon and nitrogen atoms which bear them and the optional carbon atom(s) which connect the latter two atoms, form a 4 to 6-membered heterocycloalkyl ring, whereby $R^{1a}$, optional $R^{3a}$ and optional $R^{3b}$ each represent H, $R^{2b}$ represents H, $NH_2$ or OH, and n represents 0, 1 or 2;

$U^1$ represents N or CH, $U^2$ represents N, CH, C—O($C_1$-$C_3$)alkyl, or C—CN, $U^3$ represents N or CH and $U^4$ represents N or CH, it being understood that at most three of $U^1$, $U^2$, $U^3$ and $U^4$ can represent N at the same time;

$V^1$ represents N or CH, $V^2$ represents N or CH, $V^3$ represents N or CH and $V^4$ represents N or CH, it being understood that at most three of $V^1$, $V^2$, $V^3$ and $V^4$ can represent N at the same time;

X represents CH or N;

Q represents O or S;

or a salt of this compound.

2. The compound according to claim 1, which is also a compound of formula $I_A$

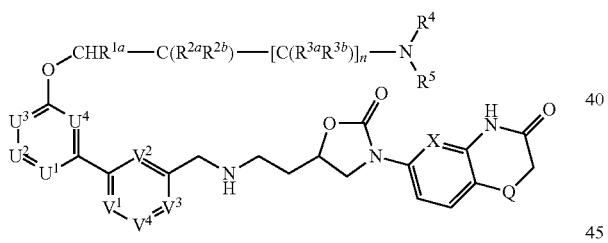

$I_A$ wherein n represents 0, 1, 2 or 3;

$R^{1a}$ represents H or ($C_1$-$C_3$)alkyl;

$R^{2a}$ and $R^{2b}$ each independently represents H or ($C_1$-$C_3$) alkyl;

$R^{3a}$ and $R^{3b}$ each independently represents H or ($C_1$-$C_3$) alkyl;

$R^4$ represents H, ($C_1$-$C_3$)alkyl, or ($C_2$-$C_3$)alkyl-$NR^{4a}R^{4b}$, wherein $R^{4a}$ and $R^{4b}$ are independently from each other H or ($C_1$-$C_3$)alkyl;

$R^5$ represents H, ($C_1$-$C_3$)alkyl, or ($C_2$-$C_3$)alkyl-$NR^{5a}R^{5b}$, wherein $R^{5a}$ and $R^{5b}$ are independently from each other H or ($C_1$-$C_3$)alkyl; or $R^{2a}$ and $R^{2b}$ together with the carbon atom which bears them, form a 3 to 6-membered cycloalkyl ring; or $R^4$ and $R^5$ together with the nitrogen atom which bears them, form a 4 to 6-membered heterocycloalkyl ring; or $R^4$ and $R^5$ together with the nitrogen atom which bears them, form a 6 to 8-membered bicyclic heterocycloalkyl ring, which bicyclic heterocycloalkyl ring may optionally be substituted by a group $NR^6R^7$, wherein $R^6$ and $R^7$ are independently from each other H or ($C_1$-$C_3$)alkyl; or $R^4$ and $R^5$ together with the nitrogen atom which bears them and the adjacent $CR^{2a}R^{2b}$ or $CR^{3a}R^{3b}$ together form an amidine group; or $R^{1a}$ and $R^{3a}$, together with the carbon atoms which bear them and the carbon atom which connects these latter two atoms, form a 4 to 6-membered cycloalkyl ring, whereby $R^{2a}$, $R^{2b}$ and $R^{3b}$ each represent H, and n represents 1;

$U^1$ represents N or CH, $U^2$ represents N, CH, C—O($C_1$-$C_3$)alkyl, or C—CN, $U^3$ represents N or CH and $U^4$ represents N or CH, it being understood that at most three of $U^1$, $U^2$, $U^3$ and $U^4$ can represent N at the same time;

$V^1$ represents N or CH, $V^2$ represents N or CH, $V^3$ represents N or CH and $V^4$ represents N or CH, it being understood that at most three of $V^1$, $V^2$, $V^3$ and $V^4$ can represent N at the same time;

X represents CH or N;

Q represents O or S;

or a salt of this compound.

3. The compound according to claim 1, which is also a compound of formula $I_B$

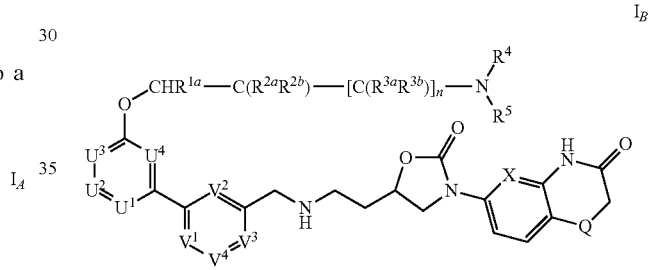

$I_B$ wherein $R^{1a}$ and $R^4$, together with the carbon and nitrogen atoms which bear them and the carbon atom(s) which connect(s) the latter two atoms, form a 4 to 6-membered heterocycloalkyl ring, whereby $R^{2a}$, $R^{2b}$, optional $R^{3a}$ and optional $R^{3b}$ each represent H, n represents 0 or 1, and said 4 to 6-membered heterocycloalkyl ring optionally comprises a substituent selected from $OCH_3$ or $CH_3$; or $R^{2a}$ and $R^4$ together with the carbon and nitrogen atoms which bear them and the optional carbon atom(s) which connect(s) the latter two atoms, form a 4 to 6-membered heterocycloalkyl ring, whereby $R^{1a}$, optional $R^{3a}$ and optional $R^{3b}$ each represent H, $R^{2b}$ represents H, $NH_2$ or OH, and n represents 0, 1 or 2;

$R^5$ represents H, ($C_1$-$C_3$)alkyl, or ($C_2$-$C_3$)alkyl-$NR^{5a}R^{5b}$, wherein $R^{5a}$ and $R^{5b}$ are independently from each other H or ($C_1$-$C_3$)alkyl;

$U^1$ represents N or CH, $U^2$ represents N, CH, C—O($C_1$-$C_3$)alkyl, or C—CN, $U^3$ represents N or CH and $U^4$ represents N or CH, it being understood that at most three of $U^1$, $U^2$, $U^3$ and $U^4$ can represent N at the same time;

$V^1$ represents N or CH, $V^2$ represents N or CH, $V^3$ represents N or CH and $V^4$ represents N or CH, it being understood that at most three of $V^1$, $V^2$, $V^3$ and $V^4$ can represent N at the same time;

X represents CH or N;
Q represents O or S;
or a salt of this compound.

4. The compound according to claim 1, wherein
$R^{1a}$ represents H or $CH_3$;
$R^{2a}$ and $R^{2b}$ each independently represents H or $CH_3$;
$R^{3a}$ and $R^{3b}$ each independently represents H or $CH_3$;
$R^4$ represents H, $CH_3$, or $CH_2CH_2NH_2$;
$R^5$ represents H, $CH_3$, or $CH_2CH_2NH_2$; and
n represents 0, 1, 2 or 3;
or a salt of this compound.

5. The compound according to claim 1, wherein
$R^{1a}$, $R^{2a}$, $R^{2b}$, $R^{3a}$ and $R^{3b}$ each represent H;
$R^4$ and $R^5$ together with the nitrogen atom which bears them, form an azetidinyl, pyrrolidinyl, piperidinyl or morpholinyl ring; and
n represents 0, 1, 2 or 3;
or a salt of this compound.

6. The compound according to claim 1, wherein
$R^{1a}$ represents H or $CH_3$;
$R^{2a}$ and $R^{2b}$, each independently from each other represents H or $CH_3$;
$R^{3a}$ and $R^{3b}$ each independently from each other represents H or $CH_3$;
$R^4$ and $R^5$ together with the nitrogen atom which bears them, form a 6-amino-3-azabicyclo[3.1.0]hexan-3-yl group; or
$R^4$ and $R^5$ together with the nitrogen atom which bears them and the adjacent $CR^{2a}R^{2b}$ or $CR^{3a}R^{3b}$ together form an amidine group; or
$R^{1a}$ and $R^{3a}$, together with the carbon atoms which bear them and the carbon atom which connects these latter two atoms, form a cyclobutyl, cyclopentyl or cyclohexyl ring;
n represents 0, 1, 2 or 3;
or a salt of this compound.

7. The compound according to claim 1, wherein
$R^{1a}$ and $R^4$, together with the carbon and nitrogen atoms which bear them and the carbon atom(s) which connect(s) the latter two atoms, form an azetinyl, pyrrolidinyl or piperidinyl ring, and said azetinyl, pyrrolidinyl or piperidinyl ring optionally comprises a substituent selected from $OCH_3$ or $CH_3$;
$R^{2a}$ and $R^{2b}$ represent H;
$R^{3a}$ and $R^{3b}$ represent H;
$R^5$ represents H or $CH_3$; and
n represents 0 or 1;
or a salt of this compound.

8. The compound according to claim 1, wherein
$R^{1a}$ represents H;
$R^{2a}$ and $R^4$ together with the carbon and nitrogen atoms which bear them and the optional carbon atom(s) which connect(s) the latter two atoms, form a azetidinyl, pyrrolidinyl or morpholinyl ring;
$R^{2b}$ represents H, $NH_2$ or OH;
$R^{3a}$ and $R^{3b}$ represent H;
$R^5$ represents H or $CH_3$; and
n represents 0, 1 or 2;
or a salt of this compound.

9. The compound according to claim 1, wherein
$U^1$ represents N or CH;
$U^2$ represents N, CH, C—$OCH_3$ or C—CN;
$U^3$ represents N or CH; and
$U^4$ represents N or CH;
it being understood that at most three of $U^1$, $U^2$, $U^3$ and $U^4$ can represent N at the same time;
or a salt of this compound.

10. The compound according to claim 1, wherein
$U^1$, $U^2$, $U^3$, $U^4$, $V^1$, $V^2$, $V^3$ and $V^4$ each represent CH; or
$U^2$ represents N; $U^1$, $U^3$, $U^4$, $V^1$, $V^2$, $V^3$ and $V^4$ each represent CH; or
$U^2$ represents C—$OCH_3$; $U^1$, $U^3$, $U^4$, $V^1$, $V^2$, $V^3$ and $V^4$ each represent CH; or
$U^3$ represents N; $U^1$, $U^2$, $U^4$, $V^1$, $V^2$, $V^3$ and $V^4$ each represent CH; or
$U^4$ represents N; $U^1$, $U^2$, $U^3$, $V^1$, $V^2$, $V^3$ and $V^4$ each represent CH; or
$U^2$ and $U^4$ represent N; $U^1$, $U^3$, $V^1$, $V^2$, $V^3$ and $V^4$ each represent CH; or
$U^4$ and $V^3$ represent N; $U^1$, $U^2$, $U^3$, $V^1$, $V^2$ and $V^4$ each represent CH;
or a salt of this compound.

11. The compound according to claim 1, wherein said compound is:
6-[(S)-5-(2-{[3'-(2-amino-ethoxy)-biphenyl-3-ylmethyl]-amino}-ethyl)-2-oxo-oxazolidin-3-yl]-4H-pyrido[3,2-b][1,4]oxazin-3-one;
6-[(S)-5-(2-{[3'-(2-dimethylamino-ethoxy)-biphenyl-3-ylmethyl]-amino}-ethyl)-2-oxo-oxazolidin-3-yl]-4H-pyrido[3,2-b][1,4]oxazin-3-one;
6-[(S)-5-(2-{[3'-(3-amino-propoxy)-biphenyl-3-ylmethyl]-amino}-ethyl)-2-oxo-oxazolidin-3-yl]-4H-pyrido[3,2-b][1,4]oxazin-3-one;
6-[(S)-5-(2-{[3'-(2-methylamino-ethoxy)-biphenyl-3-ylmethyl]-amino}-ethyl)-2-oxo-oxazolidin-3-yl]-4H-pyrido[3,2-b][1,4]oxazin-3-one;
6-[(S)-5-(2-{[3'-(4-amino-butoxy)-biphenyl-3-ylmethyl]-amino}-ethyl)-2-oxo-oxazolidin-3-yl]-4H-pyrido[3,2-b][1,4]oxazin-3-one;
6-[(S)-5-(2-{[3'-(2-amino-1-methyl-ethoxy)-biphenyl-3-ylmethyl]-amino}-ethyl)-2-oxo-oxazolidin-3-yl]-4H-pyrido[3,2-b][1,4]oxazin-3-one;
6-[(S)-5-(2-{[3'-((1R,3R)-3-amino-cyclopentyloxy)-biphenyl-3-ylmethyl]-amino}-ethyl)-2-oxo-oxazolidin-3-yl]-4H-pyrido[3,2-b][1,4]oxazin-3-one;
6-[(S)-5-(2-{3-[6-(2-amino-ethoxy)-pyridin-2-yl]-benzylamino}-ethyl)-2-oxo-oxazolidin-3-yl]-4H-pyrido[3,2-b][1,4]oxazin-3-one;
6-[(S)-2-oxo-5-(2-{3-[6-(2-pyrrolidin-1-yl-ethoxy)-pyridin-2-yl]-benzylamino}-ethyl)-oxazolidin-3-yl]-4H-pyrido[3,2-b][1,4]oxazin-3-one;
6-[(S)-5-(2-{3-[5-(2-dimethylamino-ethoxy)-pyridazin-3-yl]-benzylamino}-ethyl)-2-oxo-oxazolidin-3-yl]-4H-pyrido[3,2-b][1,4]oxazin-3-one;
6-[(S)-5-(2-{3-[5-(2-amino-ethoxy)-pyridin-3-yl]-benzylamino}-ethyl)-2-oxo-oxazolidin-3-yl]-4H-pyrido[3,2-b][1,4]oxazin-3-one;
6-[(S)-2-oxo-5-(2-{3-[6-(2-piperidin-1-yl-ethoxy)-pyridin-2-yl]-benzylamino}-ethyl)-oxazolidin-3-yl]-4H-pyrido[3,2-b][1,4]oxazin-3-one;
6-[(S)-2-oxo-5-(2-{[3'-(2-piperidin-1-yl-ethoxy)-biphenyl-3-ylmethyl]-amino}-ethyl)-oxazolidin-3-yl]-4H-pyrido[3,2-b][1,4]oxazin-3-one;
6-[(S)-5-(2-{[3'-(1-amino-cyclopropylmethoxy)-biphenyl-3-ylmethyl]-amino}-ethyl)-2-oxo-oxazolidin-3-yl]-4H-pyrido[3,2-b][1,4]oxazin-3-one;
6-[(S)-5-(2-{3-[6-(2-amino-ethoxy)-pyrazin-2-yl]-benzylamino}-ethyl)-2-oxo-oxazolidin-3-yl]-4H-pyrido[3,2-b][1,4]oxazin-3-one;
6-[(S)-5-(2-{[6-(2-amino-ethoxy)-[2,4']bipyridinyl-2'-ylmethyl]-amino}-ethyl)-2-oxo-oxazolidin-3-yl]-4H-pyrido[3,2-b][1,4]oxazin-3-one;

6-[(S)-5-(2-{3-[6-((R)-2-amino-propoxy)-pyridin-2-yl]-benzylamino}-ethyl)-2-oxo-oxazolidin-3-yl]-4H-pyrido[3,2-b][1,4]oxazin-3-one;

6-[(S)-5-(2-{3-[6-((S)-2-amino-propoxy)-pyridin-2-yl]-benzylamino}-ethyl)-2-oxo-oxazolidin-3-yl]-4H-pyrido[3,2-b][1,4]oxazin-3-one;

6-[(S)-5-(2-{3-[2-(2-amino-ethoxy)-pyridin-4-yl]-benzylamino}-ethyl)-2-oxo-oxazolidin-3-yl]-4H-pyrido[3,2-b][1,4]oxazin-3-one, 6-[(S)-5-(2-{[3'-((S)-1-azetidin-2-ylmethoxy)-biphenyl-3-ylmethyl]-amino}-ethyl)-2-oxo-oxazolidin-3-yl]-4H-pyrido[3,2-b][1,4]oxazin-3-one;

6-[(S)-2-oxo-5-(2-{[3'-((S)-1-pyrrolidin-2-ylmethoxy)-biphenyl-3-ylmethyl]-amino}-ethyl)-oxazolidin-3-yl]-4H-pyrido[3,2-b][1,4]oxazin-3-one;

6-[(S)-2-oxo-5-(2-{[3'-(pyrrolidin-3-yloxy)-biphenyl-3-ylmethyl]-amino}-ethyl)-oxazolidin-3-yl]-4H-pyrido[3,2-b][1,4]oxazin-3-one, 6-[(S)-5-(2-{[3'-((S)-1-methyl-azetidin-2-ylmethoxy)-biphenyl-3-ylmethyl]-amino}-ethyl)-2-oxo-oxazolidin-3-yl]-4H-pyrido[3,2-b][1,4]oxazin-3-one;

6-[(S)-5-(2-{[3'-(azetidin-3-yloxy)-biphenyl-3-ylmethyl]-amino}-ethyl)-2-oxo-oxazolidin-3-yl]-4H-pyrido[3,2-b][1,4]oxazin-3-one;

6-[(S)-5-(2-{3-[6-(azetidin-3-ylmethoxy)-pyridin-2-yl]-benzylamino}-ethyl)-2-oxo-oxazolidin-3-yl]-4H-pyrido[3,2-b][1,4]oxazin-3-one;

6-[(S)-5-(2-{3-[6-(azetidin-3-yloxy)-pyridin-2-yl]-benzylamino}-ethyl)-2-oxo-oxazolidin-3-yl]-4H-pyrido[3,2-b][1,4]oxazin-3-one;

6-[(S)-5-(2-{3-[6-((S)-1-azetidin-2-ylmethoxy)-pyridin-2-yl]-benzylamino}-ethyl)-2-oxo-oxazolidin-3-yl]-4H-pyrido[3,2-b][1,4]oxazin-3-one;

6-[(S)-5-(2-{3-[6-(1-morpholin-2-ylmethoxy)-pyridin-2-yl]-benzylamino}-ethyl)-2-oxo-oxazolidin-3-yl]-4H-pyrido[3,2-b][1,4]oxazin-3-one;

6-[(S)-5-(2-{3-[6-(1-morpholin-3-ylmethoxy)-pyridin-2-yl]-benzylamino}-ethyl)-2-oxo-oxazolidin-3-yl]-4H-pyrido[3,2-b][1,4]oxazin-3-one;

6-[(S)-2-oxo-5-(2-{3-[6-(piperidin-3-yloxy)-pyridin-2-yl]-benzylamino}-ethyl)-oxazolidin-3-yl]-4H-pyrido[3,2-b][1,4]oxazin-3-one;

6-[(S)-5-(2-{[3'-(2-amino-ethoxy)-5'-methoxy-biphenyl-3-ylmethyl]-amino}-ethyl)-2-oxo-oxazolidin-3-yl]-4H-pyrido[3,2-b][1,4]oxazin-3-one;

6-[(R)-5-(2-{3-[6-(2-amino-ethoxy)-pyridin-2-yl]-benzylamino}-ethyl)-2-oxo-oxazolidin-3-yl]-4H-benzo[1,4]thiazin-3-one;

6-[(S)-5-(2-{3-[6-(5-amino-pentyloxy)-pyridin-2-yl]-benzylamino}-ethyl)-2-oxo-oxazolidin-3-yl]-4H-pyrido[3,2-b][1,4]oxazin-3-one;

6-[(S)-5-(2-{3-[6-(2-morpholin-4-yl-ethoxy)-pyridin-2-yl]-benzylamino}-ethyl)-2-oxo-oxazolidin-3-yl]-4H-pyrido[3,2-b][1,4]oxazin-3-one, or (3S*,4S*)-6-[(S)-5-(2-{3-[6-(4-methoxy-pyrrolidin-3-yloxy)-pyridin-2-yl]-benzylamino}-ethyl)-2-oxo-oxazolidin-3-yl]-4H-pyrido[3,2-b][1,4]oxazin-3-one;

or a salt of this compound.

12. The compound according to of claim 1, or a pharmaceutically acceptable salt thereof, formulated as a medicament.

13. A pharmaceutical composition comprising, as active principle, the compound according to claim 1, or a pharmaceutically acceptable salt thereof, and at least one therapeutically inert excipient.

14. A method of preventing or treating a bacterial infection comprising administering to a subject an amount of the compound according to claim 1 or a pharmaceutically acceptable salt thereof.

15. The compound or pharmaceutically acceptable salt according to claim 14, wherein the bacterial infection is mediated by *Staphylococcus aureus* bacteria or *Acinetobacter baumannii* bacteria.

* * * * *